United States Patent
Han et al.

(10) Patent No.: US 12,162,931 B2
(45) Date of Patent: Dec. 10, 2024

(54) PROPERDIN BINDING PROTEIN AND USE THEREOF

(71) Applicant: LINNO PHARMACEUTICALS INC., Shanghai (CN)

(72) Inventors: Zhaozhong Han, Shanghai (CN); Lingyu Li, Shanghai (CN); Mengfan Peng, Shanghai (CN); Haiyang Li, Shanghai (CN); Jun Luo, Shanghai (CN); Hongya Pan, Shanghai (CN)

(73) Assignee: LINNO PHARMACEUTICALS INC., Shanghai (CN)

( * ) Notice: Subject to any disclaimer, the term of this patent is extended or adjusted under 35 U.S.C. 154(b) by 0 days.

(21) Appl. No.: 18/459,465

(22) Filed: Sep. 1, 2023

(65) Prior Publication Data
US 2024/0174739 A1    May 30, 2024

Related U.S. Application Data

(63) Continuation of application No. PCT/CN2023/108521, filed on Jul. 21, 2023.

(30) Foreign Application Priority Data

Nov. 25, 2022   (WO) ............... PCT/CN2022/134249

(51) Int. Cl.
| | |
|---|---|
| *C07K 16/18* | (2006.01) |
| *A61K 39/395* | (2006.01) |
| *A61P 37/02* | (2006.01) |
| *C12N 15/63* | (2006.01) |
| *G01N 33/53* | (2006.01) |
| *C07K 14/47* | (2006.01) |

(52) U.S. Cl.
CPC .......... *C07K 16/18* (2013.01); *A61K 39/3955* (2013.01); *A61P 37/02* (2018.01); *C12N 15/63* (2013.01); *G01N 33/53* (2013.01); *C07K 14/472* (2013.01); *C07K 2317/52* (2013.01); *C07K 2317/565* (2013.01); *C07K 2317/567* (2013.01); *C07K 2319/30* (2013.01); *G01N 2333/4716* (2013.01)

(58) Field of Classification Search
CPC .. C07K 16/18; C07K 14/4717; C07K 14/472; A61K 39/3955; A61K 39/395
See application file for complete search history.

(56) References Cited

U.S. PATENT DOCUMENTS

| | | |
|---|---|---|
| 7,423,128 B2 | 9/2008 | Gazit-Bornstein et al. |
| 8,664,362 B2 | 3/2014 | Bansal |
| 9,676,842 B2 | 6/2017 | Bansal |
| 9,701,742 B2 | 7/2017 | Song |
| 2013/0004485 A1 | 1/2013 | Bansal |
| 2014/0127204 A1 | 5/2014 | Bansal |
| 2014/0328846 A1 | 11/2014 | Bansal |

FOREIGN PATENT DOCUMENTS

| | | |
|---|---|---|
| CN | 103796664 A | 5/2014 |
| CN | 110831626 A | 2/2020 |
| WO | WO 2006/052591 A2 | 5/2006 |

OTHER PUBLICATIONS

Benjamini et al, 1991. Immunology: A Short Course, 2nd edition, p. 40 only.*
Ferrara et al (2015. mAbs. 7(1): 32-41) t.*
Chen et al (2018. Mol Immunol. 102: 58-72).*
Kassa et al, 2019. Expert Opinion on Biological Therapy. 19(4): 335-342.*
International Search Report issued Nov. 3, 2023 in PCT/CN2023/108521, 8 pages.

* cited by examiner

*Primary Examiner* — Zachary C Howard
(74) *Attorney, Agent, or Firm* — Merchant & Gould P.C.; Daniel J. Pereira

(57) ABSTRACT

The present disclosure provides an isolated antigen binding protein. The isolated antigen binding protein can specifically bind to properdin. The present disclosure also provides an anti-properdin antibody and a preparation method and an application thereof.

23 Claims, 77 Drawing Sheets
Specification includes a Sequence Listing.

PROPERDIN BINDING PROTEIN AND USE THEREOF

In accordance with 37 CFR § 1.833-1835 and 37 CFR § 1.77(b)(5), the specification makes reference to a Sequence Listing submitted electronically as a .xml file named "549276US_ST26.xml". The .xml file was generated on Aug. 3, 2023 and is 177,234 bytes in size. The entire contents of the Sequence Listing are hereby incorporated by reference.

FIELD OF THE INVENTION

This application is a National Stage Application and claims priority under 35 U.S.C. § 371 to Patent Cooperation Treaty application PCT/CN2023/108521, filed Jul. 21, 2023, which claims the benefit of application PCT/CN2022/134249, filed Nov. 25, 2022. Priority is claimed to these applications and the disclosures of these prior applications are considered part of the disclosure of this application and to the extent allowed the entire contents of the aforementioned applications are incorporated herein.

The present application relates to the field of biomedicine, and in particular, relates to some isolated antigen binding proteins specifically binding to properdin, and its applications thereof.

BACKGROUND OF THE INVENTION

The complement system, as a vital part of innate and adaptive immunity, plays an important role in the clearance of pathogens, cell debris and mutated cells. However, unregulated activation of this system has a significant or critical role in the pathogenesis of human diseases including eye diseases, periodontal diseases, cancer, autoimmune diseases, CNS/PNS diseases, kidney diseases and chronic hemolytic diseases. Complement inhibition has been successfully applied to clinical or experimental treatment of few human diseases such as paroxysmal nocturnal hemoglobinuria (PNH), atypical hemolytic uremic syndrome (aHUS), generalized myasthenia gravis (gMG); Neuromyelitis optica spectrum disorder (NMOSD), thrombotic microangiopathy (TMAs), age-related macular degeneration (AMD), igA nephropathy (IgAN), and Alzheimer's disease (AD).

The complement system can be activated via three routes as classical (CP), lectin (LP) or alternative (AP) pathway, respectively. The AP represents a true safeguard system that is always active and also accounts for approximately 80-90% of terminal pathway activation by forming a powerful amplification loop for the three complement pathways. The C3 convertase, either in the fluid phase or on cell surfaces, has a short half-life of around 90 seconds under physiological conditions. Properdin, a glycoprotein with low levels in plasma and high levels at inflammatory sites where it is dumped by the activated neutrophils, is the only positive regulator of the complement system by binding to and stabilizing surface-bound C3 convertases (C3bBb) and C5 convertases (C3bBbC3b) by extending the half-life of the nascent convertases by 5 to 10 fold, leading to an accelerated and efficient amplification of C3b deposition on the surface of targets. Therapeutic inhibitors of properdin would block complement at an earlier stage by interfering with the unregulated amplification of the AP and leaving CP and LP activation to physiological functions and thus potentially ameliorate human diseases more effectively and safely where the AP participates in the pathogenesis, in particular in diseases where properdin levels are increased and where properdin has been shown to play an important role in the pathogenesis.

In the past ten years, targeting complement system has been gradually gained attentions for treatment of human diseases. By interfering with terminal pathway effector generation, eculizumab (Soliris, Alexion Pharm), one humanized monoclonal antibody against human complement C5 protein, was firstly approved by the FDA in 2007 for the treatment of PNH, and subsequently expanding the indications to aHUS, gMG and NMOSD. Encouraged by such successful clinical applications, C5 antagonists in variable formats such as modified peptide, aptamer, small molecular compound (SMC), siRNA or antisense oligonucleotide (ASO) have been actively developed in clinical or preclinical settings. Molecular targets have been extended to complement proteins that are dominant in complement activation via classical, lectin or alternative pathways, including C3, complement factor B, complement factor D, MASP-2 or MASP-3, C Is, and complement factor H or 1, et. al. Particularly, OMS721 (Omeros), a human monoclonal antibody targeting mannose-binding lectin-associated serine protease-2 (MASP-2), significantly reduced the urinary albumin/creatinine ratio of patients in a phase 2 clinical trial for the treatment of IgA nephropathy. The efficacy was unprecedented in other therapies, which also earned it the FDA's breakthrough therapy designation. Furthermore, other orally bioavailable drugs are progressing through phase 2 with a focus on the amplification loop. LNPO23 (Novartis) blocks CFB and is in clinical trials for a number of indications including PNH and renal disease. Another potential target for convertase formation is properdin, a fully-human anti-properdin Fab (CLG561) was developed by Novartis for use in AMD; it had been evaluated as monotherapy or in combination with the anti-C5 mAb LFG316 in a phase 2 trial for geographic atrophy (NCT02515942).

Inhibition or modulation of properdin is an important therapeutic strategy to mitigate symptoms and slow or prevent progression of disease associated with alternative pathway. It's a viable and promising therapeutic strategy to block alternative pathway without inhibiting the classical complement pathway by depleting, neutralizing, or inactivating properdin.

SUMMARY OF THE INVENTION

The present disclosure provides an isolated antigen binding protein, which may have one or more of the following properties: 1) specifically binds to properdin, 2) inhibits alternative pathway by binding properdin, 3) inhibits interaction between properdin and C3, 4) selectively inhibits alternative pathway rather than classical pathway or lectin pathway, and 5) has species-crossing properdin-binding and complement-inhibitory activity in AP-specific pathways in mammal. The isolated antigen binding protein also shows serum stability both in plasma and formulation buffer. By multiple subcutaneous dosing said isolated antigen binding protein, properdin was depleted from serum and AP activity was inhibited consistently.

In one aspect, the present application provides an isolated antigen binding protein, comprising at least one CDR in a heavy-chain variable region VH; the VH comprises an amino acid sequence as set forth in any one of SEQ ID NO: 12, SEQ ID NO: 13, SEQ ID NO: 14, SEQ ID NO: 15, SEQ ID NO: 16, and SEQ ID NO: 17.

In some embodiments, said isolated antigen binding protein may bind to specifically epitopes domain of properdin. In some embodiments, said epitopes comprise TSR5, TSR6, and/or TSR0 of properdin.

In some embodiments, said isolated antigen binding protein may has a competitive target binding capability with reference antibodies, wherein said reference antibodies comprise CDR1, CDR2 and CDR3, said CDR1 comprises an amino acid sequence as set forth in any one of SEQ ID NO: 1, SEQ ID NO: 2, and SEQ ID NO: 3, said CDR2 comprises an amino acid sequence as set forth in any one of SEQ ID NO: 6, SEQ ID NO: 7, and SEQ ID NO: 8, said CDR3 comprises an amino acid sequence as set forth in any one of SEQ ID NO: 12, SEQ ID NO: 13, and SEQ ID NO: 14.

In some embodiments, said reference antibodies may comprise CDR1, CDR2 and CDR3, said CDR1 comprises an amino acid sequence as set forth in SEQ ID NO: 1, said CDR2 comprises an amino acid sequence as set forth in SEQ ID NO: 6, and said CDR3 comprises an amino acid sequence as set forth in SEQ ID NO: 12.

In some embodiments, said reference antibodies may comprise CDR1, CDR2 and CDR3, said CDR1 comprises an amino acid sequence as set forth in SEQ ID NO: 2, said CDR2 comprises an amino acid sequence as set forth in SEQ ID NO: 7, and said CDR3 comprises an amino acid sequence as set forth in SEQ ID NO: 13.

In some embodiments, said reference antibodies may comprise CDR1, CDR2 and CDR3, said CDR1 comprises an amino acid sequence as set forth in SEQ ID NO: 3, said CDR2 comprises an amino acid sequence as set forth in SEQ ID NO: 8, and said CDR3 comprises an amino acid sequence as set forth in SEQ ID NO: 14.

In some embodiments, said reference antibodies may comprise an amino acid sequence as set forth in any one of SEQ ID NO: 60, SEQ ID NO: 66, and SEQ ID NO: 70.

In some embodiments, said isolated antigen binding protein may comprise CDR3, said CDR3 may comprises an amino acid sequence as set forth in any one of SEQ ID NO: 12, SEQ ID NO: 13, SEQ ID NO: 14, SEQ ID NO: 15, SEQ ID NO: 16, and SEQ ID NO: 17.

In some embodiments, said isolated antigen binding protein may comprise CDR2, said CDR2 may comprises an amino acid sequence as set forth in SEQ ID NO: 55.

In some embodiments, said isolated antigen binding protein may comprise CDR2, said CDR2 may comprises an amino acid sequence as set forth in any one of SEQ ID NO: 6, SEQ ID NO: 7, SEQ ID NO: 8, SEQ ID NO: 9, SEQ ID NO: 10, and SEQ ID NO: 11.

In some embodiments, said isolated antigen binding protein may comprise CDR1, said CDR1 may comprises an amino acid sequence as set forth in X1 X2CMX5, in which X1 is H or S or T or Y, X2 is G or Y, and X5 is A or G.

In some embodiments, said isolated antigen binding protein may comprise CDR1, said CDR1 may comprises an amino acid sequence as set forth in any one of SEQ ID NO: 1, SEQ ID NO: 2, SEQ ID NO: 3, SEQ ID NO: 4, and SEQ ID NO: 5.

In some embodiments, said isolated antigen binding protein may comprise CDR1, CDR2 and CDR3, said CDR1 comprises an amino acid sequence as set forth in X1 X2CMX5, in which X1 is H or S or T or Y, X2 is G or Y, and X5 is A or G, said CDR2 comprises an amino acid sequence as set forth in SEQ ID NO: 55, and said CDR3 comprises an amino acid sequence as set forth in any one of SEQ ID NO: 12, SEQ ID NO: 13, SEQ ID NO: 14, SEQ ID NO: 15, SEQ ID NO: 16, and SEQ ID NO: 17.

In some embodiments, said isolated antigen binding protein may comprise CDR1, CDR2 and CDR3, said CDR1 comprises an amino acid sequence as set forth in any one of SEQ ID NO: 1, SEQ ID NO: 2, SEQ ID NO: 3, SEQ ID NO: 4, and SEQ ID NO: 5, said CDR2 comprises an amino acid sequence as set forth in any one of SEQ ID NO: 6, SEQ ID NO: 7, SEQ ID NO: 8, SEQ ID NO: 9, SEQ ID NO: 10, and SEQ ID NO: 11, and said CDR3 comprises an amino acid sequence as set forth in any one of SEQ ID NO: 12, SEQ ID NO: 13, SEQ ID NO: 14, SEQ ID NO: 15, SEQ ID NO: 16, and SEQ ID NO: 17.

In some embodiments, said isolated antigen binding protein may comprise CDR1, CDR2 and CDR3, said CDR1 comprises an amino acid sequence as set forth in SEQ ID NO: 1, said CDR2 comprises an amino acid sequence as set forth in SEQ ID NO: 6, and said CDR3 comprises an amino acid sequence as set forth in SEQ ID NO: 12.

In some embodiments, said isolated antigen binding protein may comprise CDR1, CDR2 and CDR3, said CDR1 comprises an amino acid sequence as set forth in SEQ ID NO: 2, said CDR2 comprises an amino acid sequence as set forth in SEQ ID NO: 7, and said CDR3 comprises an amino acid sequence as set forth in SEQ ID NO: 13.

In some embodiments, said isolated antigen binding protein may comprise CDR1, CDR2 and CDR3, said CDR1 comprises an amino acid sequence as set forth in SEQ ID NO: 3, said CDR2 comprises an amino acid sequence as set forth in SEQ ID NO: 8, and said CDR3 comprises an amino acid sequence as set forth in SEQ ID NO: 14.

In some embodiments, said isolated antigen binding protein may comprise CDR1, CDR2 and CDR3, said CDR1 comprises an amino acid sequence as set forth in SEQ ID NO: 4, said CDR2 comprises an amino acid sequence as set forth in SEQ ID NO: 9, and said CDR3 comprises an amino acid sequence as set forth in SEQ ID NO: 15.

In some embodiments, said isolated antigen binding protein may comprise CDR1, CDR2 and CDR3, said CDR1 comprises an amino acid sequence as set forth in SEQ ID NO: 5, said CDR2 comprises an amino acid sequence as set forth in SEQ ID NO: 10, and said CDR3 comprises an amino acid sequence as set forth in SEQ ID NO: 16.

In some embodiments, said isolated antigen binding protein may comprise CDR1, CDR2 and CDR3, said CDR1 comprises an amino acid sequence as set forth in SEQ ID NO: 3, said CDR2 comprises an amino acid sequence as set forth in SEQ ID NO: 11, and said CDR3 comprises an amino acid sequence as set forth in SEQ ID NO: 17.

In some embodiments, said isolated antigen binding protein may comprise FR1, wherein the C-terminus of said FR1 is linked directly or indirectly to the N-terminus of said CDR1, and said FR1 comprises an amino acid sequence as set forth in SEQ ID NO: 56.

In some embodiments, said FR1 of said isolated antigen binding protein may comprise an amino acid sequence as set forth in any one of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In some embodiments, said isolated antigen binding protein may comprise FR2, wherein said FR2 is located between said CDR1 and said CDR2, and FR2 comprises an amino acid sequence as set forth in SEQ ID NO: 57.

In some embodiments, said FR2 of said isolated antigen binding protein may comprise an amino acid sequence as set forth in any one of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In some embodiments, said isolated antigen binding protein may comprise FR3, wherein said FR3 is located between said CDR2 and said CDR3, and FR3 comprises an amino acid sequence as set forth in SEQ ID NO: 58.

In some embodiments, said FR3 of said isolated antigen binding protein may comprise an amino acid sequence as set forth in any one of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51.

In some embodiments, said isolated antigen binding protein may comprise FR4, wherein the N-terminus of said FR4 is linked directly or indirectly to the C-terminus of said CDR3, and said FR4 comprises an amino acid sequence as set forth in SEQ ID NO: 59.

In some embodiments, said FR4 of said isolated antigen binding protein may comprise an amino acid sequence as set forth in any one of SEQ ID NO: 52 and SEQ ID NO: 53.

In some embodiments, said isolated antigen binding protein comprises FR1, FR2, FR3 and FR4, said FR1 comprises an amino acid sequence as set forth in SEQ ID NO: 56, said FR2 comprises an amino acid sequence as set forth in SEQ ID NO: 57, said FR3 comprises an amino acid sequence as set forth in SEQ ID NO: 58, and said FR4 comprises an amino acid sequence as set forth in SEQ ID NO: 59.

In some embodiments, said isolated antigen binding protein comprises FR1, FR2, FR3 and FR4, said FR1 comprises an amino acid sequence as set forth in any one of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30, said FR2 comprises an amino acid sequence as set forth in any one of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40, said FR3 comprises an amino acid sequence as set forth in any one of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51, and FR4 comprises an amino acid sequence as set forth in any one of SEQ ID NO: 52 and SEQ ID NO: 53.

In some embodiments, said isolated antigen binding protein comprises FR1, FR2, FR3 and FR4, and said isolated antigen binding protein comprising any set of amino acid sequences selected from the group consisting of: FR1: SEQ ID NO: 18, FR2: SEQ ID NO: 31, FR3: SEQ ID NO: 41, FR4: SEQ ID NO: 52; FR1: SEQ ID NO: 19, FR2: SEQ ID NO: 32, FR3: SEQ ID NO: 42, FR4: SEQ ID NO: 53; FR1: SEQ ID NO: 19, FR2: SEQ ID NO: 32, FR3: SEQ ID NO: 43, FR4: SEQ ID NO: 53; FR1: SEQ ID NO: 20, FR2: SEQ ID NO: 32, FR3: SEQ ID NO: 43, FR4: SEQ ID NO: 53; FR1: SEQ ID NO: 20, FR2: SEQ ID NO: 31, FR3: SEQ ID NO: 43, FR4: SEQ ID NO: 53; FR1: SEQ ID NO: 21, FR2: SEQ ID NO: 33, FR3: SEQ ID NO: 44, FR4: SEQ ID NO: 52; FR1: SEQ ID NO: 22, FR2: SEQ ID NO: 34, FR3: SEQ ID NO: 42, FR4: SEQ ID NO: 53; FR1: SEQ ID NO: 22, FR2. SEQ ID NO: 34, FR3: SEQ ID NO: 45, FR4: SEQ ID NO: 53; FR1: SEQ ID NO: 22, FR2: SEQ ID NO: 33, FR3: SEQ ID NO: 45, FR4: SEQ ID NO: 53; FR1: SEQ ID NO: 23, FR2: SEQ ID NO: 35, FR3: SEQ ID NO: 46, FR4: SEQ ID NO: 52; FR1: SEQ ID NO: 24, FR2: SEQ ID NO: 36, FR3: SEQ ID NO: 47, FR4: SEQ ID NO: 53; FR1: SEQ ID NO: 24, FR2: SEQ ID NO: 36, FR3: SEQ ID NO: 48, FR4: SEQ ID NO: 53; FR1: SEQ ID NO: 25, FR2: SEQ ID NO: 36, FR3: SEQ ID NO: 48, FR4: SEQ ID NO: 53; FR1: SEQ ID NO: 25, FR2: SEQ ID NO: 35, FR3: SEQ ID NO: 48, FR4: SEQ ID NO: 53; FR1: SEQ ID NO: 26, FR2. SEQ ID NO: 37, FR3: SEQ ID NO: 49, FR4: SEQ ID NO: 52; FR1: SEQ ID NO: 27, FR2: SEQ ID NO: 38, FR3: SEQ ID NO: 42, FR4: SEQ ID NO: 53; FR1: SEQ ID NO: 27, FR2: SEQ ID NO: 39, FR3: SEQ ID NO: 42, FR4: SEQ ID NO: 53; FR1: SEQ ID NO: 28, FR2: SEQ ID NO: 39, FR3: SEQ ID NO: 42, FR4: SEQ ID NO: 53: FR1: SEQ ID NO: 28, FR2: SEQ ID NO: 39, FR3: SEQ ID NO: 43, FR4: SEQ ID NO: 53; FR1: SEQ ID NO: 28, FR2: SEQ ID NO: 37, FR3: SEQ ID NO: 43, FR4: SEQ ID NO: 53; FR1: SEQ ID NO: 29, FR2: SEQ ID NO: 31, FR3: SEQ ID NO: 50, FR4: SEQ ID NO: 52; and FR1: SEQ ID NO: 30, FR2. SEQ ID NO: 40, FR3: SEQ ID NO: 51, FR4: SEQ ID NO: 52.

In some embodiments, said isolated antigen binding protein comprises a heavy chain variable region VH, which comprises an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

In some embodiments, said heavy chain variable region is VHH.

In some embodiments, said isolated antigen binding protein may comprise an antibody heavy-chain constant region.

In some embodiments, said heavy-chain constant region may comprise a human Fc region.

In some embodiments, said heavy-chain constant region may comprise an amino acid sequence as set forth in SEQ ID NO: 109.

In some embodiments, said isolated antigen binding protein may be directly or indirectly linked to a second antigen binding domain.

In some embodiments, said isolated antigen binding protein may be linked to a second antigen binding domain by a linker.

In some embodiments, said linker of said isolated antigen binding protein may be a poly-glycine linker.

In some embodiments, said linker of said isolated antigen binding protein may comprise an amino acid sequence as set forth in SEQ ID NO: 108: GGGGSGGGGSGGGGS.

In some embodiments, said second antigen binding domain of said isolated antigen binding protein may bind to properdin.

In some embodiments, said second antigen binding domain of said isolated antigen binding protein may bind to different epitopes of properdin from said isolated antigen binding protein.

In some embodiments, said second antigen binding domain of said isolated antigen binding protein may bind to the same epitopes of properdin with the isolated antigen binding protein.

In some embodiments, said second antigen binding domain of said isolated antigen binding protein may comprise an amino acid sequence as set forth in of any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

In some embodiments, said isolated antigen binding protein may comprise an amino acid sequence as set forth in SEQ ID NO: 81.

In some embodiments, said isolated antigen binding protein may comprise an antibody or an antigen binding fragments thereof.

In some embodiments, said isolated antigen binding fragment may comprise Fab, Fab', F(ab)$_2$, Fv fragments, F(ab')$_2$, scFv, di-scFv, VHH and/or dAb.

In some embodiments, said antibody may be selected from the group consisting of: monoclonal antibodies, single chain antibodies, chimeric antibodies, humanized antibodies, and fully human antibodies.

In some embodiments, said antibody may be a camelid antibody.

In another aspect, the present application provides a fusion protein, comprising the isolated antigen binding protein.

In some embodiments, said fusion protein may comprise a functionally active protein.

In some embodiments, said isolated antigen binding protein may be directly or indirectly linked to said functionally active protein.

In some embodiments, said isolated antigen binding protein may be linked to said functionally active protein by a linker.

In some embodiments, said isolated antigen binding protein may be linked to said functionally active protein by more than one linker.

In some embodiments, said linker of said isolated antigen binding protein and said functionally active protein may be a poly-glycine linker.

In some embodiments, said linker of said isolated antigen binding protein and said functionally active protein may be more than one poly-glycine linker.

In some embodiments, said linker of said isolated antigen binding protein and said functionally active protein may comprise an amino acid sequence as set forth in SEQ ID NO: 108: GGGGSGGGGSGGGGS.

In some embodiments, said functionally active protein of said fusion protein may be factor H.

In some embodiments, said factor H of said fusion protein may comprise an amino acid sequence as set forth in SEQ ID NO: 110.

In some embodiments, said factor H of said fusion protein may comprise its functional active fragment, ortholog, and variant. In some embodiments, the sequence similarity may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

In some embodiments, said fusion protein may comprise an amino acid sequence as set forth in SEQ ID NO: 82.

In some embodiments, said functionally active protein of said fusion protein may be VEGF inhibiting protein.

In some embodiments, said VEGF inhibiting protein, of said fusion protein may comprise an amino acid sequence as set forth in SEQ ID NO: 113.

In some embodiments, said VEGF inhibiting protein of said fusion protein may comprise its functional active fragment, ortholog, and variant. In some embodiments, the sequence similarity may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

In some embodiments, said fusion protein may comprise an amino acid sequence as set forth in SEQ ID NO: 114.

In some embodiments, said functionally active protein of said fusion protein may be transferrin inhibiting protein.

In some embodiments, said transferrin inhibiting protein of said fusion protein may comprise an amino acid sequence as set forth in SEQ ID NO: 115.

In some embodiments, said transferrin inhibiting protein of said fusion protein may comprise its functional active fragment, ortholog, and variant. In some embodiments, the sequence similarity may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

In some embodiments, said fusion protein may comprise an amino acid sequence as set forth in SEQ ID NO: 117.

In some embodiments, said fusion protein may comprise an amino acid sequence as set forth in SEQ ID NO: 118.

In another aspect, the present application provides a polypeptide, comprising the isolated antigen binding protein.

In another aspect, the present application provides an immunoconjugate, comprising the isolated antigen binding protein or the polypeptide.

In another aspect, the present application provides an isolated nucleic acid molecule or isolated nucleic acid molecules, encoding the isolated antigen binding protein.

In another aspect, the present application further provides a vector, comprising the nucleic acid molecule(s).

In another aspect, the present application provides a cell, comprising said nucleic acid molecule(s), said polypeptide, said immunoconjugate, said isolated nucleic acid molecule, and/or said vector.

In another aspect, the present application provides a method of producing said isolated antigen binding protein or said polypeptide, wherein said method comprises culturing the cell under conditions that allow expression of said isolated antigen binding protein or said polypeptide.

In another aspect, the present application provides a method for detecting properdin, wherein said method comprises using said isolated antigen binding protein or said polypeptide.

In some embodiments, said isolated antigen binding protein of said methods comprises an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118.

In another aspect, the present application provides a detection kit for properdin, comprising said isolated antigen binding protein or said polypeptide.

In some embodiments, said isolated antigen binding protein of said detection kit comprises an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118.

In another aspect, the present application provides the use of said isolated antigen binding protein or said polypeptide in the preparation of a kit.

In some embodiments, said isolated antigen binding protein of said use comprises an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118.

In another aspect, the present application provides a pharmaceutical composition, comprising said isolated antigen binding protein, said polypeptide, said immunoconjugate, said isolated nucleic acid molecule, said vector, said cell, and/or a pharmaceutically acceptable adjuvant and/or excipient.

In another aspect, the present application provides a pharmaceutical combination comprising said isolated antigen binding protein.

In another aspect, the present application provides a method of inhibiting alternative complement pathway, comprising administering an effective amount of said isolated antigen binding protein, said polypeptide, said immunoconjugate, said isolated nucleic acid molecule, said vector, said cell, and/or said pharmaceutical composition, and/or a pharmaceutically acceptable therapeutic agent.

In another aspect, the present application provides a method of inhibiting alternative complement pathway, comprising administering an effective amount of said pharmaceutical combination and/or a pharmaceutically acceptable therapeutic agent.

In another aspect, the present application provides said isolated antigen binding protein, said polypeptide, said immunoconjugate, said isolated nucleic acid molecule, said vector, said cell and/or said pharmaceutical composition, and/or said pharmaceutical combination for use in the prevention and/or treatment of diseases.

In some embodiments, said diseases may be caused by properdin.

In some embodiments, said diseases may be mediated by alternative pathway.

In some embodiments, said diseases may include autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the present application provides the use of said isolated antigen binding protein, said polypeptide, said immunoconjugate, said isolated nucleic acid molecule, said vector, said cell, said pharmaceutical composition, and/or pharmaceutical combination in the manufacture of a medicament for the prevention and/or treatment of a disease.

In some embodiments, said diseases of said use may be caused by properdin.

In some embodiments, said diseases of said use may be mediated by alternative pathway.

In some embodiments, said diseases of said use may include autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the present application provides a method of preventing and/or treating a disease, comprising administering to a patient in need thereof an effective amount of said isolated antigen binding protein, said polypeptide, said immunoconjugate, said isolated nucleic acid molecule, said vector, said cell, said pharmaceutical composition, and/or said pharmaceutical combination.

In some embodiments, said diseases of said method may be caused by properdin.

In some embodiments, said diseases of said method may be mediated by alternative pathway.

In some embodiments, said diseases of said method may include autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1:
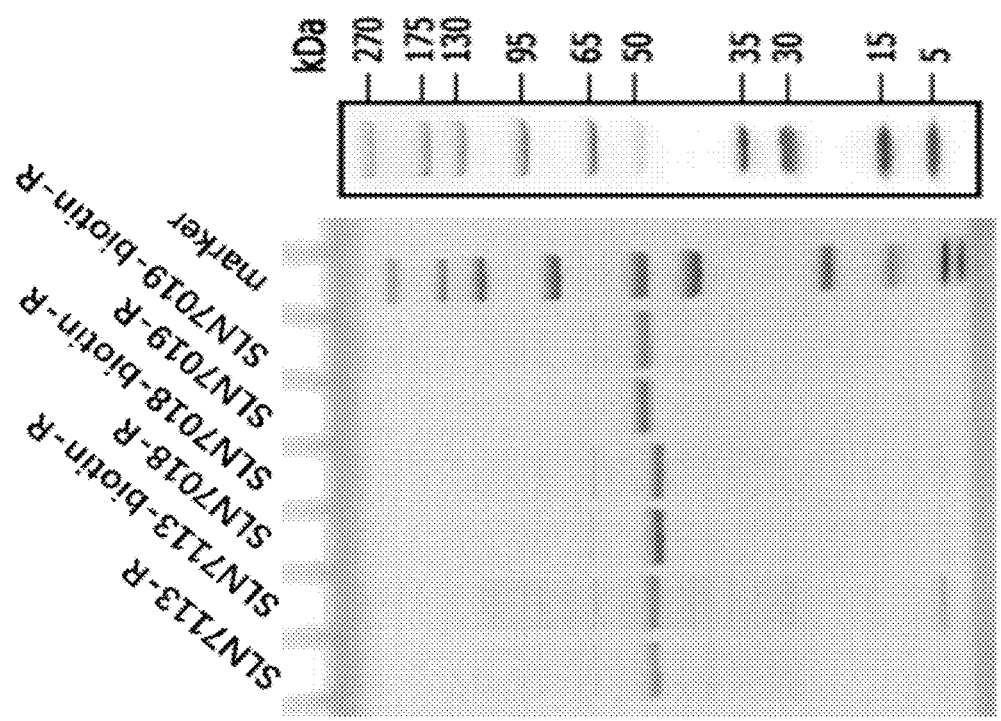
FIG. 1 Illustrates production of human, mouse and cyno properdin analysis on non-reducing and reducing SDS-PAGE.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Terms & Definitions

The term "antibody" is used in the broadest sense, and may include but not limited to monoclonal antibodies (including full-length monoclonal antibodies containing two light chains and two heavy chains), polyclonal antibodies, multi-specific antibodies (e.g., bispecific antibodies), murine antibodies, human antibodies (fully human antibodies), humanized antibodies, chimeric antibodies, single chain antibodies (e.g., scFv), antibody derivatives, and antibody fragments that bind to an antigen (e.g., Fab', VHH, and (Fab)$_2$ fragments). The term "antibody" may also include all recombinant forms of antibodies, such as antibodies expressed in prokaryotic cells, unglycosylated antibodies, and any antigen-binding antibody fragments and derivatives thereof described herein. The "antibody" may generally comprise a protein in which at least two heavy chains (HC) and two light chains (LC) are linked to each other by disulfide bonds, or an antigen-binding fragment thereof. Each heavy chain may be composed of a heavy chain variable region (VH) and a heavy chain constant region. The VH region can be further distinguished as hypervariable regions, termed complementarity determining region (CDR), interspersed with more conserved regions termed framework region (FR). Each VH may be composed of three CDRs and four FRs regions, which may be arranged from amino-terminus to carboxy-terminus in the following order: FR1, CDR1, FR2, CDR2, FR3, CDR3 and FR4. The variable regions of the heavy chains contain binding domains that interact with an antigen (e.g., properdin). In the art, the CDR of an antibody may be defined by a variety of methods, for example, the Kabat definition rules based on sequence variability (see, Kabat et al., Sequences of Proteins of Immunological Interest, Fifth Edition, National Institutes of Health, Besse Star, Maryland (1991)), the Chothia definition rules based on the location of the structural loop regions (see, Al-Lazikani et al., J Mol Biol 273: 927-48, 1997), and the IMGT definition rules based on the concepts in IMGT-ONTOLOGY and IMGT Scientific chart rules. In the present application, the CDRs may be defined by the Kabat definition rules.

The term "antigen binding domain" herein generally refers to a domain capable of binding to a target. For example, the binding may require some complementarity in binding sequence. For example, the binding may require special structure. For example, in the present application, the antigen binding domain of antigen binding protein may specifically bind to antigen (e.g., properdin, VEGF family, transferrin). For example, the antigen binding domain may belong to an antibody or an antigen binding fragment, and make them bind to the target with greater affinity, avidity, easiness, and/or duration than it binds to other targets. For example, the antigen binding domain may have a measurable and reproducible interaction, such as the binding between an antigen and an antibody, whereby the existence of a target may be determined in the presence of a heterogeneous population of molecules (including biomolecules). "Binding sequence" refers to a specific amino sequence on the target (e.g., antigen), which is complementary to the antigen binding protein.

The term "antigen binding fragment" herein generally refers to one or more fragments of an antibody that specifically bind to antigen. The antigen binding function of an antibody can be achieved by a full-length fragment of the antibody. The antigen binding function of an antibody can also be achieved by: a heavy chain comprising a fragment of Fv, scFv, dsFv, Fab' or F(ab')$_2$, or a light chain comprising a fragment of Fv, scFv, dsFv, Fab' or F(ab')$_2$. The term "Fab" generally refers to a fragment comprising a heavy-chain variable domain and a light-chain variable domain, and also comprising a light-chain constant domain and a heavy-chain first constant domain (CHI). The term "Fab'" generally refers to a fragment that is different from Fab by the addition of a few residues (comprising one or more cysteines from the hinge region of an antibody) to a carboxyl terminus of the heavy-chain CHI. The term "F(ab')2" generally refers to a dimer of Fab', comprising an antibody fragment in which two Fab fragments are linked by a disulfide bridge on the hinge region. The term "Fv" generally refers to the smallest antibody fragment that comprises a complete antigen recognition and binding site. In some cases, this fragment may consist of a dimer in which one heavy-chain variable region and one light-chain variable region are tightly non-covalently bound. The term "dsFv" generally refers to a disulfide-stabilized Fv fragment, with a disulfide bond between a single light-chain variable region and a single heavy-chain variable region. The term "dAb fragment" generally refers to an antibody fragment consisting of a VH domain. The term "scFv" generally refers to a molecule produced by covalently linking and pairing one heavy-chain variable domain with one light-chain variable domain of an antibody by means of a flexible peptide linker. The term "Fd" generally refers to a fragment consisting of the VH and CH domains. For example, the term "antigen binding fragment" may include one class of antibody VHHs, which lacks the antibody light chain and has only the heavy chain variable region.

The term "antigen binding protein" herein generally refers to a polypeptide molecule capable of specifically recognizing and/or neutralizing a particular antigen. For example, in the present application, the term "antigen binding protein" may include an "antibody" or an "antigen binding fragment", as long as they exhibit the desired antigen-binding activity. For example, the said isolated antigen binding protein may comprise a single domain protein, for example, the said isolated antigen binding protein may include any molecule comprising an antigen-binding portion thereof. For example, the said isolated antigen binding protein may comprise a VHH-Fc protein or a Fc-VHH-VHH protein.

The term "camelid antibody" generally refers to an antibody derived from a camelid species. For example, in a camel, dromedary, llama, alpaca or guanaco. Camelid antibody lacks a light chain, and thus includes only heavy chains with complete and diverse antigen binding capabilities.

The term "VHH", also known as VHH domains, VHH antibody fragments, and VHH antibodies, generally refers to the antigen binding immunoglobulin (variable) domain of "heavy chain antibodies". For example, having the structure of FR1-CDR1-FR2-CDR2-FR3-CDR3-FR4 and specifically binding to an epitope without requiring the presence of a second immunoglobulin variable domain.

The term "cell" generally refers to an individual cell, a cell line or a cell culture, which may contain or already contain a plasmid or vector comprising a nucleic acid molecule of the present application, or which is capable of expressing the antibody or antigen binding fragment thereof in the present application. The cell may include a progeny of a single host cell. Due to natural, accidental or deliberate mutations, progeny cells and original parent cells may not be necessarily identical in terms of morphology or genome, as long as they are capable of expressing the antibody or antigen-binding fragment thereof in the present application. The cells may be obtained by transfecting cells in vitro using the vector of the present application. The cells may be prokaryotic cells (e.g., *Escherichia coli*), or eukaryotic cells (e.g., yeast cells; e.g., COS cells, Chinese hamster ovary (CHO) cells, HeLa cells, HEK293 cells, COS-1 cells, NS0 cells, or myeloma cells). In some cases, the cells may be mammalian cells. For example, the mammalian cells may be CHO-K1 cells.

The term "chimeric antibodies" generally refers to an antibody in which the variable region is derived from one species and the constant region is derived from another species. Generally, the variable region is derived from an antibody ("parent antibody") in an experimental animal such as a rodent, and the constant region is derived from a human antibody, such that the possibility of causing an adverse immune response in an individual human by the resulting chimeric antibody is reduced as compared with the parental (e.g., mouse-derived) antibody.

The term "derivative" "variant" or "analogue" are used interchangeably, and generally refers to a polypeptide or polynucleotide of the present application, including any substitution, variation, modification, substitution, deletion and/or addition of one (or more) amino acid residues from/to the sequence, so long as the resulting polypeptide or polynucleotide substantially retains at least one of its endogenous functions. For example, the derivative may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

The term "epitopes" generally refers to a domain or an amino acid sequence specifically bind to antigen binding protein. For example, the term "epitopes" may include chemically active surface molecular groups (e.g., a sugar side chain, a phosphoryl group, or a sulfonyl group). For example, the term "epitope" may have specific tertiary structural features, and/or specific charge features.

The term "fully human antibodies" generally refers to an antibody that contains only the sequence of human immunoglobulin proteins. The fully human antibody can greatly reduce the side immune effects caused by heterologous antibodies on the human body. Methods for obtaining the fully human antibody in the art may include the phage display technology, the transgenic mouse technology, the ribosome display technology, the RNA-polypeptide technology, etc.

The term "bi-paratopic antigen-binding protein" generally refers to an antigen-binding molecule comprising a first antigen-binding domain and a second antigen-binding domain. For example, the two antigen-binding domain binds to two different epitopes. For example, non-overlapping epitopes of the respective antigen. For example, the first antigen-binding domain and the second antigen-binding domain may target the same antigen. For example, the first antigen-binding domain and the second antigen-binding domain target different epitopes of the same antigen. The part of an antigen-binding protein that recognize the epitope is called a paratope.

The term "fusion protein" generally refers to a protein composed of two or more polypeptides. The two or more polypeptide components can be bound directly or indirectly through a peptide linker/spacer. For example, said polypeptides are not normally bound in their natural state, they are held together by peptide bonds through their respective amino and carboxyl termini to form a contiguous polypeptide. For example, the term "fusion protein" comprises an antigen binding protein which is prepared by the method described in present application, and a functionally active protein. For example, the said functionally active protein may be factor H. For example, the said functionally active protein may be VEGF inhibiting protein. For example, the said functionally active protein may be transferrin inhibiting protein. For example, the fusion protein may include a prophylactic or therapeutic drug fused to a heterologous protein, polypeptide, or peptide. Wherein, the heterologous protein, polypeptide or peptide may or may not be different types or therapeutic drugs. For example, the fusion protein may comprise two different proteins, polypeptides or peptides with immunomodulatory activity. For example, the fusion protein may retain or improve the activity compared to the activity of the original polypeptide or protein. Typically, the fusion protein can be produced by in vitro recombinant techniques well known in the art. For example, the fusion protein may comprise the antigen binding protein. For example, the fusion protein may comprise biologic molecules. For example, the fusion protein may compose of properdin inhibiting proteins and VEGF inhibiting proteins.

For example, the fusion protein may compose of properdin inhibiting proteins and transferrin inhibiting proteins.

The term "blood-brain barrier (BBB)", generally refers to the physiological barrier between the peripheral circulation and the brain and spinal cord. It is formed by the tight junctions in the plasma membrane of brain capillary endothelial cells and constitutes a tight barrier that restricts the transport of molecules to the brain, even very small molecules such as urea (60 Daltons). For example, the brain capillary endothelial cells may have weaker pinocytosis. For example, the blood-brain barrier may include the BBB in the brain, the blood-spinal cord barrier in the spinal cord, and the blood-retinal barrier in the retina. For example, the BBB may also include the blood-CSF barrier (choroid plexus), where the barrier is composed of ependymal cells instead of capillary endothelial cells.

The term "humanized antibodies" generally refers to an antibody in which some or all of the amino acids outside the CDR of a non-human antibody (e.g., a mouse antibody) have been replaced by corresponding amino acids derived from human immunoglobulins. In the CDR, small additions, deletions, insertions, substitutions, or modifications to the amino acids may also be allowed, as long as they still retain the capability of the antibody to bind to a specific antigen. The humanized antibody may optionally comprise at least a portion of a constant region of a human immunoglobulin. The "humanized antibody" reserves the antigen specificity similar to that of the original antibody. The "humanized" form of a non-human (e.g., a mouse) antibody may minimally comprise a chimeric antibody derived from a non-human immunoglobulin sequence. In some cases, CDR residues in a human immunoglobulin (receptor antibody) may be replaced with CDR residues from a non-human species (donor antibody) (e.g., a mouse, a rat, a rabbit, or a non-human primate) with the desired properties, affinity, and/or capability. In some cases, FR residues of the human immunoglobulin may be replaced with corresponding non-human residues. In addition, the humanized antibody may comprise an amino acid modification that is not present in the receptor antibody or in the donor antibody. These modifications may be made to further improve the properties such as binding affinity of the antibody.

The term "immunoconjugate" generally refers to a conjugate formed by conjugating (e.g., covalently linking via a linking molecule) the additional therapeutic agent to the isolated antigen binding protein, which conjugate can deliver the additional therapeutic agent to a target cell via specific binding of the isolated antigen binding protein to an antigen on the target cell.

The term "isolated" antigen binding protein generally refers to an antigen binding protein that has been identified, isolated, and/or recovered from (e.g., native or recombinant) components of the environment in which it is produced. Contaminant components of the environment in which it is produced are generally substances that interfere with its investigational, diagnostic or therapeutic use, and may include enzymes, hormones, and other proteinaceous or non-proteinaceous solutes. An isolated antigen binding protein or an antibody is generally prepared by at least one purification step. The isolated antigen binding protein of the present application generally specifically binds to properdin.

The term "isolated nucleic acid molecule" generally refers to a genome, an mRNA, a cDNA, or a synthetic-origin DNA or RNA or a certain combination thereof. It is not associated with the all or some of polynucleotides found in nature, or is linked to polynucleotides to which it is not linked in nature.

The term "monoclonal antibodies" generally refers to an antibody obtained from a group of substantially homogeneous antibodies, that is, a cluster in which several antibodies are the same, except for a few natural mutants that may exist. The monoclonal antibody is generally highly specific for a single antigen site. Moreover, unlike conventional polyclonal antibody preparations (which generally comprise different antibodies directed against different determinants), each monoclonal antibody is directed against a single determinant on the antigen. In addition to their specificity, the advantage of monoclonal antibodies lies in that they may be synthesized by hybridoma culture, without being contaminated by other immunoglobulins. The modifier "monoclonal" indicates the characteristics of an antibody obtained from a substantially homogeneous antibody population, and is not construed as requiring the production of the antibody by any specific method. For example, the monoclonal antibodies may be prepared in hybridoma cells, or may be prepared by recombinant DNA methods.

The term "patient" generally refers to a human or non-human animal, including but not limited to a cat, dog, horse, pig, cow, sheep, rabbit, mouse, rat, or monkey.

The term "pharmaceutically acceptable adjuvant" generally comprises pharmaceutically acceptable carriers, excipients, or stabilizers, which are nontoxic for the cells or mammals that are exposed to them at the dose and concentration used Generally, the physiologically acceptable carrier is a PH buffered aqueous solution. Examples of the physiologically acceptable carrier may comprise: buffers, such as phosphate, citrate, and other organic acids; antioxidants, including ascorbic acid; low-molecular-weight (less than about 10 residues) polypeptides, and proteins, such as serum albumin, gelatin, or immunoglobulin; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrin; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™.

The term "pharmaceutical combination" and "combination product" is used interchangeably, and generally refers to a product resulting from the admixture or combination of more than one active ingredients, and includes both fixed and non-fixed combinations of active ingredients. The term "fixed combination" means that the active ingredients, and one or more combination partners are both administered to a patient simultaneously in the form of a single entity or dose. The term "non-fixed combination" means that the active ingredients and one or more combination partners are administered to a patient simultaneously, jointly or sequentially (without a specific time limit) as separate entities, wherein such administration provides two compounds at therapeutically effective levels in the patient's body. For example, one active ingredient of pharmaceutical combination may be an antigen binding protein prepared by the method described in present application.

The term "pharmaceutical composition" generally refers to a composition suitable for administration to a patient. For example, the term "pharmaceutical composition" contains one or more antigen binding proteins, which is generally prepared by the method described in present application. A pharmaceutical composition may also contain one or more suitable (pharmaceutically effective) carriers, stabilizers, excipients, diluents, solubilizers, surfactants, emulsifiers, preservatives and/or adjuvants. For example, an acceptable component of a composition is nontoxic to the patient at the dose and concentration used. The pharmaceutical composition in present application includes, but is not limited to liquid, frozen and lyophilized compositions.

The term "polypeptide", "polypeptide", "peptide" and "protein" are used interchangeably, and generally refer to a polymer of amino acids of any length. The polymer may be linear or branched, it may comprise modified amino acids, and it may be interrupted by non-amino acids. These terms also encompass amino acid polymers that have been modified. These modifications may comprise: disulfide bond formation, glycosylation, lipidation, acetylation, phosphorylation, or any other manipulation (e.g., binding to a labeling component). The term "amino acid" includes natural and/or unnatural or synthetic amino acids, including glycine, D and L optical isomers, amino acid analogs and peptidomimetics.

The term "properdin", "factor P", and "Pillemer molecular" are used interchangeably, and are positive regulator of the alternative complement activation. For example, the term "properdin" may be oligomerization of a rod-like monomer into cyclic dimers, trimers, and tetramers. For example, the term "properdin" may be human properdin, which is a 469 amino acid soluble glycoprotein found in plasma that has seven thrombospondin type I repeats (TSR) with the N-terminal domain, TSR0, being a truncated domain. For example, the term "properdin" may be a mouse properdin, which is a 457 amino acid soluble glycoprotein found in plasma that has seven TSRs with the N-terminal domain, TSR0, being truncated. Said TSRs can be divided according to the common sense of people in the field. For example, the term "properdin" may comprise full length, truncated, and variant properdin.

The term "VEGF", or "vascular endothelial growth factor" are used interchangeably, and generally refers to a family of signaling proteins that can stimulate for example angiogenesis, vasculogenesis and/or lymphangiogenesis. Members of the VEGF family include VEGF-A, VEGF-B, VEGF-C, VEGF-D, and PIGF (Placental Growth Factor). In the present application, the term "VEGF" may comprise its functional active fragment, ortholog, analogue, and variant.

The term "transferrin" generally refers to a glycoprotein which can bind to and transport multivalent ions. For example, the transferrin may be a single-chain glycoprotein. For example, the transferrin may have a molecular weight of about 77,000D. For example, the transferrin may have a polysaccharide. For example, the transferrin may have two ion binding sites. For example, the ion binding sites may have different affinity with iron ions. For example, the multivalent ion may be an iron ion, a chromium ion, a manganese ion, a cadmium ion or a nickel ion thereof. For example, each molecule of transferrin may bind two trivalent iron atoms. For example, transferrin could be iron-containing holo-transferrin, or iron-free apo-transferrin. For example, the transferrin may be a mice transferrin. For example, the amino sequence of mice transferrin may be as set forth in GenBank: EDL21066.1, AAL34533.1, or AAL34533.1. For example, the transferrin may be a human transferrin. For example, the amino sequence of human transferrin may be as set forth in GenBank: AAH59367.1, AAH59367.1, or AAB22049.1. In the present application, the term "transferrin" may comprise its functional active fragment, ortholog, and variant.

The term "transferrin receptor" generally refers to a carrier protein of transferrin. For example, the transferrin may be a transmembrane glycoprotein. For example, the transferrin receptor may mediate endocytosis of transferrin associated to two iron ions. For example, the transferrin receptor may maintain iron homeostasis in cells. For example, the transferrin receptor may be transferrin receptor 1 (TfR1) or transferrin receptor 2 (TfR2). For example, TfR1 and TfR2 may show homologies around 45-66% in the extracellular domain but present with different expression patterns in the body. For example, the TfR1 may have higher affinity to transferrin than that of TfR2. For example, TfR2 may have a 25-fold lower affinity with transferrin compared to that of TfR1. For example, the TfR2 may mainly express in tissues involved in regulating iron metabolism, such as the liver and small intestines, while the TfR1 is generally found on the surface of most body cells. The term "transferrin receptor 1" generally refers to a 97-kDa type2 membrane protein expressed as a homodimer in the cell membrane. TfR1-mediated transferrin internalization is classically described as the canonical iron import pathway. For example, the transferrin receptor may be a mouse transferrin receptor. For example, the amino sequence of mouse transferrin receptor may be as set forth in GenBank. AAH54522.1, CAA40624.1, or NP_001344227.1. For example, the transferrin receptor may be a human transferrin receptor. For example, the amino sequence of human transferrin receptor may be as set forth in GenBank: AAA61153.1, AAF04564.1, or AAB19499.1. In the present application, the term "transferrin receptor" may comprise its functional active fragment, ortholog, and variant.

The term "ortholog" generally refers to an amino acid sequence that shares a certain percentage of sequence identity and functional similarity with the reference amino acid sequence. For example, orthologs may comprise structurally similar sequences in different species due to evolution from a common ancestor. Ortholog may be identified using any method known in the art, preferably by using the BLAST tool to compare a reference sequence to a separate second sequence or sequence fragment or sequence database. For example, the ortholog may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

The term "treatment" generally refers to the administration of an internal or external therapeutic agent to a patient who has one or more disease symptoms, and furthermore, the therapeutic agent is known to show a therapeutic effect against these symptoms. Generally, therapeutic agent is administered to the patient at an amount (therapeutically effective amount) for effectively alleviating one or more disease symptoms. The desired therapeutic effect comprises reducing the rate of disease progression, ameliorating or alleviating the disease state, and regressing or improving the prognosis.

The term "vector" generally refers to a nucleic acid molecule capable of self-replication in a suitable host. It transfers an inserted nucleic acid molecule into and/or between host cells. The vector may include a vector mainly for inserting DNA or RNA into cells, a vector mainly for replicating DNA or RNA, and a vector mainly for expressing DNA or RNA transcription and/or translation. The vector also includes a vector having a variety of the functions defined above. The vector may be a polynucleotide that may be transcribed and translated into a polypeptide when introduced into a suitable host cell. Generally, the vector may produce a desired expression product by culturing a suitable host cell containing the vector.

The term "optional" or "optionally" means that the event or situation described subsequently may occur but does not have to occur.

The term "comprise" generally refers to the meaning of including, inclusive, containing, or encompassing. In some cases, it also means "is/are" and "consist of".

The term "about" generally refers to a variation within a range of 0.5%-10% above or below a specified value, for example, a variation within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, and 10% above or below a specified value.

Details Description of the Invention

Isolated Antigen Binding Protein

In one aspect, the present application provides an isolated antigen binding protein, which may specifically bind to properdin in an ELISA binding assay with an isolated antigen binding protein concentration of about 100 ng/ml or less (e.g., said concentration is no greater than about 50 ng/ml, no greater than about 55 ng/ml, no greater than about 60 ng/ml, no greater than about 65 ng/ml, no greater than about 70 ng/ml, no greater than about 75 ng/ml, no greater than about 80 ng/ml, no greater than about 85 ng/ml, no greater than about 90 ng/ml, or no greater than about 95 ng/ml or less). For example, said properdin may comprise human properdin, cyno properdin, and mouse properdin.

In the present application, said isolated antigen binding protein may inhibit alternative pathway by binding protein to induce hemolysis. For example, percent of hemolysis in alternative pathway experiments can be determined by co-incubation of complement-preserved serum and erythrocytes. For example, said complement-preserved serum may derived from human or mouse. For example, said percent of hemolysis may be about 60% or less (e.g., said percent of hemolysis is no greater than about 55%, no greater than about 50%, no greater than about 45%, no greater than about 40%, no greater than about 35%, no greater than about 30%, no greater than about 25%, no greater than about 20%, no greater than about 15%, no greater than about 10%, or no greater than about 5% or less) at the isolated antigen binding protein concentration of 500 nM.

In the present application, said isolated antigen binding protein may specifically bind to TSR5, TSR6, and/or TSR0 domain of properdin. For example, the binding epitopes can be determined by combination between truncated variants of human properdin-biotin and thrombospondin repeats (TSRs).

In the present application, said isolated antigen binding protein may inhibit interaction between properdin and C3. For example, the inhibition activity of said isolated antigen binding protein can be determined by competitive binding assay. The isolated binding protein can competitively bind to properdin, so that inhibit the combination of properdin and C3. For example, said isolated antigen binding protein shows inhibition activity with properdin binding to C3 in dose-dependent manner.

In the present application, said isolated antigen binding protein may selectively inhibit alternative pathway rather than classical pathway or lectin pathway. For example, the pathway selectivity can be determined by percent of hemolysis. For example, said isolated antigen binding protein can inhibit alternative pathway with IC50 of about 50 nM or less (e.g., said 1C50 is no greater than about 45 nM, no greater than about 40 nM, no greater than about 35 nM, no greater than about 30 nM, no greater than about 25 nM, no greater than about 20 nM, no greater than about 15 nM, no greater than about 10 nM, or no greater than about 5 nM or less). For example, said isolated antigen binding protein exhibits no inhibitory activity in the classical pathway, while control shows inhibitory ability, with IC50 of 57 nM. For example, said isolated antigen binding protein exhibits no inhibitory activity in the lectin pathway, while control shows inhibitory ability, with IC50 of 45 nM.

In the present application, said isolated antigen binding protein may have species-crossing properdin-binding and complement-inhibitory activity in AP-specific pathways in mammal. For example, the species-crossing complement inhibitory activity can be determined by detecting hemolysis in different species. For example, said species can be human, cyno, mouse and rat.

In one aspect, the present application provides an isolated antigen binding protein, which may comprise at least one CDR in a heavy-chain variable region VH. The VH may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

In the present application, the CDR of the isolated antigen binding protein may be divided in any form, and any form of divided CDR may fall within the scope of the present application, as long as the VH is identical to an amino acid sequence shown in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

The CDRs of an antibody, also known as complementarity determining regions, are part of the variable region. The amino acid residues of this region may be in contact with an antigen or an antigenic epitope. The CDRs can be determined by a variety of coding systems, such as CCG, Kabat, Chothia, IMGT, AbM, consensus Kabat/Chothia, and the like. These coding systems are known in the art and the person skilled in the art can determine the CDR regions using different coding systems depending on the sequence and structure of the antibody. Using different coding systems, the CDR regions may differ. In the present application, the CDR encompasses CDR sequences divided according to any CDR division manner; and variants thereof are also contemplated. The said variants comprise an amino acid sequence of the CDR substituted, deleted and/or added with one or more amino acids (e.g., 1-30, 1-20 or 1-10; further e.g., 1, 2, 3, 4, 5, 6, 7, 8 or 9 amino acid substitutions, deletions and/or insertions). Homologs are also encompassed, comprising an amino acid sequence having at least about 85% (e.g., having at least about 85%, about 90%, about 91%, about 92%, about 93%, about 94%, about 95%, about 96%, about 97%, about 98%, about 99% or more) sequence homology to an amino acid sequence of the CDR. In some embodiments, the isolated antigen binding protein described herein is defined by the Kabat coding system.

In the present application, said isolated antigen binding protein may bind to properdin. For example, human properdin, cyno properdin, mouse properdin, rat properdin and the like.

In the present application, said isolated antigen binding protein may comprise a heavy chain variable region VH, which may comprise at least one, two or three of CDR3, CDR2 and CDR1.

In the present application, said CDR3 of said isolated antigen binding protein may comprise an amino acid sequence as set forth in any one of SEQ ID NO: 12, SEQ ID NO: 13, SEQ ID NO: 14, SEQ ID NO: 15, SEQ ID NO: 16, and SEQ ID NO: 17. For example, the CDR3 sequence of said isolated antigen binding protein may be defined according to the Kabat coding system.

In the present application, said CDR2 of said isolated antigen binding protein may comprise an amino acid sequence as set forth in SEQ ID NO: 55: $X_1X_2X_3X_4X_5X_6X_7X_8X_9YX_{11}DSVKG$, in which $X_1$ is F or I or absent, $X_2$ is D or I, $X_3$ is D or N or R or T, $X_4$ is G or R or S or T, $X_5$ is D or E, $X_6$ is G or R, $X_7$ is G or R or S or V or W, $X_8$ is E or K or T, $X_9$ is R or S or W or Y, and $X_{11}$ is A or T. For example, the CDR2 sequence of said isolated antigen binding protein may be defined according to the Kabat coding system.

In the present application, said CDR2 of said isolated antigen binding protein may comprise an amino acid sequence as set forth in any one of SEQ ID NO: 6, SEQ ID NO: 7, SEQ ID NO: 8, SEQ ID NO: 9, SEQ ID NO: 10, and SEQ ID NO: 11.

In the present application, said CDR1 of said isolated antigen binding protein may comprise an amino acid sequence as set forth in $X_1 X_2CMX_5$, in which $X_1$ is H or S or T or Y, $X_2$ is G or Y, and $X_5$ is A or G. For example, the CDR1 sequence of said isolated antigen binding protein may be defined according to the Kabat coding system.

In the present application, said CDR1 of said isolated antigen binding protein may comprise an amino acid sequence as set forth in any one of SEQ ID NO: 1, SEQ ID NO: 2, SEQ ID NO: 3, SEQ ID NO: 4, and SEQ ID NO: 5.

For example, said CDR3 of said isolated antigen binding protein may comprise an amino acid sequence as set forth in any one of SEQ ID NO: 12, SEQ ID NO: 13, SEQ ID NO: 14, SEQ ID NO: 15, SEQ ID NO: 16, and SEQ ID NO: 17, said CDR2 of said isolated antigen binding protein may comprise an amino acid sequence as set forth in any one of SEQ ID NO: 6, SEQ ID NO: 7, SEQ ID NO: 8, SEQ ID NO: 9, SEQ ID NO: 10, and SEQ ID NO: 11, and said CDR1 of said isolated antigen binding protein may comprise an amino acid sequence as set forth in any one of SEQ ID NO: 1, SEQ ID NO: 2, SEQ ID NO: 3, SEQ ID NO: 4, and SEQ ID NO: 5.

For example, said CDR3 of said isolated antigen binding protein may comprise an amino acid sequence as set forth in SEQ ID NO: 12, said CDR2 of said isolated antigen binding protein may comprise an amino acid sequence as set forth in SEQ ID NO: 6, and said CDR1 of said isolated antigen binding protein may comprise an amino acid sequence as set forth in SEQ ID NO: 1. For example, said CDR3 of said isolated antigen binding protein may comprise an amino acid sequence as set forth in SEQ ID NO: 13, said CDR2 of said isolated antigen binding protein may comprise an amino acid sequence as set forth in SEQ ID NO: 7, and said CDR1 of said isolated antigen binding protein may comprise an amino acid sequence as set forth in SEQ ID NO: 2. For example, said CDR3 of said isolated antigen binding protein may comprise an amino acid sequence as set forth in SEQ ID NO: 14, said CDR2 of said isolated antigen binding protein may comprise an amino acid sequence as set forth in SEQ ID NO: 8, and said CDR1 of said isolated antigen binding protein may comprise an amino acid sequence as set forth in SEQ ID NO: 3. For example, said CDR3 of said isolated antigen binding protein may comprise an amino acid sequence as set forth in SEQ ID NO: 15, said CDR2 of said isolated antigen binding protein may comprise an amino acid sequence as set forth in SEQ ID NO: 9, and said CDR1 of said isolated antigen binding protein may comprise an amino acid sequence as set forth in SEQ ID NO: 4. For example, said CDR3 of said isolated antigen binding protein may comprise an amino acid sequence as set forth in SEQ ID NO: 16, said CDR2 of said isolated antigen binding protein may comprise an amino acid sequence as set forth in SEQ ID NO: 10, and said CDR1 of said isolated antigen binding protein may comprise an amino acid sequence as set forth in SEQ ID NO: 5. For example, said CDR3 of said isolated antigen binding protein may comprise an amino acid sequence as set forth in SEQ ID NO: 17, said CDR2 of said isolated antigen binding protein may comprise an amino acid sequence as set forth in SEQ ID NO: 11, and said CDR1 of said isolated antigen binding protein may comprise an amino acid sequence as set forth in SEQ ID NO: 3. For example, said isolated antigen binding protein may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93, or an antibody having the same CDR (e.g., CDR1, CDR2 or CDR3).

In the present application, said isolated antigen binding protein may further comprise framework regions FR1, FR2, FR3, and FR4.

In the present application, said FR1 of said isolated antigen binding protein may comprise an amino acid sequence as set forth SEQ ID NO: 56: $X_1VQLVESGGGX_{11}V$ $X_{13}X_{14}GGSLRLSCX_{23}X_{24}X_{25}X_{25}YX_{28}X_{29}X_{30}$, in which $X_1$ is D or E or H or Q, $X_{11}$ is L or S or V, $X_{13}$ is H or Q, $X_{14}$ is A or P or S or V, $X_{23}$ is A or E or V, $X_{24}$ is A or D or H or V, $X_{25}$ is F or P or S, $X_{26}$ is A or E or G, $X_{28}$ is I or T or absent, $X_9$ is H or S or Y or absent, and $X_{30}$ is G or S or T or absent. For example, said FR1 sequence of said isolated antigen binding protein may be defined according to the Kabat coding system.

In the present application, said FR1 of said isolated antigen binding protein may comprise an amino acid sequence as set forth in any one of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In the present application, said FR2 of said isolated antigen binding protein may comprise an amino acid sequence as set forth SEQ ID NO: 57: $WX_2RQAPG X_8X_9X_{10}EX_{12}VX_{14}X_{15}$, in which $X_2$ is F or I, $X_8$ is E or K, $X_8$ is E or G, $X_{10}$ is L or R, $X_{12}$ is G or R, $X_{14}$ is A or S, and $X_{15}$ is A or S or V. For example, said FR2 sequence of said isolated antigen binding protein may be defined according to the Kabat coding system.

In the present application, said FR2 of said isolated antigen binding protein may comprise an amino acid sequence as set forth in any one of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In the present application, said FR3 of said isolated antigen binding protein may comprise an amino acid sequence as set forth SEQ ID NO: 58: RFTIS$X_6$D$X_8$$X_9$$X_{10}$$X_{11}$TLYL$X_{16}$MN$X_{19}$L$X_{21}$$X_{22}$EDTA$X_{27}$YYCA$X_{32}$, in which $X_6$ is K or L or Q or R, $X_8$ is I or N, $X_9$ is A or S, $X_{10}$ is E or K or T, $X_{11}$ is N or S, $X_{11}$ is E or Q, $X_{19}$ is I or N or S, $X_{21}$ is K or Q or R, $X_{22}$ is A or P or S, $X_7$ is M or V, and $X_{32}$ is A or T. For example, the FR3 sequence of said isolated antigen binding protein may be defined according to the Kabat coding system.

In the present application, said FR3 of said isolated antigen binding protein may comprise an amino acid sequence as set forth in any one of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51.

In the present application, said FR4 of said isolated antigen binding protein may comprise an amino acid sequence as set forth SEQ ID NO: 59: WGQGT$X_6$VTVSS, in which $X_6$ is L or Q. For example, said FR4 sequence of said isolated antigen binding protein may be defined according to the Kabat coding system.

In the present application, said FR4 of said isolated antigen binding protein may comprise an amino acid sequence as set forth in any one of SEQ ID NO: 52 and SEQ ID NO: 53.

For example, said FR1 of said isolated antigen binding protein may comprise an amino acid sequence as set forth in any one of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30; said FR2 of said isolated antigen binding protein may comprise an amino acid sequence as set forth in any one of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40; said FR3 of said isolated antigen binding protein may comprise an amino acid sequence as set forth in any one of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51, and said FR4 of said isolated antigen binding protein may comprise an amino acid sequence as set forth in any one of SEQ ID NO: 52 and SEQ ID NO: 53.

For example, said FR1 of said isolated antigen binding protein may comprise an amino acid sequence as set forth in SEQ ID NO: 18; said FR2 of said isolated antigen binding protein may comprise an amino acid sequence as set forth in SEQ ID NO: 31; said FR3 of said isolated antigen binding protein may comprise an amino acid sequence as set forth in SEQ ID NO: 41, and said FR4 of said isolated antigen binding protein may comprise an amino acid sequence as set forth in SEQ ID NO: 52. For example, said isolated antigen binding protein may comprise an amino acid sequence as set forth in SEQ ID NO: 60, or an antibody having the same FR (e.g., FR1, FR2, FR3, or FR4).

For example, said FR1 of said isolated antigen binding protein may comprise an amino acid sequence as set forth in SEQ ID NO: 19; said FR2 of said isolated antigen binding protein may comprise an amino acid sequence as set forth in SEQ ID NO: 32; said FR3 of said isolated antigen binding protein may comprise an amino acid sequence as set forth in SEQ ID NO: 42, and said FR4 of said isolated antigen binding protein may comprise an amino acid sequence as set forth in SEQ ID NO: 53. For example, said isolated antigen binding protein may comprise an amino acid sequence as set forth in SEQ ID NO: 61, or an antibody having the same FR (e.g., FR1, FR2, FR3, or FR4).

For example, said FR1 of said isolated antigen binding protein may comprise an amino acid sequence as set forth in SEQ HD NO: 19; said FR2 of said isolated antigen binding protein may comprise an amino acid sequence as set forth in SEQ ID NO: 32; said FR3 of said isolated antigen binding protein may comprise an amino acid sequence as set forth in SEQ ID NO: 42, and said FR4 of said isolated antigen binding protein may comprise an amino acid sequence as set forth in SEQ ID NO: 53. For example, said isolated antigen binding protein may comprise an amino acid sequence as set forth in SEQ ID NO: 62, or an antibody having the same FR (e.g., FR1, FR2, FR3, or FR4).

For example, said FR1 of said isolated antigen binding protein may comprise an amino acid sequence as set forth in SEQ ID NO: 19; said FR2 of said isolated antigen binding protein may comprise an amino acid sequence as set forth in SEQ ID NO: 32; said FR3 of said isolated antigen binding protein may comprise an amino acid sequence as set forth in SEQ ID NO: 43, and said FR4 of said isolated antigen binding protein may comprise an amino acid sequence as set forth in SEQ ID NO: 53. For example, said isolated antigen binding protein may comprise an amino acid sequence as set forth in SEQ ID NO: 63, or an antibody having the same FR (e.g., FR1, FR2, FR3, or FR4).

For example, said FR1 of said isolated antigen binding protein may comprise an amino acid sequence as set forth in SEQ ID NO: 20; said FR2 of said isolated antigen binding protein may comprise an amino acid sequence as set forth in SEQ ID NO: 32; said FR3 of said isolated antigen binding protein may comprise an amino acid sequence as set forth in SEQ ID NO: 43, and said FR4 of said isolated antigen binding protein may comprise an amino acid sequence as set forth in SEQ ID NO: 53. For example, said isolated antigen binding protein may comprise an amino acid sequence as set forth in SEQ ID NO: 64, or an antibody having the same FR (e.g., FR1, FR2, FR3, or FR4).

For example, said FR1 of said isolated antigen binding protein may comprise an amino acid sequence as set forth in SEQ ID NO: 20; said FR2 of said isolated antigen binding protein may comprise an amino acid sequence as set forth in SEQ ID NO: 31; said FR3 of said isolated antigen binding protein may comprise an amino acid sequence as set forth in SEQ ID NO: 43, and said FR4 of said isolated antigen binding protein may comprise an amino acid sequence as set forth in SEQ ID NO: 53. For example, said isolated antigen binding protein may comprise an amino acid sequence as set forth in SEQ ID NO: 65 or an antibody having the same FR (e.g., FR1, FR2, FR3, or FR4).

For example, said FR1 of said isolated antigen binding protein may comprise an amino acid sequence as set forth in SEQ ID NO: 21; said FR2 of said isolated antigen binding protein may comprise an amino acid sequence as set forth in SEQ ID NO: 33, said FR3 of said isolated antigen binding protein may comprise an amino acid sequence as set forth in SEQ ID NO: 44, and said FR4 of said isolated antigen binding protein may comprise an amino acid sequence as set forth in SEQ ID NO: 52. For example, said isolated antigen binding protein may comprise an amino acid sequence as set forth in SEQ ID NO: 66, or an antibody having the same FR (e.g., FR1, FR2, FR3, or FR4).

For example, said FR1 of said isolated antigen binding protein may comprise an amino acid sequence as set forth in SEQ ID NO: 22; said FR2 of said isolated antigen binding protein may comprise an amino acid sequence as set forth in SEQ ID NO: 34; said FR3 of said isolated antigen binding protein may comprise an amino acid sequence as set forth in SEQ ID NO: 42, and said FR4 of said isolated antigen binding protein may comprise an amino acid sequence as set forth in SEQ ID NO: 53. For example, said isolated antigen binding protein may comprise an amino acid sequence as set forth in SEQ ID NO: 67, or an antibody having the same FR (e.g., FR1, FR2, FR3, or FR4).

For example, said FR1 of said isolated antigen binding protein may comprise an amino acid sequence as set forth in SEQ ID NO: 22; said FR2 of said isolated antigen binding protein may comprise an amino acid sequence as set forth in SEQ ID NO: 34; said FR3 of said isolated antigen binding protein may comprise an amino acid sequence as set forth in SEQ ID NO: 45, and said FR4 of said isolated antigen binding protein may comprise an amino acid sequence as set forth in SEQ ID NO: 53. For example, said isolated antigen binding protein may comprise an amino acid sequence as set forth in SEQ ID NO: 68, or an antibody having the same FR (e.g., FR1, FR2, FR3, or FR4).

For example, said FR1 of said isolated antigen binding protein may comprise an amino acid sequence as set forth in SEQ ID NO: 22; said FR2 of said isolated antigen binding protein may comprise an amino acid sequence as set forth in SEQ ID NO: 33; said FR3 of said isolated antigen binding protein may comprise an amino acid sequence as set forth in SEQ ID NO: 45, and said FR4 of said isolated antigen binding protein may comprise an amino acid sequence as set forth in SEQ ID NO: 53. For example, said isolated antigen binding protein may comprise an amino acid sequence as set forth in SEQ ID NO: 69, or an antibody having the same FR (e.g., FR1, FR2, FR3, or FR4).

For example, said FR1 of said isolated antigen binding protein may comprise an amino acid sequence as set forth in SEQ ID NO: 23; said FR2 of said isolated antigen binding protein may comprise an amino acid sequence as set forth in SEQ ID NO: 35, said FR3 of said isolated antigen binding protein may comprise an amino acid sequence as set forth in SEQ ID NO: 46, and said FR4 of said isolated antigen binding protein may comprise an amino acid sequence as set forth in SEQ HD NO: 52. For example, said isolated antigen binding protein may comprise an amino acid sequence as set forth in SEQ ID NO: 70, or an antibody having the same FR (e.g., FR1, FR2, FR3, or FR4).

For example, said FR1 of said isolated antigen binding protein may comprise an amino acid sequence as set forth in SEQ ID NO: 24; said FR2 of said isolated antigen binding protein may comprise an amino acid sequence as set forth in SEQ ID NO: 36; said FR3 of said isolated antigen binding protein may comprise an amino acid sequence as set forth in SEQ ID NO: 47, and said FR4 of said isolated antigen binding protein may comprise an amino acid sequence as set forth in SEQ ID NO: 53. For example, said isolated antigen binding protein may comprise an amino acid sequence as set forth in SEQ ID NO: 71, or an antibody having the same FR (e.g., FR1, FR2, FR3, or FR4).

For example, said FR1 of said isolated antigen binding protein may comprise an amino acid sequence as set forth in SEQ ID NO: 24; said FR2 of said isolated antigen binding protein may comprise an amino acid sequence as set forth in SEQ ID NO: 36; said FR3 of said isolated antigen binding protein may comprise an amino acid sequence as set forth in SEQ ID NO: 48, and said FR4 of said isolated antigen binding protein may comprise an amino acid sequence as set forth in SEQ ID NO: 53. For example, said isolated antigen binding protein may comprise an amino acid sequence as set forth in SEQ ID NO: 72, or an antibody having the same FR (e.g., FR1, FR2, FR3, or FR4).

For example, said FR1 of said isolated antigen binding protein may comprise an amino acid sequence as set forth in SEQ ID NO: 25; said FR2 of said isolated antigen binding protein may comprise an amino acid sequence as set forth in SEQ ID NO: 36; said FR3 of said isolated antigen binding protein may comprise an amino acid sequence as set forth in SEQ ID NO: 48, and said FR4 of said isolated antigen binding protein may comprise an amino acid sequence as set forth in SEQ ID NO: 53. For example, said isolated antigen binding protein may comprise an amino acid sequence as set forth in SEQ ID NO: 73, or an antibody having the same FR (e.g., FR1, FR2, FR3, or FR4).

For example, said FR1 of said isolated antigen binding protein may comprise an amino acid sequence as set forth in SEQ ID NO: 25; said FR2 of said isolated antigen binding protein may comprise an amino acid sequence as set forth in SEQ ID NO: 35; said FR3 of said isolated antigen binding protein may comprise an amino acid sequence as set forth in SEQ ID NO: 48, and said FR4 of said isolated antigen binding protein may comprise an amino acid sequence as set forth in SEQ ID NO: 53. For example, said isolated antigen binding protein may comprise an amino acid sequence as set forth in SEQ ID NO: 74, or an antibody having the same FR (e.g., FR1, FR2, FR3, or FR4).

For example, said FR1 of said isolated antigen binding protein may comprise an amino acid sequence as set forth in SEQ ID NO: 26; said FR2 of said isolated antigen binding protein may comprise an amino acid sequence as set forth in SEQ ID NO: 37; said FR3 of said isolated antigen binding protein may comprise an amino acid sequence as set forth in SEQ ID NO: 49, and said FR4 of said isolated antigen binding protein may comprise an amino acid sequence as set forth in SEQ ID NO: 52. For example, said isolated antigen binding protein may comprise an amino acid sequence as set forth in SEQ ID NO: 75, or an antibody having the same FR (e.g., FR1, FR2, FR3, or FR4).

For example, said FR1 of said isolated antigen binding protein may comprise an amino acid sequence as set forth in SEQ ID NO: 27; said FR2 of said isolated antigen binding protein may comprise an amino acid sequence as set forth in SEQ ID NO: 38; said FR3 of said isolated antigen binding protein may comprise an amino acid sequence as set forth in SEQ ID NO: 42, and said FR4 of said isolated antigen binding protein may comprise an amino acid sequence as set forth in SEQ ID NO: 53. For example, said isolated antigen binding protein may comprise an amino acid sequence as set forth in SEQ ID NO: 76, or an antibody having the same FR (e.g., FR1, FR2, FR3, or FR4).

For example, said FR1 of said isolated antigen binding protein may comprise an amino acid sequence as set forth in SEQ ID NO: 27; said FR2 of said isolated antigen binding protein may comprise an amino acid sequence as set forth in SEQ ID NO: 39; said FR3 of said isolated antigen binding protein may comprise an amino acid sequence as set forth in SEQ ID NO: 42, and said FR4 of said isolated antigen binding protein may comprise an amino acid sequence as set forth in SEQ ID NO: 53. For example, said isolated antigen binding protein may comprise an amino acid sequence as set forth in SEQ ID NO: 77, or an antibody having the same FR (e.g., FR1, FR2, FR3, or FR4).

For example, said FR1 of said isolated antigen binding protein may comprise an amino acid sequence as set forth in SEQ ID NO: 28; said FR2 of said isolated antigen binding protein may comprise an amino acid sequence as set forth in SEQ ID NO: 39; said FR3 of said isolated antigen binding protein may comprise an amino acid sequence as set forth in SEQ ID NO: 42, and said FR4 of said isolated antigen binding protein may comprise an amino acid sequence as set forth in SEQ ID NO: 53. For example, said isolated antigen binding protein may comprise an amino acid sequence as set forth in SEQ ID NO: 78, or an antibody having the same FR (e.g., FR1, FR2, FR3, or FR4).

For example, said FR1 of said isolated antigen binding protein may comprise an amino acid sequence as set forth in SEQ HD NO: 28; said FR2 of said isolated antigen binding protein may comprise an amino acid sequence as set forth in SEQ ID NO: 39; said FR3 of said isolated antigen binding protein may comprise an amino acid sequence as set forth in SEQ ID NO: 43, and said FR4 of said isolated antigen binding protein may comprise an amino acid sequence as set forth in SEQ ID NO: 53. For example, said isolated antigen binding protein may comprise an amino acid sequence as set forth in SEQ ID NO: 79, or an antibody having the same FR (e.g., FR1, FR2, FR3, or FR4).

For example, said FR1 of said isolated antigen binding protein may comprise an amino acid sequence as set forth in SEQ ID NO: 28; said FR2 of said isolated antigen binding protein may comprise an amino acid sequence as set forth in SEQ ID NO: 37; said FR3 of said isolated antigen binding protein may comprise an amino acid sequence as set forth in SEQ ID NO: 43, and said FR4 of said isolated antigen binding protein may comprise an amino acid sequence as set forth in SEQ ID NO: 53. For example, said isolated antigen binding protein may comprise an amino acid sequence as set forth in SEQ ID NO: 80, or an antibody having the same FR (e.g., FR1, FR2, FR3, or FR4).

For example, said FR1 of said isolated antigen binding protein may comprise an amino acid sequence as set forth in SEQ ID NO: 29; said FR2 of said isolated antigen binding protein may comprise an amino acid sequence as set forth in SEQ ID NO: 31; said FR3 of said isolated antigen binding protein may comprise an amino acid sequence as set forth in SEQ ID NO: 50, and said FR4 of said isolated antigen binding protein may comprise an amino acid sequence as set forth in SEQ ID NO: 52. For example, said isolated antigen binding protein may comprise an amino acid sequence as set forth in SEQ ID NO: 92, or an antibody having the same FR (e.g., FR1, FR2, FR3, or FR4).

For example, said FR1 of said isolated antigen binding protein may comprise an amino acid sequence as set forth in SEQ ID NO: 30; said FR2 of said isolated antigen binding protein may comprise an amino acid sequence as set forth in SEQ ID NO: 40; said FR3 of said isolated antigen binding protein may comprise an amino acid sequence as set forth in SEQ ID NO: 51, and said FR4 of said isolated antigen binding protein may comprise an amino acid sequence as set forth in SEQ ID NO: 52. For example, said isolated antigen binding protein may comprise an amino acid sequence as set forth in SEQ ID NO: 93, or an antibody having the same FR (e.g., FR1, FR2, FR3, or FR4).

In the present application, said heavy-chain variable region may comprise VHH. The VHH may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

In the present application, said isolated antigen binding protein may comprise a heavy-chain constant region.

For example, the Fc region of said isolated antigen binding protein may be a human Fc region. For example, said human Fc region may be modified to achieve the desired property (e.g., an amino acid mutation). For example, said human Fc region may comprise an amino acid sequence as set forth in SEQ ID NO: 109.

In the present application, said isolated antigen binding protein may be directly or indirectly linked to a second antigen binding domain.

For example, said isolated antigen binding protein may be linked by its N-terminus or C-terminus to the N-terminus or C-terminus of said second antigen binding domain. For example, said isolated antigen binding protein may be linked by its N-terminus or C-terminus to the N-terminus or C-terminus of said second antigen binding domain with a linker. For example, said linker of said isolated antigen binding protein may be a simple covalent bond (e.g., a peptide bond), a synthetic polymer (e.g., a polyethylene glycol (PEG) polymer), or any kind of bond created from a chemical reaction. For example, said linker of said isolated antigen binding protein may be a poly-glycine linker. For example, said linker of said isolated antigen binding protein may comprises an amino acid sequence as set forth in SEQ ID NO: 108: GGGGSGGGGSGGGGS.

In the present application, said second antigen binding domain of said isolated antigen binding protein may bind to a different target from said isolated antigen binding protein.

In the present application, said second antigen binding domain of said isolated antigen binding protein may bind to the same target as said isolated antigen binding protein.

For example, said second antigen binding domain of said isolated antigen binding protein may bind to properdin. For example, said second antigen binding domain of said isolated antigen binding protein may bind to different epitopes of properdin from the isolated antigen binding protein. For example, said second antigen binding domain of said isolated antigen binding protein may bind to the same epitopes of properdin with the isolated antigen binding protein. For example, said second antigen binding domain of said isolated antigen binding protein may bind to TSR5, TSR6, and/or TSR0 domain of properdin. For example, said second antigen binding domain of said isolated antigen binding protein may comprises an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

For example, said isolated antigen binding protein may comprise an amino acid sequence as set forth in SEQ ID NO: 81.

For example, said isolated antigen binding protein may comprise an amino acid sequence as set forth in SEQ ID NO: 116.

For example, said isolated antigen binding protein may comprise an antibody or an antigen binding fragment thereof. For example, said isolated antigen binding protein may comprise Fab, Fab', F(ab)$_2$, Fv fragments, F(ab')$_2$, scFv, di-scFv, VHH and/or dAb. For example, said isolated antigen binding protein may be selected from the group consisting of: monoclonal antibodies, single chain antibodies, chimeric antibodies, humanized antibodies, and fully human antibodies.

For example, said isolated antigen binding protein may be a camelid antibody.

In the present application, said isolated antigen binding protein may have a competitive target binding capability with reference antibodies, wherein said reference antibodies may comprise a heavy chain variable region VH, which may comprise at least one, two or three of CDR3, CDR2 and CDR1.

In the present application, the CDR3 of said reference antibodies may comprise an amino acid sequence as set forth in any one of SEQ ID NO: 12, SEQ ID NO: 13, and SEQ ID NO: 14. For example, the CDR3 sequence of said reference antibodies may be defined according to the Kabat coding system.

In the present application, the CDR2 of said reference antibodies may comprise an amino acid sequence as set forth in SEQ ID NO: 55: $X_1X_2X_3X_4X_5X_6X_7X_8X_9YX_{11}DSVKG$, in which $X_1$ is F or I or absent, $X_2$ is D or I, $X_3$ is D or N or R or T, $X_4$ is G or R or S or T, $X_5$ is D or E, $X_6$ is G or R, $X_7$ is G or R or S or V or W, $X_8$ is E or K or T, $X_9$ is R or S or W or Y, and $X_{11}$ is A or T. For example, the CDR2 sequence of said reference antibodies may be defined according to the Kabat coding system.

In the present application, the CDR2 of said reference antibodies may comprise an amino acid sequence as set forth in any one of SEQ ID NO: 6, SEQ ID NO: 7, and SEQ ID NO: 8.

In the present application, the CDR1 of said reference antibodies may comprise an amino acid sequence as set forth in $X_1 X_2CMX_5$, in which $X_1$ is H or S or T or Y, $X_2$ is G or Y, and $X_5$ is A or G. For example, the CDR1 sequence of said reference antibodies may be defined according to the Kabat coding system.

In the present application, the CDR1 of said reference antibodies may comprise an amino acid sequence as set forth in any one of SEQ ID NO: 1, SEQ ID NO: 2, and SEQ ID NO: 3.

For example, the CDR3 of said reference antibodies may comprise an amino acid sequence as set forth in any one of SEQ ID NO: 12, SEQ ID NO: 13, and SEQ ID NO: 14, the CDR2 of said reference antibodies may comprise an amino acid sequence as set forth in any one of SEQ ID NO: 6, SEQ ID NO: 7, and SEQ ID NO: 8, and the CDR1 of said reference antibodies may comprise an amino acid sequence as set forth in any one of SEQ ID NO: 1, SEQ ID NO: 2, and SEQ ID NO: 3.

For example, the CDR3 of said reference antibodies may comprise an amino acid sequence as set forth in SEQ ID NO: 12, the CDR2 of said reference antibodies may comprise an amino acid sequence as set forth in SEQ ID NO: 6, and the CDR1 of said reference antibodies may comprise an amino acid sequence as set forth in SEQ ID NO: 1. For example, the CDR3 of said reference antibodies may comprise an amino acid sequence as set forth in SEQ ID NO: 13, the CDR2 of said reference antibodies may comprise an amino acid sequence as set forth in SEQ ID NO: 7, and the CDR1 of said reference antibodies may comprise an amino acid sequence as set forth in SEQ ID NO: 2. For example, the CDR3 of said reference antibodies may comprise an amino acid sequence as set forth in SEQ ID NO: 14, the CDR2 of said reference antibodies may comprise an amino acid sequence as set forth in SEQ ID NO: 8, and the CDR1 of said reference antibodies may comprise an amino acid sequence as set forth in SEQ ID NO: 3. For example, said isolated antigen binding protein may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, and SEQ ID NO: 74, or an antibody having the same CDR (e.g., CDR1, CDR2 or CDR3).

For example, the isolated antigen binding protein may comprise its functional active fragment, ortholog, and variant, which keep the similar biologic activity. For example, the sequence similarity may have at least 30%, at least 35%, at least 40%, at least 45%, at least 50/a, at least 55%, at least 60%, at least 65%, at least 70%, at least 75%, at least 80%, at least 85%, at least 90%, at least 95% or at least 99% similarity to its corresponding sequence.

Fusion Protein

In another aspect, the present application provides a fusion protein that may comprise the isolated antigen binding protein of the present application.

In the present application, said fusion protein may comprise a functionally active protein.

In the present application, said functionally active protein of said fusion protein may be directly or indirectly linked to said isolated antigen binding protein.

For example, said functionally active protein may be linked by its N-terminus or C-terminus to the N-terminus or C-terminus of said isolated antigen binding protein. For example, said functionally active protein may be linked by its N-terminus or C-terminus to the N-terminus or C-terminus of said isolated antigen binding protein with a linker. For example, said linker may be a simple covalent bond (e.g., a peptide bond), a synthetic polymer (e.g., a polyethylene glycol (PEG) polymer), or any kind of bond created from a chemical reaction. For example, said linker may be a polyglycine linker. For example, said linker may comprises an amino acid sequence as set forth in SEQ ID NO: 108: GGGGSGGGGSGGGGS.

For example, said functionally active protein may be factor H. For example, said factor H may comprise an amino acid sequence as set forth in SEQ ID NO: 110. For example, said factor H of said fusion protein may comprise its functional active fragment, ortholog, and variant. For example, the sequence similarity may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

For example, said fusion protein may comprise an amino acid sequence as set forth in SEQ ID NO: 82.

For example, said functionally active protein of said fusion protein may be VEGF inhibiting protein. For example, said VEGF inhibiting protein, of said fusion protein may comprise an amino acid sequence as set forth in SEQ ID NO: 113. For example, said VEGF inhibiting protein of said fusion protein may comprise its functional active fragment, ortholog, and variant. In some embodiments, the sequence similarity may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

For example, said fusion protein may comprise an amino acid sequence as set forth in SEQ ID NO: 114.

For example, said functionally active protein of said fusion protein may be transferrin inhibiting protein. For example, said factor H of said fusion protein may comprise an amino acid sequence as set forth in SEQ ID NO: 115. For example, said transferrin inhibiting protein of said fusion protein may comprise its functional active fragment, ortholog, and variant. In some embodiments, the sequence similarity may have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% similarity to its corresponding sequence.

For example, said fusion protein may comprise an amino acid sequence as set forth in SEQ ID NO: 117.

For example, said fusion protein may comprise an amino acid sequence as set forth in SEQ ID NO: 118.

For example, the fusion protein may include a prophylactic or therapeutic drug fused to a heterologous protein, polypeptide, or peptide. Wherein, the heterologous protein, polypeptide or peptide may or may not be different types or therapeutic drugs.

For example, the fusion protein may comprise two or more different proteins, polypeptides or peptides with immunomodulatory activity. For example, the fusion protein may retain or improve the activity compared to the activity of the original polypeptide or protein. Typically, the fusion protein can be produced by in vitro recombinant techniques well known in the art. For example, the fusion protein may comprise the antigen binding protein.

Polypeptides and Immunoconjugates

In another aspect, the present application provides one or more polypeptides that may comprise the isolated antigen binding protein of the present application.

In another aspect, the present application provides one or more immunoconjugates that may comprise the isolated antigen binding protein of the present application. In certain embodiments, the immunoconjugate may further comprise a pharmaceutically acceptable therapeutic agent.

Nucleic Acid, Vector and Cell

In another aspect, the present application further provides an isolated nucleic acid molecule or isolated nucleic acid molecules. The nucleic acid molecule(s) may encode the antigen binding protein of the present application. For example, each of the nucleic acid molecule(s) may encode the complete antigen binding protein, or a portion thereof (e.g., one or more of CDR1-3, FR1-4, VH, VHH or heavy chain).

The nucleic acid molecule(s) of the present application may be isolated. For example, it may be produced or synthesized by the following methods: (i) in vitro amplification, for example by polymerase chain reaction (PCR) amplification, (ii) clonal recombination, (iii) purification, for example, by fractionation through restriction digestion and gel electrophoresis, or (iv) synthesis, for example, by chemical synthesis. In some embodiments, the isolated nucleic acid(s) is/are a nucleic acid molecule(s) prepared by the recombinant DNA technology.

In the present application, the nucleic acid(s) encoding the antibody and the antigen-binding fragment thereof may be prepared by a variety of methods known in the art. These methods include, but are not limited to, the overlap extension PCR using restriction fragment operations or using synthetic oligonucleotides. For specific operations, see Sambrook et al., Molecular Cloning, A Laboratory Manual, Cold Spring Harbor Laboratory Press, Cold Spring Harbor, N.Y., 1989; and Ausube et al., Current Protocols in Molecular Biology, Greene Publishing and Wiley-Interscience, New York N.Y., 1993.

In another aspect, the present application provides a vector or vectors, each of which comprises the nucleic acid molecule(s) of the present application. Each vector may comprise one or more said nucleic acid molecule(s). In addition, the vector may also comprise other genes, for example, a marker gene that is allowed to select this vector in a suitable host cell and under a suitable condition. In addition, the vector may also comprise an expression control element that allows a coding region to be expressed correctly in a suitable host. Such a control element is well known to those skilled in the art, which, for example, may include a promoter, a ribosome binding site, an enhancer, and other control elements that regulate gene transcription or mRNA translation. In some embodiments, the expression control sequence is a regulatable element. A specific structure of the expression control sequence may vary depending on the function of the species or cell type, but generally includes a 5' non-transcribed sequence and 5' and 3' non-translated sequences, for example, a TATA box, a capped sequence, a CAAT sequence, etc., which are involved in transcription and translation initiation, respectively. For example, the 5' non-transcribed expression control sequence may include a promoter region, and the promoter region may include a promoter sequence for functionally linked to the nucleic acid for transcriptional control. The expression control sequence may further comprise an enhancer sequence or an upstream activator sequence. In the present application, suitable promoters may comprise, for example, promoters for SP6, T3, and T7 polymerases, human U6 RNA promoters, CMV promoters, and their artificial hybrid promoters (such as CMV), wherein a portion of a promoter may be fused with a portion of a promoter of an additional cellular protein (such as human GAPDH and glyceraldehyde-3-phosphate dehydrogenase) gene, and the promoter may or may not contain additional introns. The nucleic acid molecule(s) of the present application may be operably linked to the expression control element. The vector may comprise, for example, a plasmid, a cosmid, a virus, a bacteriophage, or other vectors commonly used in, for example, genetic engineering. For example, the vector is an expression vector.

In another aspect, the present application provides a host cell, which may comprise the nucleic acid molecule(s) of the present application and/or the vector or vectors of the present application. In some embodiments, each type of or each host cell may comprise one or one type of the nucleic acid molecule or vector of the present application. In some embodiments, each type of or each cell may comprise a plurality of (e.g., 2 or more) or a plurality of types of (e.g., 2 or more types of) vectors of the present application. For example, the vector of the present application may be introduced into the host cell, for example, a eukaryotic cell, such as a plant-originated cell, a fungal cell, or a yeast cell, etc. The vector of the present application may be introduced into the host cell by methods known in the art, such as electroporation, lipofectine transfection, lipofectamin transfection, etc.

Preparation Method

In another aspect, the present application provides a preparation method for the isolated antigen binding protein. The method may comprise culturing the host cell of the present application under such a condition that the isolated antigen binding protein is expressed. For example, an appropriate medium, an appropriate temperature, a culture time and the like may be used, and these methods are understood by those of ordinary skills in the art.

Any method suitable for producing a monoclonal antibody may be used to produce the isolated antigen binding protein (e.g., the anti-properdin antibody) of the present application. For example, animals may be immunized with linked or naturally occurring properdin or fragments thereof. Suitable immunization methods may be used, including adjuvants, immunostimulants, and repeated booster immunizations, and one or more routes may be used.

Any suitable form of properdin may be used as an immunogen (antigen) to produce a non-human antibody specific to properdin and to screen the biological activity of the antibody. An eliciting immunogen may be a human properdin, a recombinant mouse, or peptides containing single/multiple epitopes. The immunogen may be used alone, or in combination with one or more immunogenicity enhancers known in the art. The immunogen may be purified from a natural source, or produced in a genetically modified cell. An DNA encoding the immunogen may be genomic or non-genomic (e.g. cDNA) in source. A suitable genetic vector may be used to express the DNA encoding the immunogen, and the vector comprises, but is not limited to, an adenovirus vector, an adeno-associated virus vector, a baculovirus vector, a material, and a non-viral vector.

An exemplary method for discovering the isolated antigen binding protein of the present application is described in Example 1.

Immunization may be performed using recombinant mouse properdin in healthy camels. An essential constant domain sequence may be optimized by screening antibodies with the biological assays described in the Examples below, so as to produce the desired biological activity.

An exemplary method for humanizing the isolated antigen binding protein of the present application is described in Example 2.

The sequence of the DNA molecule of the isolated antigen binding protein or the fragment thereof in the present application may be obtained by conventional techniques, such as methods using PCR amplification or genomic library screening and the like.

Once relevant sequences are obtained, they may be obtained on a large scale by recombination. This is generally done by cloning them into vectors, then transferring then into cells, and then isolating the relevant sequences from the proliferated host cell by means of a conventional method.

In addition, the relevant sequences may also be synthesized by using an artificial synthesis method, especially when a fragment is short. Generally, a fragment with a very long sequence may be obtained by first synthesizing multiple small fragments, and then linking these small fragments. Then, the nucleic acid molecules may be introduced into various existing DNA molecules (or such as vectors) and cells known in the art.

The present application also relates to vectors comprising the aforementioned appropriate nucleic acid molecules and appropriate promoters or control sequences. These vectors may be used for transforming appropriate host cells to enable them to express proteins. The host cells may be prokaryotic cells, such as bacterial cells; or lower eukaryotic cells, such as yeast cells; or higher eukaryotic cells, such as mammalian cells. For example, the animal cells may comprise (but are not limited to): CHO-S, CHO-K1, and HEK-293 cells.

The step of transforming the host cells with recombinant DNAs in the present application may be performed using techniques well known in the art. An obtained transformant may be cultured by a conventional method, and it expresses the polypeptide encoded by the nucleic acid molecule(s) of the present application. According to the host cells used, they are cultured in a conventional medium under suitable conditions. Generally, the host cells are cultured and transformed under conditions suitable for the expression of the isolated antigen binding protein of the present application. Then, the isolated antigen binding protein of the present application is purified and obtained using conventional immunoglobulin purification steps, such as protein A-Sepharose, hydroxyapatite chromatography, gel electrophoresis, dialysis, ion exchange chromatography, hydrophobic chromatography, molecular sieve chromatography, or affinity chromatography, and other conventional separation and purification means well known to those skilled in the art.

The resulting monoclonal antibody may be identified by a conventional means. For instance, the binding specificity of the monoclonal antibody may be determined by immunoprecipitation or in vitro binding assays, such as fluorescence activated cell sorting (FACS), radioimmunoassay (RIA), or enzyme-linked immunosorbent assay (ELISA).

Pharmaceutical Composition and Pharmaceutical Combination

In another aspect, the present application provides a pharmaceutical composition. The pharmaceutical composition may comprise the isolated antigen binding protein, the polypeptide, the immunoconjugate, the isolated nucleic acid molecule, the vector, the cell, and/or a pharmaceutically acceptable adjuvant and/or excipient described herein. In the present application, the pharmaceutically acceptable adjuvant may include a buffer, an antioxidant, a preservative, a low molecular weight polypeptide, a protein, a hydrophilic polymer, an amino acid, a sugar, a chelating agent, a counter ion, a metal complex, and/or a non-ionic surfactant. Except insofar as any conventional media or agent is incompatible with the cells described herein, its use in the pharmaceutical compositions of the present application is contemplated. In the present application, the pharmaceutically acceptable excipient may include an additive other than the main drug in the pharmaceutical preparation, and may also be referred to as an auxiliary material. For example, the excipients may include binders, fillers, disintegrants, lubricants in tablets. For example, the excipients may include wine, vinegar, medicinal juices, etc. in a traditional Chinese medicine pill. For example, the excipient may comprise a base portion of a semisolid formulation ointment, cream. For example, the excipients may include preservatives, antioxidants, flavoring agents, fragrances, cosolvents, emulsifiers, solubilizers, tonicity adjusting agents, colorants in liquid formulations. A pharmaceutical preparation should match the mode of administration. The pharmaceutical composition of the present application may be prepared into an injection form, for example, by means of a conventional method using normal saline or an aqueous solution containing glucose and other adjuvants. The pharmaceutical composition such as an injection and a solution should be manufactured under an aseptic condition. The dosage of an active ingredient is a therapeutically effective amount. In addition, the isolated antigen binding protein of the present application may also be used together with other therapeutic agents.

In another aspect, the present application provides a pharmaceutical combination comprising the isolated antigen binding protein and one or more active ingredients.

The isolated antigen binding protein, pharmaceutical composition or pharmaceutical combination described herein may be formulated, dosed, and administered in line with good medical practices. The considerations in this case comprise the specific disorder being treated, the specific mammal being treated, the clinical condition of a single patient, the cause of the disorder, the site of agent delivery, the method of administration, the schedule of administration, and other factors known to a medical practitioner. A therapeutic agent (e.g., an anti-properdin antibody) does not need to be but is optionally formulated and/or administered together with one or more agents that are currently used for preventing or treating the disorder in question. The effective amount of such other agents depends on the amount of the therapeutic agent (e.g., an anti-properdin antibody) existing in the preparation, the type of disorder or treatment, and other factors discussed above. Generally, these agents may be used at any dose that is empirically/clinically determined to be appropriate and via any route that is empirically/clinically determined to be appropriate. Compared with a single therapy, the dose of the antibody administered in a combination therapy may be reduced. The progress of such a therapy may be easily monitored by conventional techniques.

Kit, Use and Method

In another aspect, the present application provides a method for detecting or determining properdin, which method may comprise using said isolated antigen binding protein or said polypeptide.

In the present application, the methods may include in vitro methods, ex vivo methods, methods of non-diagnostic or non-therapeutic interest. For example, the method may include a method for detecting the presence and/or amount of properdin for non-diagnostic purposes, which may include the steps of:

1) contacting a sample with an antigen binding protein of the present application; and
2) detecting the presence and/or amount of the antigen binding protein bound by the sample to determine the presence and/or level of expression of properdin in the sample obtained from the subject.

For example, said isolated antigen binding protein of said method may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118.

For example, said isolated antigen binding protein of said method may comprise an amino acid sequence as set forth in any one of SEQ ID NO: 92, and SEQ ID NO: 93.

For example, said isolated antigen binding protein of said method may comprise an amino acid sequence as set forth in SEQ ID NO: 92.

For example, said isolated antigen binding protein of said method may comprise an amino acid sequence as set forth in SEQ ID NO: 93.

In another aspect, the present application provides a kit for properdin that may include use of the isolated antigen binding protein or the polypeptide. In the present application, the kit may further comprise instructions that document a method for detecting the presence and/or amount of properdin. For example, the methods may include in vitro methods, ex vivo methods, methods of non-diagnostic or non-therapeutic interest.

For example, said kit may be an ELISA kit comprising said isolated antigen binding protein or the polypeptide. For example, said ELISA kit may detect properdin by direct ELISA, indirect ELISA, Sandwich ELISA or competitive ELISA.

For example, said isolated antigen binding protein or said polypeptide may be used as capture antibodies.

For example, said isolated antigen binding protein or said polypeptide may be used as detecting antibodies. For example, said detecting antibodies may link to HRP (horse radish peroxidase). For example, said detecting antibodies may link to ALP (alkaline phosphatase).

For example, said capture antibodies may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118. For example, said capture antibodies may comprise an amino acid sequence as set forth in any one of SEQ ID NO: 92, and SEQ ID NO: 93.

For example, said capture antibodies may comprise an amino acid sequence as set forth in SEQ ID NO: 92. For example, said capture antibodies may comprise an amino acid sequence as set forth in SEQ ID NO: 93.

For example, said detecting antibodies may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118.

In another aspect, the application provides a use of the isolated antigen binding protein or the polypeptide in the preparation of a kit for use in a method of detecting the presence and/or amount of properdin. For example, the methods may include in vitro methods, ex vivo methods, methods of non-diagnostic or non-therapeutic interest.

For example, said isolated antigen binding protein of said use may comprise an amino acid sequence as set forth in any one of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 92, SEQ ID NO: 93, SEQ ID NO: 116, SEQ ID NO: 117 and SEQ ID NO: 118. For example, said isolated antigen binding protein of said use may comprise an amino acid sequence as set forth in any one of SEQ ID NO: 92, and SEQ ID NO: 93. For example, said isolated antigen binding protein of said use may comprise an amino acid sequence as set forth in SEQ ID NO: 92. For example, said isolated antigen binding protein of said use may comprise an amino acid sequence as set forth in SEQ ID NO: 93.

In another aspect, the present application provides a method of inhibiting alternative complement pathway comprising administering to a subject in need thereof an effective amount of the isolated antigen binding protein, the polypeptide, the immunoconjugate, the isolated nucleic acid molecule, the vector, the cell and/or the pharmaceutical composition, and/or a pharmaceutically acceptable therapeutic agent. In the present application, the method of modulating an immune response may include in vitro methods, ex vivo methods, methods of non-diagnostic or non-therapeutic interest.

In another aspect, the present application provides a method of inhibiting alternative complement pathway comprising administering to a subject in need thereof an effective amount of the pharmaceutical composition, pharmaceutical combination, and/or a pharmaceutically acceptable therapeutic agent. In the present application, the method of modulating an immune response may include in vitro methods, ex vivo methods, methods of non-diagnostic or non-therapeutic interest.

In another aspect, the present application provides a method of inhibiting properdin binding to C3 comprising administering to a subject in need thereof an effective amount of the isolated antigen binding protein, the polypeptide, the immunoconjugate, the isolated nucleic acid molecule, the vector, and/or the cell. The method may be an ex vivo or in vitro method.

In another aspect, the present application provides an isolated antigen binding protein, said polypeptide, said immunoconjugate, said isolated nucleic acid molecule, said vector, said pharmaceutical composition for preventing and/or treating diseases. For example, said diseases may be caused by properdin. For example, said diseases may be mediated by alternative pathway. For example, said diseases may comprise autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACT), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the kit, the pharmaceutical composition and/or the pharmaceutical combination is used for the prevention and/or treatment of diseases in the present application. For example, said diseases may be caused by properdin. For example, said diseases may be mediated by alternative pathway. For example, said diseases may comprise autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACT), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the present application provides a use of the isolated antigen binding protein, the polypeptide, the immunoconjugate, the isolated nucleic acid molecule, the vector, the cell and/or the pharmaceutical composition for the preparation of a medicament for the prevention and/or treatment of diseases in the present application. For example, said diseases may be caused by properdin. For example, said diseases may be mediated by alternative pathway. For example, said diseases may comprise autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the present application provides the use of a pharmaceutical combination for the manufacture of a medicament for the prevention and/or treatment of diseases in the present application. For example, said diseases may be caused by properdin. For example, said diseases may be mediated by alternative pathway. For example, said diseases may comprise autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the present application provides a method of preventing and/or treating a disease or disorder comprising administering the isolated antigen binding protein, the isolated nucleic acid molecule, the vector, the cell, the pharmaceutical composition to a subject in need thereof. For example, said diseases may be caused by properdin. For example, said diseases may be mediated by alternative pathway. For example, said diseases may comprise autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

In another aspect, the present application provides a method of preventing and/or treating a disease or disorder comprising administering the pharmaceutical combination to a subject in need thereof. For example, said diseases may be caused by properdin. For example, said diseases may be mediated by alternative pathway. For example, said diseases may comprise autoimmune thrombotic thrombocytopenic purpura (TTP), hemolytic uremic syndrome (HUS), atypical hemolytic uremic syndrome (aHUS), paroxysmal nocturnal hemoglobinuria (PNH), C3 glomerulopathy (C3G), asthma, Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACT), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMO), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA).

The pharmaceutical compositions, pharmaceutical combinations, and methods described herein can be used in conjunction with other types of therapies, such as chemotherapy, surgery, radiation, gene therapy, and the like.

In the present application, the subject and/or patients may include a human or non-human animal. For example, the non-human animal may be selected from the group consisting of: monkey, chicken, goose, cat, dog, mouse and rat. Furthermore, non-human animals may also include any animal species other than humans, such as livestock animals, or rodents, or primates, or domestic animals, or poultry animals. The human may be caucasian, african, asian, amphibian, or other ethnicity, or a hybrid of various ethnicities. As another example, the person may be an elderly person, an adult, a teenager, a child, or an infant.

An effective amount in humans can be presumed from an effective amount in experimental animals. For example, Freiich et al describe the dose correlation between animals and humans (based on milligrams per square meter of body surface) (Freirich et al, Cancer Chemother. Rep. 50, 219 (1966)). The body surface area can be approximately determined from the height and weight of the patient. See, e.g., Scientific Tables, Geigy Pharmaceuticals, Ardsley, N.Y., 537 (1970).

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly), and the like.

Example 1 Discovery of Properdin-Binding Antibody Fragments 1.1 Human, Mouse and Cyno Properdin Generation The sequence of human, mouse and cyno properdin from Uniprot database synthesized by GENEWIZ were subcloned to expression vector. Protein expression was performed using transient expression of HEK293 cells transfected using PEI (Polysciences, cat #24765-1). Cultures were grown in shaking flasks media at scales ranging from 100-200 ml for 5-7 days. Cells were removed by centrifugation and culture supernatants were used for protein purification by Ni sepharose with elution using a pH 7.4 PBS buffer. Purified proteins were analyzed with 4-12% SDS-PAGE under non-reduced and reduced conditions (FIG. 1).

1.2 VHH Immune Library Constructions

Immunization was performed using recombinant mouse properdin in two healthy camels. On day 60 after finishing 4 rounds of immunization, phage-displayed VHH library was constructed of PMBCs from immunized camels by following a standardized protocol. The final phage-displayed VHH library had $2.1 \times 10^9$ independent clones, with 92% of them encoding VHH-gp3 fusion proteins.

1.3 Phage Panning Method

As previously prepared, an immune VHH library was used for VHH selection and was subjected to four rounds of panning in 1.5 ml Eppendorf tubes. About $10^{12}$ CFU phages were incubated with 10 μg of biotinylated properdin within 1 ml of blocking buffer (1% BSA in PBS) at RT for 1 h to make phages/target mixture. At the same time, 100 μl of streptavidin-coated Dynabeads M-280 (Invitrogen, 11206D) were washed with 1 ml of blocking buffer for five times in an Eppendorf microtube. Thereafter, the phage/target mixture was incubated with the Mag-beads prepared as above on a rotator at RT for 30 min. To recover the phages binding to the Mag-beads, the reaction tube was placed on a magnetic rack for 30 s. After the supernatant was removed, the beads were washed with PBS containing 0.5% Tween20 (0.5% PBST) for 10 times, followed by three-times by PBS. The phages were eluted with 1 ml of trypsin (10 μg/ml in PBS) at 37° C. for 30 min. After each round of selection, 100 μl of eluted phages were used to infect mid-log phase E. coli TIG1 ($OD_{600}$=0.6) grown at 37° C. for phage titration. Enrichment value of properdin-specific VHHs was also assessed to monitor the progress of the selection process. Remaining eluted phages were used to infect E. coli TG1 ($O_{600}$=0.6) for subsequent amplification. The bacteria were subsequently superinfected with M13KO7 helper phage at a ratio of 20:1 (phage: bacteria) to rescue phage particles. A mixture of kanamycin (50 μg/mL) and ampicillin (100 μg/mL) was added to the culture, and bacteria were further grown 4 h with shaking at 220 rpm at 30° C. The cultures were centrifuged at 4,000 g for 20 min, and the supernatants were added to 20% (w/v) polyethylene glycol 6000/2.5M NaCl (PEG/NaCl) to precipitate the phages. The samples were incubated on ice overnight and then centrifuged for 20 min at 8,000 g at 4° C. The pellets were resuspended in PBS, PEG precipitation was repeated once as described above. The final phage pellets were resuspended in 1 ml of PBS, and $10^{12}$ phages were used in subsequent rounds of panning. The general panning procedure was repeated for another three rounds. The variation was the antigens derived from different species to have cross-reactive and affinity matched phage clones. Panning summary was listed in Table 1.

TABLE 1

Panning summary

| Campaign | Input (CFU) | Output (CFU) | Output/Input |
|---|---|---|---|
| 1st round with biotin-mouse FP | 4E12 | 4E7 | 1E-5 |
| 2nd round with biotin-cyno FP | 1.8E12 | 6E8 | 3.3E-4 |
| 3rd round panning with biotin-mouse FP and cyno FP | 6E11 | 1.6E9 | 2.6E-3 |
| 4th round panning with biotin-cyno FP and mouse FP | 4E12 | 7E9 | 1.75E-3 |

1.4 Phage Screening Method

For phage-based Elisa screening, individual bacterial colonies were picked and inoculated into 200 μl 2×YT-GA medium, cultured at 37° C. with shaking (250 rpm) for 4-5 h. Then 10 μl of culture was transferred into a new deep 96-well plate containing 200 μl of 2×YT-GA medium and incubated as above till $OD_{600}$ reached around 0.6. VHH expression was induced with 1 mM IPTG (Sangon Biotech) for 16 h at 30° C. with shaking (250 rpm). After the overnight culture was spun at 4.000 rpm at 4° C. for 30 min, the supernatants were collected for phage ELISA.

Following four rounds of panning, output from 2nd, 3rd and 4th round was screened by phage enzyme-linked immunosorbent assay (ELISA). Wells of MaxiSorp 96-well plates were coated with 1 μg/ml streptavidin in coating buffer overnight at 4° C. An equivalent concentration of BSA was used as a control for nonspecific binding. After washing with PBST, the remaining protein-binding sites in the wells were blocked for 1 h at 37° C. with 1% BSA. The blocking reagent was discarded and washed by 0.05% PBST for three times. The 5 μg/ml biotin-human/mouse/cyno properdin were added in the wells for 1 h at 37° C. The supernatant was discarded, and washed for three times with 0.05% PBST. 100 μl supernatants prepared above were added to appropriate wells and incubated while shaking for 1 h at 37° C. The supernatant was discarded, and nonspecific phages were eliminated by washing three times with 0.05% PBST. Detection of the interaction between antigen and the phage-VHH was performed using a 5000-fold diluted solution of anti-Myc-HRP (Abcam, ab62928). After incubation for 1 h at 37° C., plates were then washed as before and 100 μl of TMB substrate solution were added and incubated at RT for 15 min. 100 μl/well of stop solution were added to stop the reaction before the plates were scanned with a microplate reader at 450 nm. ELISA-positive clones were defined as those that exhibited at least three times stronger ELISA signals on antigen coated plates in comparison to signals on BSA-coated plates. In parallel, the genetic diversity of the ELISA positive clones was determined using DNA sequencing, and phages with different amino acid sequences of VHH were considered as unique clones. In total, 76 unique clones with different CDR sequences were identified as positive in target-binding assays with phage ELISA and 37 selected expression and purification in HEK293 cells.

TABLE 2

Screening summary

| Plate ID | Panning output | Sequenced | Functional seq | Unique seq | New seq |
|---|---|---|---|---|---|
| P1P2 | 2nd round output | 74 | 57 | 13 | 13 |
| P3P4 | 4th round output | 44 | 6 | 5 | 2 |
| P5 | 4th round output | 18 | 16 | 7 | 0 |

TABLE 2-continued

Screening summary

| Plate ID | Panning output | Sequenced | Functional seq | Unique seq | New seq |
|---|---|---|---|---|---|
| P6 | 4$^{th}$ round output | 24 | 18 | 7 | 0 |
| P7 | 2$^{nd}$ round output | 64 | 64 | 9 | 4 |
| P8 | 2$^{nd}$ round output | 29 | 28 | 7 | 2 |
| P9 | 4$^{th}$ round output | 54 | 52 | 6 | 0 |
| P10 | 4$^{th}$ round output | 37 | 37 | 7 | 0 |
| P11 | 1$^{st}$ round output | 60 | 54 | 7 | 23 |
| P12 | 2$^{nd}$ round output | 57 | 50 | 7 | 19 |
| P13 | 1$^{st}$ round output | 37 | 30 | 6 | 10 |
| P14 | 2$^{nd}$ round output | 38 | 34 | 10 | 3 |
| Total | | 536 | 446 | 91 | 76 |

The properdin-binding VHH sequences were as follows:
SLN7150 (SEQ ID NO: 60); SLN12066 (SEQ ID NO: 61); SLN12067 (SEQ ID NO: 62);
SLN12068 (SEQ ID NO: 63); SLN12069 (SEQ ID NO: 64); SLN12070 (SEQ ID NO: 65);
SLN7160 (SEQ ID NO: 66); SLN12075 (SEQ ID NO: 67); SLN12076 (SEQ ID NO: 68);
SLN12077 (SEQ ID NO: 69); SLN7162 (SEQ ID NO: 70); SLN12078 (SEQ ID NO: 71);
SLN12079 (SEQ ID NO: 72); SLN12080 (SEQ ID NO: 73); SLN12081 (SEQ ID NO: 74);
SLN12036 (SEQ ID NO: 75), SLN12082 (SEQ ID NO: 76); SLN12083 (SEQ ID NO: 77);
SLN12084 (SEQ ID NO: 78); SLN12085 (SEQ ID NO: 79); SLN12086 (SEQ ID NO: 80);
SLN7151 (SEQ ID NO: 83); SLN7152 (SEQ ID NO: 84); SLN7153 (SEQ ID NO: 85);
SLN7154 (SEQ ID NO: 86); SLN7155 (SEQ ID NO: 87); SLN7156 (SEQ ID NO: 88);
SLN7159 (SEQ ID NO: 89); SLN7161 (SEQ ID NO: 90); SLN12027 (SEQ ID NO: 91);
SLN12030 (SEQ ID NO: 92); SLN12039 (SEQ ID NO: 93); SLN12041 (SEQ ID NO: 94);
SLN12042 (SEQ ID NO: 95); SLN12044 (SEQ ID NO: 96); SLN12045 (SEQ ID NO: 97).

Example 2 Identification of Properdin-Binding Antibodies with Inhibitory Effects on Complement Activation Through Alternative Pathway 2.1 Expression and Purification of VHHs-FC Unique VHH clones were selected for subcloning to create recombinant plasmids to produce VHH-FC proteins, degenerated primers (Forward: SEQ ID NO: 111, Reverse: SEQ ID NO: 112) were used. After the DNA sequences were verified with DNA sequencing, the recombinant plasmids were prepared and fusion protein expressed and purified by following standard protocols.

To express the recombinant VHH-Fc proteins, 100 ml of Expi293F™ Cells in OPM-CD05 Medium (OPM, cat #81075-001) were cultured to reach a cell density of approximately 3×10$^6$ viable cells/ml with viability more than 95%. Plasmids were diluted with OPM-CD05 Medium to a concentration of 1.5 µg/ml in a total volume of 5 ml. Transfection reagent PEI was diluted with OPM-CD05 Medium to a same volume of 5 ml to have a DNA:PEI ratio as 1:4 (m/m) when the diluted DNA and PEI were mixed together. After being incubated at RT for 15 minutes, the DNA/PEI complex were added onto the prepared Expi293F™ cells by swirling gently. Then the cells cultures were placed in a 37° C. incubator with >80% relative humidity and 5% CO$_2$ on an orbital shake. At 24 h post the transfection, 5% peptone (1 mg/ml) and 2% glucose (330 g/l) were added to the culture slowly. After days of culturing, the cell culture supernatant was collected by sequential centrifugations at 1,200 rpm for 10 min and 3,900 rpm for 20 min before being used for Protein A purification.

VHH-Fcs were purified with Protein A (BIOON, HZ1011-2). 1 ml of Protein A slurry were loaded onto a 20-ml column (G-bios, C006197-0025). After the columns were equilibrated with PBS of 10-fold of CV (column volume), the cell culture supernatant prepared as above were loaded and flow throw the Protein-A columns by gravity for 2 times. After the columns were washed with PBS for 10 times of CV, 10 ml of 0.1 M Glycine-HCl buffer (pH 3.0) were used to elute the VHH-Fc proteins. The eluted proteins were neutralized with 100 µl of 1 M (pH 8.5) Tris-HCL buffer the pH was adjusted to 7.4. The Protein A affinity column was regenerated and preserved by washing with PBS, ddH$_2$O and 20% ethanol sequentially. For the eluted protein, it was desalted through an Amicon UltraCel 30K centrifugal device (Milipore, UFC903016). Briefly, eluted protein was diluted in 10 ml PBS and concentrated to 1.5 ml by centrifugation for 3 times at least. The final protein solution was formulated in PBS to less than 1 ml and filtrated with 0.22-µm filters.

Figure 2:
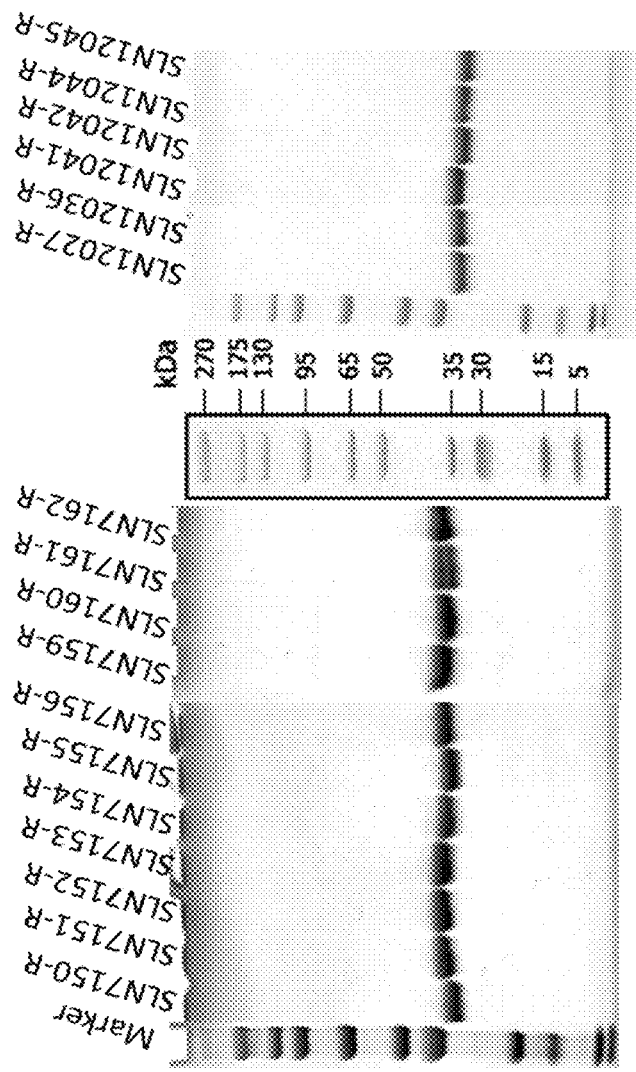
FIG. 2 Illustrates production of the recombinant VHH-Fc analysis on non-reducing and reducing SDS-PAGE.

Purity of VHH-Fcs were analyzed with SDS-PAGE. Briefly, 2 µg protein in 4×LDS Sample buffer was loaded and analyzed with SurePAGE gel in Tris-MOPS SDS buffer (Genscript, M00138) at a constant voltage of 160-V for 50 min. Proteins were visualized with Coomassie stain (TIANGEN, cat #PA101) following the manufacturer's instructions. The purified proteins were analyzed with 4-12% gradient SDS-PAGE gel under non-reducing or reducing conditions (FIG. 2).

2.2 ELISA Binding

Figure 3A:
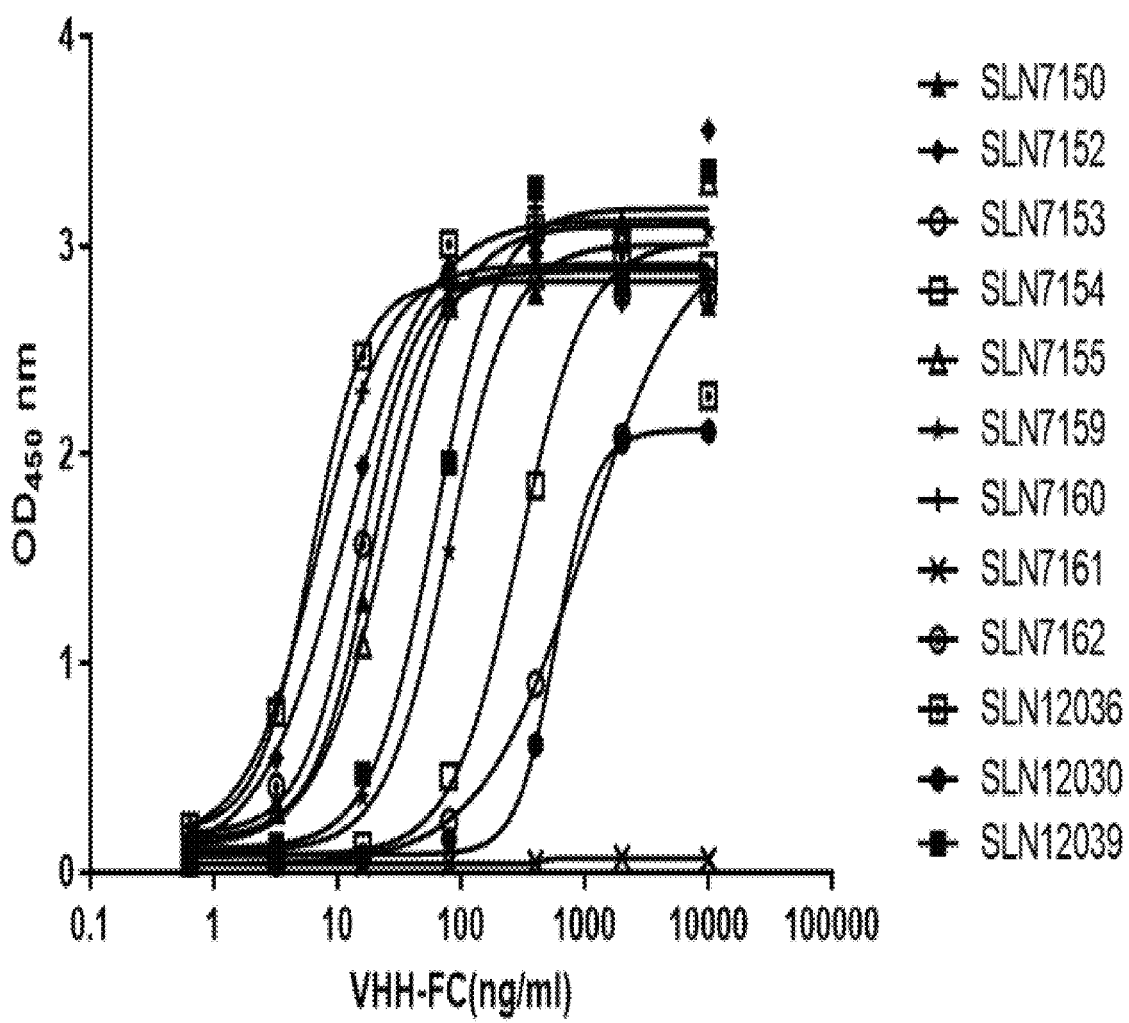
FIG. 3 Illustrates ELISA binding of the recombinant VHH-Fc to human (FIG. 3A), cyno (FIG. 3B) or mouse (FIG. 3C) properdin.
Figure 3B:
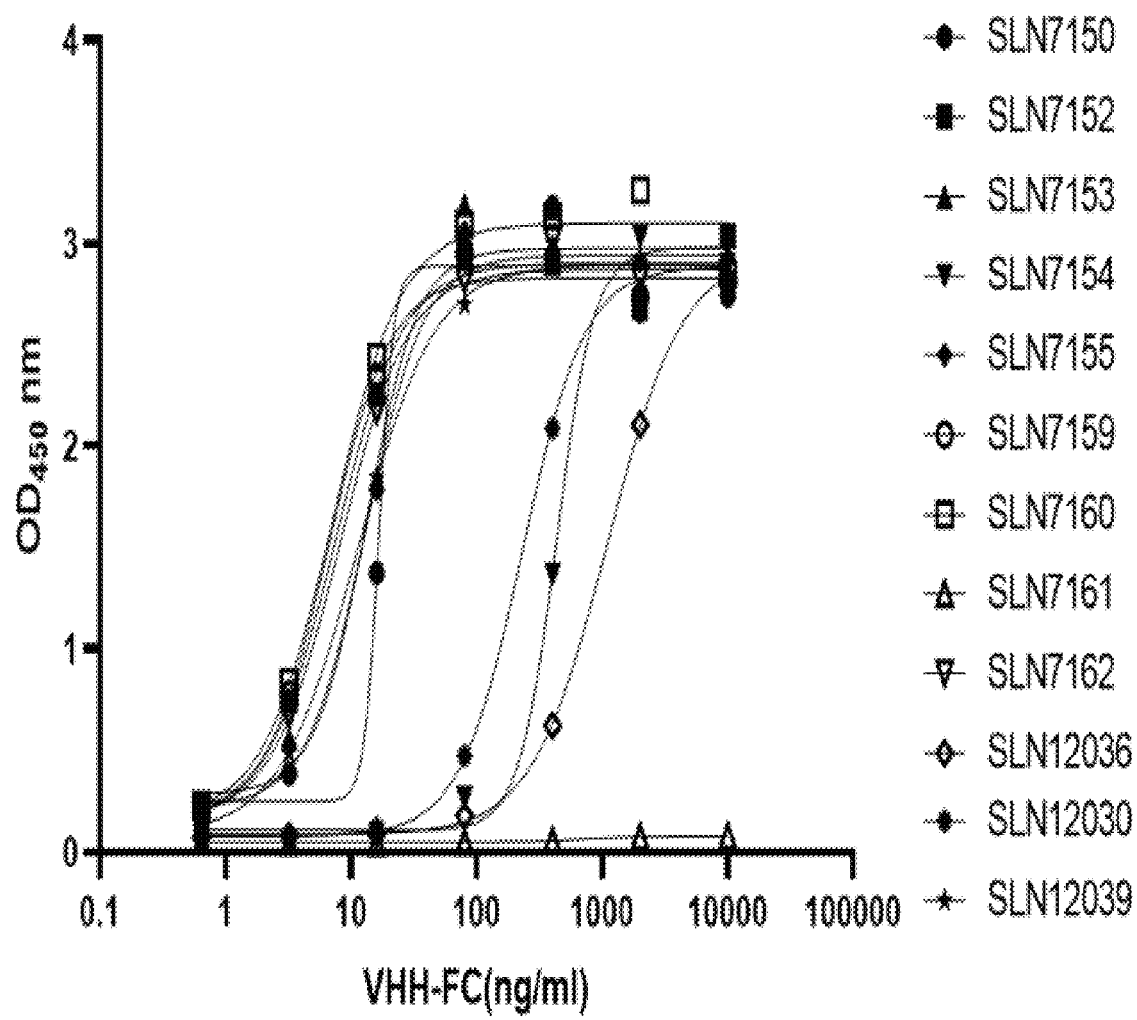
Figure 3C:
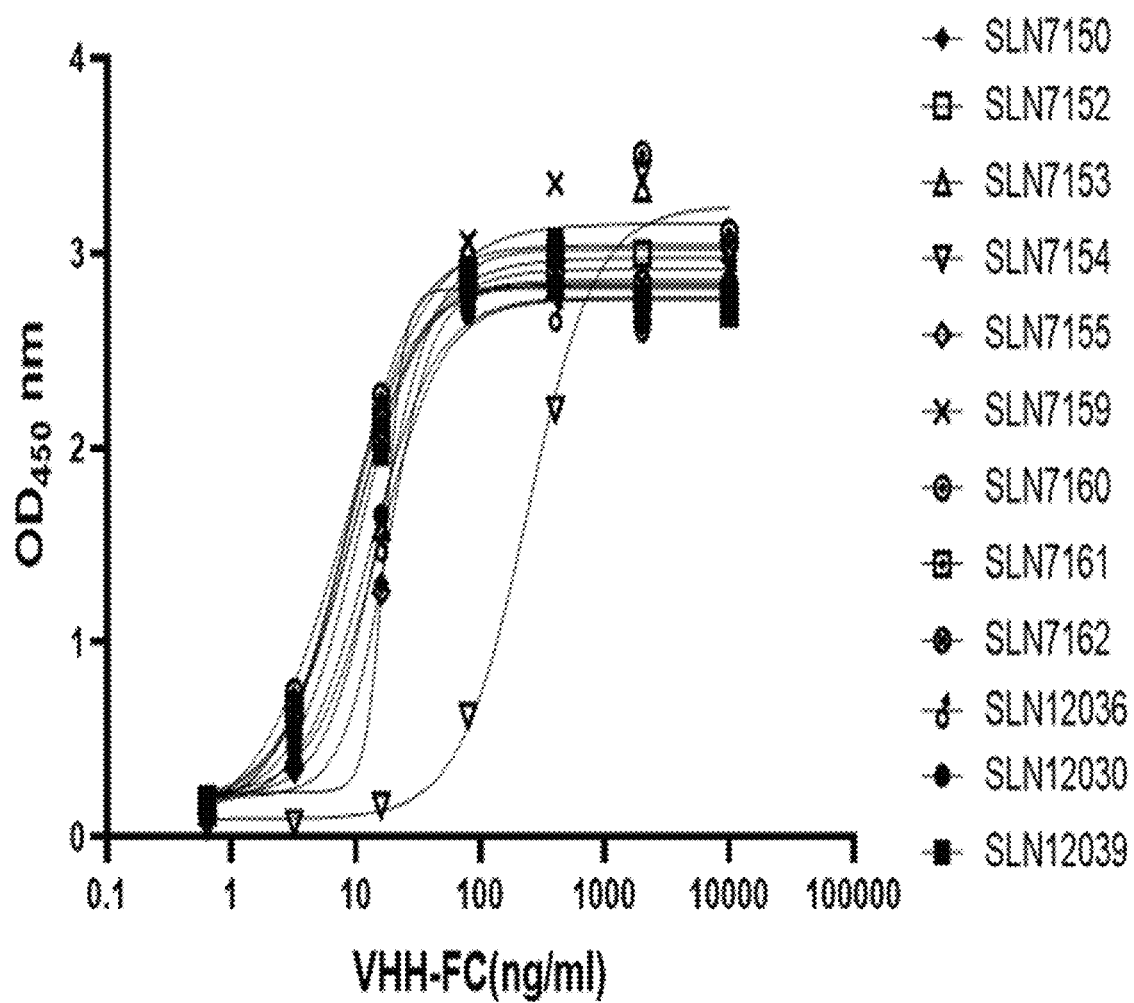

For binding ELISA, 96-well immunoplates were coated with 100 µl/well 1 µg/ml streptavidin and incubate at 4° C. overnight. Wells were washed with PBST for 3 times and blocked with 200 µl of 1% BSA/PBS at RT for 1 h Washed with PBST for 3 times and add human properdin-biotin, mouse properdin-biotin or cyno properdin-biotin (5 µg/ml) 100 µl/well and incubated at RT for 1 h. Plates were washed with PBST for 3 times, 100 µl/well 5-fold serially diluted VHH-Fcs from 10 µg/ml was added, and incubate at RT for 1 h. Plates were washed with PBST for 3 times and add 100 µl goat anti-human Fc-HRP (Sigma, A0170) diluted 1/5000 in 1% BSA/PBST to each well and incubate at RT for 1 h. Plates were then washed as before and add 100 µl TMB substrate and incubate at RT for 15 min. 100 µl per well stop solution was added to stop the reaction, and the plates were read with microplate reader at 450 nm. 37 recombinant VHH-Fc clones were showed human properdin binding activity (FIG. 3A), cyno properdin binding activity (FIG. 3B) and mouse properdin binding activity (FIG. 3C), all of the clones showed cross binding and affinity matched activity.

2.3 AP Activity

For human alternative pathway experiments, all test samples were diluted by PBS and added in duplicate (50 µl/well) to a U-bottom 96-well microtiter plate. At the same time, human complement-preserved serum (Quidel, A113) was diluted to 20% vol/vol in GVBS-EGTA (1×AP buffer: 0.1% gelatin, 145 mM NaCl, 2.5 mM sodium barbital, pH7.4 with 10 mM Mg/EGTA), incubate on ice for 30 minutes and added (50 µl/well) to the rows of the same 96-well plate such that the final concentration of human serum in each well was 10%. Then prepare the rabbit erythrocytes (4×10$^8$/ml) were washed three times with 1 ml of 1-AP buffer and resuspended to a final concentration of $5\times10^7$/ml (6 ml) in 1×AP buffer. After that, 50 µl aliquots of rabbit erythrocytes ($2.5\times10^6$ cells) were added to the plate as described above, mixed well, and incubated at 37° C. for 30 min. Each plate contained two wells of 50 µl of identically prepared rabbit erythrocytes, incubated with 50 µl PBS+50 µl 1×AP buffer alone (negative control) as a control for spontaneous hemolysis, two wells containing 100 µl ddH$_2$O serving as a control for 100% lysis and two wells containing 10 mM EDTA (Thermo 15575-038) as a serum blank control. After incubating, the plate was then centrifuged at 600 rpm for 2 min and 100 µl of the supernatant transferred to a new flat bottom 96-well plate. Hemoglobin release was determined at OD 405 nm using a microplate reader, and the percent hemolysis was determined using the following formula:

Percent hemolysis (%): 100×(OD sample–OD of EDTA)/(OD 100% lysis–OD negative control)

Figure 4A:
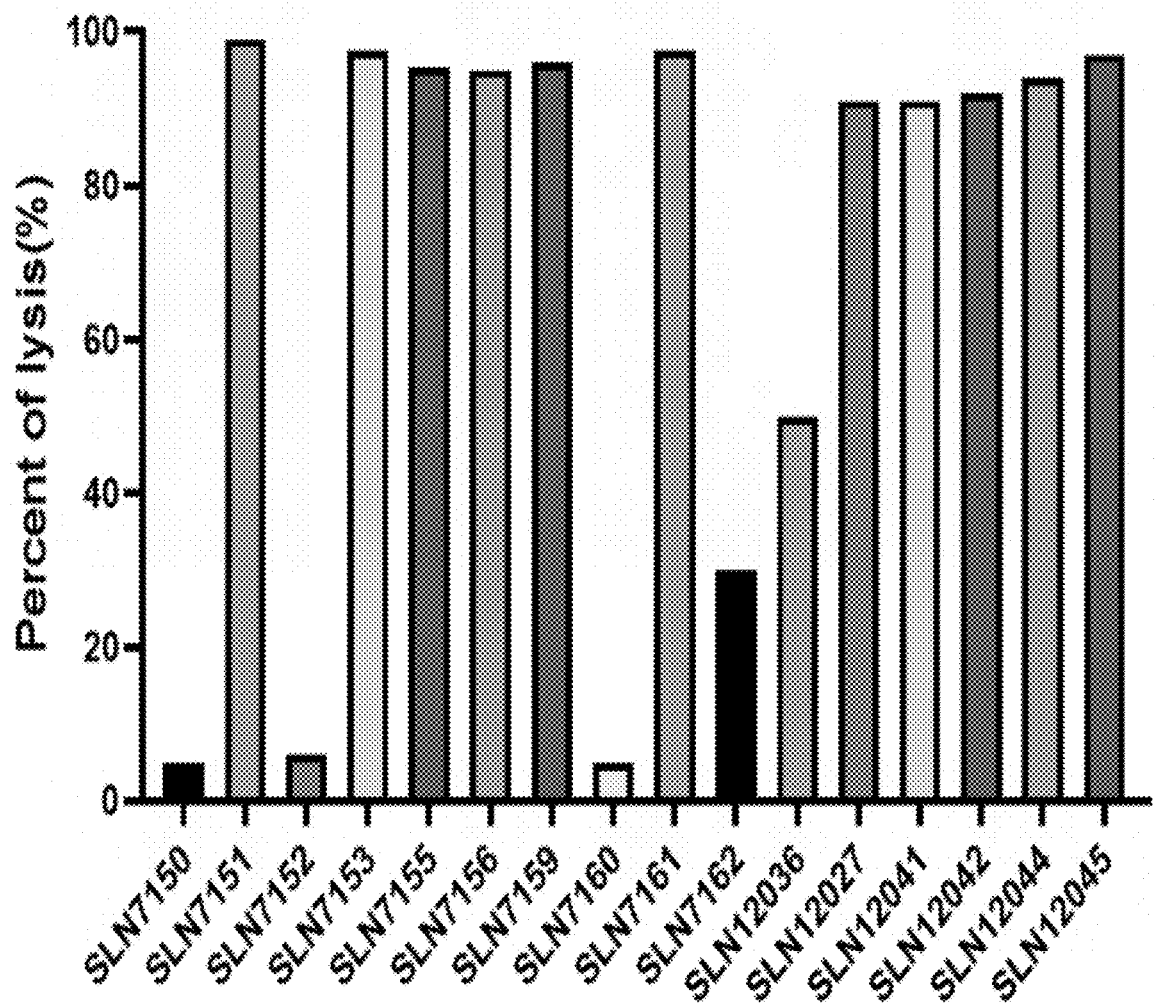
FIG. 4 Illustrates complement-inhibitory activities of the recombinant VHH-Fc within human (FIG. 4A) or mouse (FIG. 4B) serum.
Figure 4B:
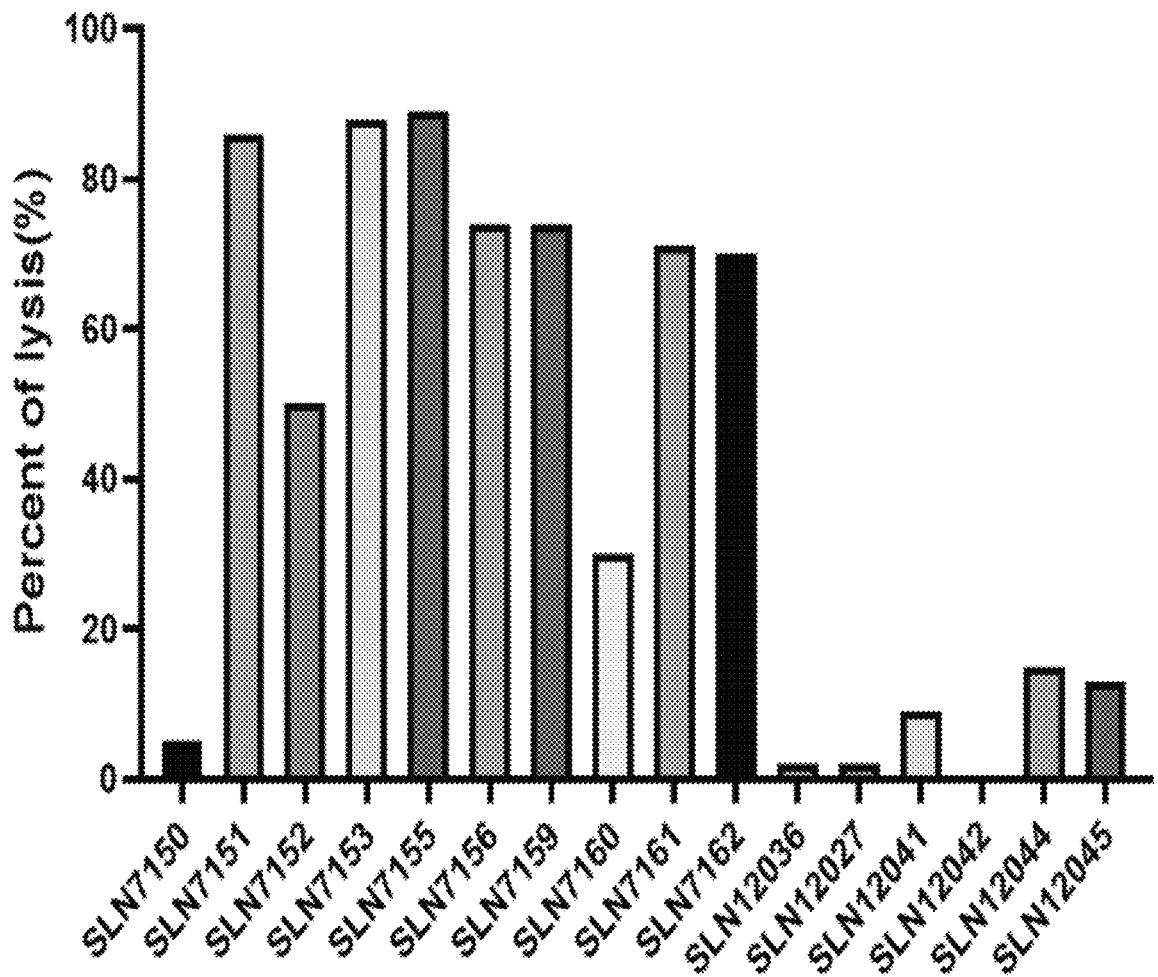

For mouse alternative pathway experiments, the process is basically the same as the above process, the difference is that the final concentration of mouse serum is 30% and that of human serum is 10%, and the incubation time is replaced by 30 min for 1 h in mouse alternative pathway assay (FIG. 4). Some clones showed complement inhibitory activity in human (FIG. 4A) and mouse (FIG. 4B) serum at 500 nM.

Figure 5:
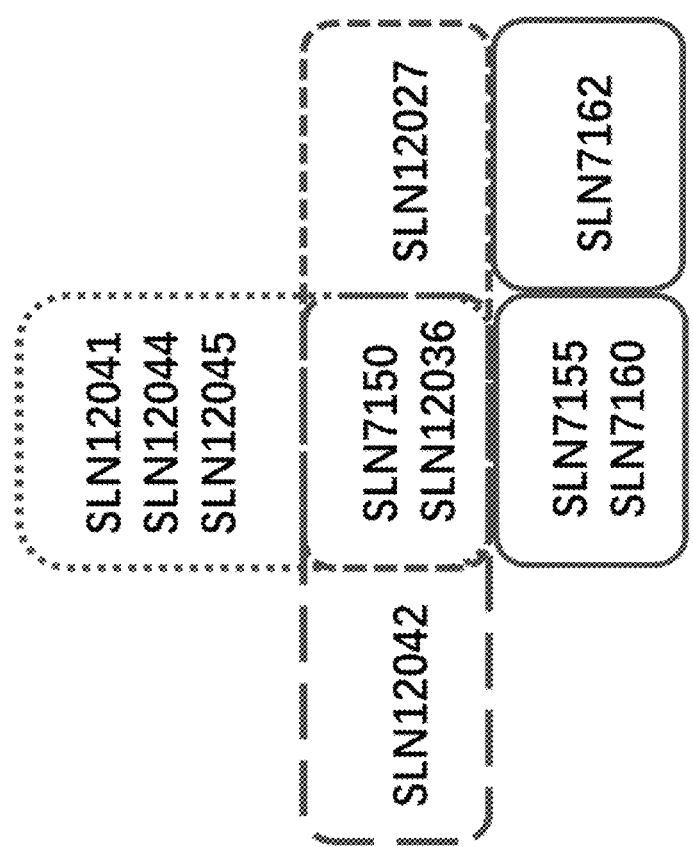
FIG. 5 Illustrates epitope binning of the properdin (full length)-binding VHH's.

Example 3 Bi-Paratopic Engineering of Properdin-Binding Antibody Fragments 3.1 Epitope Binning Assay with Full Length of Human/Mouse Properdin well immunoplates were coated with 100 µl/well of 5 µg/ml VHH Fc fusion protein and incubate at 4° C. overnight. Wells were washed with PBST for 3 times and blocked with 200 µl of 1% BSA/PBS at RT for 1 h. 60 µl human properdin-biotin or mouse properdin-biotin (0.5 µg/ml) and 60 µl VHH-Fc fusion protein (20 µg/ml) were pre-mixed and transfer 100 µl to each well that had been coated with VHH-Fc and blocked with BSA, and continued incubation at RT for 1 h. Plates were washed with PBST for 3 times and add 100 µl SA-HRP (Sigma, S5512) diluted 1/5000 in 1% BSA/PBST to each well and incubate at RT for 1 h. Plates were then washed as before and add 100 µl TMB substrate and incubate at RT for 15 min. 100 µl/well of stop solution was added to stop the reaction, and the plates were read with microplate reader at 450 nm. VHHs with competitive target binding capabilities were grouped to a same Bin. The results indicated SLN7150, SLN12036 and SLN12042 belong to Bin #1, SLN7150, SLN12036 and SLN12027 belong to Bin #2, SLN7150, SLN12036, SLN12041, SLN12044 and SLN12045 belong to Bin #3, SLN7160 and SLN7155 belong to Bin #4, SLN7162 might have different epitope with most of other VHH-Fcs belong to Bin #5 (FIG. 5).

3.2 Production of Bi-Paratopic VHH's

Figure 6:
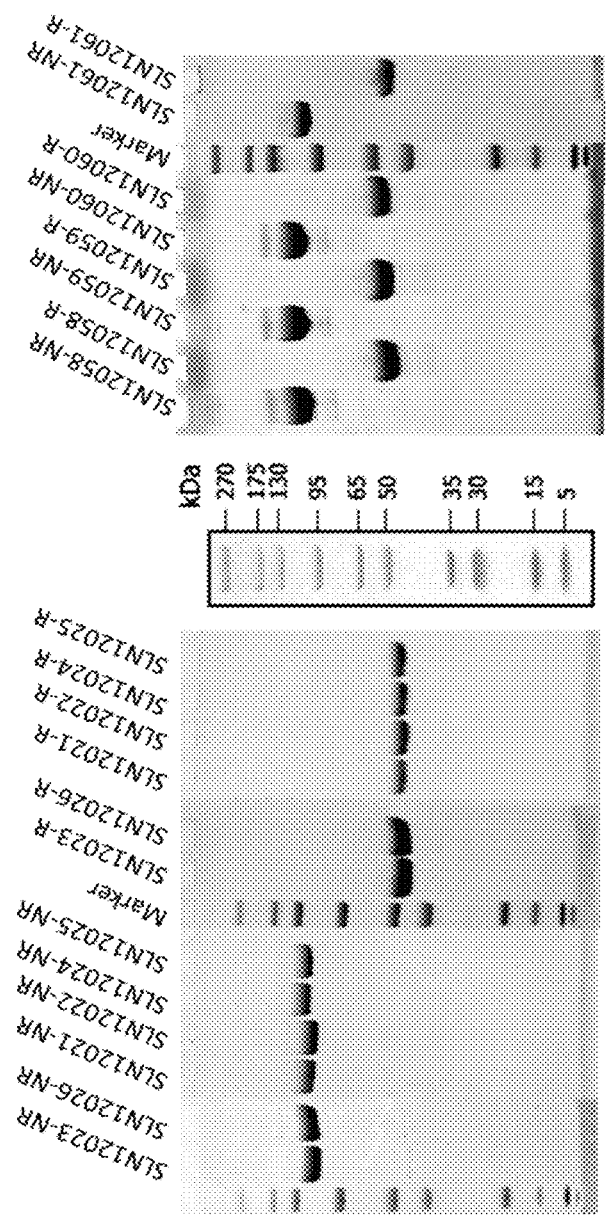
FIG. 6 Illustrates production of bi-paratopic VHH's analysis on non-reducing and reducing SDS-PAGE.

VHHs from different bins were combined with G4S linker to make bi-paratopic Fc-VHH-VHH fusion proteins as listed in Table 3. Plasmid construction and protein purification procedures can refer to the above. SDS-PAGE analysis and characterization result showed in FIG. 6.

TABLE 3

List of bi-paratopic VHHs

| Protein No. | Feature |
|---|---|
| SLN12021 | Fc-SLN7150-(G4S)$_3$-SLN7155 |
| SLN12022 | Fc-SLN7150-(G4S)$_3$-SLN7160 |
| SLN12023 | Fc-SLN7150-(G4S)$_3$-SLN7162 |
| SLN12024 | Fc-SLN7152-(G4S)$_3$-SLN7155 |
| SLN12025 | Fc-SLN7152-(G4S)$_3$-SLN7160 |
| SLN12026 | Fc-SLN7152-(G4S)$_3$-SLN7162 |
| SLN12058 | Fc-SLN12036-(G4S)$_3$-SLN7155 |
| SLN12059 | Fc-SLN12036-(G4S)$_3$-SLN7160 |
| SLN12060 | Fc-SLN12036-(G4S)$_3$-SLN7162 |
| SLN12061 | Fc-SLN7150-(G4S)$_3$-SLN12036 |

3.3 Characteristics of Bi-Paratopic VHH's

Figure 7A:
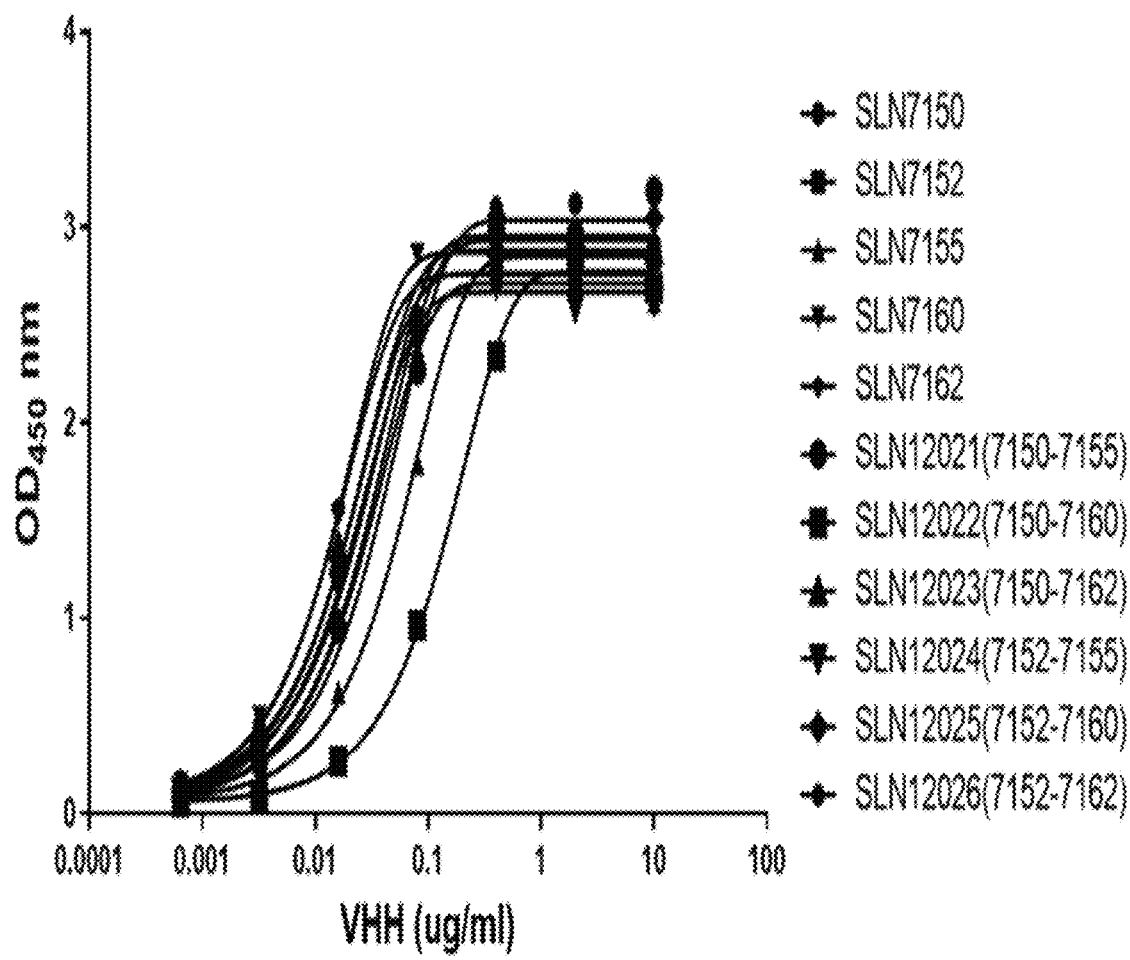
FIG. 7 Illustrates binding of the bi-paratopic VHH's to human (FIG. 7A and FIG. 7C) or mouse (FIG. 7B and FIG. 7D) properdin.
Figure 7B:
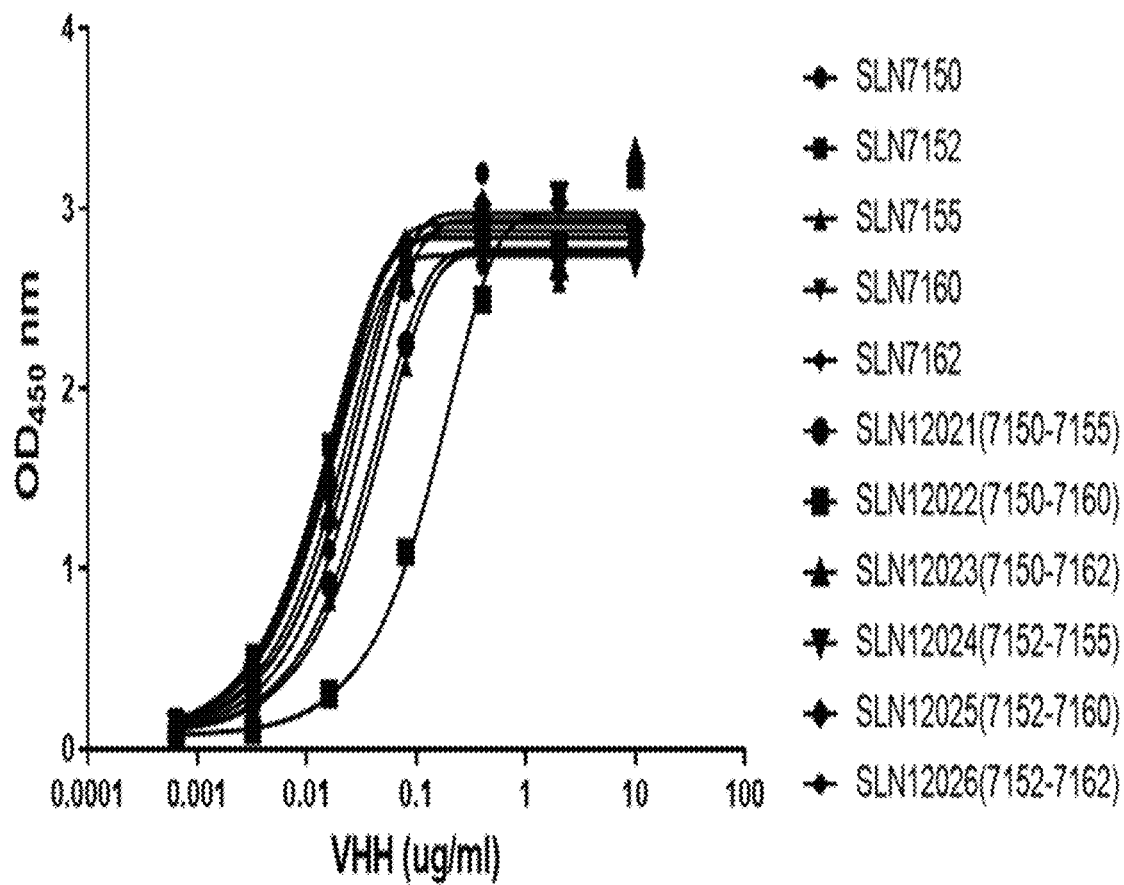
Figure 7C:
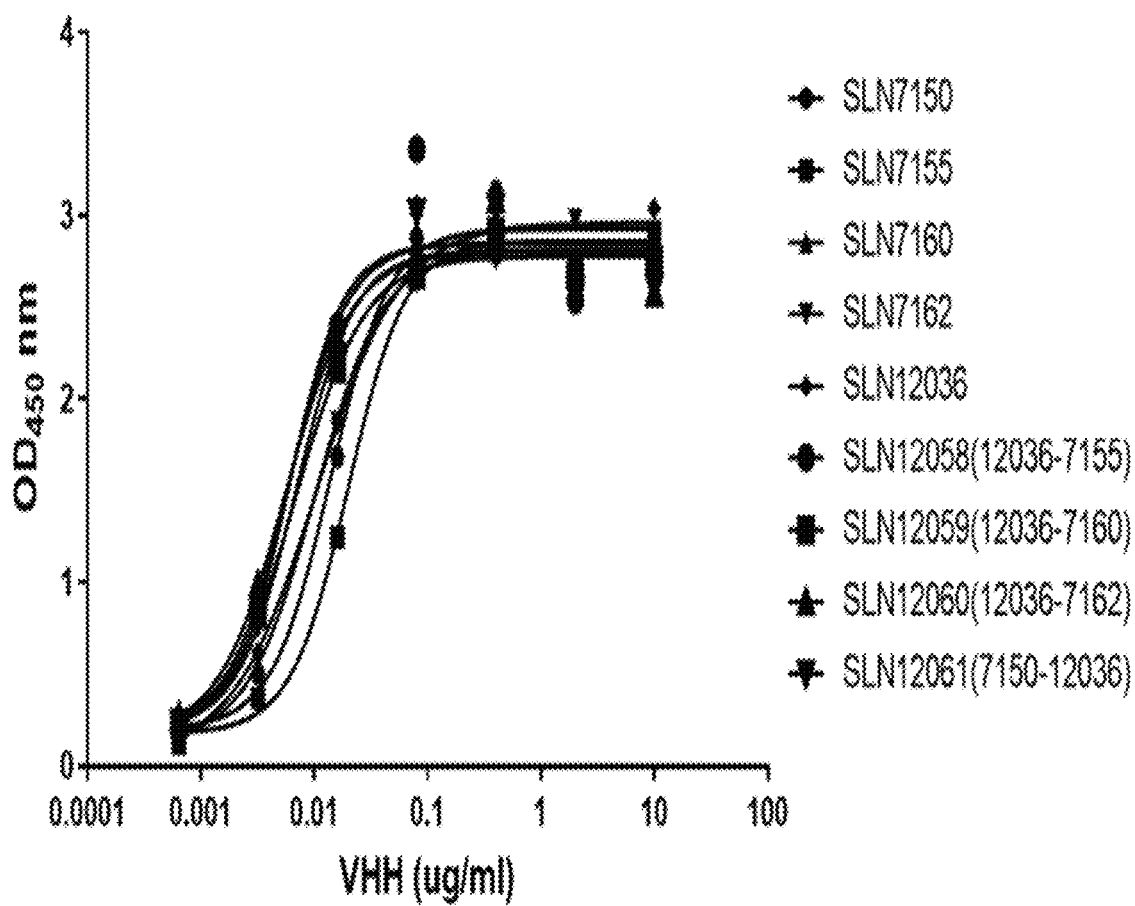
Figure 7D:
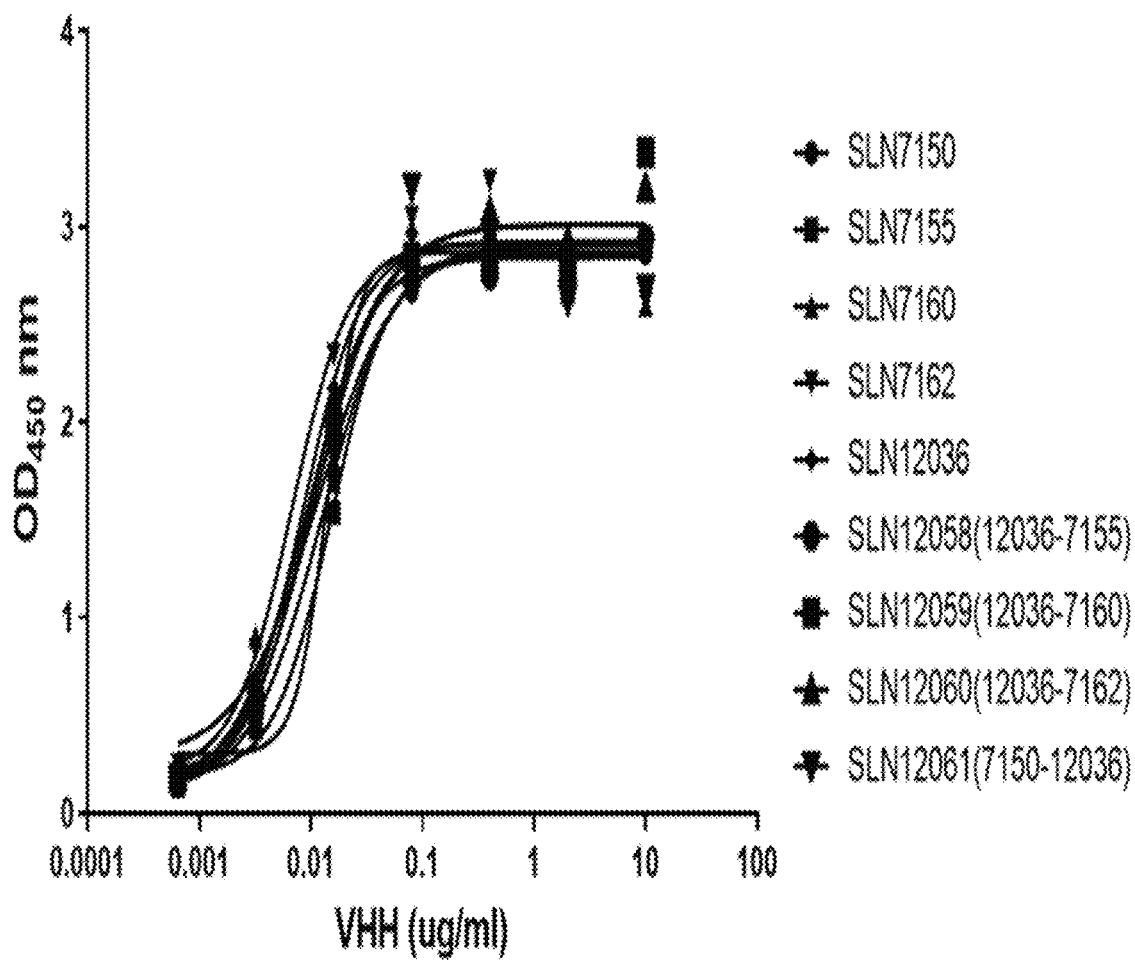
Figure 8A:
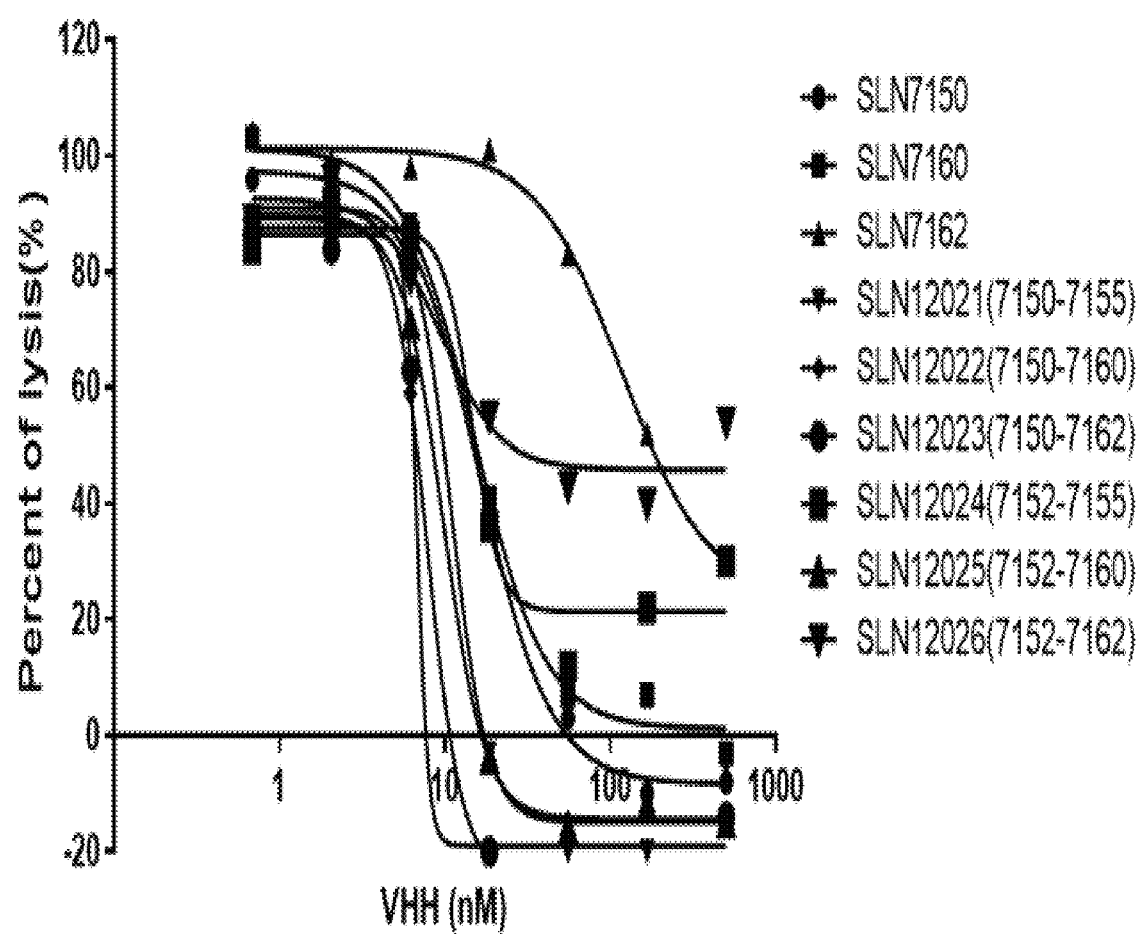
FIG. 8 Illustrates complement-inhibitory activities of the bi-paratopic VHH's within human (FIG. 8A and FIG. 8C) or mouse (FIG. 8B and FIG. 8D) serum.
Figure 8B:
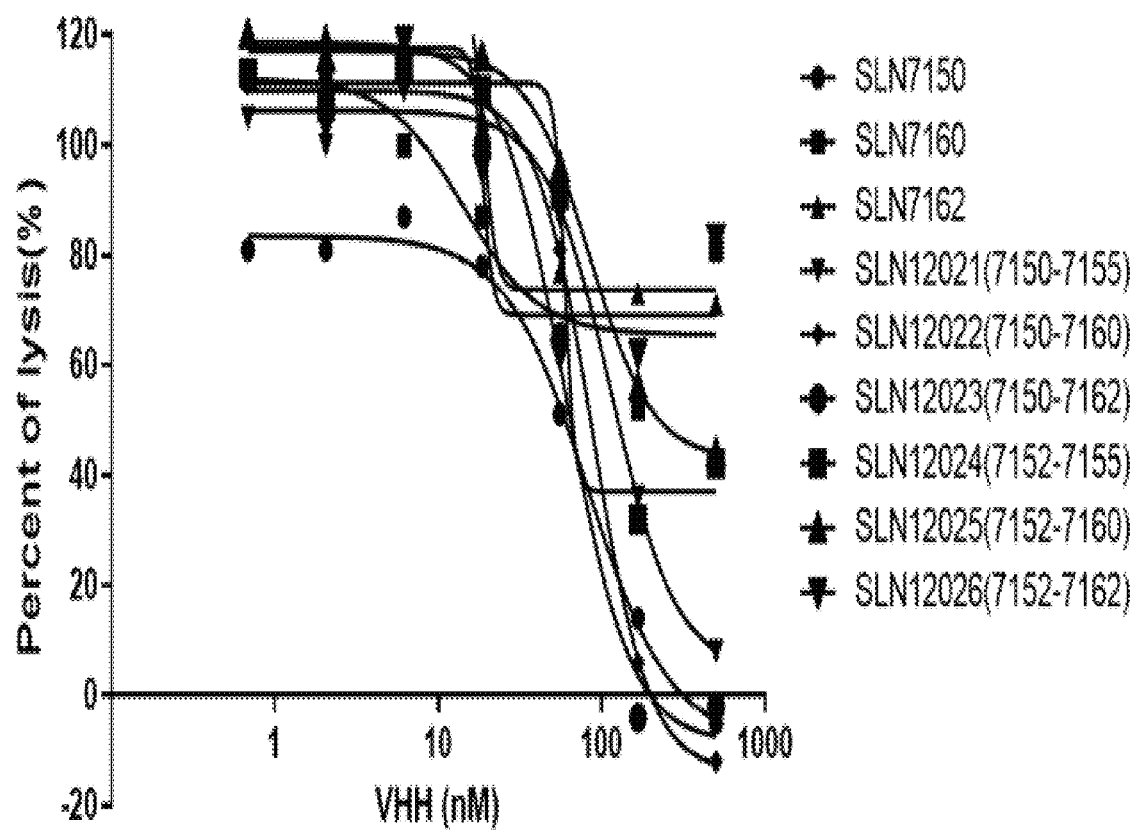
Figure 8C:
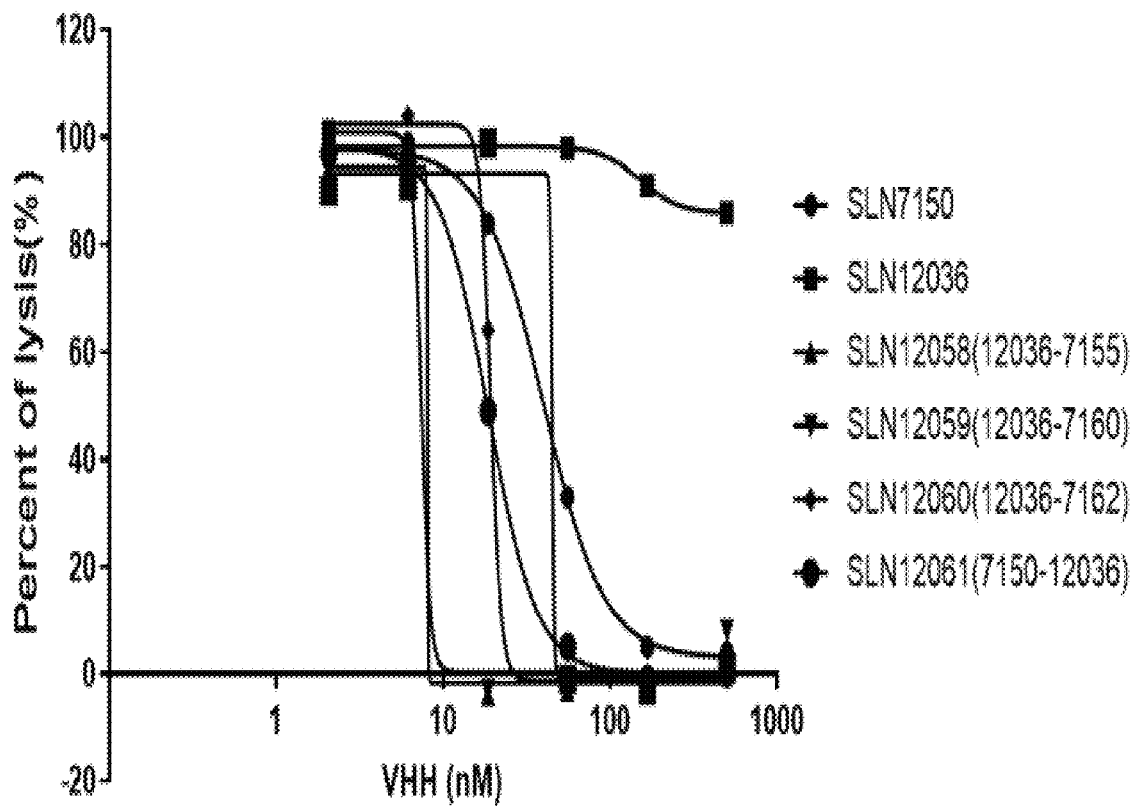
Figure 8D:
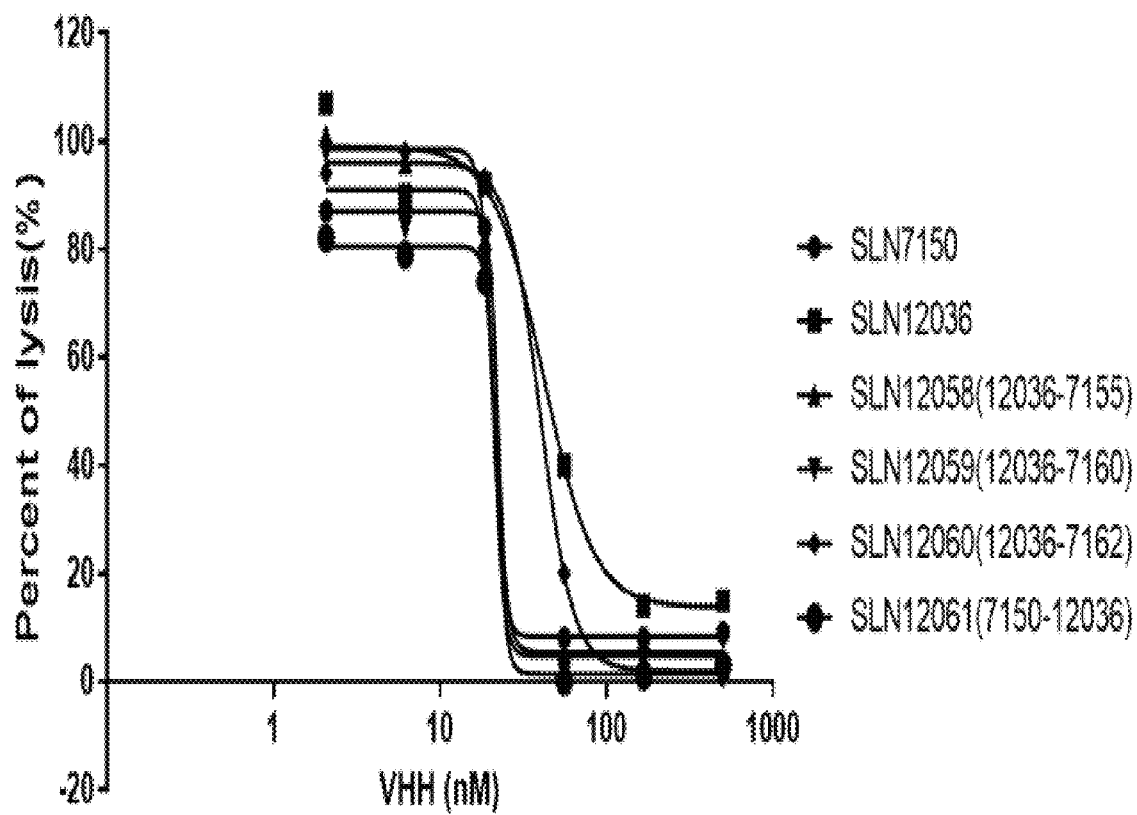

In the target-binding assays, as is shown in FIG. 8, the 10 bi-paratopic VHHs demonstrated negligible effect than those of single VHHs whether in human (FIG. 7A & FIG. 7C) or mice (FIG. 7B & FIG. 7D). In contrast, in the alternative pathway activity assays, as is shown in FIG. 8, bi-paratopic VHH's shows better complement inhibitory activity than monovalent, especially in human serum.

Example 4 Humanization of the Properdin-Binding VHH's

Figure 9A:
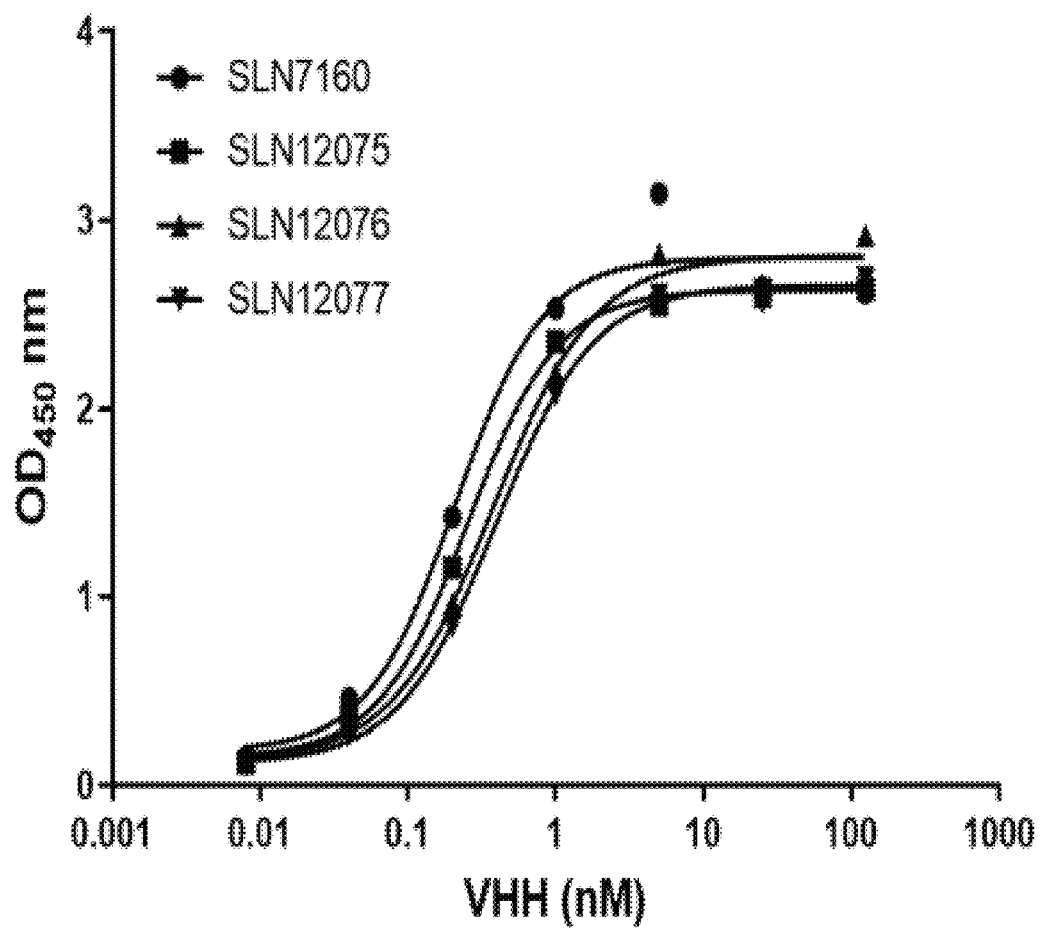
FIG. 9 Illustrates humanization of the selected properdin-binding VHH's. Human properdin binding (FIG. 9A and FIG. 9C), mouse properdin binding (FIG. 9B and FIG. 9D), human AP activity (FIG. 9E and FIG. 9F), mouse AP activity (FIG. 9G and FIG. 9H).
Figure 9B:
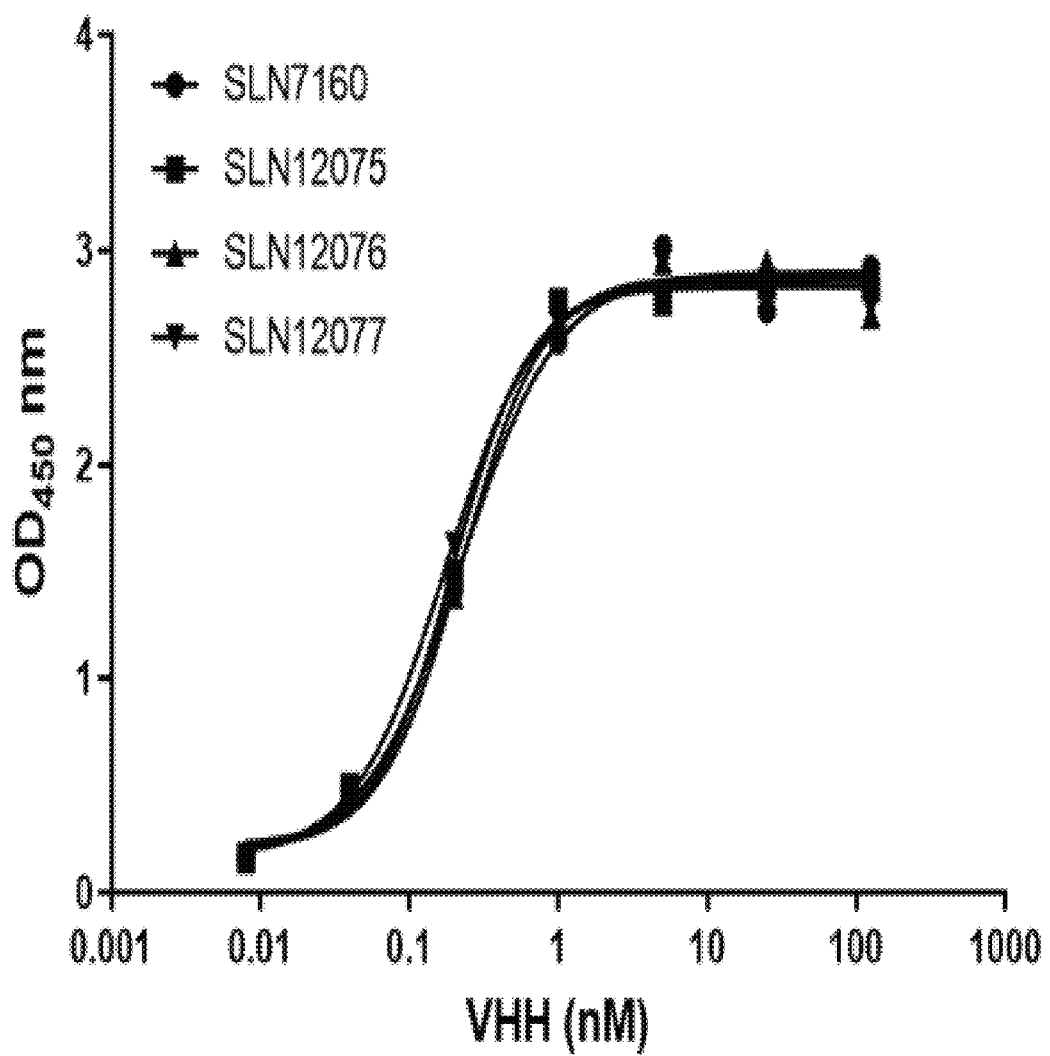
Figure 9C:
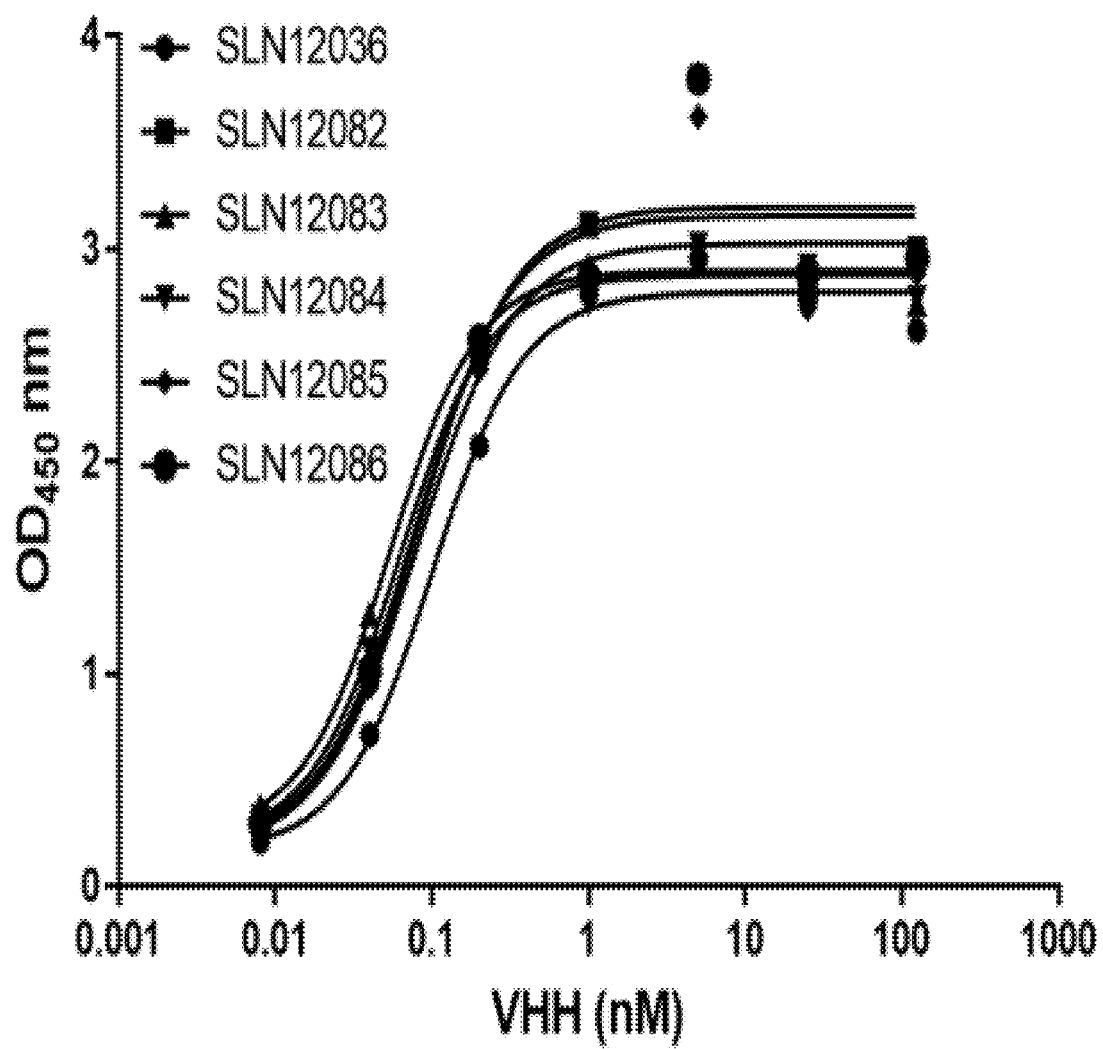
Figure 9D:
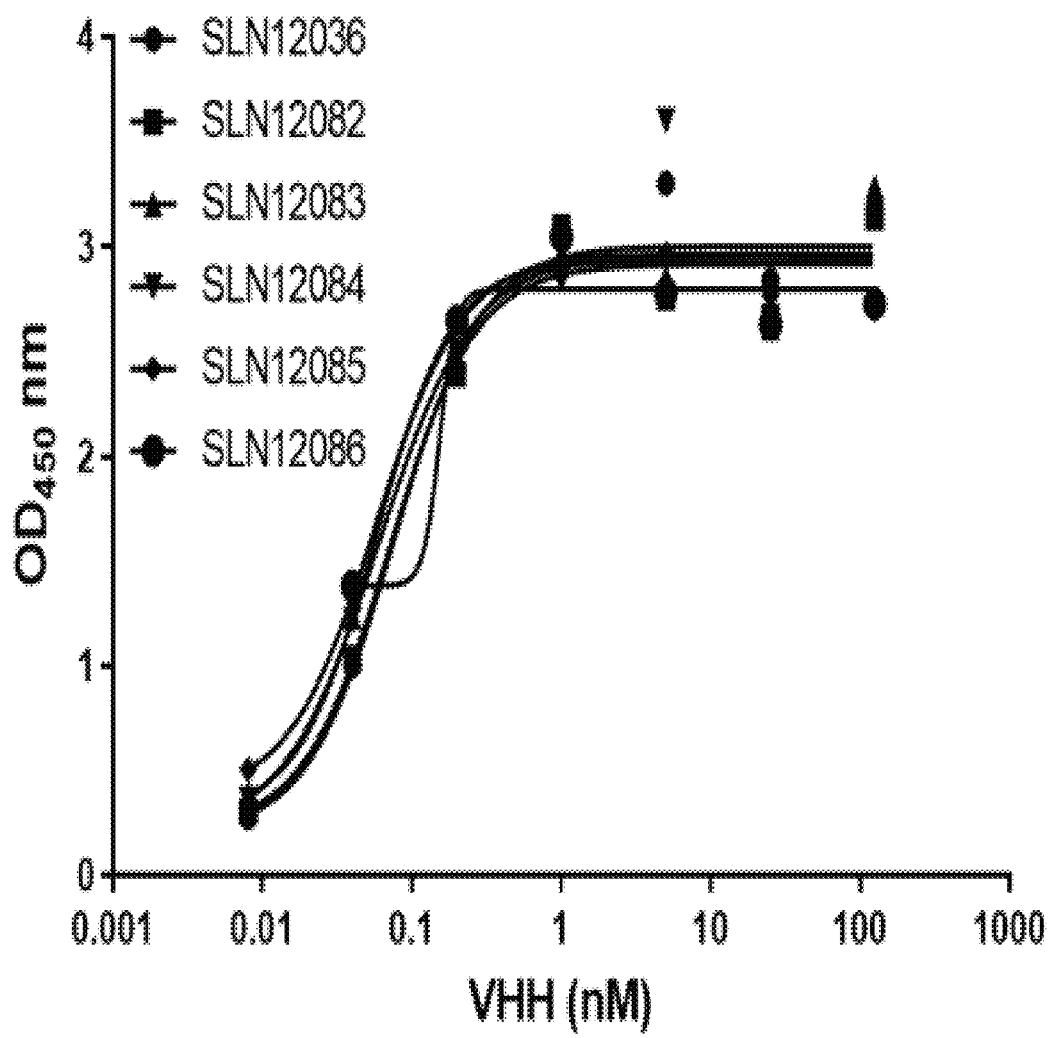
Figure 9E:
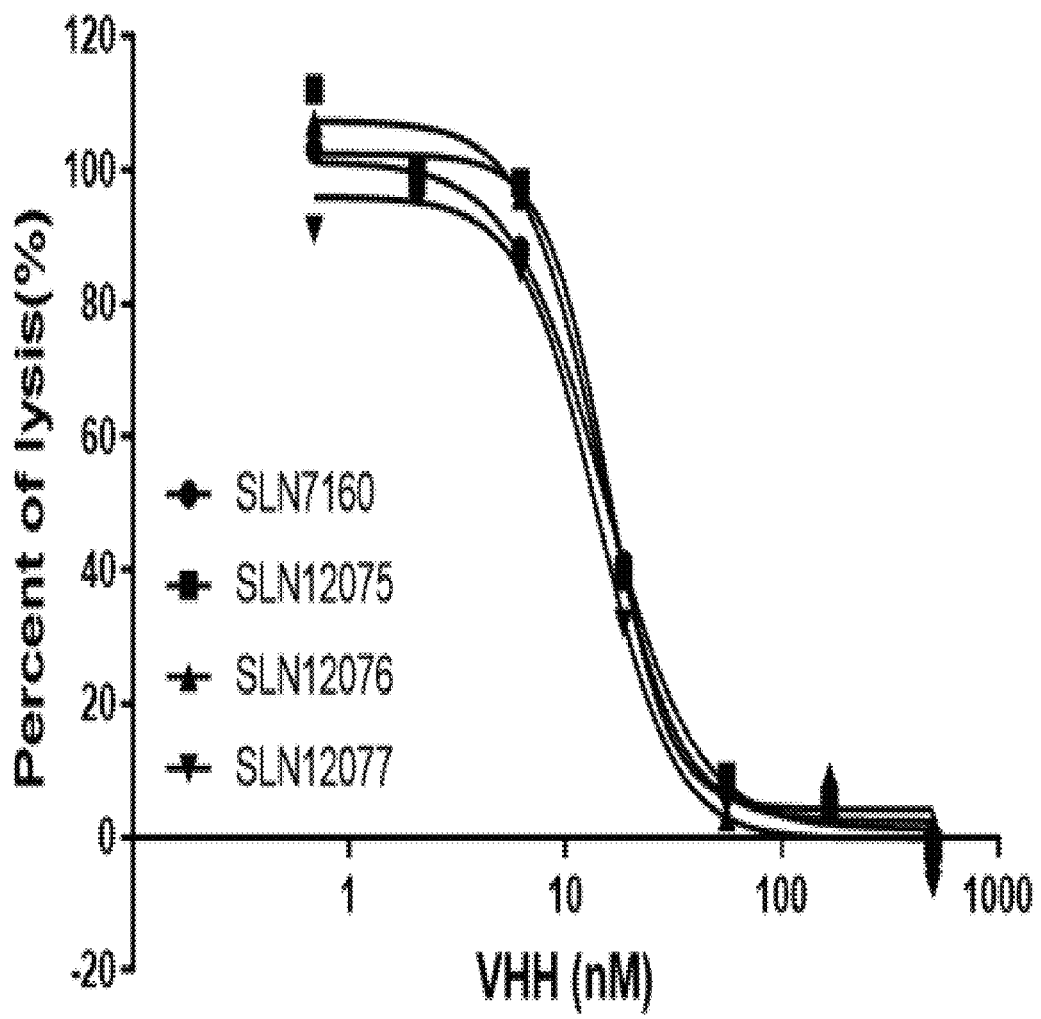
Figure 9F:
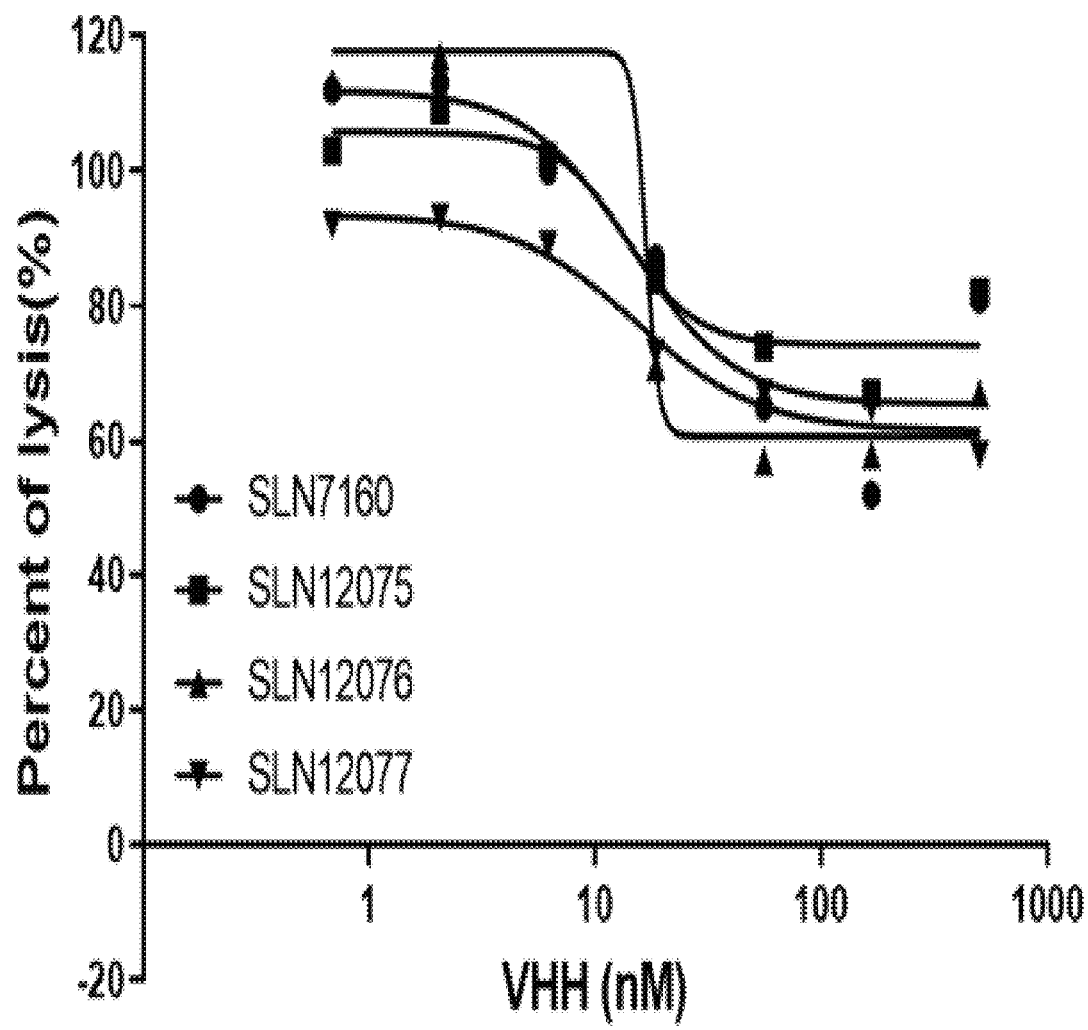
Figure 9G:
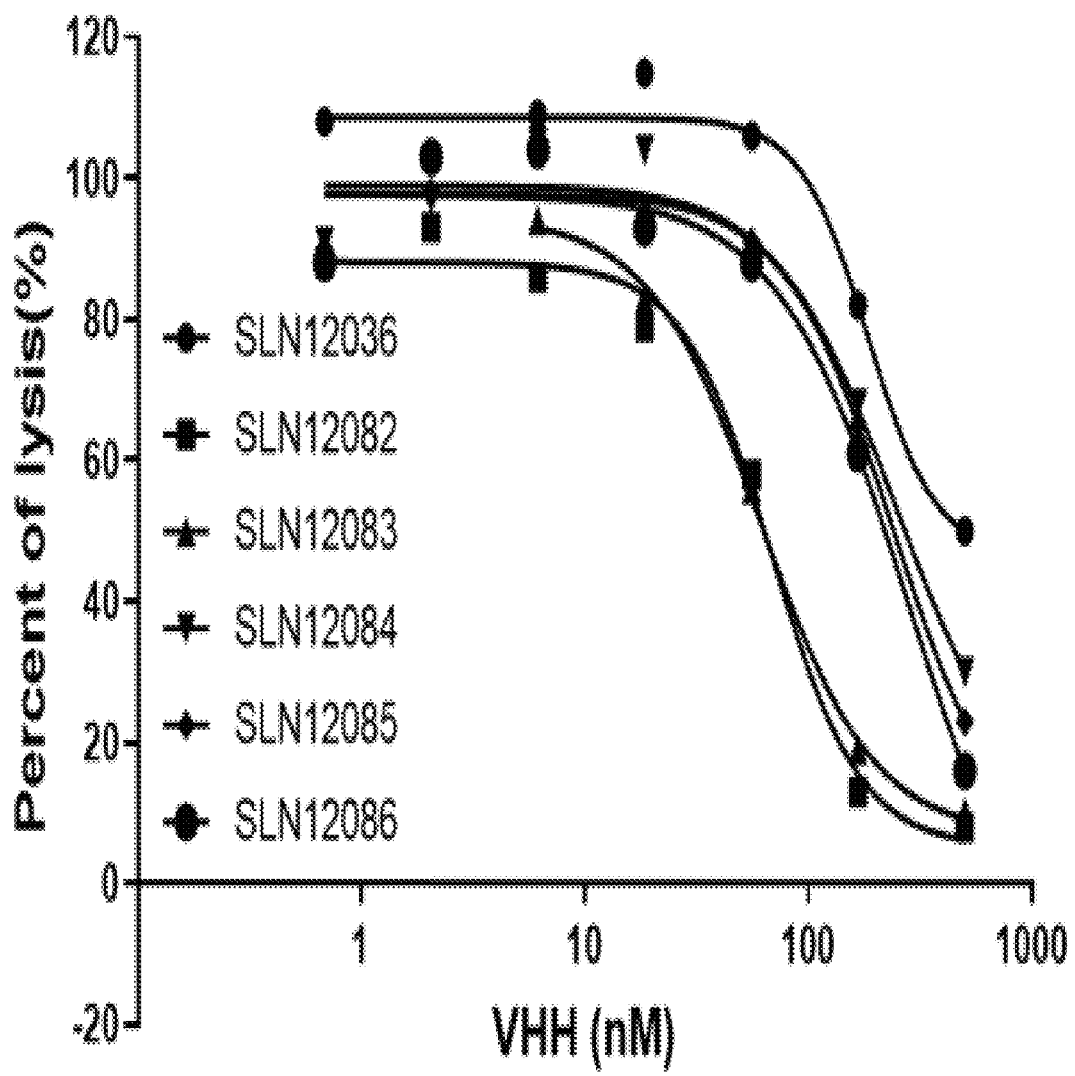
Figure 9H:
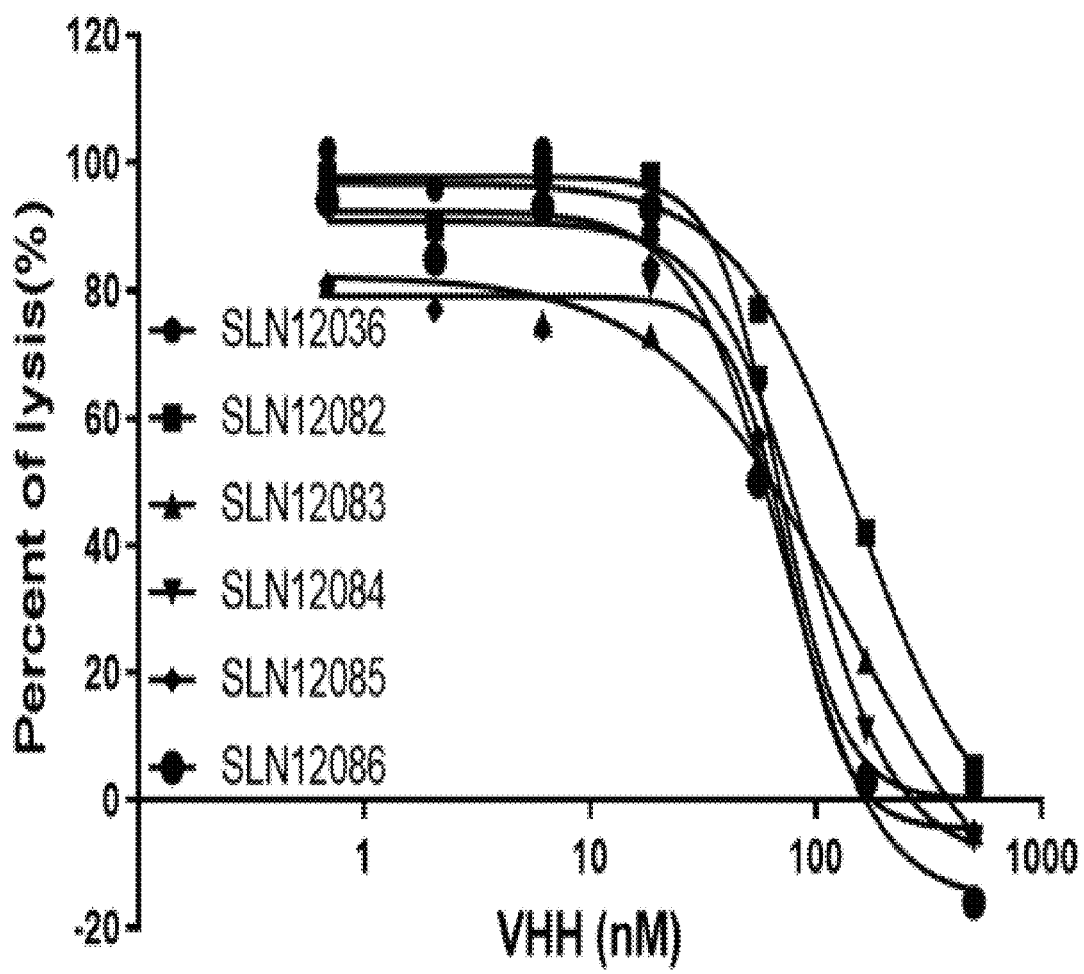

VHH humanization was conducted by standard procedures of CDR grafting and structural refinement. Upon the humanization design, recombinant DNA constructs were created to produce recombinant constructs as described above. The humanized sequences with an affinity equal to or better than that of the original VHH to properdin having acceptable expression and stability levels were selected for further development. FIG. 9 indicated that the humanized VHH variant SLN7160 possess similar profile as the parental VHH regarding its binding to human (FIG. 9A) and mouse properdin (FIG. 9B). VHH variant SLN12036 possess similar profile as the parental VHH regarding its binding to human (FIG. 9C) and mouse properdin (FIG. 9D). Meanwhile, SLN7160 possess negligible effect of complement inhibition activity in human (FIG. 9E) and mouse serum (FIG. 9F), and it was noteworthy that humanized SLN12083 showed better human alternative pathway activity than the original VHH SLN12036 (FIG. 9G & FIG. 9H).

Figure 10:
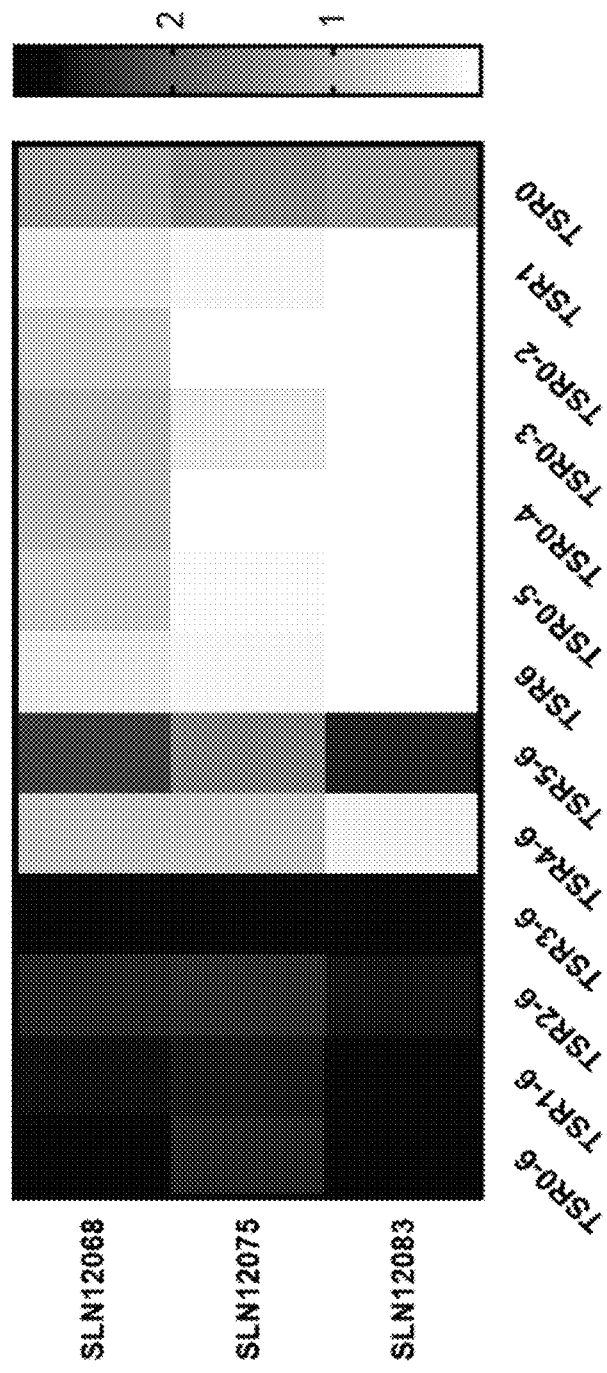
FIG. 10 Illustrates epitope mapping of the properdin (truncated variants)-binding VHH's.

Example 5 Epitope Mapping Assay with Truncated Human Properdin 96-well immunoplates were coated with 100 µl/well 1 g/ml streptavidin and incubate at 4° C. overnight. Wells were washed with PBST for 3 times and blocked with 200 µl of 1% BSA/PBS at RT for 1 h. Washed with PBST for 3 times and add truncated variants of human properdin-biotin (50 µg/ml) 100 µl/well and incubated at RT for 1 h. Plates were washed with PBST for 3 times, 100 µl/well 10 µg/ml VHH-Fcs were added and incubate at RT for 1 h. Plates were washed with PBST for 3 times and add 100 µl goat anti-human Fc-HRP (Sigma, A0170) diluted 1/5000 in 1% BSA/PBST to each well and incubate at RT for 1 h. Plates were then washed as before and add 100 µl TMB substrate and incubate at RT for 15 min. 100 µl per well stop solution was added to stop the reaction, and the plates were read with microplate reader at 450 nm. Result was shown in FIG. 10, SLN12068, SLN12075 and SLN12083 binding with different thrombospondin repeats (TSRs) respectively by TSR0, TSR1, TSR2, TSR3, TSR4, TSR5, TSR6, TSR 0-6, TSR1-6, TSR2-6, TSR3-6, TSR4-6 TSR 5-6 and TSR6, and the biologically active TSR5-6 and TSR 0 domains play the important role in the binding of properdin with SLN12068, SLN12075 and SLN12083.

Example 6 Impact of Properdin Inhibitors on Interactions Between C3 and Properdin 6.1 C3 Binding Assay Maxisorp 96-well plates were coated with human C3 (Sigma, C2910-.1MG) 2 µg/ml, 100 µl/well in PBS, pH 7.4, and left overnight at 4° C. After washing 3 times with PBST, the wells were blocked with 2% BSA in PBS for 1 h at 37° C. Serial three-fold dilution (100 µl/well) of biotin human Properdin (starting at 90 µg/ml) were added to wells and incubated for 1 h at 37° C. The wells were washed three times with PBST and HRP-labeled streptavidin (1/5000 dilution) (sigma, s5512) was added to the wells. The plate was incubated for 1 h at 37° C. Plates were then washed as before and add 100 µl TMB substrate and incubate at RT for 15 min. 100 µl per well stop solution was added to stop the reaction, and the plates were read with microplate reader at 450 nm.

6.2 Competitive Binding Assay

Figure 11A:
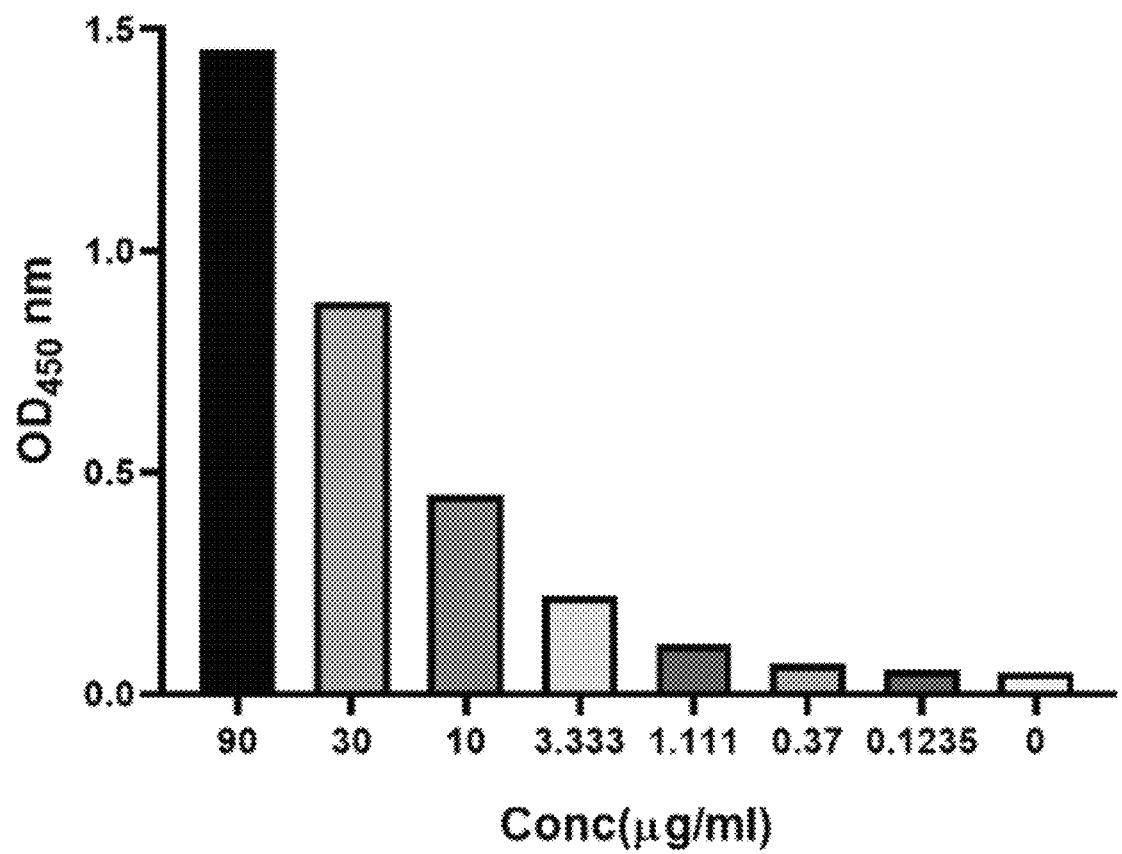
FIG. 11 Illustrates impact of properdin inhibitors on interactions between C3 and properdin. Properdin binding assay (FIG. 11A), Competition assay (FIG. 111B).
Figure 11B:
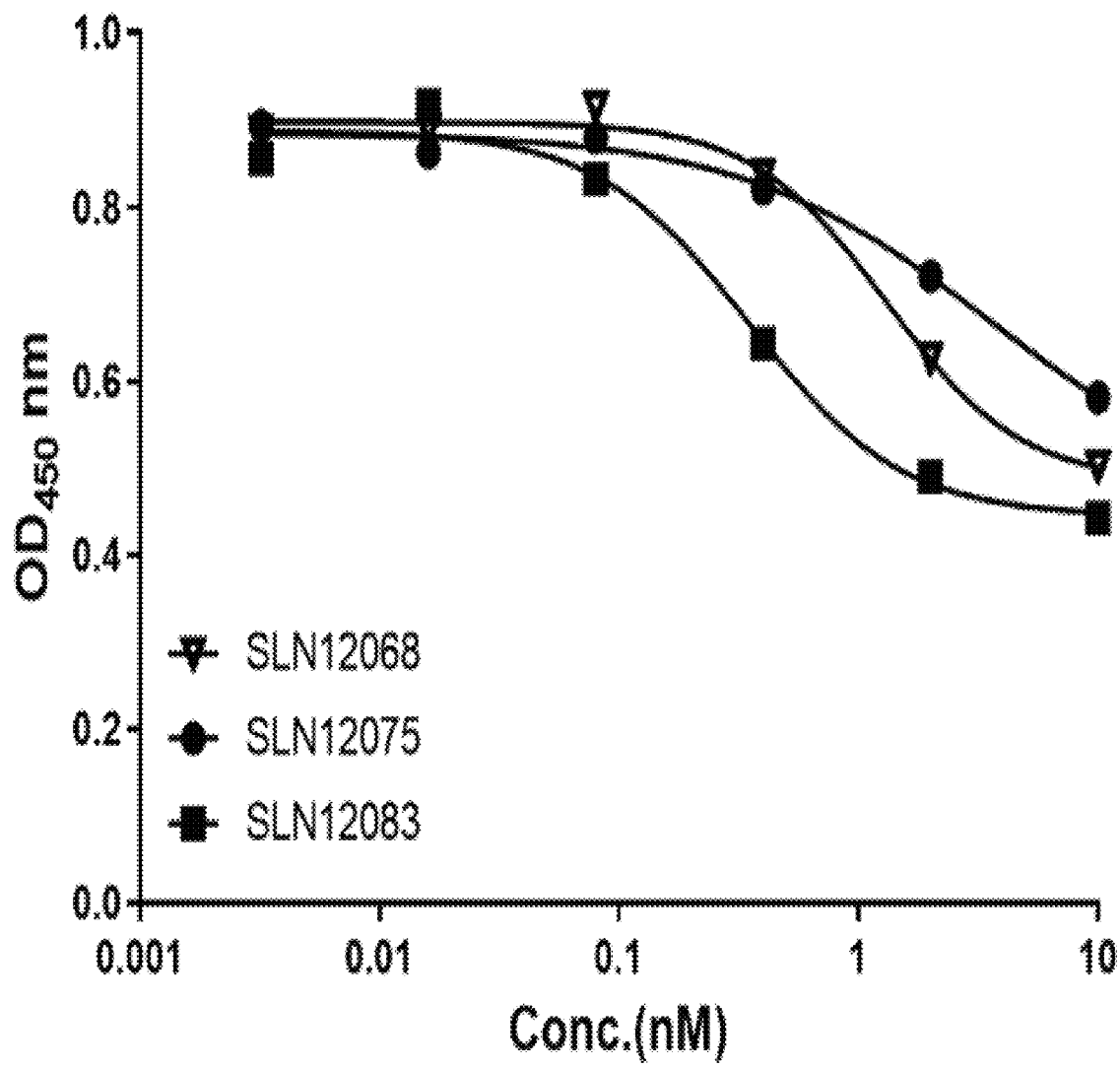

Maxisorp 96-well plates were coated with C3 (see binding assays), blocked with 1% BSA in PBST, and washed three times with PBST. Serially five-fold dilution FP inhibitors (starting at 50 nM), 100 µl/well, and a constant amount of properdin (20 µg/ml) 100 µl/well (in PBS) was added to each well, and incubated at 37° C. for 1 h. Wells were washed again three times with PBST, incubated with HRP-labeled Streptavidin (1/5000 dilution) (sigma, s5512) was added to the wells. The plate was incubated for 1 h at 37° C. Plates were then washed as before and add 100 µl TMB substrate and incubate at RT for 15 min. 100 µl per well stop solution was added to stop the reaction, and the plates were read with microplate reader at 450 nm. As is shown in FIG. 11A, properdin showed binding to C3 in dose-dependent manner. In addition, SLN12068, SLN12075 and SLN12083 also showed inhibition activity with properdin binding to C3. (FIG. 11B)

Figure 12:
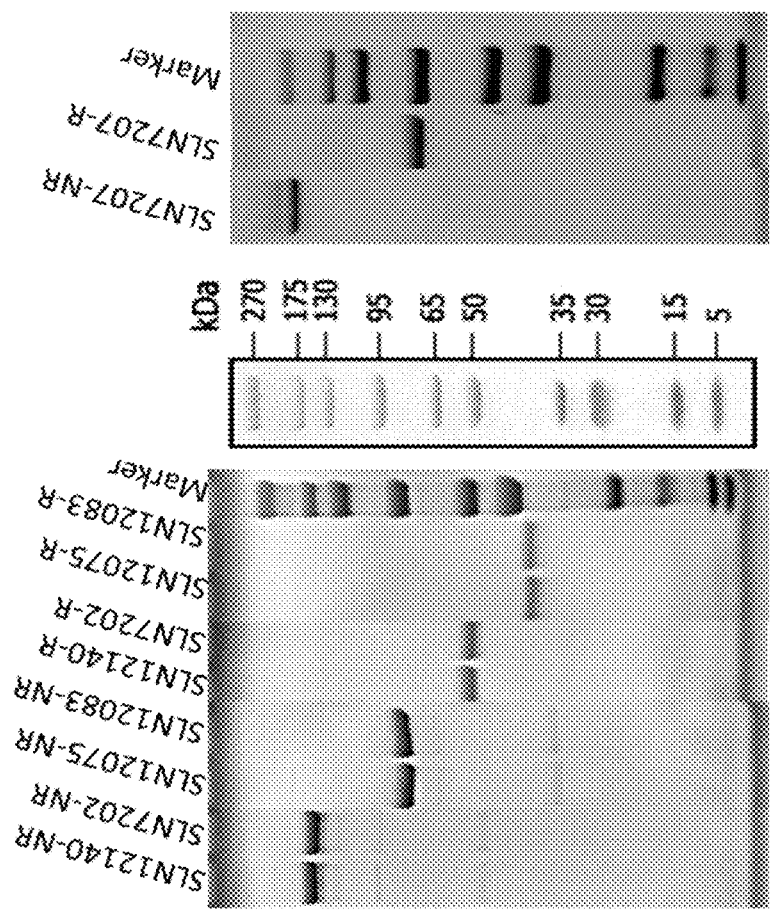
FIG. 12 Illustrates production of the VHH-CFH analysis on non-reducing and reducing SDS-PAGE.

Example 7 Fusion Protein of VHH to Engineered Factor H as a Dual-Inhibitor of Alternative Pathway 7.1 Bi-Paratopic Engineering of Humanized VHH Sequence Bi-paratopic VHHs with humanized sequences through a G4S linker, by procedures as described above were created. Purified proteins were analyzed with 4-12% SDS-PAGE under non-reduced and reduced conditions (FIG. 12).

Figure 13A:
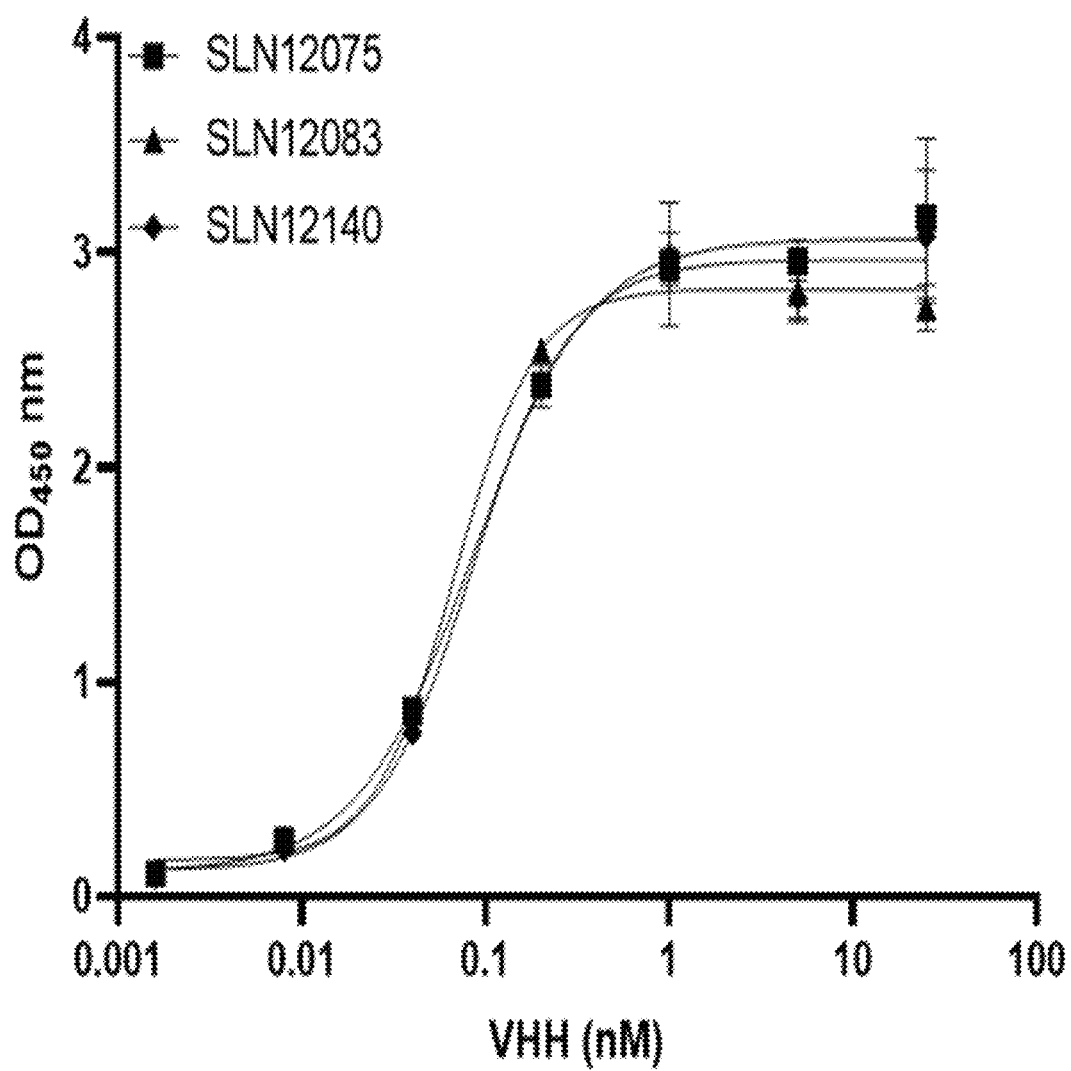
FIG. 13 Illustrates properdin-binding activities of SLN12140 and SLN7207 in human (FIG. 13A and FIG. 13C) and mouse (FIG. 13B and FIG. 13D) serum.
Figure 13B:
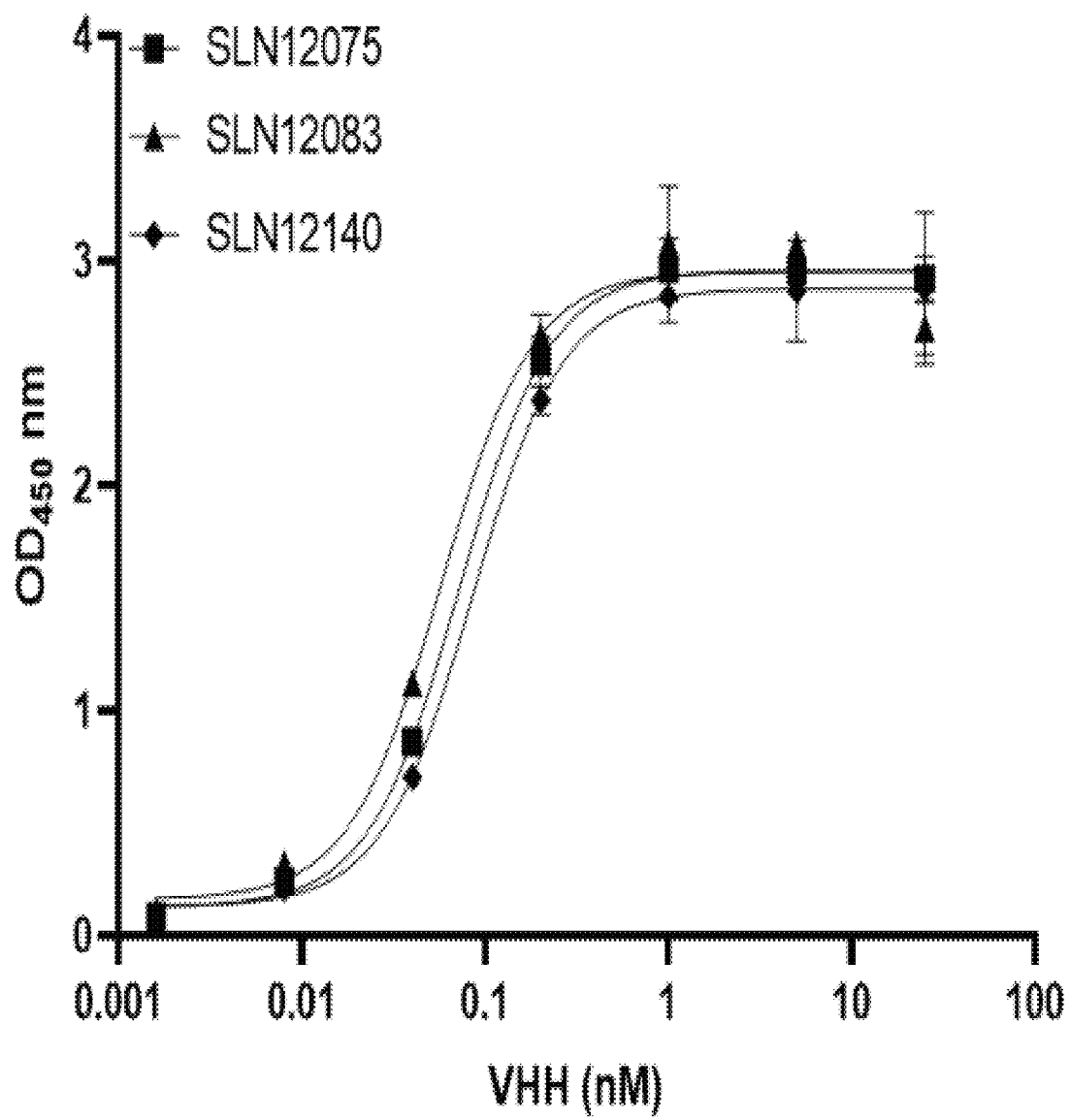
Figure 13C:
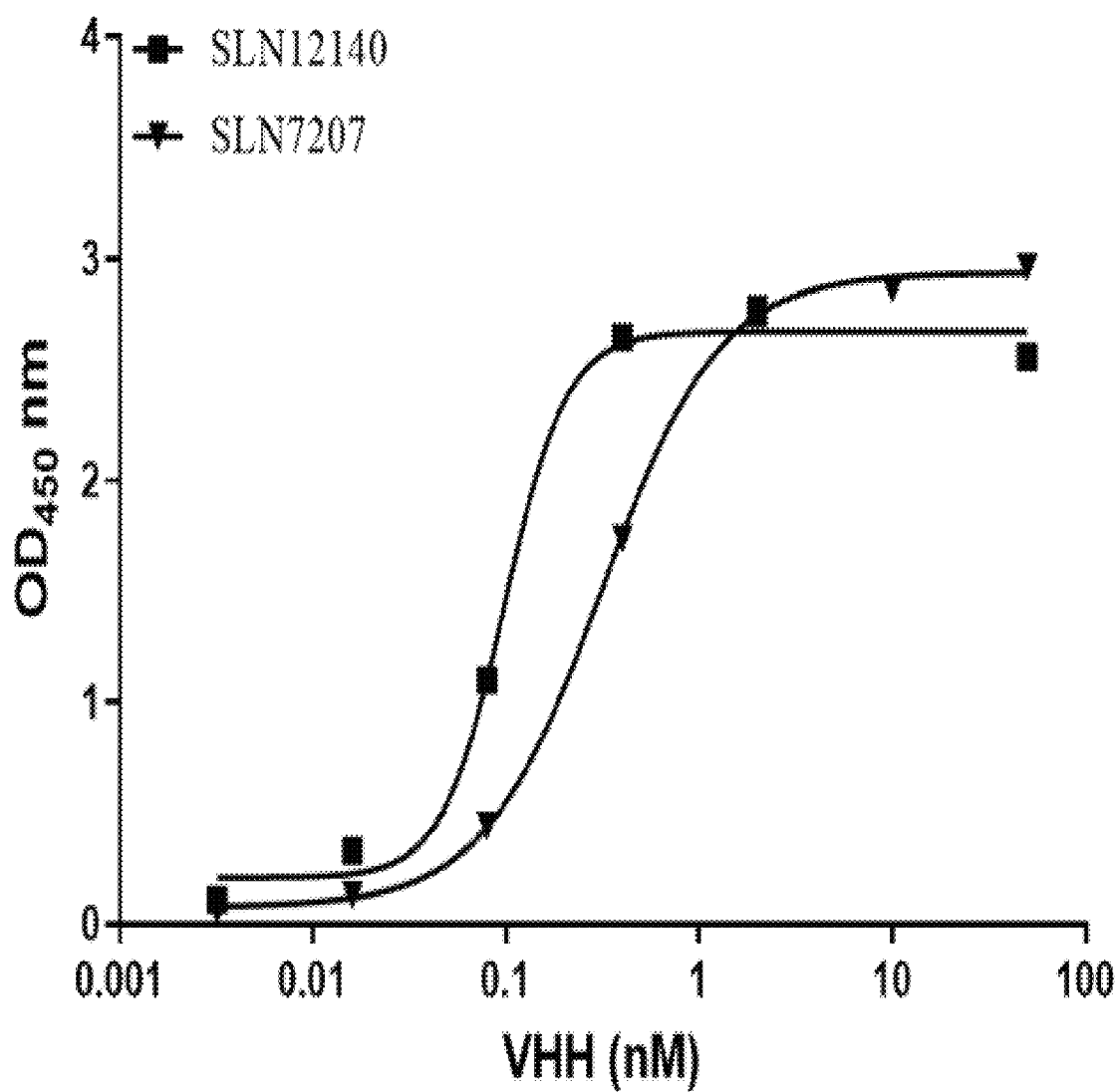
Figure 13D:
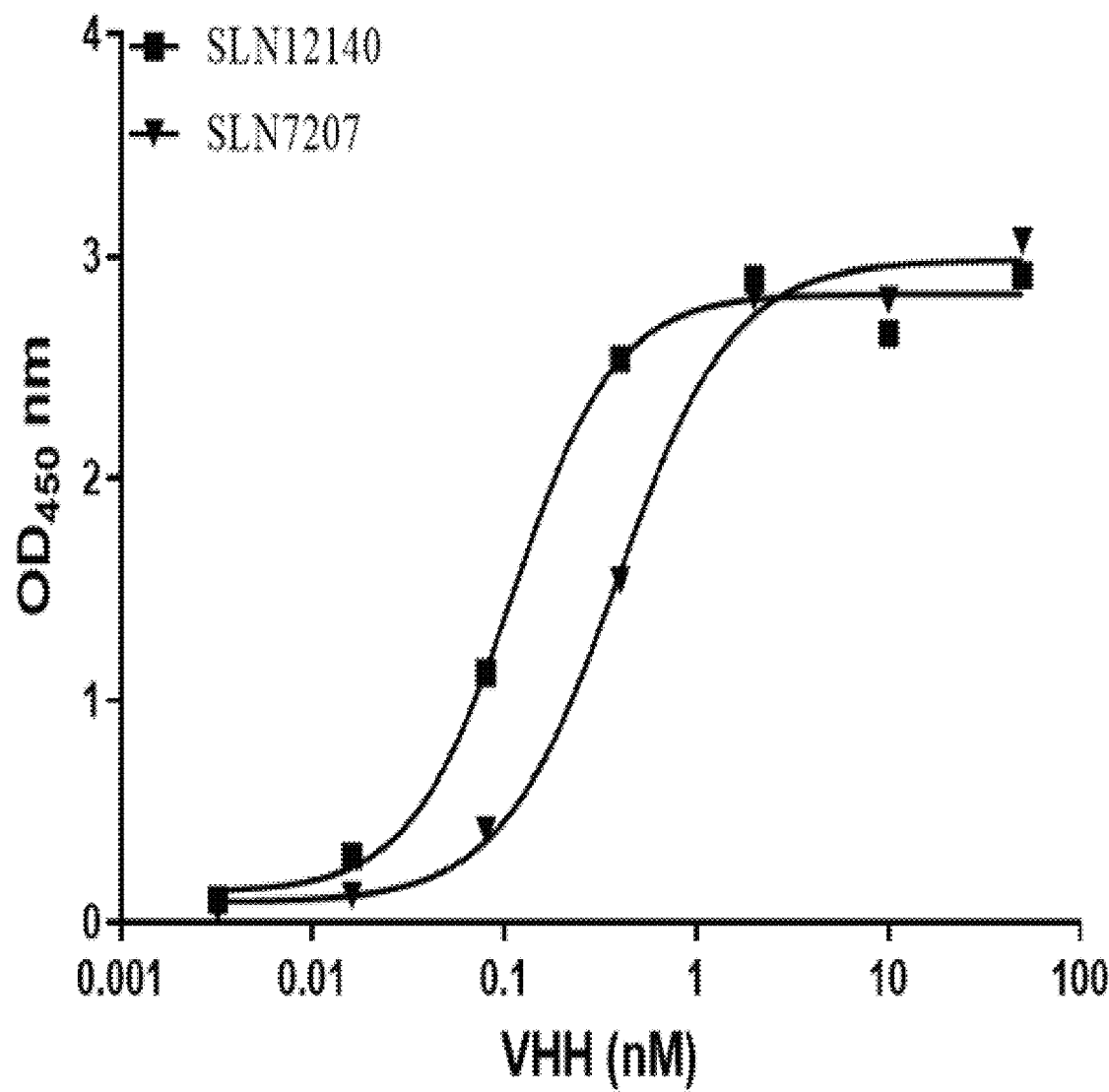
Figure 14A:
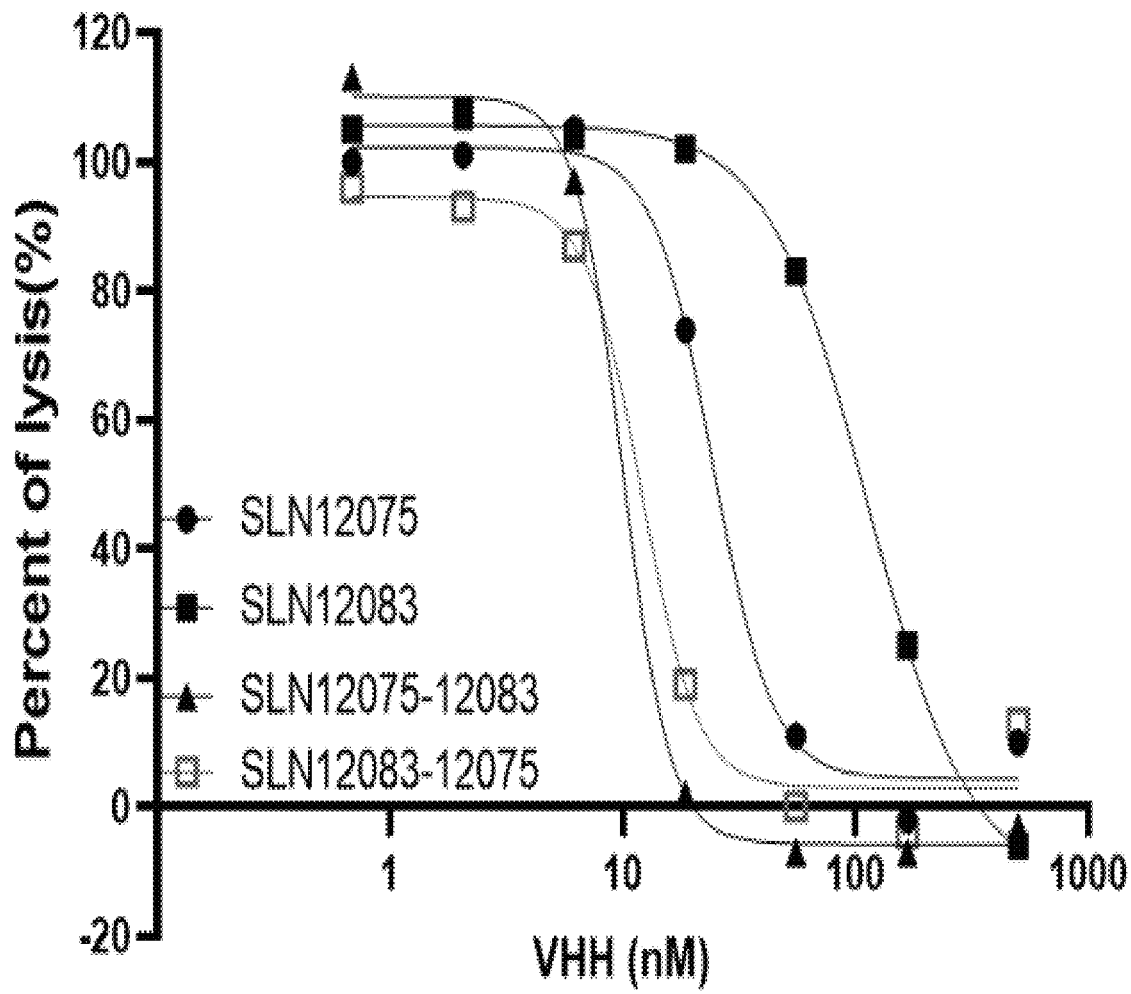
FIG. 14 Illustrates AP inhibiting activities of SLN12140 and SLN7207 in human (FIG. 14A and FIG. 14C) and mouse (FIG. 14B and FIG. 14D) serum.
Figure 14B:
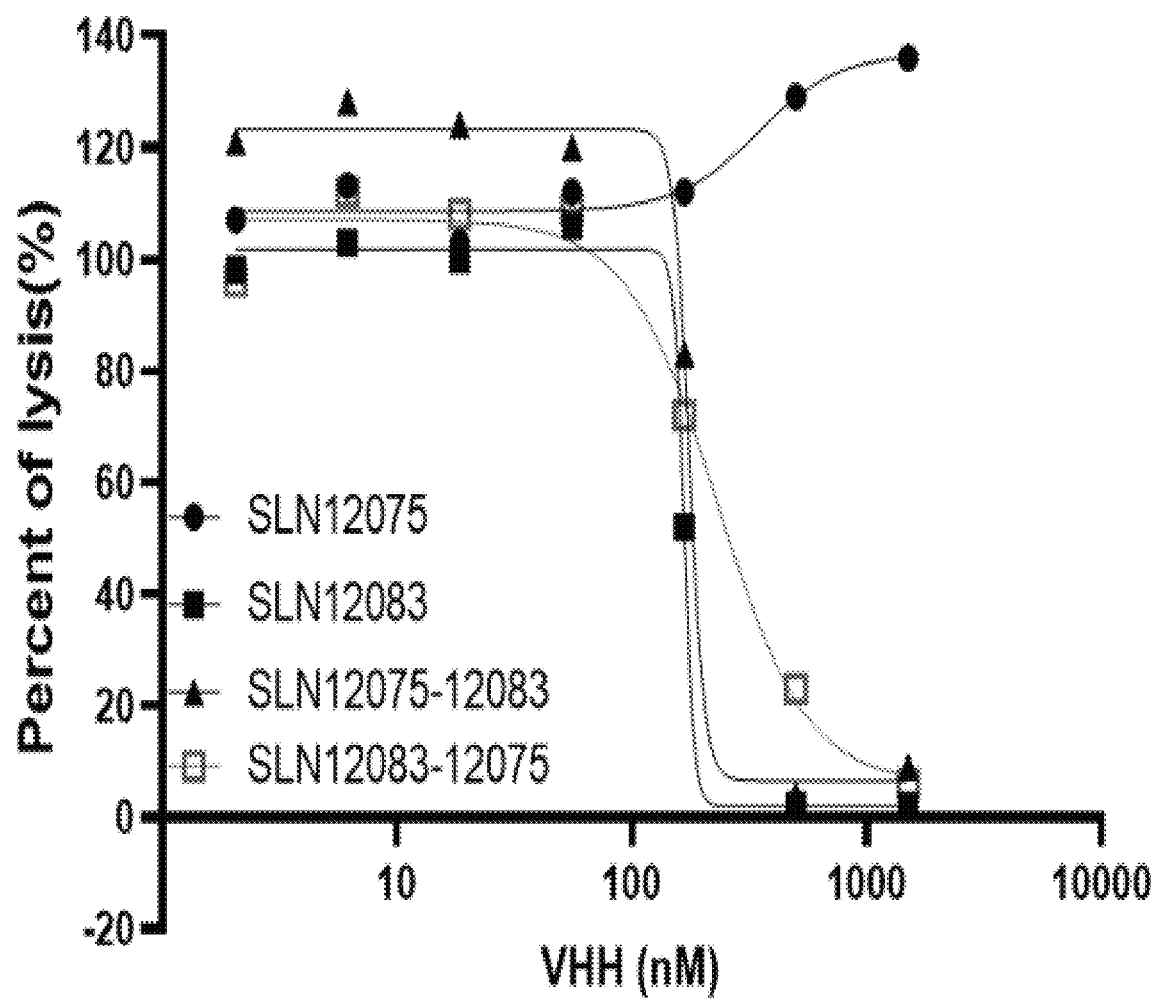
Figure 14C:
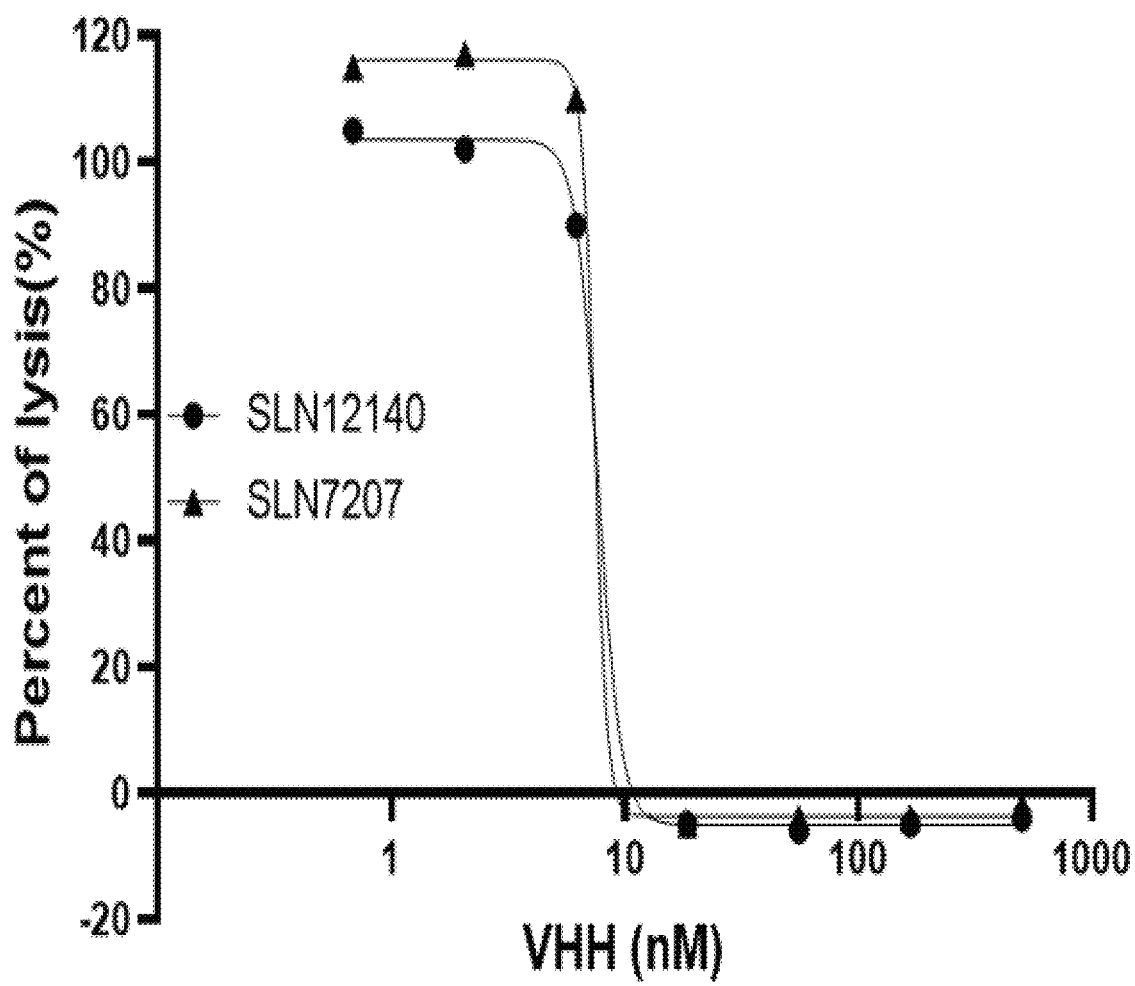
Figure 14D:
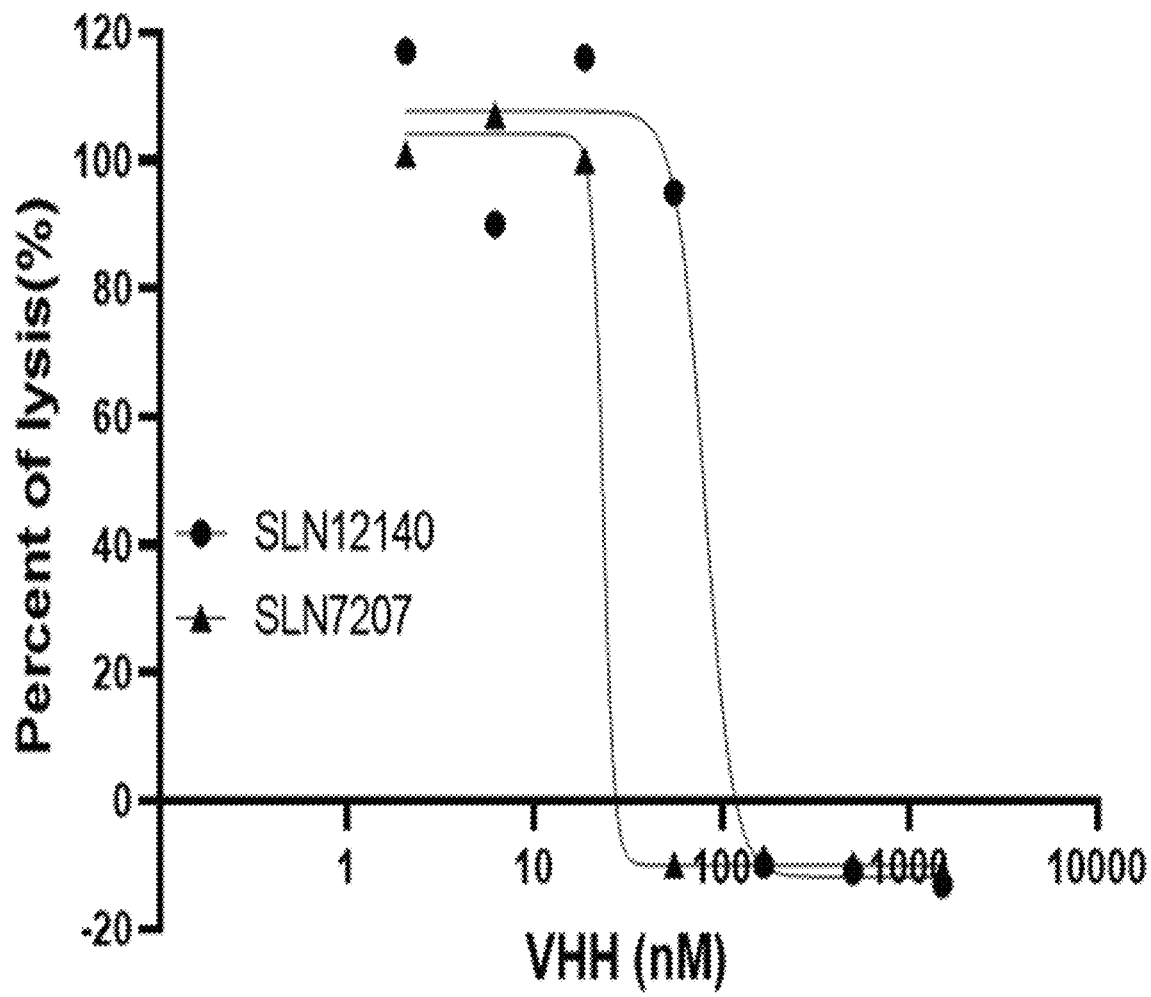

Target-binding ELISA shown in FIG. 13 indicated that such humanized bi-paratopic VHHs had negligible effect on the single VHH by human properdin binding (FIG. 13A) assay and mouse properdin binding assay (FIG. 13B). Alternative pathway activity indicated that the SLN12140 AP activity of bi-paratopic was better than that of single VHH (FIG. 14A & FIG. 14B).

7.2 Fusion Protein of VHH to Engineered Factor H

Truncated CFH (domain 1-4) was fused to the C-terminus of SLN12140 to form SLN7207 to make a dual functional recombinant protein inhibiting complement activation. The results were shown in FIG. 13. Panel of (C) and (D) shows binding activity of SLN7207 and SLN12140 to human properdin-biotin and mouse properdin-biotin. Panel of (C) and (D) of FIG. 14 shows human and mouse alternative pathway activity of SLN12140 and SLN7207. Fusion with CFH (domain 1-4) at the C-terminus of SLN12140 showed negligible effect on that of SLN12140 by human serum, however it showed about three times biological activity increased by mouse serum. In any case, both SLN12140 and SLN7207 showed both human and mouse alternative pathway inhibition activity at nM level especially in humans with an IC50 of 17 nM. Such functional protein provides a potential therapeutical strategy for complement hyperactivation disease.

Example 8 Pathway Selectivity and Species Cross Activity of SLN12140

8.1 Pathway Selectivity in Complement Inactivation
8.1.1 Complement Inactivation in Alternative Pathway For alternative pathway assay, procedure refer to 2.3. The inhibition curves of single VHH SLN12075, SLN12083 and bi-paratopic SLN12140 exhibited consistent alternative pathway complement inhibitory activity, and SLN12140 showed superior activity compared to single VHH with IC50 of 17 nM. Eculizumab (Targetmol, T9915), a recombinant humanized monoclonal antibody against the complement protein C5 was as a control also showed inhibitory ability in the AP pathway, with IC50 of 50 nM.

8.1.2 Complement Inactivation in Classical Pathway

For classical pathway assay, all test samples were serially diluted 1:3 in PBS and added in duplicate (50 µl/well) to a U-bottom 96-well microtiter plate. Human complement-preserved serum (Quidel A113) was diluted to 20% vol/vol with GVB2+ buffer (0.1% gelatin, 141 mM NaCl, 0.5 mM $MgCl_2$, 0.15 mM $CaCl_2$, 1.8 mM sodium barbital) (Comp Tech B100) and added (50 µl/well) to the rows of the same 96-well plate such that the final concentration of human serum in each well was 10%. The plate was then incubated at RT for 30 min. Then chicken erythrocytes ($1-4\times10^8$) based on the samples were washed three times with 1 ml of GVBS2+ buffer and resuspended to a final concentration of $1\times10^8$/ml in GVBS2+ buffer. After that, 1-6 ml of the chicken erythrocytes were sensitized by the addition of an anti-chicken red blood cell polyclonal antibody (Rockland, 103-4139) at 3% and the cells were incubated on ice for 15 min with frequent mixing. The cells were then washed twice with 1 ml of GVBS2+ buffer and resuspended to $1\times10^8$/ml in GVBS2+ buffer. 30 µl aliquots of chicken erythrocytes ($3\times10^6$ cells) were added to the plate as described above, mixed well, and incubated at 37° C. for 30 min. Then, each plate contained two wells of 50 µl of identically prepared chicken erythrocytes, one incubated with 50 µl PBS+50 µl GVBS2+ buffer alone (negative control) as a control for spontaneous hemolysis, two wells containing 10 mM EDTA (Thermo 15575-038) as the serum blank and two wells normal NHS as 100% lysis. The plate was then centrifuged at 600 rpm for 2 min and 100 µl of the supernatant transferred to a new flat bottom 96-well plate. Hemoglobin release was determined at OD 405 nm using a microplate reader, and the percent hemolysis was determined using the following formula:

Hemolysis (%): 100×(OD sample−OD EDTA blank)/ (OD 100% lysis−OD EDTA blank)

Figure 15A:
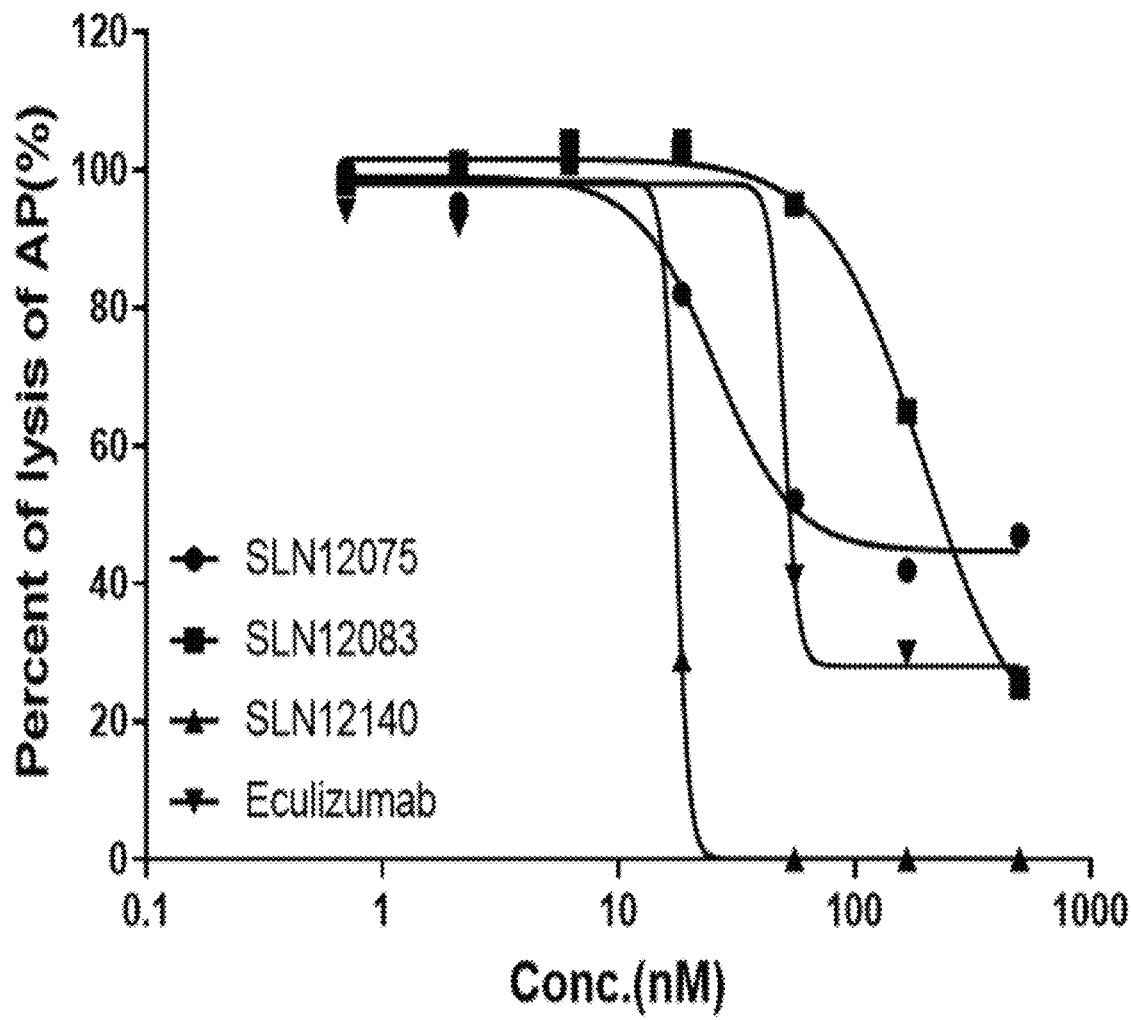
FIG. 15 Illustrates pathway-selectivity of SLN12140 in complement inactivation. AP (FIG. 15A), CP (FIG. 15B), and LP (FIG. 15C).
Figure 15B:
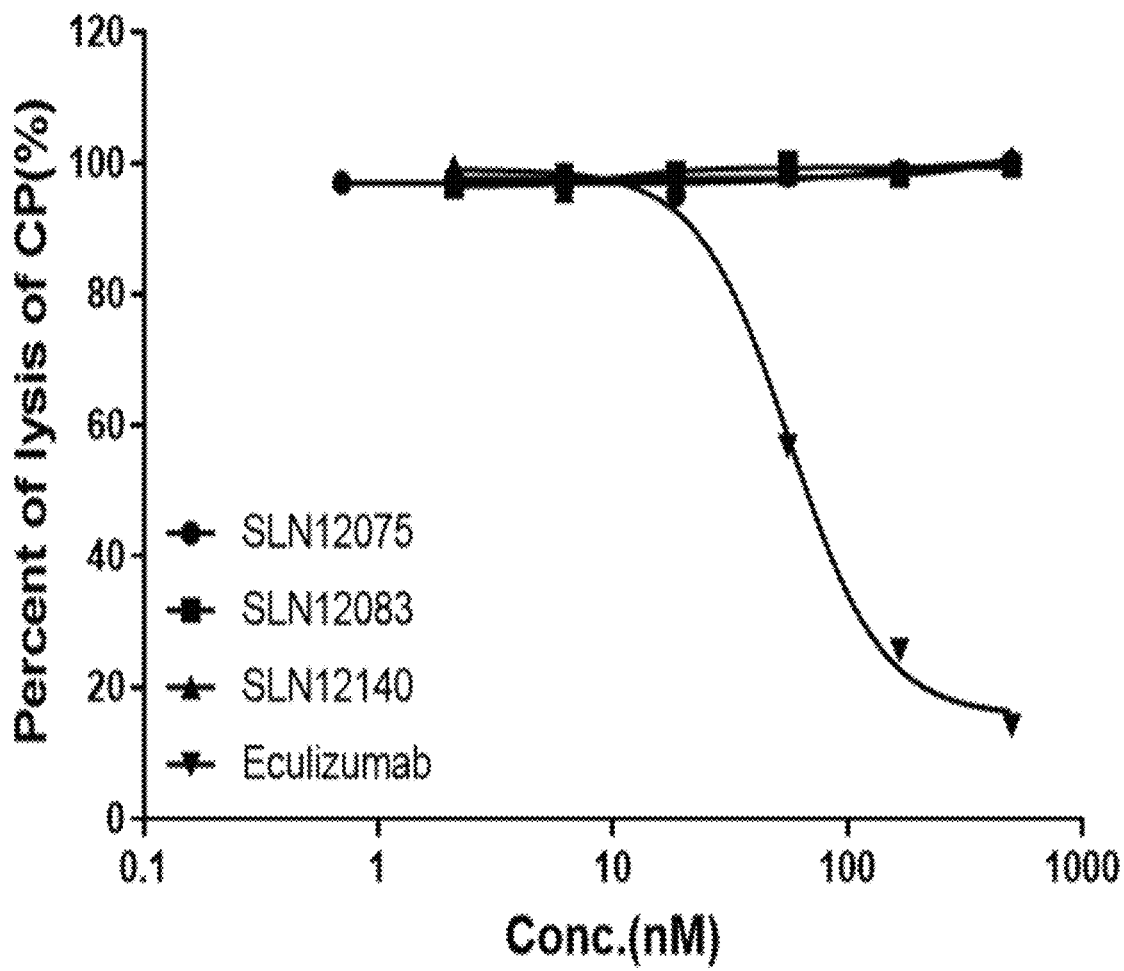

As shown in FIG. 15B, VHHs either single or bi-paratopic of the alternative pathway specific antibody, exhibited no inhibitory activity in the classical pathway. Eculizumab (Targetmol, T9915), a recombinant humanized monoclonal antibody against the complement protein C5 was as a control also showed inhibitory ability in the CP pathway, with IC50 of 57 nM.

8.1.3 Complement Inactivation in Lectin Pathway

For lectin pathway assay: 0.3 ml aliquots of mannan solution (0.5 mg/ml) were mixed with an equal volume of $CrCl_3$ solution (0.5 mg/ml) (Sigma 27096-100G-F, Lot #BCCB5331), an equal volume of the chicken erythrocyte suspension (1×10$^9$ cells) was added, and the mixture was incubated with occasional mixing for 15 min at 25° C. Then wash with 1.0 ml of ice-cold GVBS2+. The erythrocytes coated with mannan (ME) (sigma M7604-100MG, Lot #SLOF4977) were washed three times by centrifugation with GVBS2+(gelatin-Veronal-buffered saline, 5 mM Veronal buffer, pH 7.4, containing 0.145 M NaC 1, 0.1% gelatin, 0.15 M $CaCl_2$ and 0.5 mM $MgCl_2$) (Comp Tech, B100), resuspended to a final concentration of 5×10$^7$ cells/ml in GVBS2+ and store on ice. All test samples were serially diluted 1:3 (from 500 nM to 0.2 nM) in PBS and added in duplicate (50 µl/well) to a U-bottom 96-well microtiter plate. Human complement-preserved serum was diluted to 20% vol/vol with GVBS2+ and added (50 µl/well) to the rows of the same 96-well plate, such that the final concentration of human serum in each well was 10%. 100 µl dd$H_2O$ or serum only and 50 µl PBS+50 µl GVBS2+ was used as 100% lysis and 0% blank controls, respectively, 10 mM EDTA was used as serum blank. 50 µl aliquots of chicken erythrocytes (2.5×10$^6$ cells) was added to the plate as described above, mixed well, and incubated at 37° C. for 60 min. The plate was then centrifuged at 1,000 g for 2 min and 100 µl of the supernatant transferred to a new flat bottom 96-well plate. Hemoglobin release was determined at OD 405 nm using a microplate reader, and the percent hemolysis was determined using the following formula:

Percent hemolysis (%): 100×(OD sample−OD of EDTA)/(OD 100% lysis−OD of EDTA)

Figure 15C:
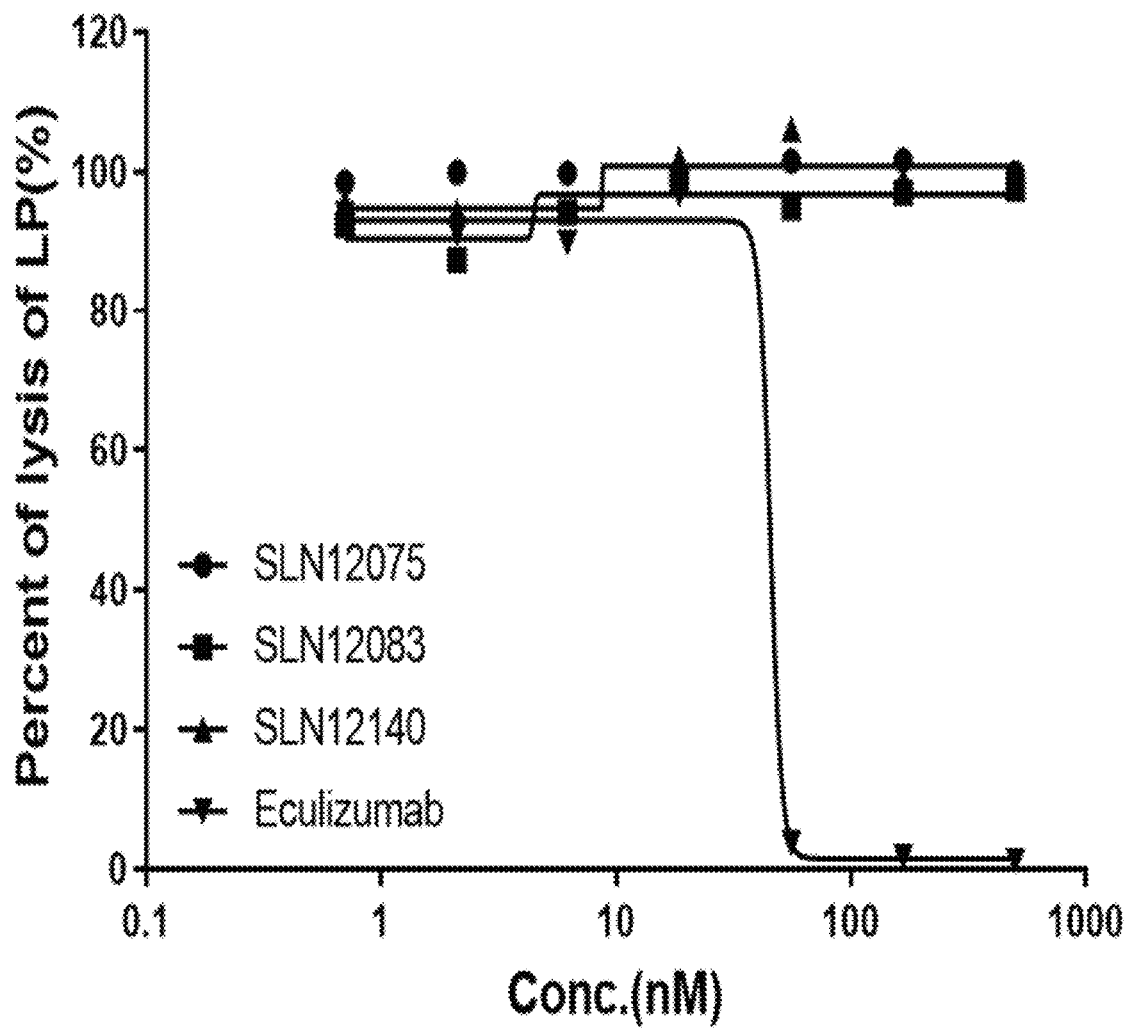
Figure 16A:
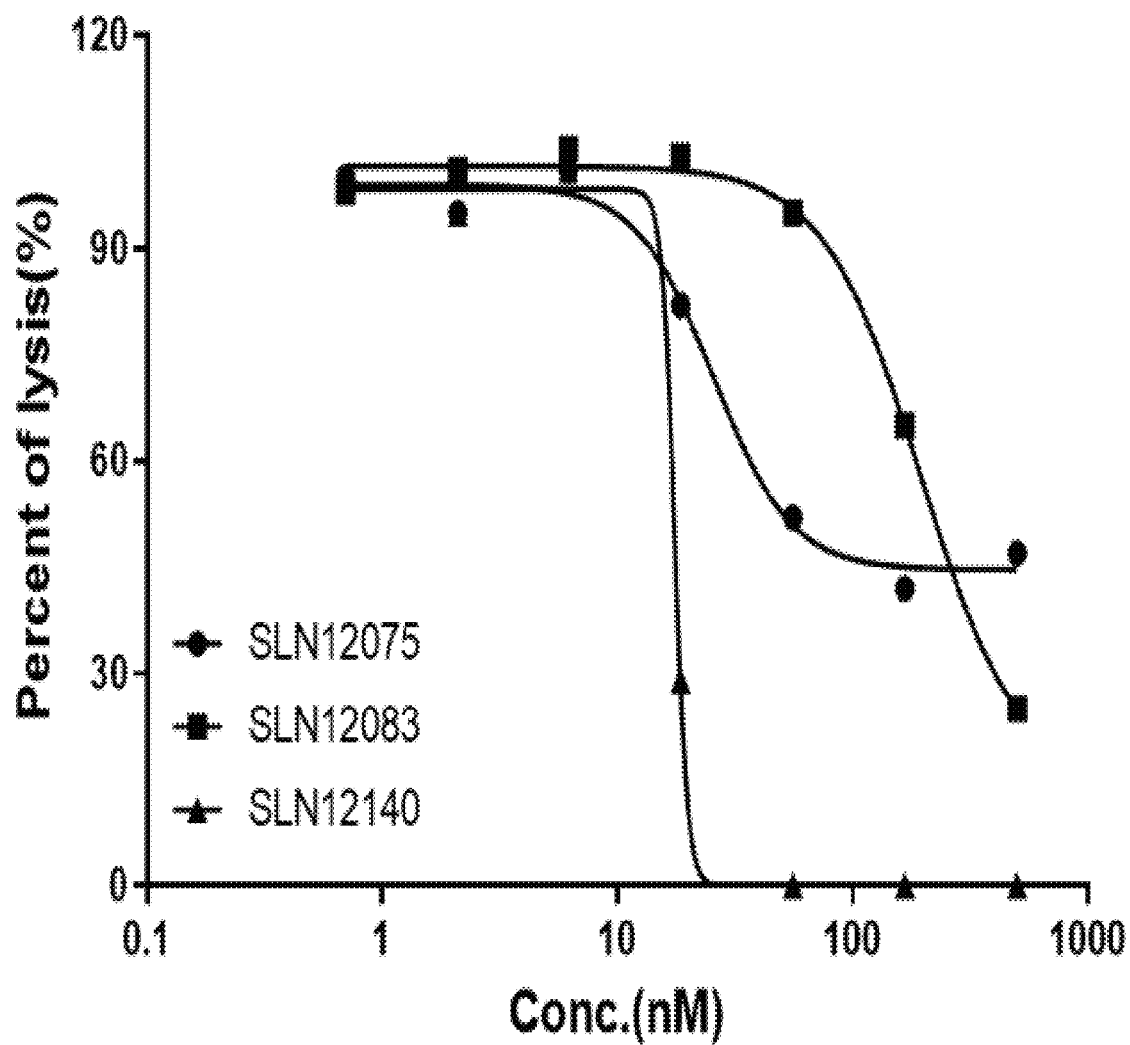
FIG. 16 Illustrates cross-species reactivity of SLN12140 upon AP activity assay. AP activity in human serum (FIG. 16A), AP activity in cyno serum (FIG. 16B), AP activity in mouse serum (FIG. 16C) and AP activity in rat serum (FIG. 16D).
Figure 16B:
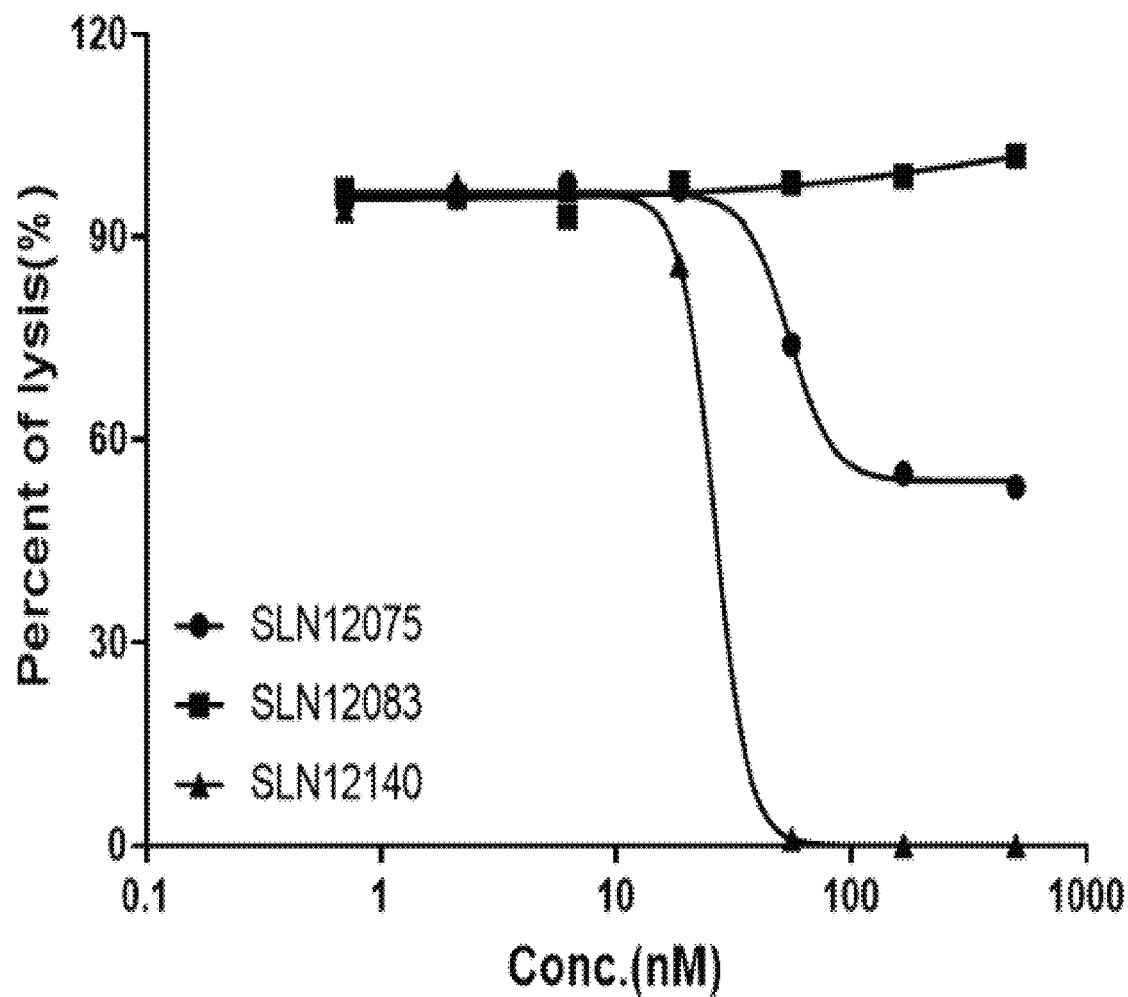
Figure 16C:
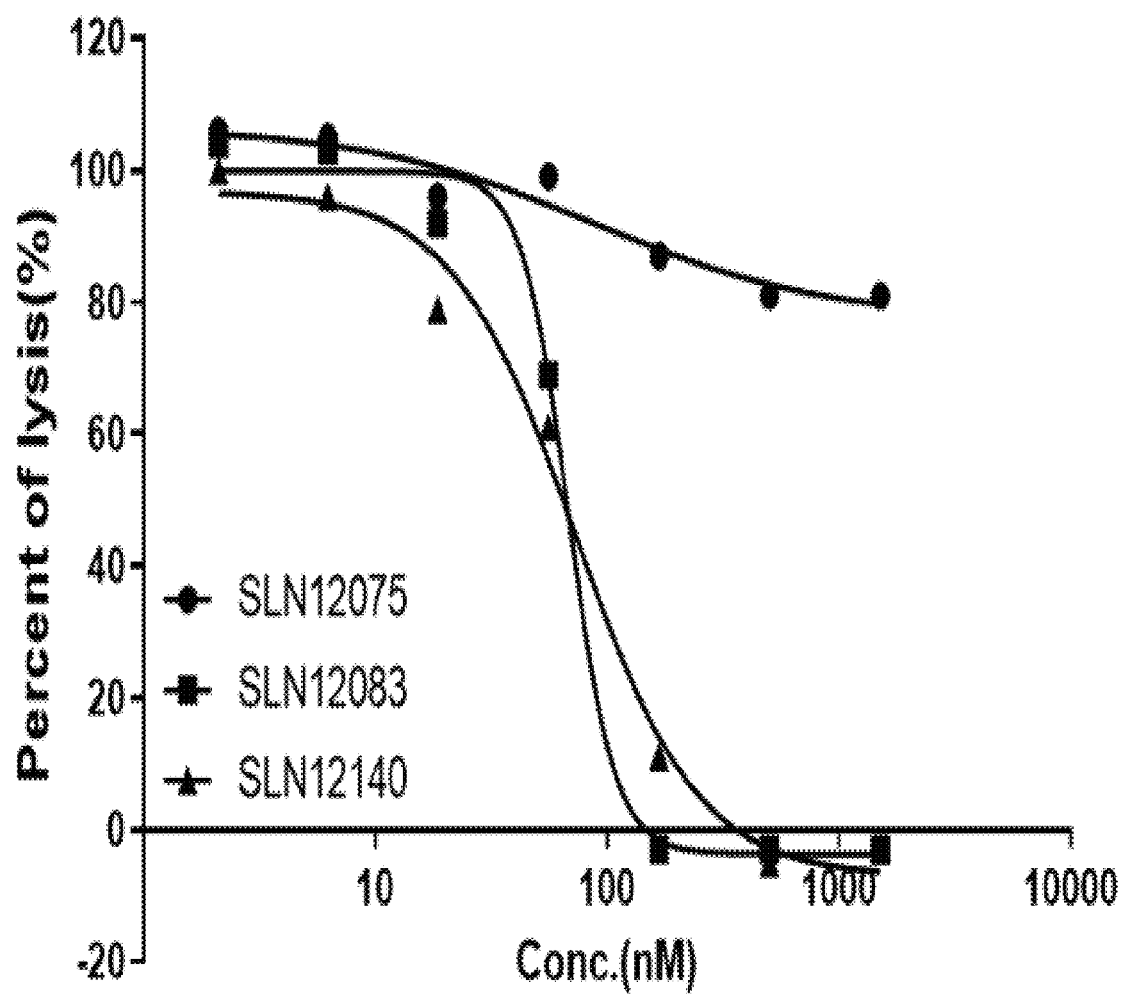
Figure 16D:
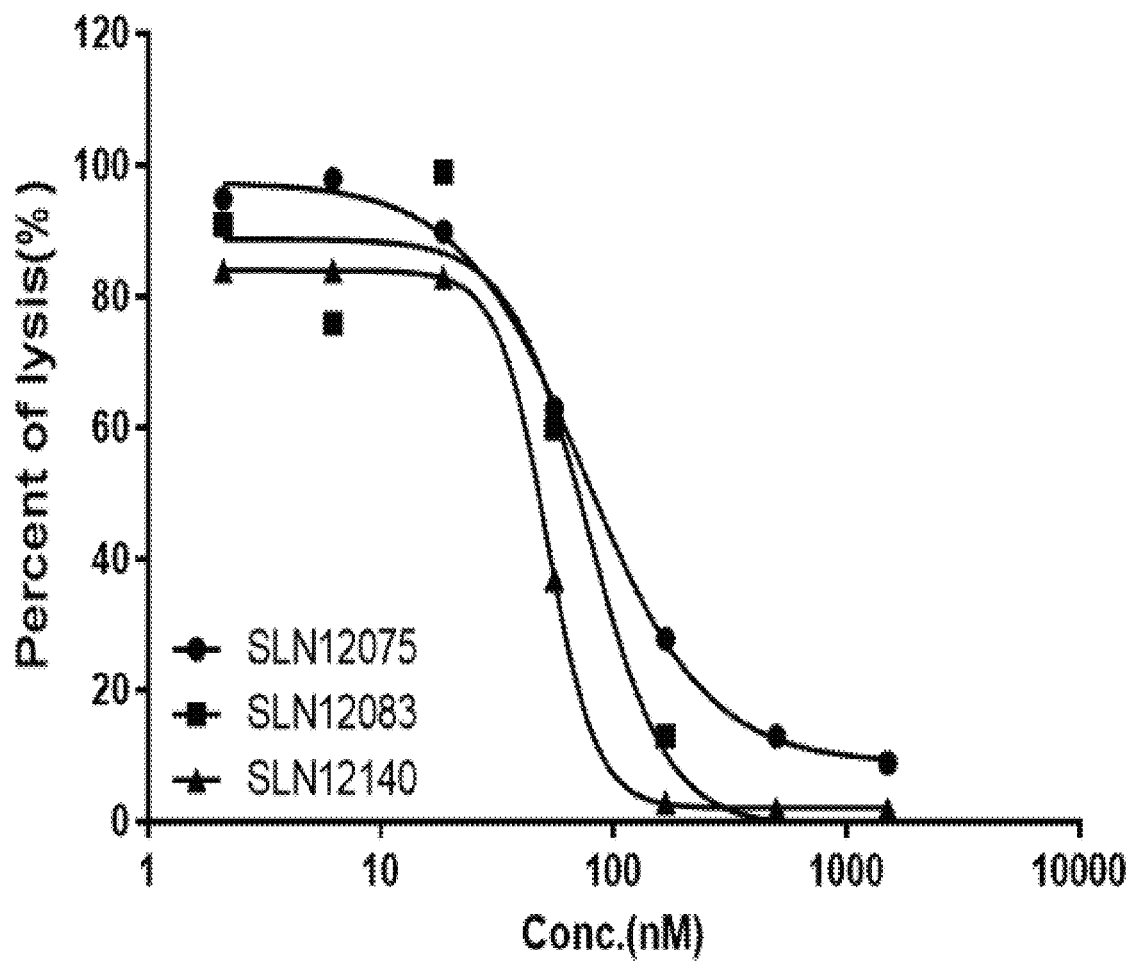

The inhibition curves of VHHs were shown in FIG. 15C, VHHs either single or bi-paratopic exhibited no inhibitory activity in the lectin pathway showing specificity in the alternative pathway. Eculizumab (Targetmol, T9915), a recombinant humanized monoclonal antibody against the complement protein C5 was as a control also showed inhibitory ability in the LP pathway, with IC50 of 45 nM.

8.2 Human, Cyno, Mouse and Rat Species Cross Activity of SLN12140

For alternative pathway assay, procedure refer to 2.3. The inhibition curves of VHHs shown in FIG. 16, Panel of (A), (B), (C) and (D) of FIG. 15 shows human, cyno, mouse and rat alternative pathway activity of SLN12075, SLN12083 and SLN12140 respectively. SLN12140 shows good species-crossing complement inhibitory activity in AP-specific pathways including human, mouse, monkey and rat. And all showed the characteristics of bivalent activity higher than single VHH.

Figure 17:
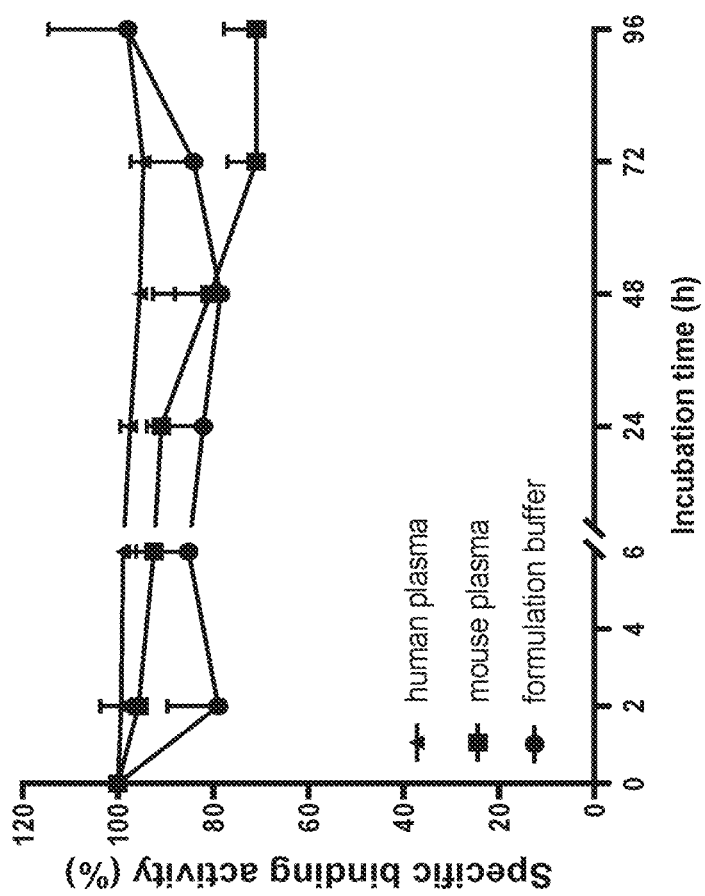
FIG. 17 Illustrates serum stability of SLN12140 both in plasma and formulation buffer.

Example 9 Serum Stability of SLN12140 and It's PK Profiles in Mice 9.1 Serum Stability of SLN12140 in Mouse Plasma Test compound SLN12140 was prepared with C57BL/6 mouse plasma, human plasma and protein formulation buffer to a concentration of 10 µg/mL, and the samples were prepared and stored at −80° C. After that, samples were incubated at 37° C. with constant temperature and moisturizing conditions, and were collected at each time points (96, 72, 48, 24, 6, 2 and 0 h). Supernatant of each sample was obtained and analyzed for quantification by analytical Elisa as described below. All assays were performed in triplicate. FIG. 17 illustrates the buffer stability and plasma stability in human and mouse plasma. SLN12140 (SEQ ID NO: 81) maintain a stable concentration in formulation buffer within 96 h and maintain stable concentration until 96 h still 70% of SLN12140 can be detected.

9.2 Sample Analysis Method Establishment 9.2.1 Total Drug Pk Assay Development and QC Verification Goat F(ab')2 anti-human IgG-Fc (Abeam, CAT #Ab98587) was coated on a 96-well enzyme-linked plate, washed 3 times with PBST (Tween-20, 0.1%) and washed with 200 µl of PBST containing 1% BSA at 37° C. blocked for 1 h. After washing 3 times with PBST, serial dilutions of SLN12140 standard, serum samples and quality control samples in PBST containing 1% BSA were added. After incubation at 37° C. for 1 h. The cells were washed 3 times with PBST, horseradish peroxidase (HRP)-labeled goat anti-human IgG (FC-specific) antibody (Sigma, CAT #A0170) was added, and the cells were incubated at 37° C. for 1 h. After washing 3 times with PBST, 100 µl of TMB substrate solution was added to incubate for 15 min, and the absorbance at 450 nm was read after adding stop solution. The accuracy and accuracy of the standard curve and quality control materials were verified by SoftMax software, and the sample concentration was calculated. The validation of the PK method with three standard concentrations (high, medium, and low) showing the precision (CV %<20%) and accuracy (RE %+/−25%) of this method) meet the sample testing requirements.

9.2.2 Total mFP assay development and QC verification

SLN12039 (SEQ ID NO: 93) was coated on a 96-well enzyme-linked plate, washed three times with PBST (Tween-20, 0.1%) and blocked with 200 µl of PBST containing 1% BSA for 1 h at 37° C. After washing 3 times with PBST, serially diluted mFP (Linno) with 1% BSA in PBST was added, incubated at 37° C. for 1 h, washed 3 times with PBST, and added with biotinylated SLN12030 antibody (Linno), incubate at 37° C. for 1 h, wash three times with PBST, add horseradish peroxidase (HRP)-labeled streptavidin antibody (Sigma, CAT #S5512), and incubate at 37° C. for 1 h. After washing 3 times with PBST, 100 si of TMB substrate solution was added to incubate for 15 minutes, and the absorbance at 450 nm was read after adding stop solution. The accuracy and accuracy of the standard curve and quality control materials were verified by SoftMax software, and the sample concentration was calculated, the validation of the PK method with three standard concentrations (high, medium, and low) showing the precision (CV %<20%) and accuracy (RE %+/−25%) of this method) meet the sample testing requirements.

9.3 Subcutaneous and intravenous single dose pharmacokinetic studies in mice

Figure 18:
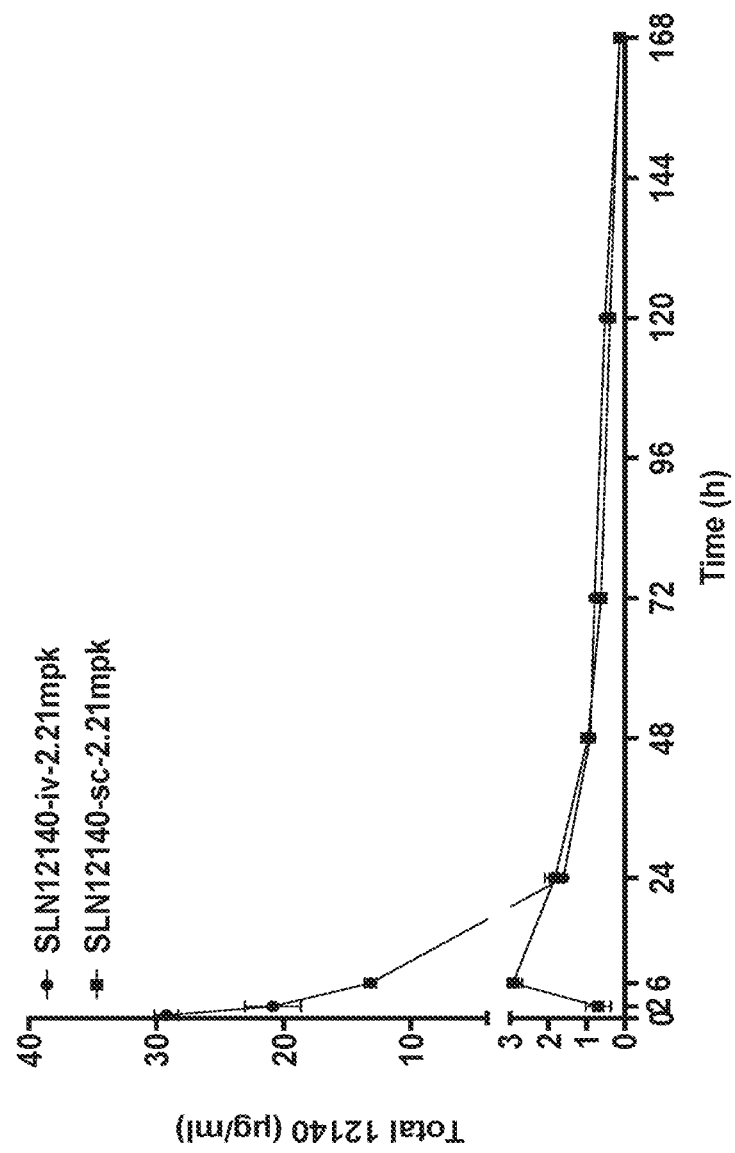
FIG. 18 Illustrates subcutaneous and intravenous single dose pharmacokinetic studies in mice.

PK studies were performed in 8 weeks old male C57BL/6 mice. The study consisted of two groups, 4 animals each group and administered by a single-dose subcutaneous or intravenous injection with 2.21 mpk SLN12140 respectively. Collected at Pro-dose (0), 0.5 h, 2 h, 6 h, 24 h (D1), 48 h (D2), 72 h (D3), 120 h (D5), 144 h (D7) and 240 h (D10), serum was separated from blood samples, and the above-mentioned PK method was used for quantitative analysis of drugs in serum, and PK solver software was used to calculate PK parameters. As shown in FIG. 18, the terminal elimination half-lives of SLN12140 after i.v and s.c administration in mouse was 2.5d. SLN12140 was rapidly absorbed after s.c. administration and the bioavailability based on $AUC_{0-4}$ was 40% for s.c. These results demonstrated that SLN12140 (SEQ ID NO: 81) exhibited a suitable half-time and favorable bioavailability.

9.4 Subcutaneous dose dependent pharmacokinetic studies in mice

Figure 19A:
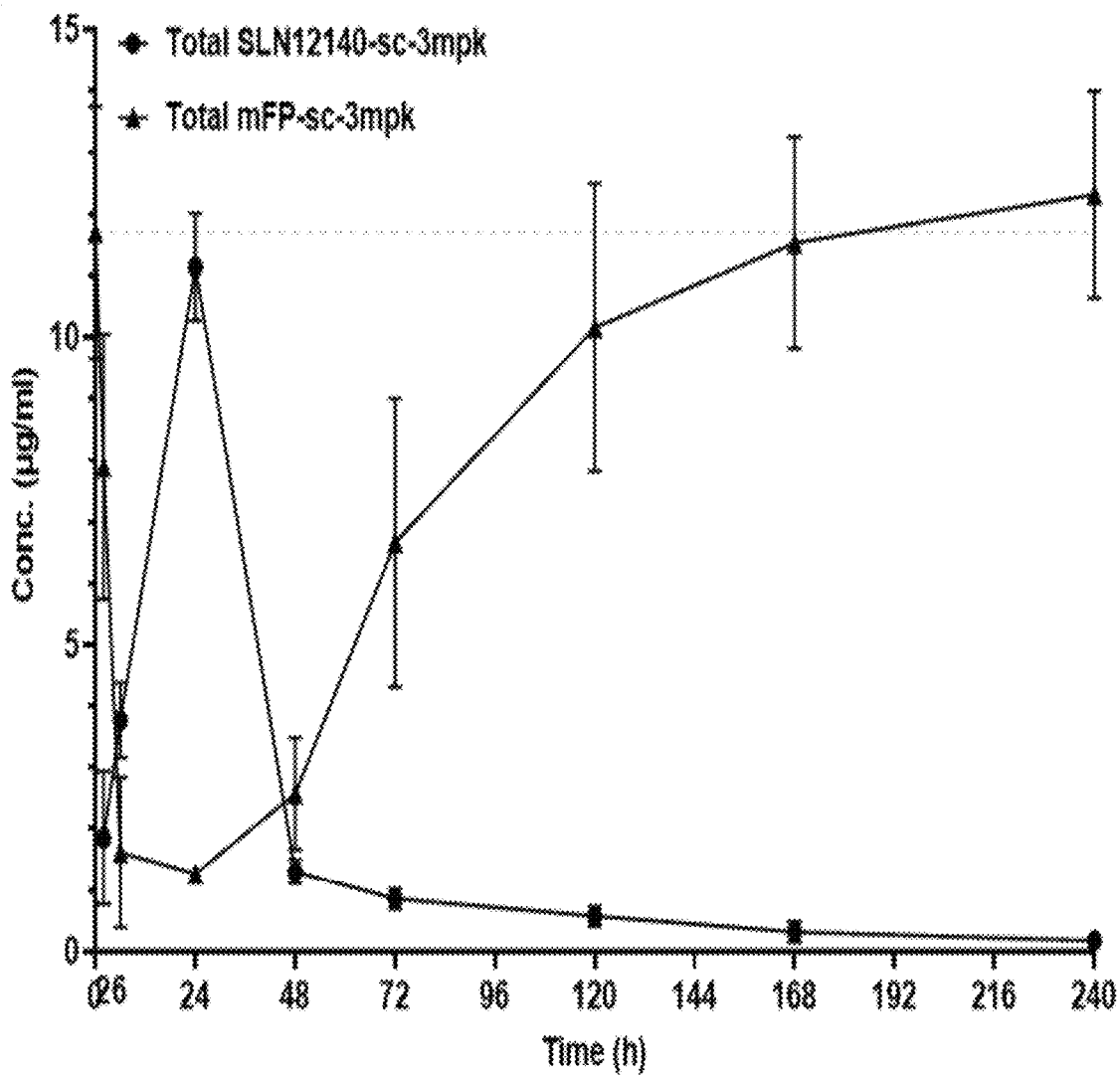
FIG. 19 Illustrates dose-dependent subcutaneous PK of SLN12140 at a dosage of 3 mpk (FIG. 19.A), 10 mpk (FIG. 19.B) or 30 mpk (FIG. 19.C), respectively.
Figure 19B:
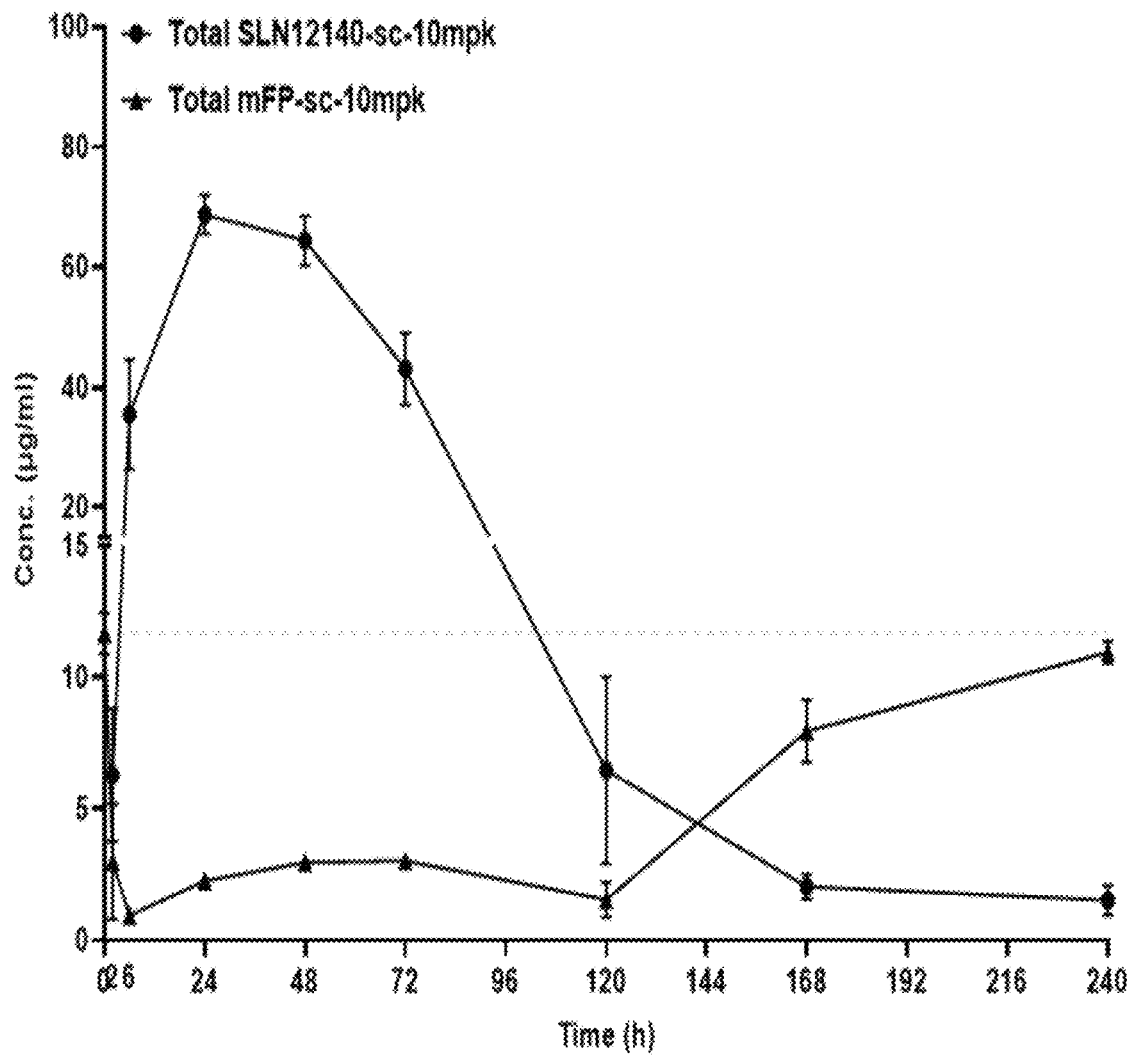
Figure 19C:
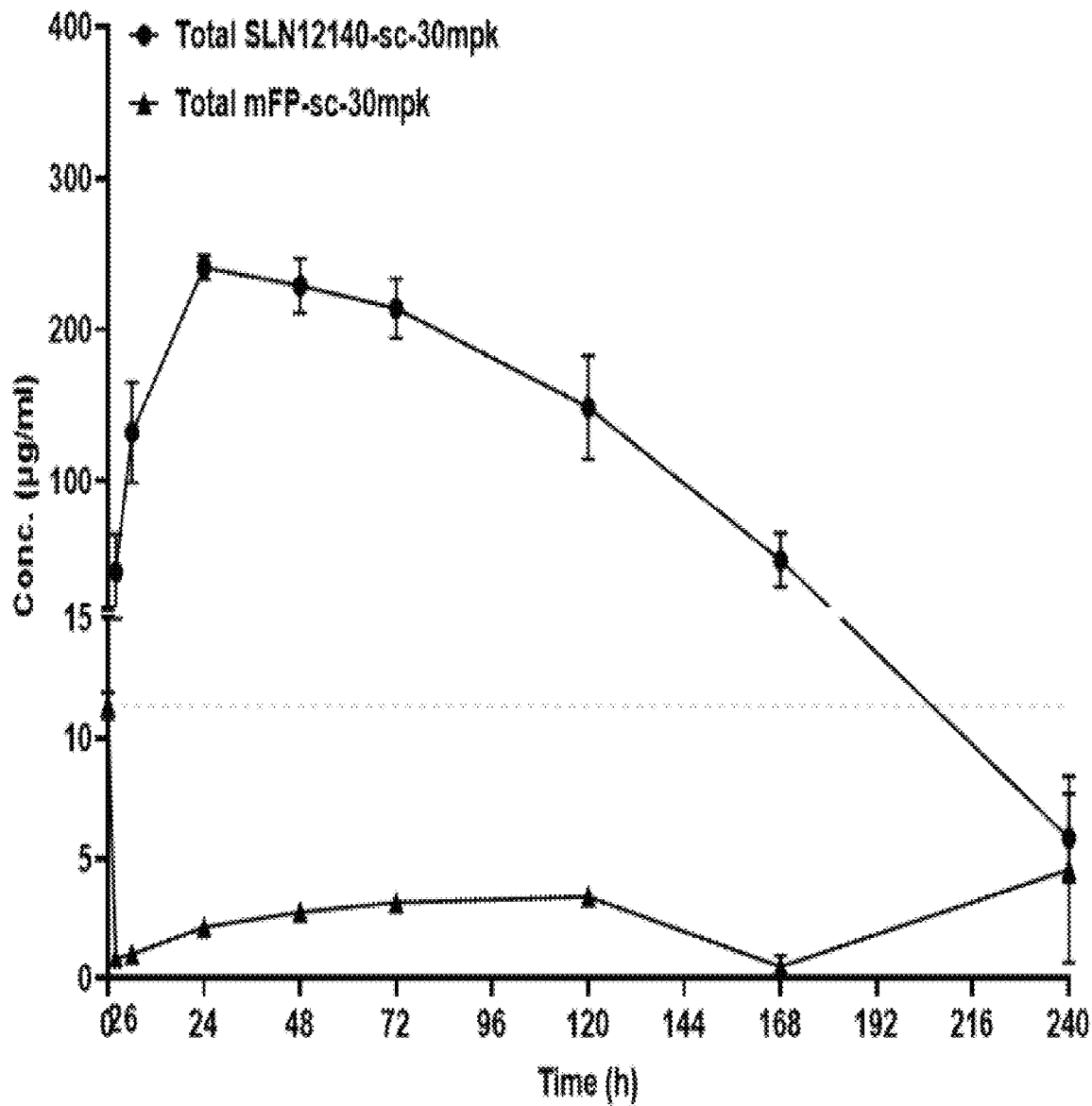

Dose dependent PK studies were performed in 8 weeks old male C57BL/6 mice. The study consisted of three groups, 5 animals each group and administered by a single-dose subcutaneous with 3, 10 and 30 mpk respectively. Blood samples were collected at pro-dose (0 h) and 8 sampling times post dosing: 2 h, 6 h, 24 h (D1), 48 h (D2), 72 h (D3), 120 h (D5), 144 h (D7) and 240 h (D10). Once collected, blood samples were centrifuged at 4° C. for 10 min at 1500 g and stored at −80° C. prior to analysis, and the above-mentioned PK method was used for quantitative analysis of drugs in serum, and PK solver software was used to calculate PK parameters. As results shown in FIG. 19A-C, the exposure of SLN12140 (SEQ ID NO: 81) in terms of AUC increased more than proportional with dose in the entire dose range between 3, 10 and 30 mpk. The concentration of the mFP also maintains a very consistent correspondence with the drug concentration. Low level FP concentration can be maintained for 48 h at 3 mpk, 120 h at 10 mpk, 168 h at 30 mpk respectively and showed good target inhibitory activity and good safety profile.

9.5 Multiple Dose Pharmacokinetic Studies in Mice

Figure 20:
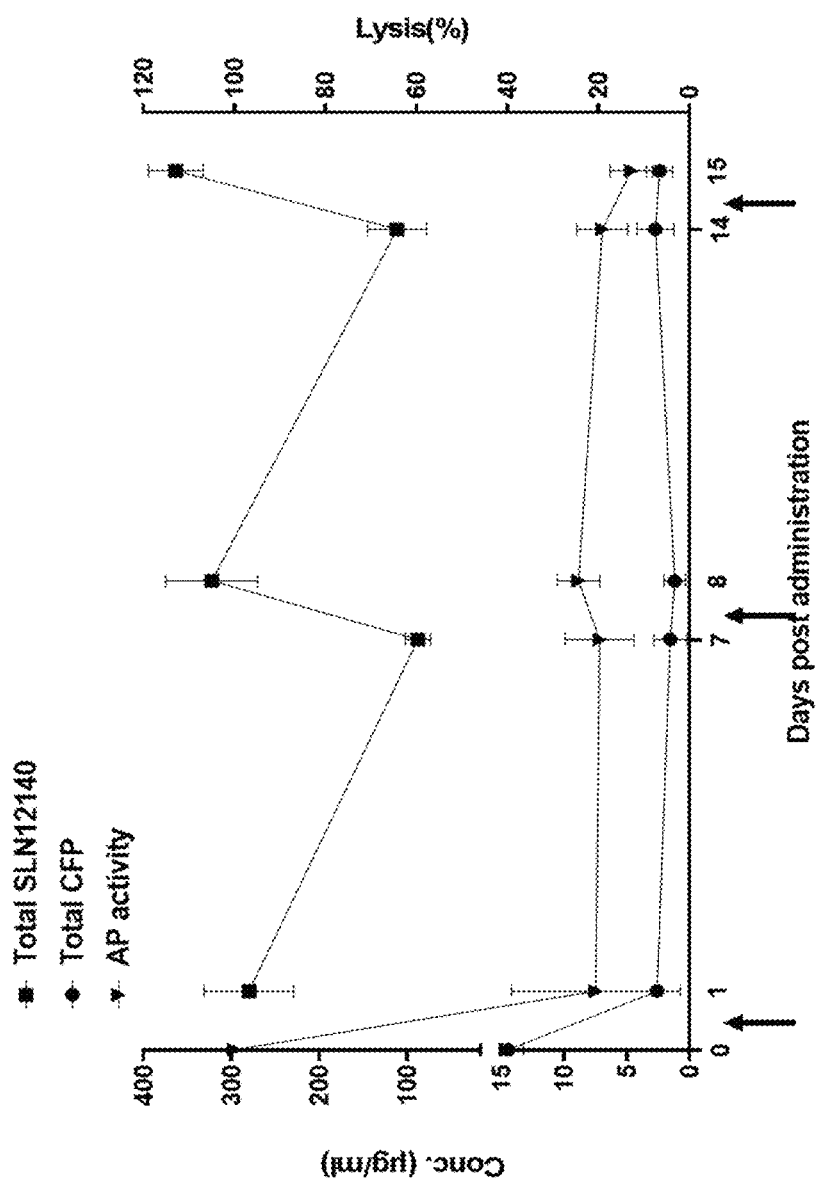
FIG. 20 Illustrates multiple subcutaneous dosing SLN12140 once a week for 3 weeks sustainably reduce the target concentration to a low level and consistently inhibit AP activity.

PK studies were performed in 8 weeks old male C57BL/6 mice. The subcutaneous doses of SLN12140 of 30 mpk, administered once every 7 days for four consecutive doses. Blood samples were collected at before each dose (0 h), 24 h post each dose. Once collected, after 2 hours of natural agglutination at room temperature, blood samples were centrifuged at 4° C. for 10 min at 1500 g and stored at −80° C. prior to analysis, and the above-mentioned PK method was used for quantitative analysis of drugs in serum, and PK solver software was used to calculate PK parameters. At the same time, AP activity was measured at different sampling time points using the method described above. As results shown in the FIG. 20, FP concentration decreased significantly 24 h after administration and remained below physiological levels 7 days after administration, an no risk of increased FP after multiple administrations was observed. The AP activity detected by the erythrocyte lysis method was highly consistent with the FP concentration, and the AP activity decreased significantly when the FP concentration decreased and SLN12140 (SEQ ID NO: 81) showed good and sustained AP pathway inhibitory activity after multiple dosing.

9.6 Multiple Dose Pharmacokinetic Studies in hCD89 Tg Mice

Figure 21:
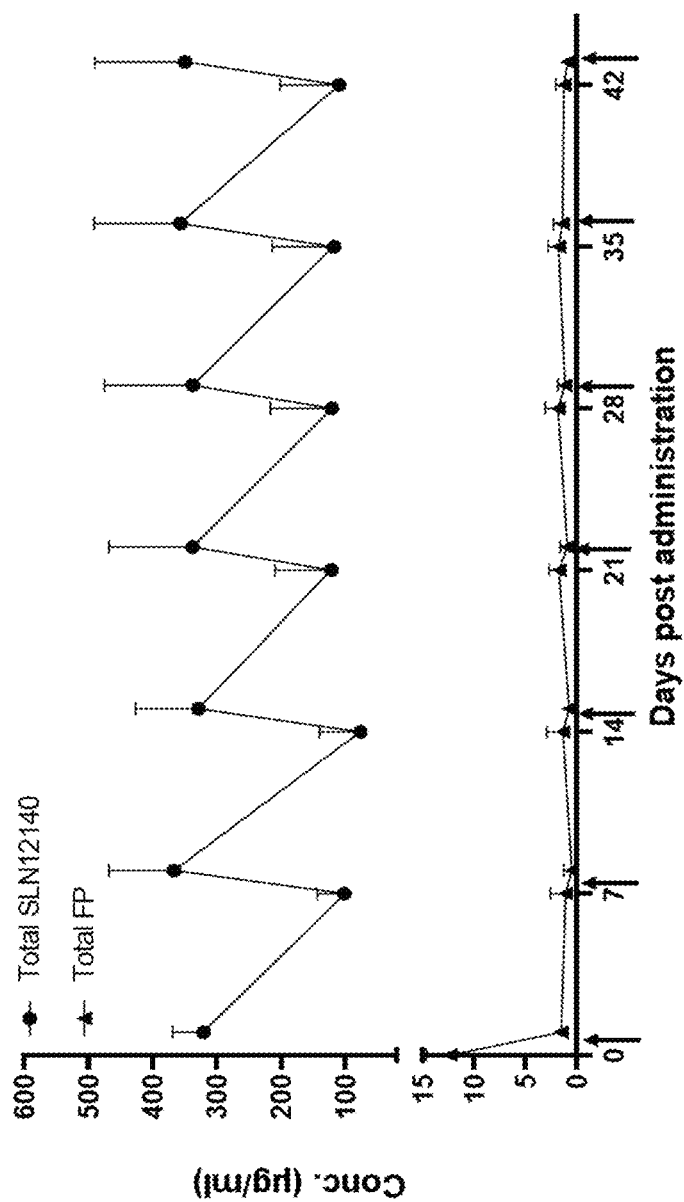
FIG. 21 Illustrates multiple subcutaneous dosing SLN12140 once a week for 7 weeks in hCD89 Tg mice sustainably reduce the target concentration to a low level and stable pharmacokinetic characteristics of SLN12140.

PK studies were performed in 13-14 weeks old male hCD89 Tg C57BL/6 mice. The hCD89 transgenic (Tg) mice expressed human CD89 on macrophage/monocytes and the key role of soluble CD89 in the pathogenesis of IgAN has been demonstrated in the literature. The subcutaneous doses of 30 mpk SLN12140, administered once every 7 days for seven consecutive doses. Blood samples were collected at before each dose (0 h), 24 h post each dose. Once collected, after 2 hours of natural agglutination at room temperature, blood samples were centrifuged at 4° C. for 10 min at 1500 g and stored at −80° C. prior to analysis, and the above-mentioned PK method was used for quantitative analysis of drugs in serum, and PK solver software was used to calculate PK parameters. At the same time, AP activity was measured at different sampling time points using the method described above. As results shown in FIG. 21, with 7 consecutive doses, the SLN12140 (SEQ ID NO: 81) serum concentration shows a continuous and stable pharmacokinetic character, and the weekly dosing can continuously decrease the target concentration at a low level, and there is no risk of immune complex formation according to blood concentration analysis and target concentration analysis. At the same time, mice are generally well observed.

Figure 22:
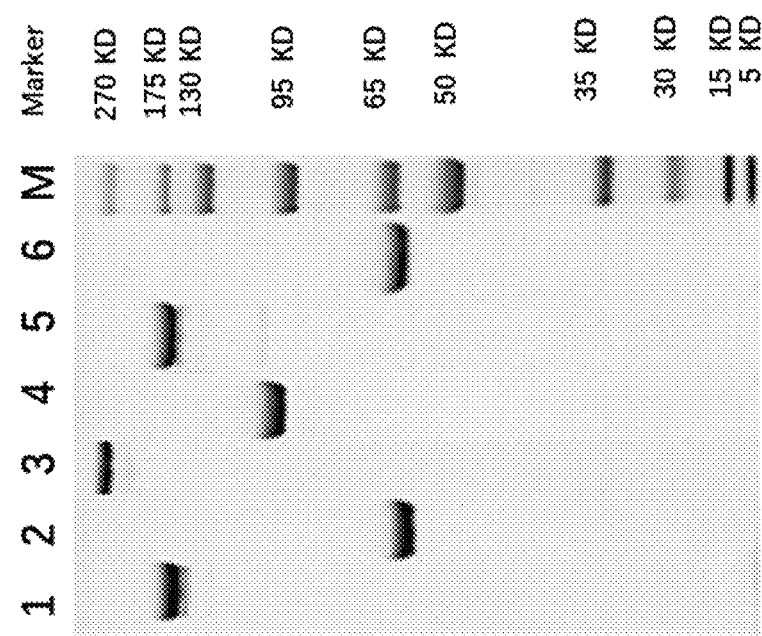
FIG. 22 Illustrates representative SDS-PAGE gels of the fusion proteins expressed in HEK293 cells. Purified fusion proteins SLN6073, SLN8284, SLN12140 under non-reducing conditions (lane 1,3,5) and reducing conditions (lane 2,4,6).

Example 10 SLN12140 Fusion with VEGF Inhibitors 10.1 Production of Recombinant Anti-Complement Protein VHH-G4Fc, Anti-VEGF Protein VHH-G4Fc, Bispecific Protein that Inhibited Both Complement and VEGF Pathways A nucleotide sequence corresponding to the amino acid of the bispecific fusion protein with VEGF inhibiting domain fused to N-terminal and complement inhibiting domain fused to C-terminal of Fc domain (SLN8284, SEQ ID NO: 114) and complement inhibiting protein (SLN12140, SEQ ID NO: 81) or VEGF inhibiting protein (SLN6073, SEQ ID NO: 113) with an G4Fc domain fused to C-terminal were constructed into the plasmid pCDNA3.4 or pCP. After these plasmids sequence were verified by sequencing, small scale production of recombinant proteins was performed using transient transfection of HEK293 cells with the recombinant plasmid using lipofectamine or PEI as transfection reagent. Cultures were grown in shaking flasks media at scales ranging from 30 ml to 100 ml for 5-7 days. Cells were removed by centrifugation and culture supernatants were used for protein purification via Protein A chromatography. The purified proteins were quantified by Coomassie Plus (Bradford) Assay Kit and analyzed with 4-12% gradient SDS-PAGE gel under non-reducing (lanes 1, lane3 and lane 5) or reducing conditions (lanes 2, lane 4 and lane 6) (FIG. 22).

Figure 23A:
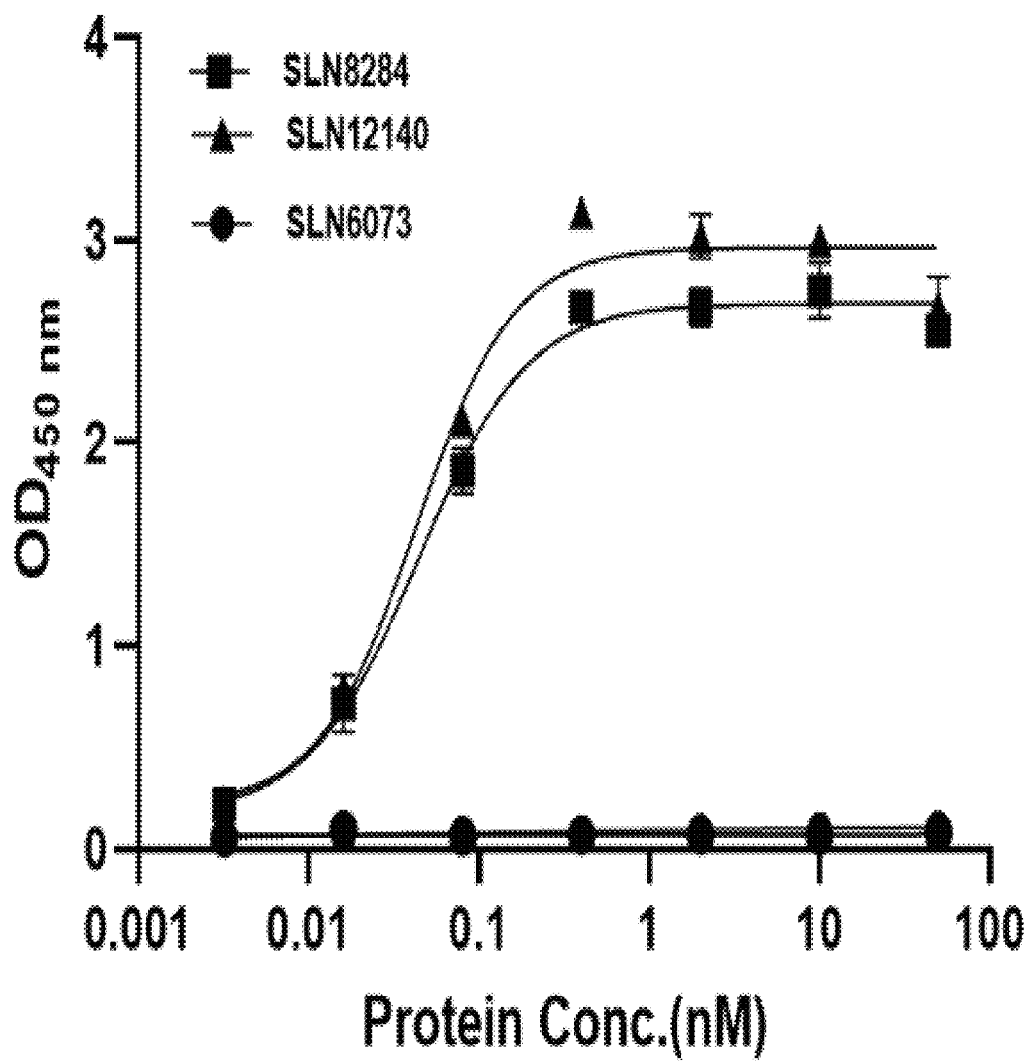
FIG. 23A-C Illustrates representative binding of SLN8284, SLN12140, SLN6073 to different species' properdin in vitro. A) Human properdin binding of SLN8284, SLN6073, SLN12140. B) Cynomolgus macaques properdin binding of SLN8284, SLN6073, SLN12140. C) Mouse properdin binding of SLN8284, SLN6073, SLN12140.
Figure 23B:
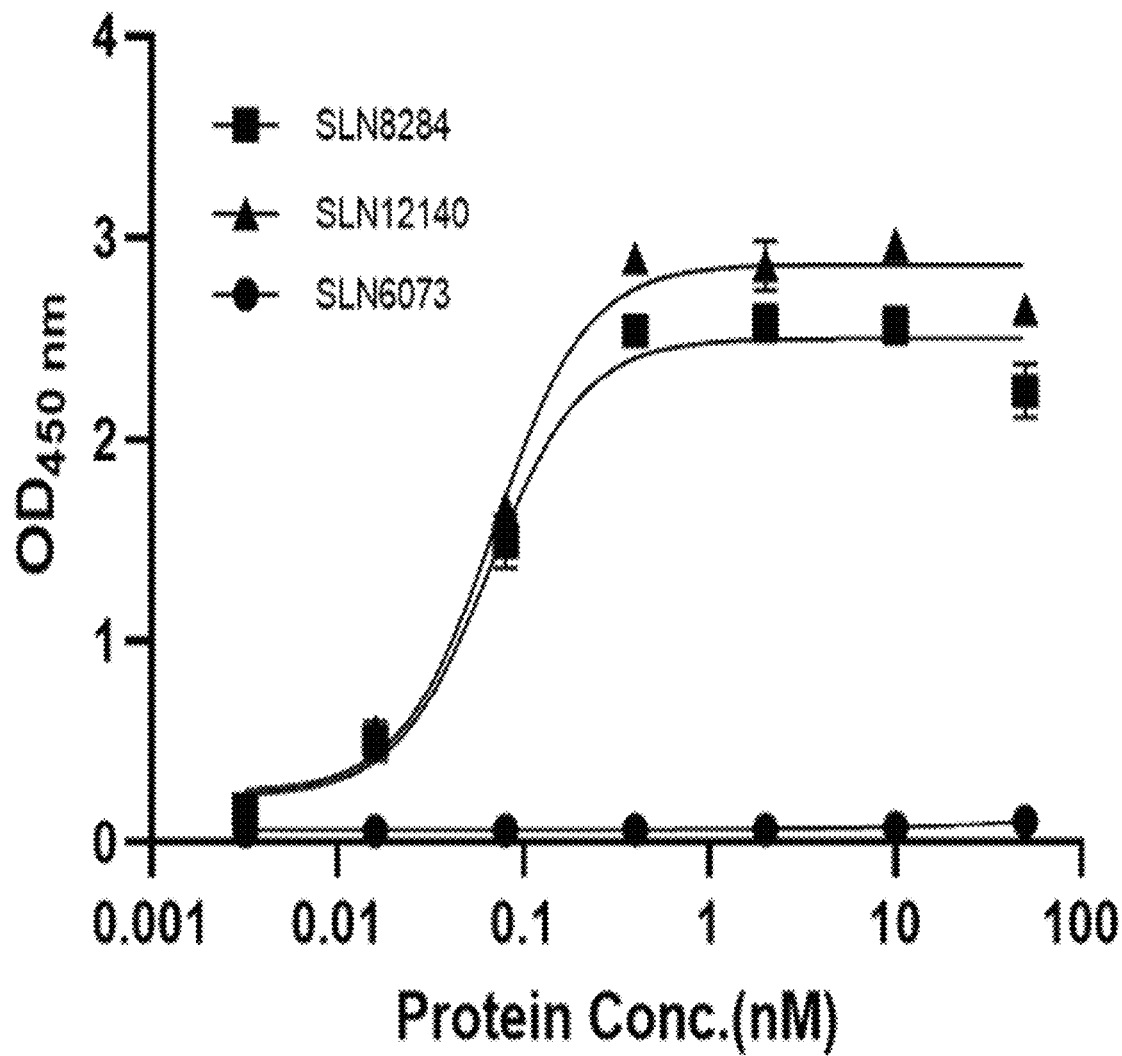
Figure 23C:
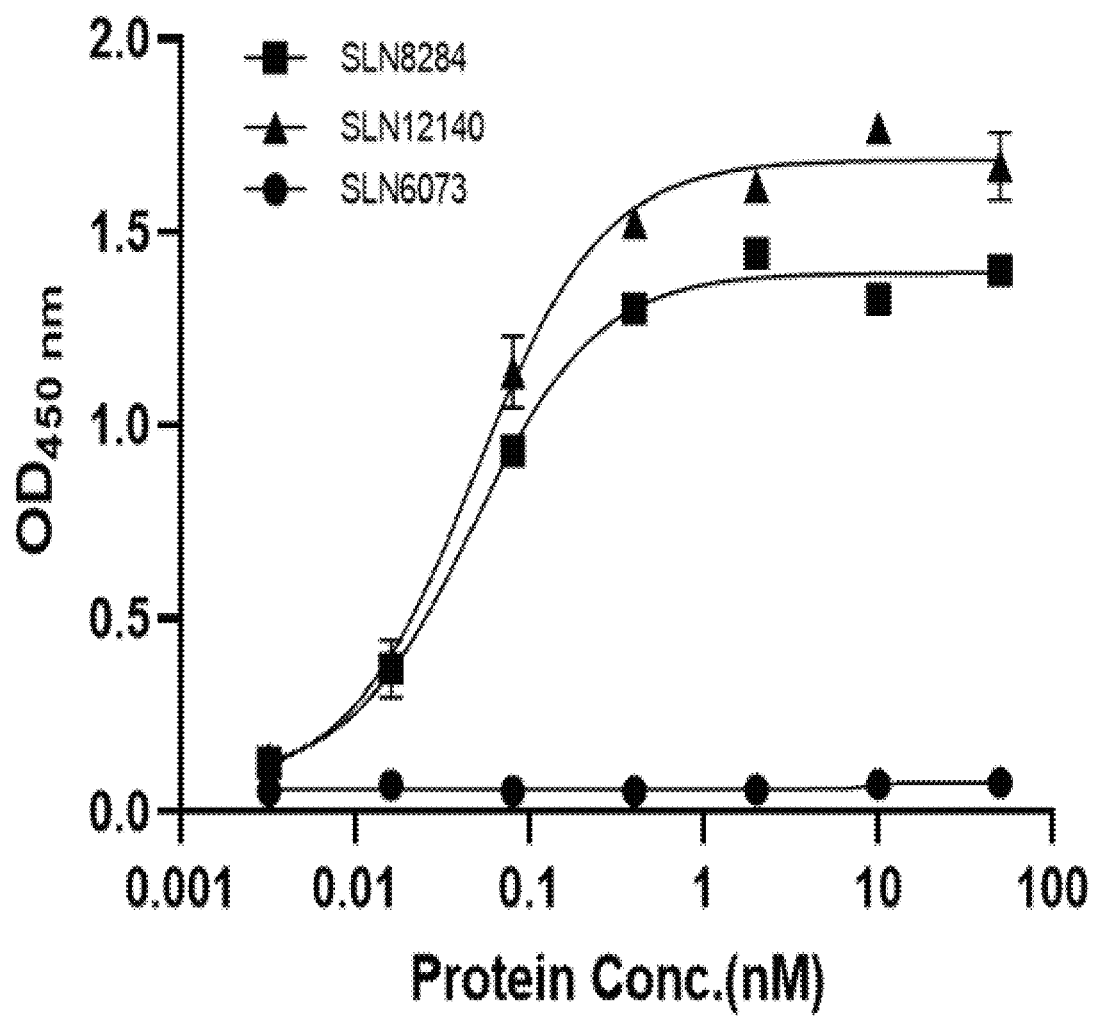

10.2 In Vitro Binding of SLN8284. SLN12140, SLN6073 to Different Species' Properdin ELISAs were performed to determine whether proteins bind directly to properdin. Briefly, the wells of a 96-well ELISA plate were coated with streptavidin (1 µg/ml in CBS, 100 µl/well) and incubated at 4° C. overnight. After 3 times of washing with PBST, the plates were blocked with 1% BSA in PBST at RT for 1 hour. After 3 times of washing with PBST, biotinylated human or Cynomolgus macaques or mouse properdin protein (2 µg/ml in BSA, 100 µL/well) was added and incubate at RT for 1 hour. After 3 times of washing with PBST, the purified SLN8284 (SEQ ID NO: 114), SLN12140 (SEQ ID NO: 81), SLN6073 (SEQ ID NO: 113) (serially diluted in BSA, starting from 50 nM) were added and incubated at RT for 1 hour. After 3 times of washing with PBST, ANTI-HUMAN IGG (FC SPECIFIC) PEROXIDASE (Sigma Catalog No. A0170-1ML) were added to each well for incubation of 1 hour. After 3 times of washing with PBST, stop reagent for TMB Substrate was added to each well, and OD absorption at 450 nm was measured. The data was analyzed by sigmoidal curve fitting using GraphPad Prism 8.0. As shown in FIG. 23. SLN8284, 12140 exhibited strong binding to human or Cynomolgus macaques or mouse properdin respectively, and SLN6073 (SEQ ID NO: 113) can't exhibit binding to human or Cynomolgus macaques properdin or mouse (FIG. 23A, 23B, 23C)

10.3 Inhibition of the Alternative Complement Pathway by SLN8284, SLN12140, SLN6073

In contrast to the classical and lectin complement pathways, which require both magnesium and calcium ions for activation, activation of the alternative complement pathway requires only magnesium ions. Thus, to quantify alternative complement activity in the presence of fusion proteins, the assay described above was modified such that rabbit erythrocytes (Er) were incubated with serum, 0-1500 nM fusion proteins, 5 mM Mg2+, and 5 mM EGTA, which preferentially chelates calcium ions.

Figure 24A:
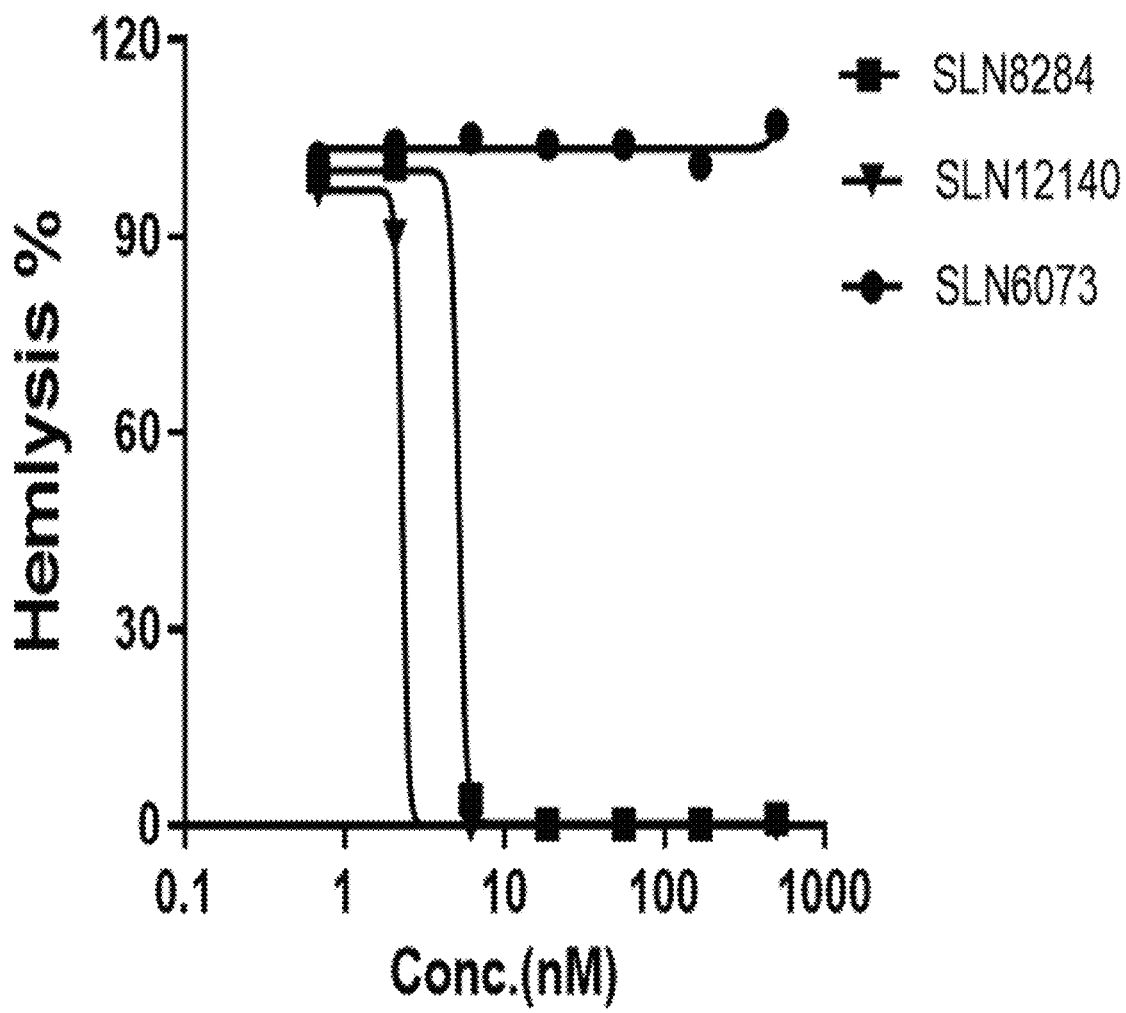
FIG. 24A-B Illustrates inhibition of the alternative complement pathway in rabbit erythrocytes by various concentrations of fusion proteins SLN8284, SLN6073, SLN12140. A) Inhibition of the alternative complement pathway of SLN8284, SLN6073, SLN12140 in human serum. B) Inhibition of the alternative complement pathway of SLN8284, SLN6073, SLN12140 in mouse serum.
Figure 24B:
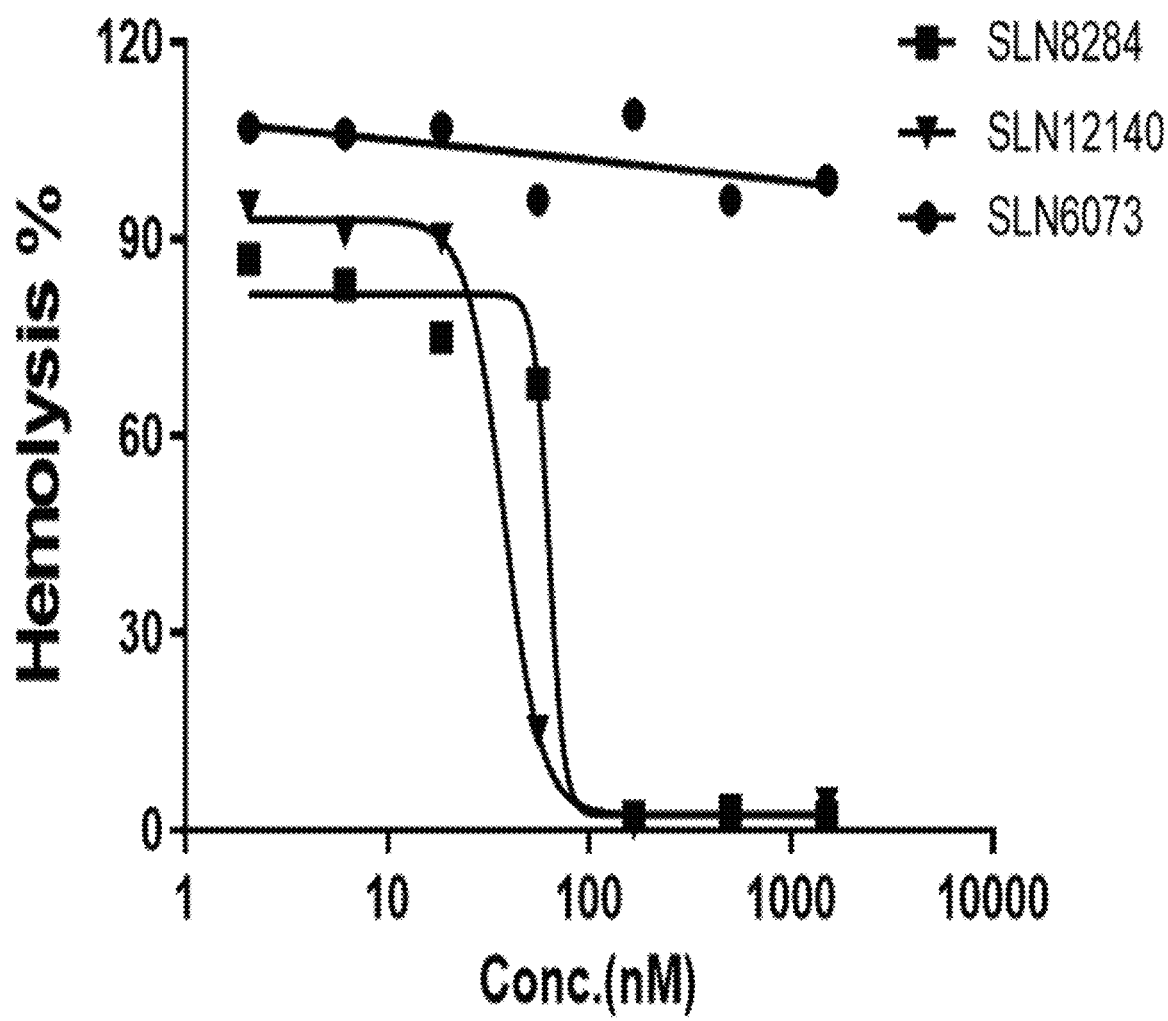

For this assay, all fusion proteins samples were serially diluted in PBS and added to a U-bottom 96-well microtiter plate, normal human serum (Complement Technology Catalog No. NHS A113) or complement-preserved mouse serum was diluted to the right concentration in assay buffer AP (20 mM Mg/EGTA in GVB0) and incubated on ice for 30 min. Then prepared of $5\times10^7$ rabbit erythrocytes/ml (SenBeiJia Biological Technology Co., Ltd. Catalog No. SBJ-RBC-RAB003-10 mL) in assay buffer. Inhibition of the alternative complement pathway was initiated by mixing 0-1500 nM of SLN8284, SLN6073, SLN12140 with the dilution of normal human serum or mouse serum with $2.5\times10^6$ rabbit erythrocytes for 30 min or 1 hour at 37° C. Hemolysis of Er was then assayed by measuring absorption at OD405 nm. The data was analyzed by sigmoidal curve fitting using Prism 8. Analysis of the percentage of hemolysis of the EA in the presence of the fusion proteins demonstrated that SLN8284 exhibited a high inhibitory activity with IC50 of 5.166 nM or 63.4 nM (FIG. 24A, 24B, closed square). SLN12140 (SEQ ID NO: 81) exhibited an improved inhibitory effect (2.3 or 1.7-fold) to IC50 of 2.293 nM or 37.83 nM (FIG. 24A, 24B, inverted triangle). SLN6073 (SEQ ID NO: 113) can't exhibit an inhibitory effect (FIG. 24A, 24B, closed circle).

10.4 In Vitro Binding of SLN8284, SLN12140, SLN6073 to Human and Mouse VEGF

Figure 25A:
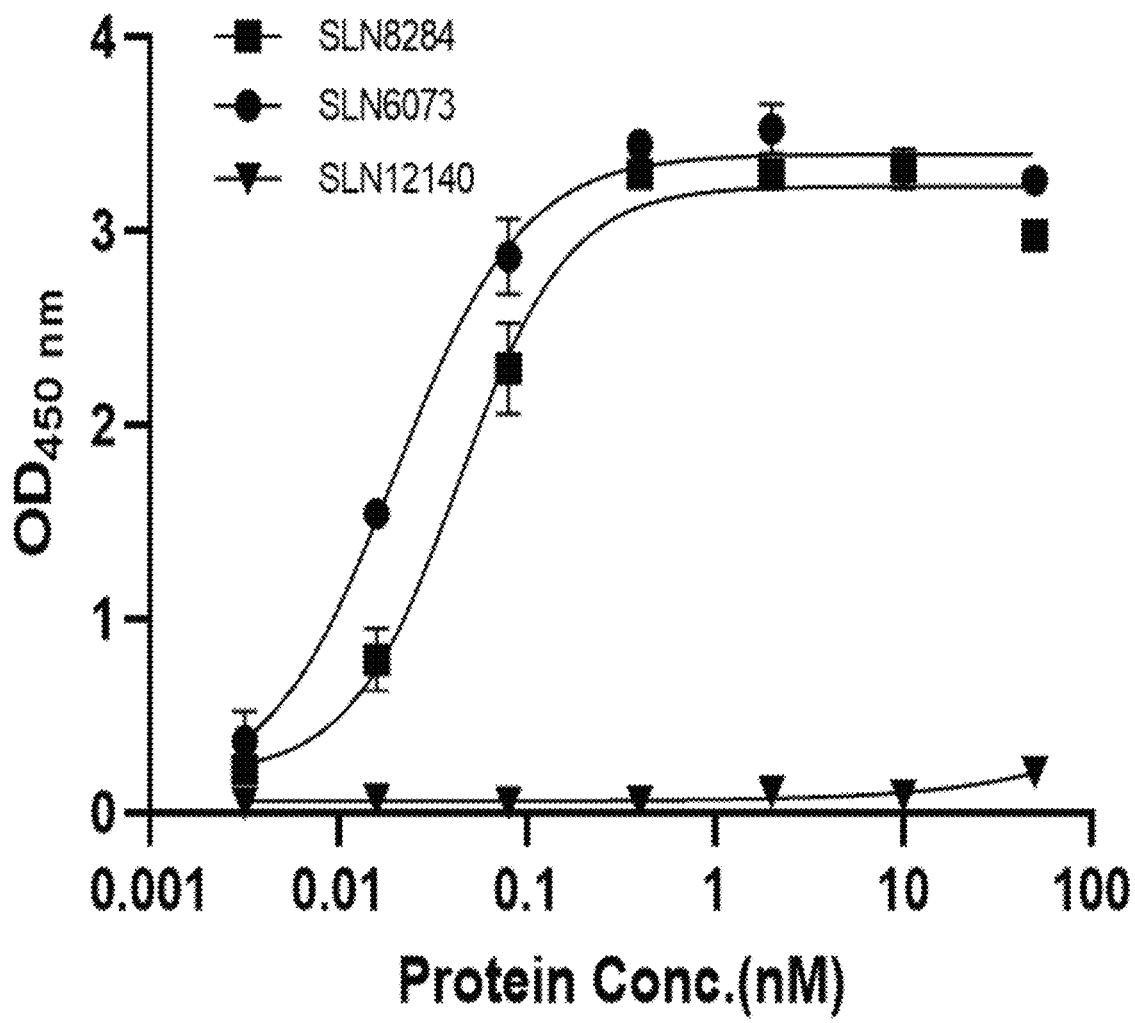
FIG. 25A-B Illustrates in vitro binding of a VEGF by SLN8284, SLN6073, SLN12140 as detected by ELISA. A) Human VEGF121 binding of SLN8284, SLN6073, SLN12140. B) Mouse VEGF120 binding of SLN8284, SLN6073, SLN12140.
Figure 25B:
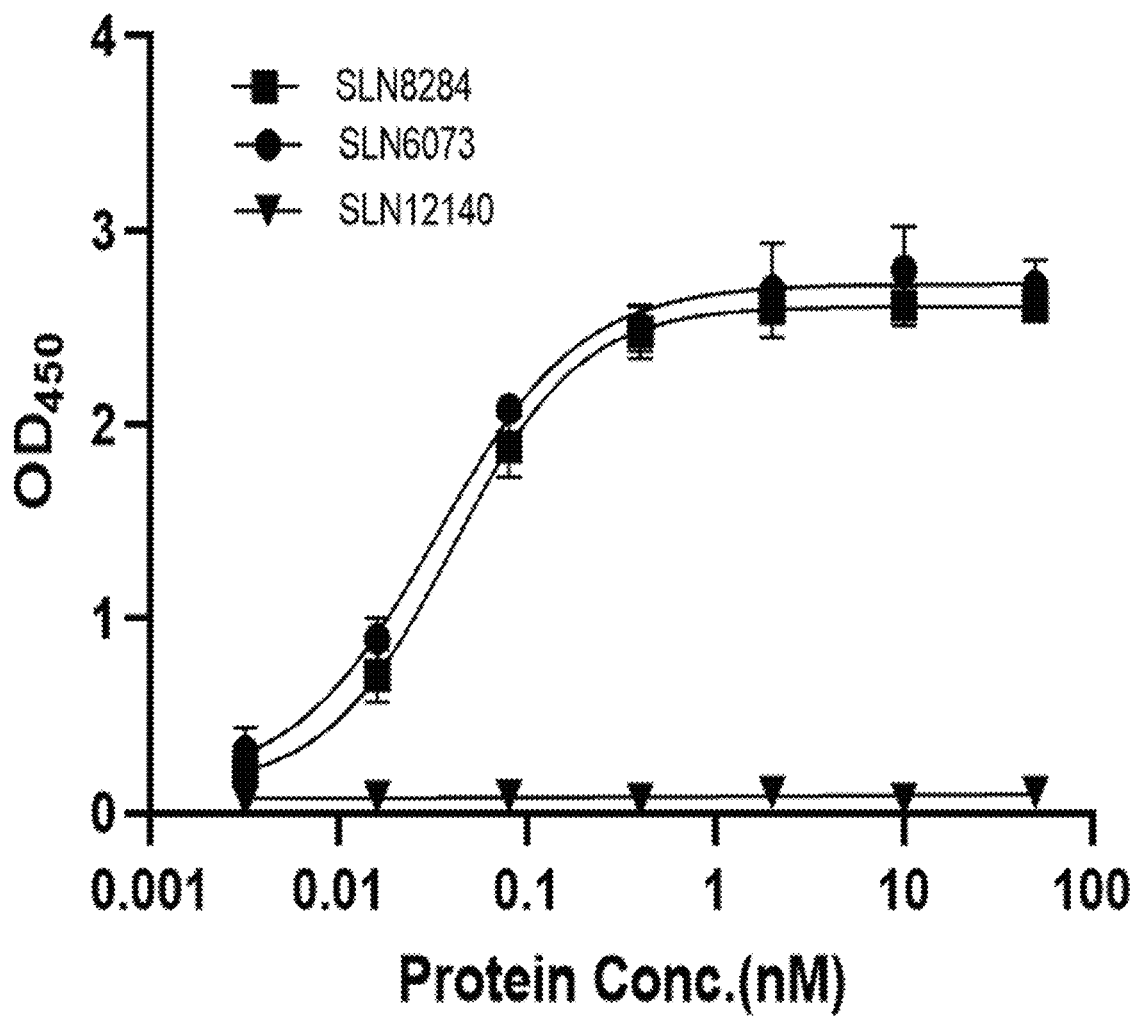

ELISAs were performed to determine whether proteins bind directly to VEGF. Briefly, the wells of a 96-well ELISA plate were coated with streptavidin (1 µg/mL in CBS, 100 µL/well) and incubated at 4° C. overnight. After 3 times of washing with PBST, the plates were blocked with 1% BSA in PBST at RT for 1 hr. After 3 times of washing with PBST, biotinylated human or mouse VEGF protein (0.5 µg/ml in BSA, 100 µL/well) was added and incubate at RT for 1 h. After 3 times of washing with PBST, the purified SLN8284 (SEQ ID NO: 114), SLN12140 (SEQ ID NO: 81), SLN6073 (SEQ ID NO: 113) proteins (serially diluted in BSA, starting from 50 nM) were added and incubated at RT for 1 h. After 3 times of washing with PBST, ANTI-HUMAN IGG (FC SPECIFIC) PEROXIDASE (Sigma Catalog No. A0170-1ML) were added to each well for incubation of 1 hour. After 3 times of washing with PBST, stop reagent for TMB Substrate was added to each well, and OD absorption at 450 nm was measured. The data was analyzed by sigmoidal curve fitting using GraphPad Prism 8.0. As shown in FIG. 25. SLN8284 (SEQ ID NO: 114), SLN6073 (SEQ ID NO: 113) exhibited strong binding to human or mouse VEGF respectively, and SLN12140 (SEQ ID NO: 81) can't exhibit binding to human or Cynomolgus macaques properdin or mouse (FIG. 25A, 25B).

(Human VEGF121: Accession #: P15692-9; VEGF120: Accession #: Q00731-3)

10.5 Blocking the Interaction Between VEGFA and VEGFR2 of SLN8284, SLN6073, SLN12140

Figure 26A:
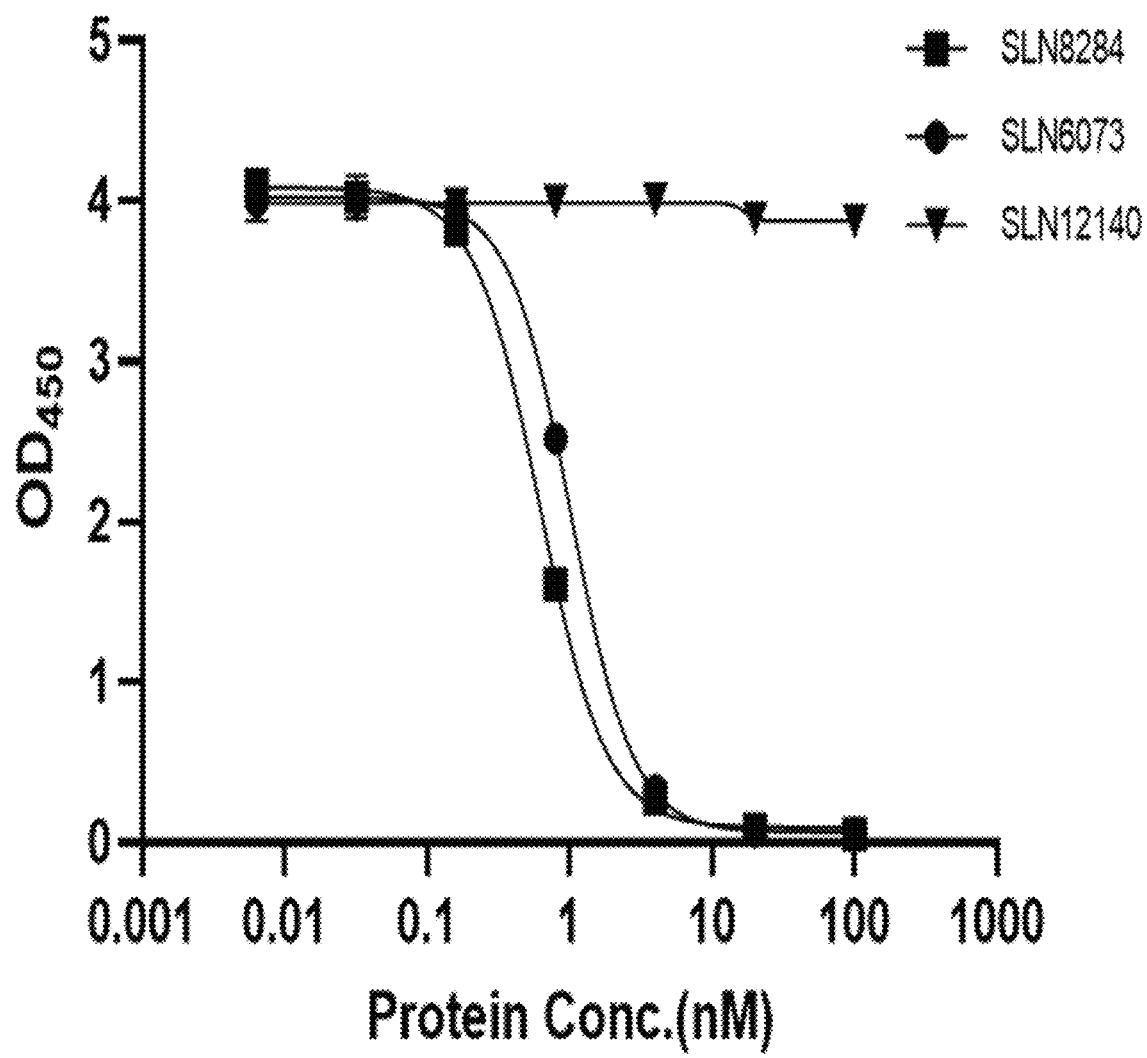
FIG. 26A-B Illustrates effect of blocking the interaction between VEGFA and VEGFR2 by SLN8284, SLN6073, SLN12140. A) Blocking the interaction between hVEGFA and hVEGFR2 by SLN8284, SLN6073, SLN12140. B) Blocking the interaction between mVEGFA and mVEGFR2 by SLN8284, SLN6073, SLN12140.
Figure 26B:
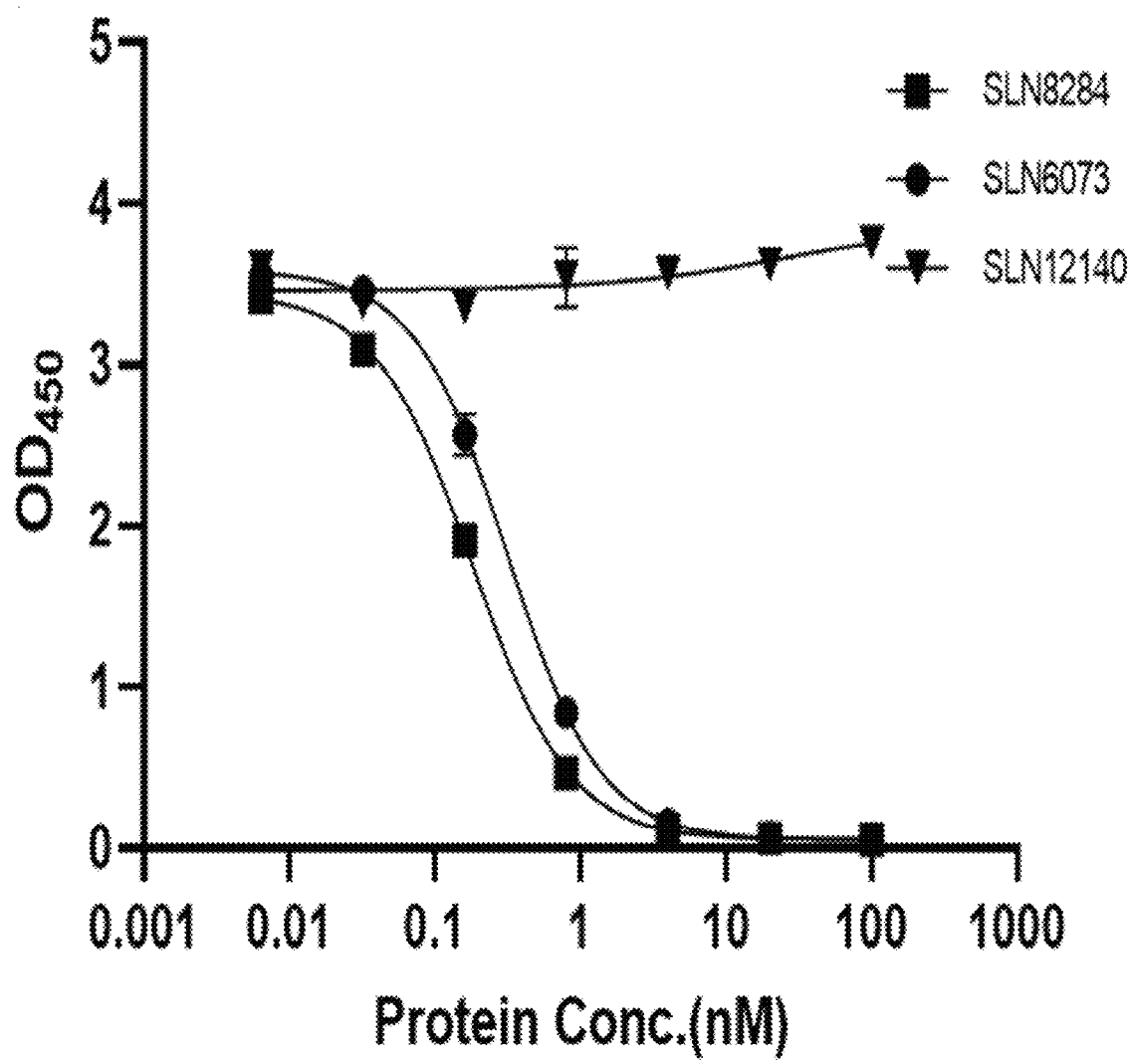

ELISAs were performed to determine whether proteins can block the interaction between VEGFA and VEGFR2 Briefly, the wells of a 96-well FLISA plate were coated with streptavidin (1 µg/ml in CBS, 100 µl/well) and incubated at 4° C. overnight. After 3 times of washing with PBST, the plates were blocked with 1% BSA in PBST at RT for 1 hour. After 3 times of washing with PBST, biotinylated human or mouse VEGF protein (0.07 µg/mL in BSA) was added and incubate at RT for 1 hour. After 3 times of washing with PBST, human or mouse VEGFR1 (0.14 µg/mL or 0.07 µg/mL in BSA) mixed with purified SLN8284, SLN12140, SLN6073 (a serially diluted in BSA, starting from 100 nM) was added and incubate at RT for 1 hour After 3 times of washing with PBST, anti-mouse IgG Fc-HRP (Abcam, lot #GR3396448-2) were added to each well for incubation of 1 hour. After 3 times of washing with PBST, stop reagent for TMB Substrate was added to each well, and OD absorption at 450 nm was measured. The data was analyzed by sigmoidal curve fitting using GraphPad Prism 8.0. As shown in FIG. 26. SLN8284, 6073 can block the interaction between human or mouse VEGFA and human or mouse VEGFR2 effectively. SLN12140 can't block the interaction between human or mouse VEGFA and human or mouse VEGFR2 (FIG. 26A and FIG. 26B).

(hVEGFR2: Accession #: P35968-1; mVEGFR2: Accession #: P35918-1)

10.6 Inhibition of VEGF-Dependent HUVEC Proliferation Assay by SLN8284, SLN12140, SLN6073

Figure 27:
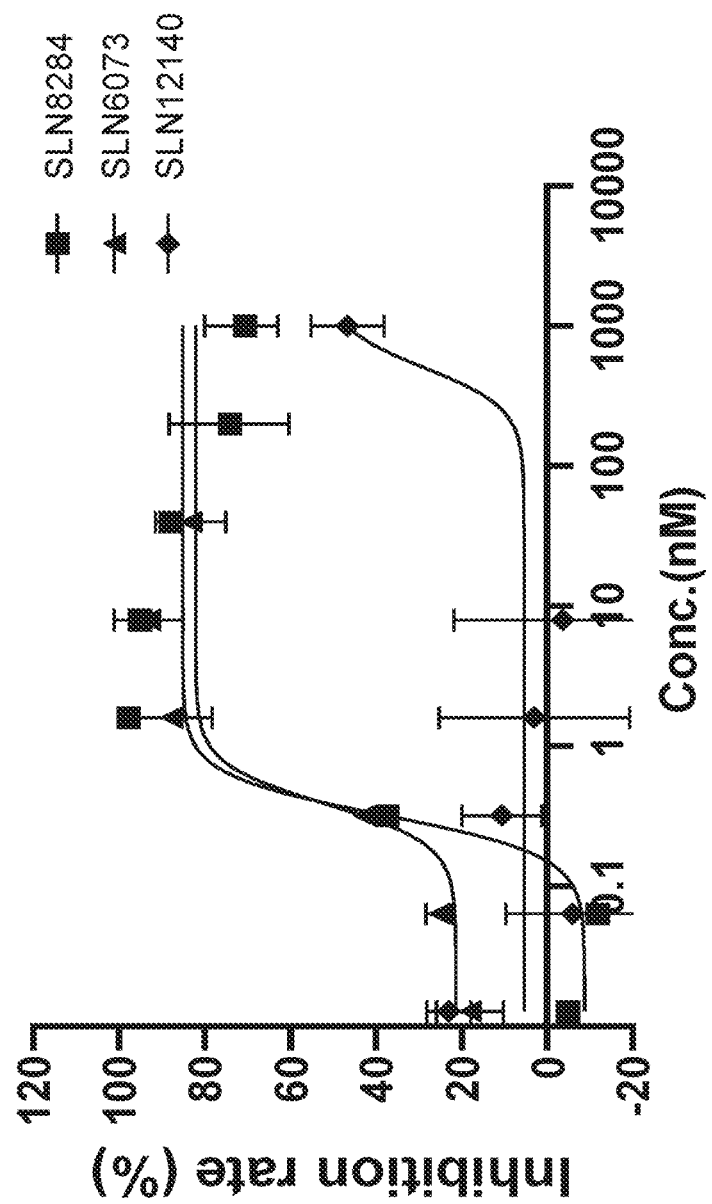
FIG. 27 Illustrates inhibition of VEGF-induced proliferation of human umbilical vein endothelial cells (HUVECs) by SLN8284, SLN6073, SLN12140.

All proteins are tested for the ability to inhibit VEGF signaling pathway (e.g., inhibition of VEGF activity) in a cell-based assay. For example, SLN8284 was tested for the ability to inhibit VEGF signaling pathway (e.g, inhibition of VEGF activity) in this cell-based assay and compared to the VEGF inhibitory activity of SLN6073 and SLN12140. Human Umbilical Vein Endothelial Cells are often used to demonstrate VEGF-dependent cell proliferation which can be inhibited by binding of fusion proteins to VEGF. In this assay, HUVECs are maintained in Endothelial Cell Growth Medium with 1% FBS. A 96-well flat bottom microtiter plate is seeded 3000 HUVEC cells each well in complete medium (1% FBS), and culture overnight. Discard the medium from the cell plate and add 100 µL of various concentrations of fusion proteins (serially diluted in PBS, starting from 1000 nM) from mixed with 50 ng/mL VEGF-A in each well and incubate for 72 hours at 37° C. Cell proliferation is assayed by adding 10 µL of CCK-8 (Dojindo, Inc.) to each well and incubate for 2.5 hours at 37° C. Cell proliferation is measured at OD absorption of 450 nm. Results showed that SLN8284 and SLN6073 significantly inhibited VEGF-induced HUVEC proliferation as compared to the control (SLN12140) and the inhibitory effect of SLN8284 was similar to SLN6073 (FIG. 27).

SLN8284 (SEQ ID NO: 114)
SLN6073 (SEQ ID NO: 113)

Example 11 SLN12140 Fusion with hTf Binding VHH (9056VHH)

11.1 Production of Anti-CFP Recombinant Antibodies with/without 9056VHH Domain

Figure 28:
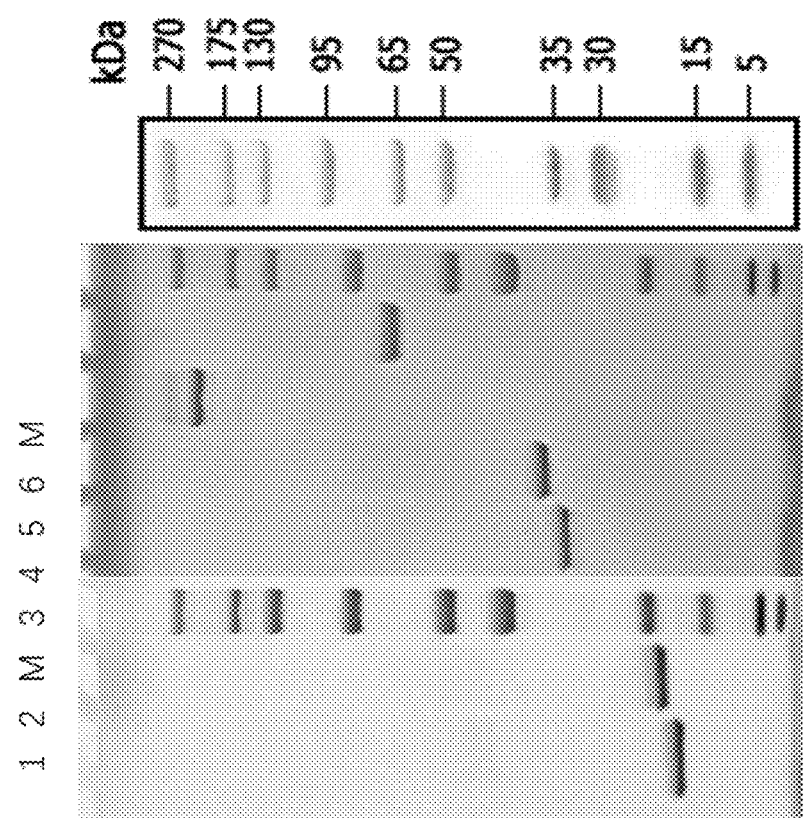
FIG. 28 Illustrates representative SDS-PAGE gels of the fusion proteins expressed in HEK293 cells. Purified fusion proteins SLN12147, SLN12149, SLN12150 under non-reducing conditions (lane 1,3,5) and reducing conditions (lane 2,4,6).

SLN12149(12075-(G4S)3-12083-(G4S)3-9056-G4S-His) and SLN12150 (12075-(G4S)3-12083-(G4S)3-Fc-(G4S)3-9056) fusion protein was constructed from SLN12147 (12075-(G4S)3-12083-(G4S)3-His) and SLN12140(12075-(G4S)3-12083-(G4S)3-Fc). Small scale production of recombinant proteins was performed using transient transfection of HEK293 cells with the recombinant plasmid using PEI as transfection reagent. Cultures were grown in 100 ml shaking flasks media for 5-7 days. Cells were removed by centrifugation and culture supernatants were used for protein purification by Ni-NTA or protein A sepharose. The purified proteins were analyzed with 4-12% gradient SDS-PAGE gel under non-reducing or reducing conditions (FIG. 28).

11.2 CFP Binding Assay with the Recombinant Antibodies in Different Species

Figure 29A:
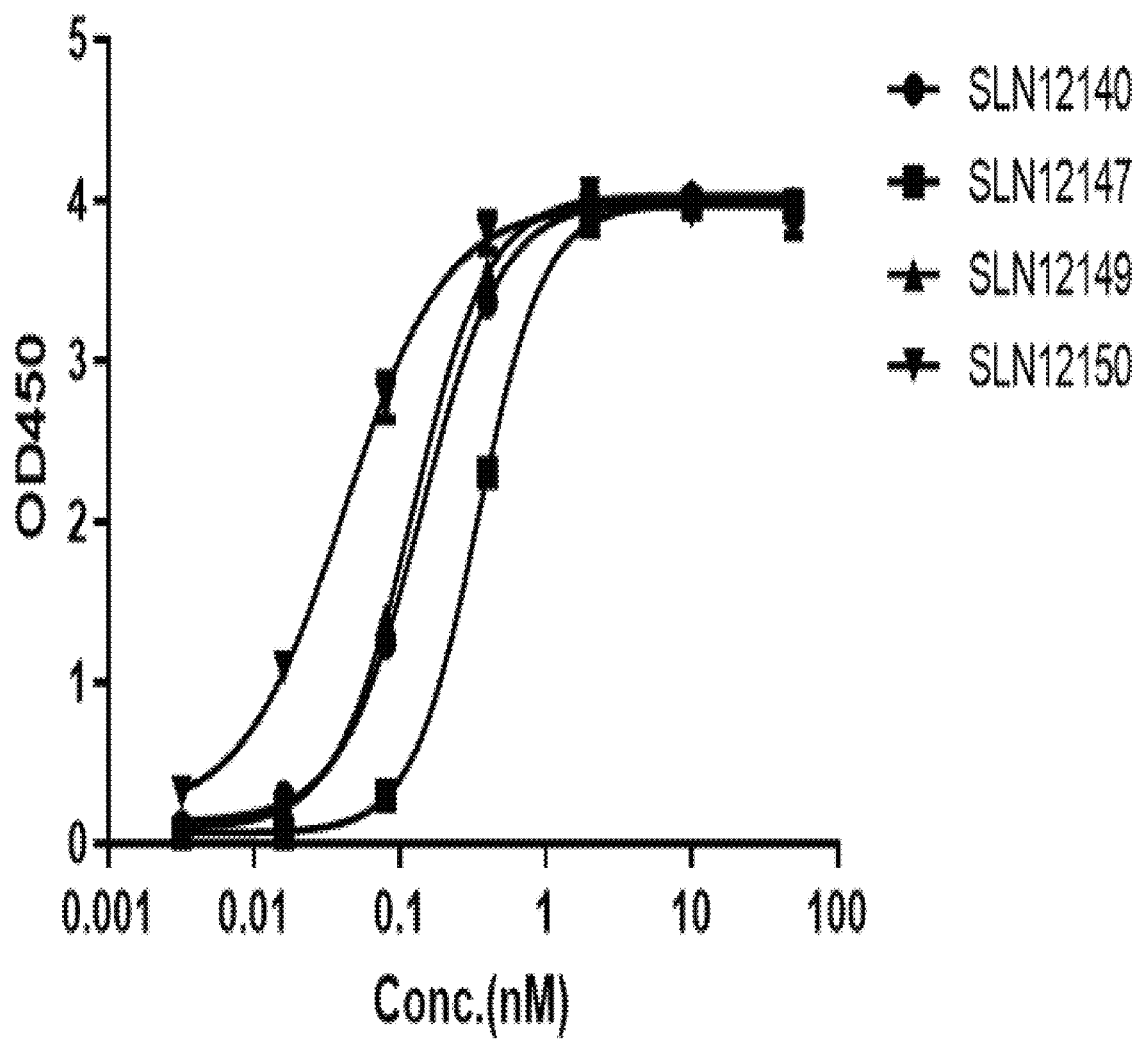
FIG. 29 Illustrates Elisa Binding results of SLN12140, SLN12147, SLN12149 and SLN12150 to different species' properdin in vitro. A) Human properdin binding. B) Cynomolgus macaques properdin binding. C) Mouse properdin binding.
Figure 29B:
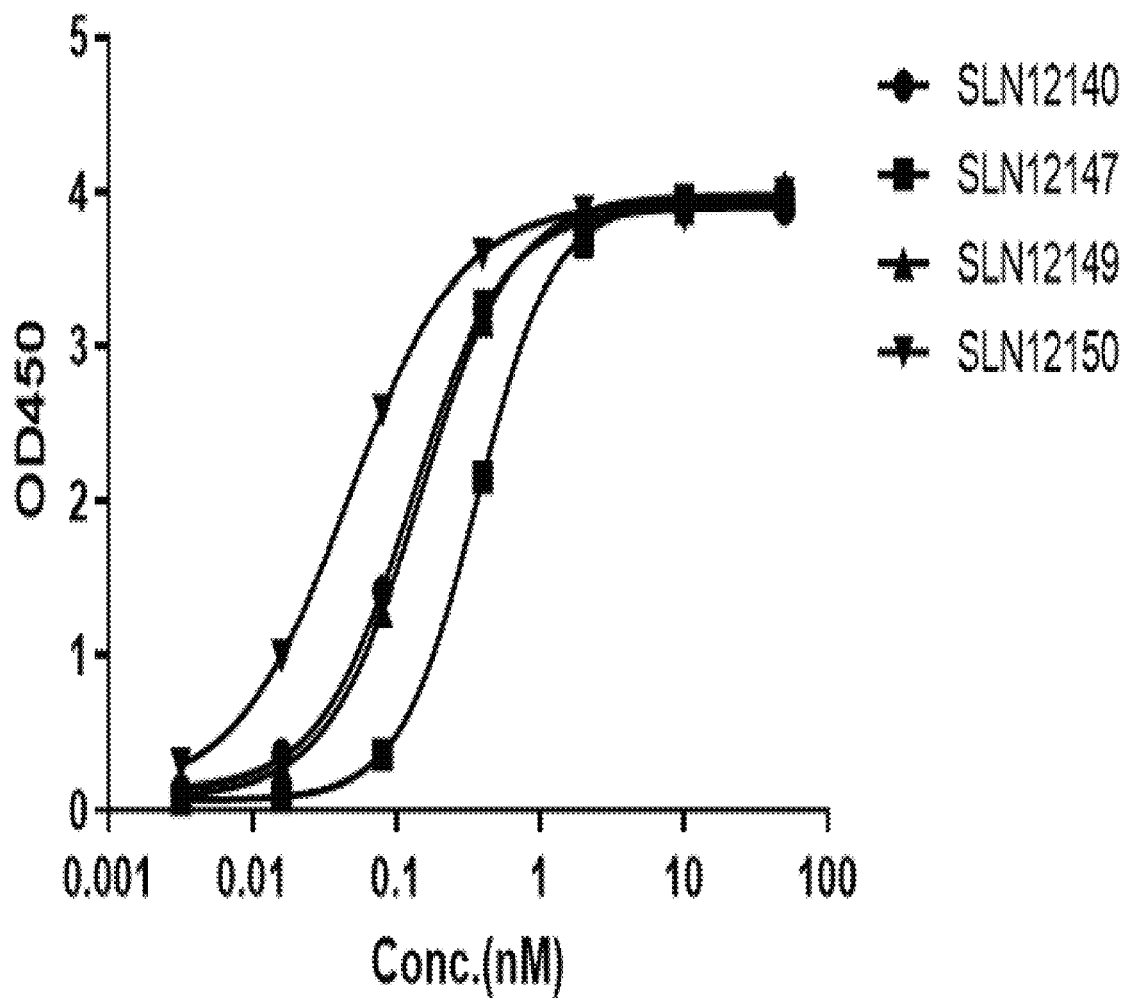
Figure 29C:
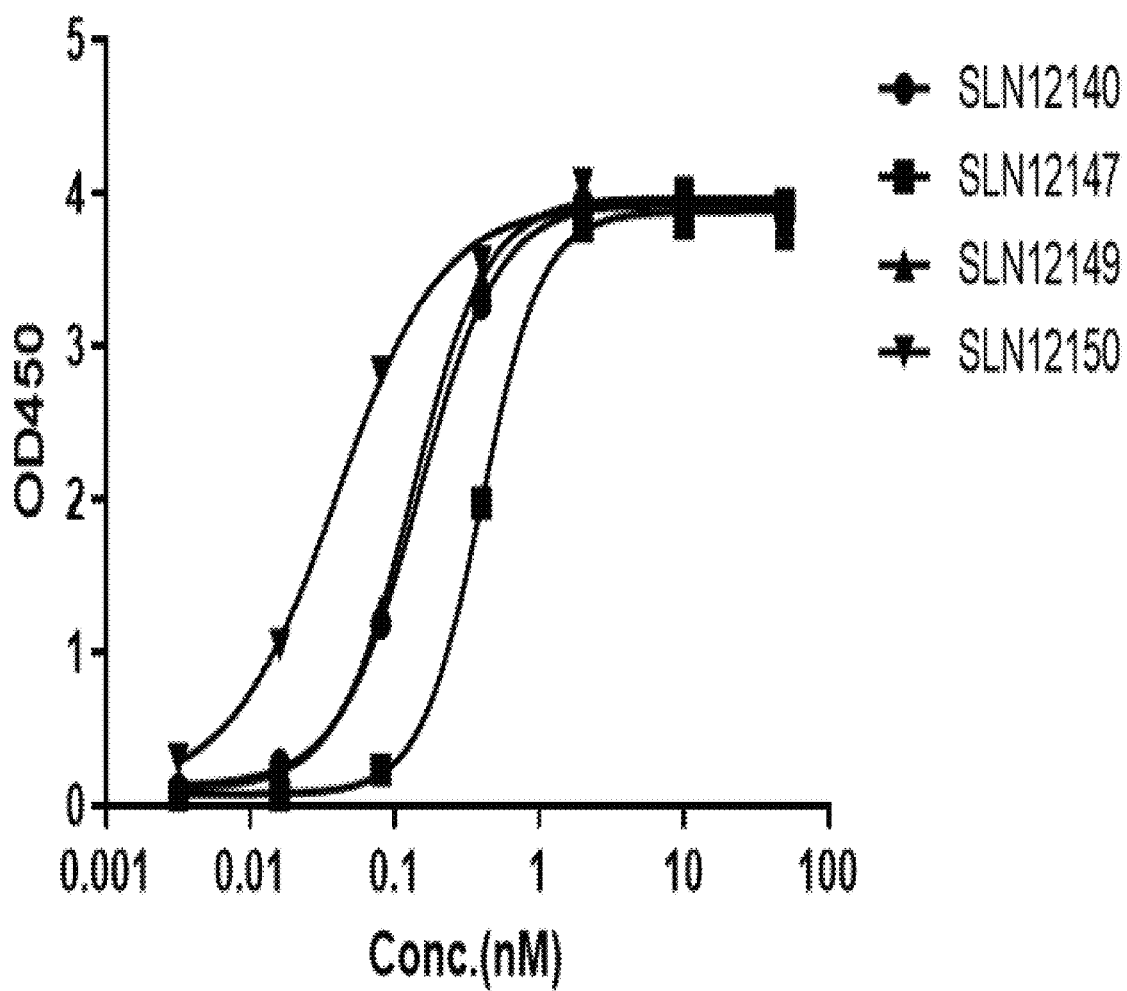
Figure 30A:
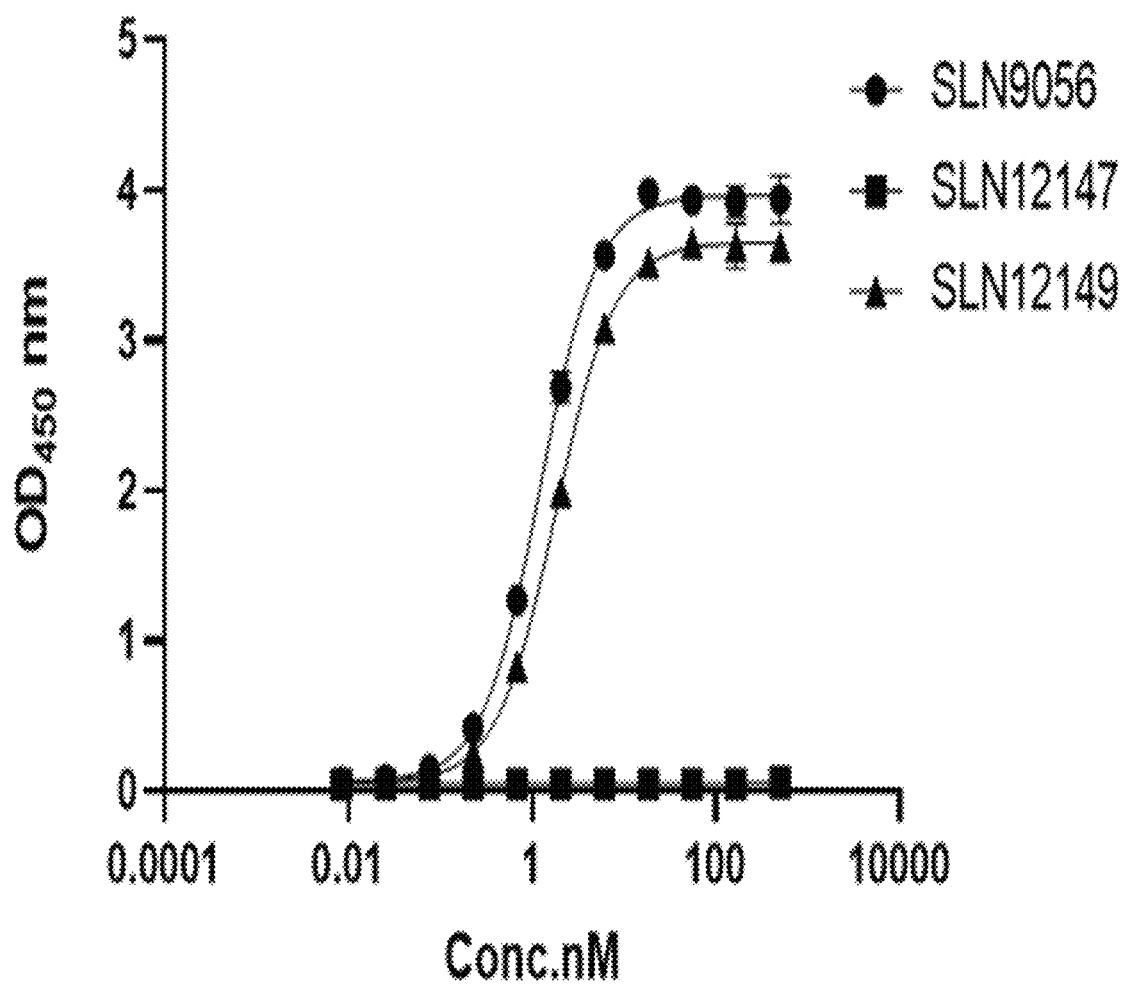
FIG. 30 Illustrates ELISA binding results of SLN12140, SLN12147, SLN12149, SLN12150 and SLN9056 to human transferrin (hTf) in vitro. A) Binding results of SLN12147, SLN12149 and SLN9056 with hTf at pH7.4; B) Binding results of SLN12147, SLN12149 and SLN9056 with hTf at pH6.0; C) Binding results of SLN12140, SLN12150 with hTf at pH7.4; D) Binding results of SLN12140, SLN12150 with hTf at pH6.0
Figure 30B:
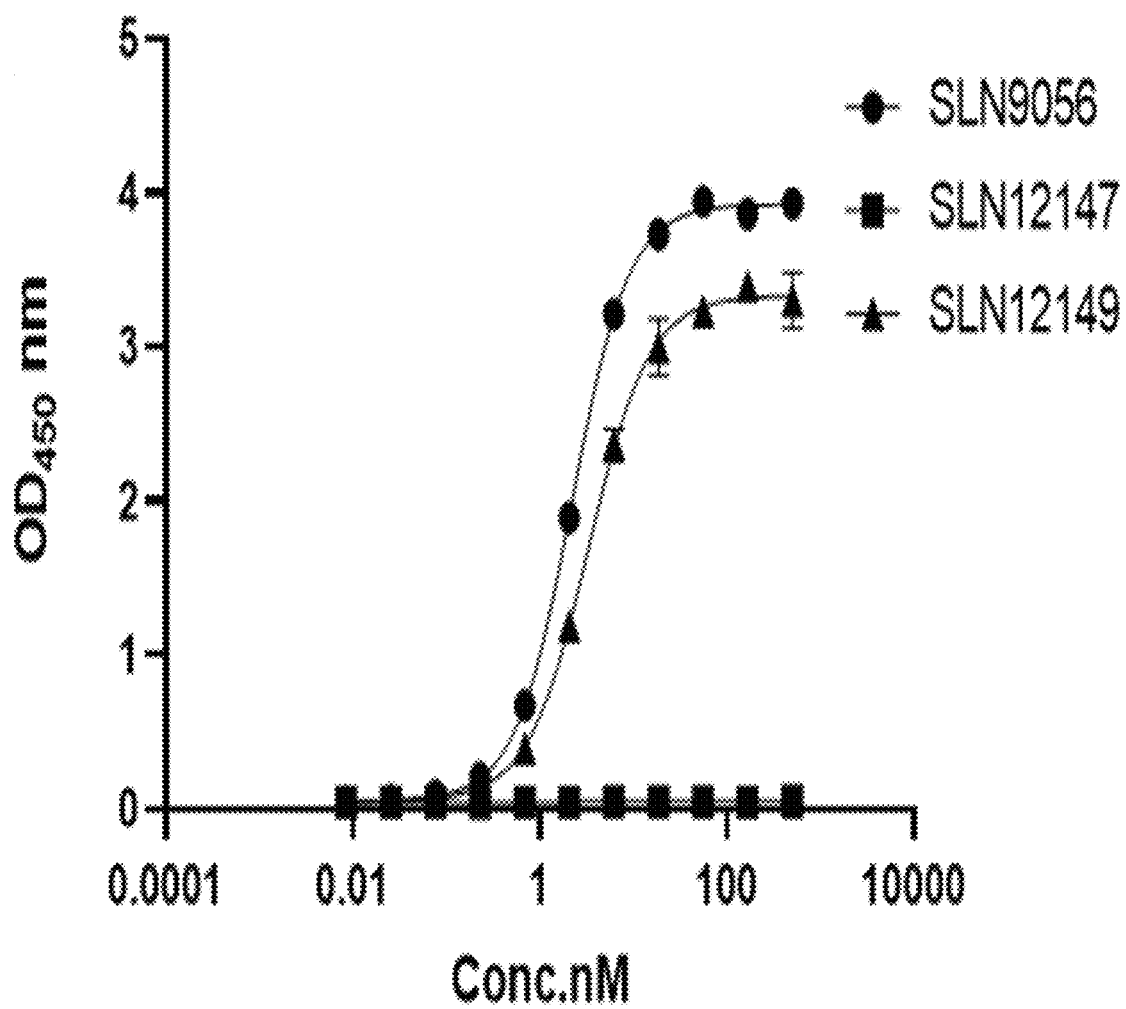
Figure 30C:
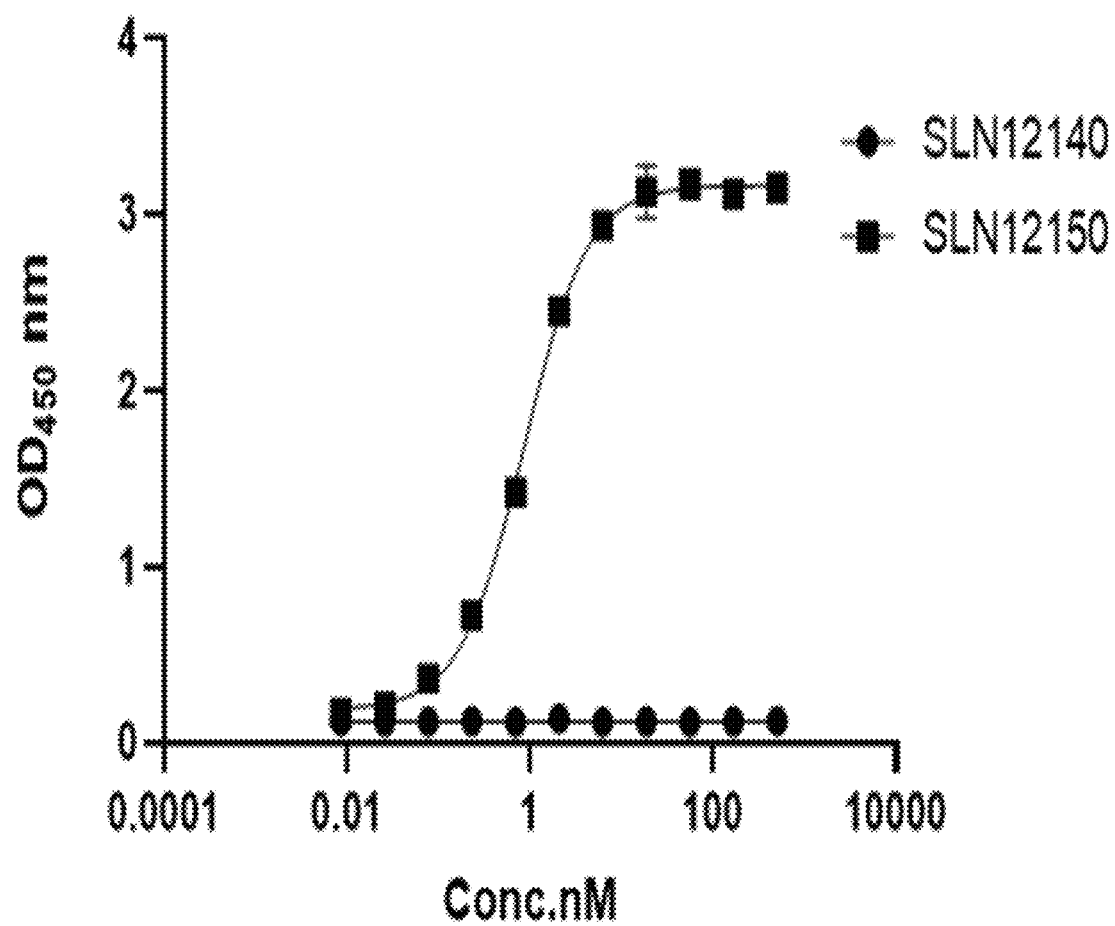
Figure 30D:
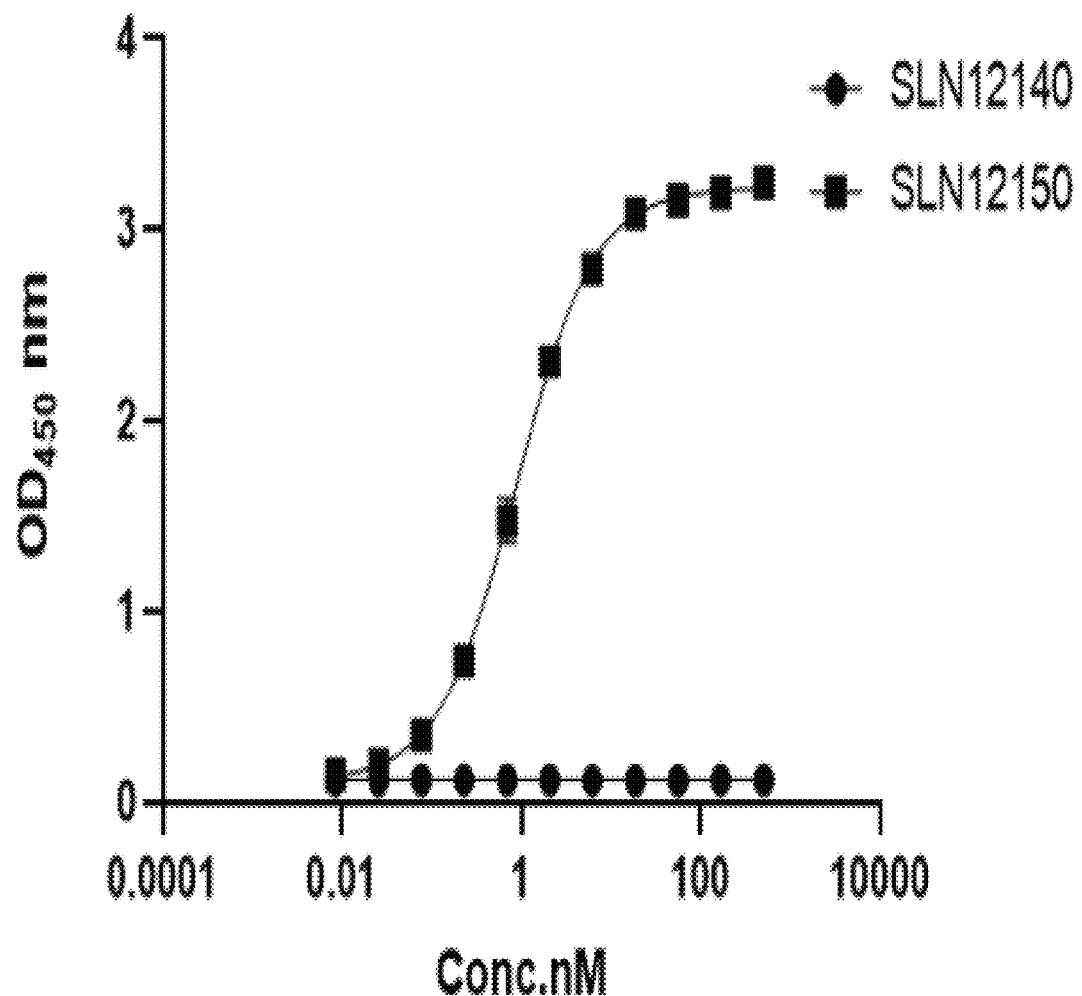

To test the binding activities of recombinant antibodies to CFP, 96-well microplates were coated with streptavidin (1 µg/ml in PBS, 100 µl/well) and incubated at 4° C. overnight. After 3 times of washing with PBST, the plates were blocked with 1% BSA in PBST at RT for 1 hr. After 3 times of washing with PBST, biotinylated human/rhesus/mouse CFP (10/5/2 µg/ml in 1% BSA, 100 µl/well) was added and incubate at RT for 1 h. After 3 times of washing with PBST, the recombinant antibodies were added and incubated at RT for 1 h (50 nM, 5× dilution, serially diluted in 1% BSA, 100 µl/well). SLN12143 (1 µg/ml, binding 12075/12083 humanized framework) and a secondary anti-mFc-HRP were incubated sequentially, before the plates were washed with PBST 3 times and incubated with substrate solution and stop solution as described above for ELISA (FIG. 29).

11.3 Human Transferrin Binding Assay with the Recombinant Antibodies

To test the binding activities of recombinant antibodies to human transferrin, 96-well microplates were coated with streptavidin (1 µg/ml in PBS, 100 µl/well) and incubated at 4° C. C overnight. After 3 times of washing with PBST, the plates were blocked with 1% BSA in PBST at RT for 1 hr. After 3 times of washing with PBST, was added and incubate at RT for 1 h. After 3 times of washing with PBST, the recombinant antibodies (1000 nM, 5× dilution, serially diluted in 1% BSA) were premixed with biotinylated human transferrin (2 ug/ml in 1% BSA), added the mixture (100 µl/wel) into the plates and incubated at RT for 1 h. Then, the secondary anti-hFc-HRP/anti-6×his-HRP were incubated sequentially, before the plates were washed with PBST 3 times and incubated with substrate solution and stop solution as described above for ELISA. (FIG. 30).

Figure 31A:
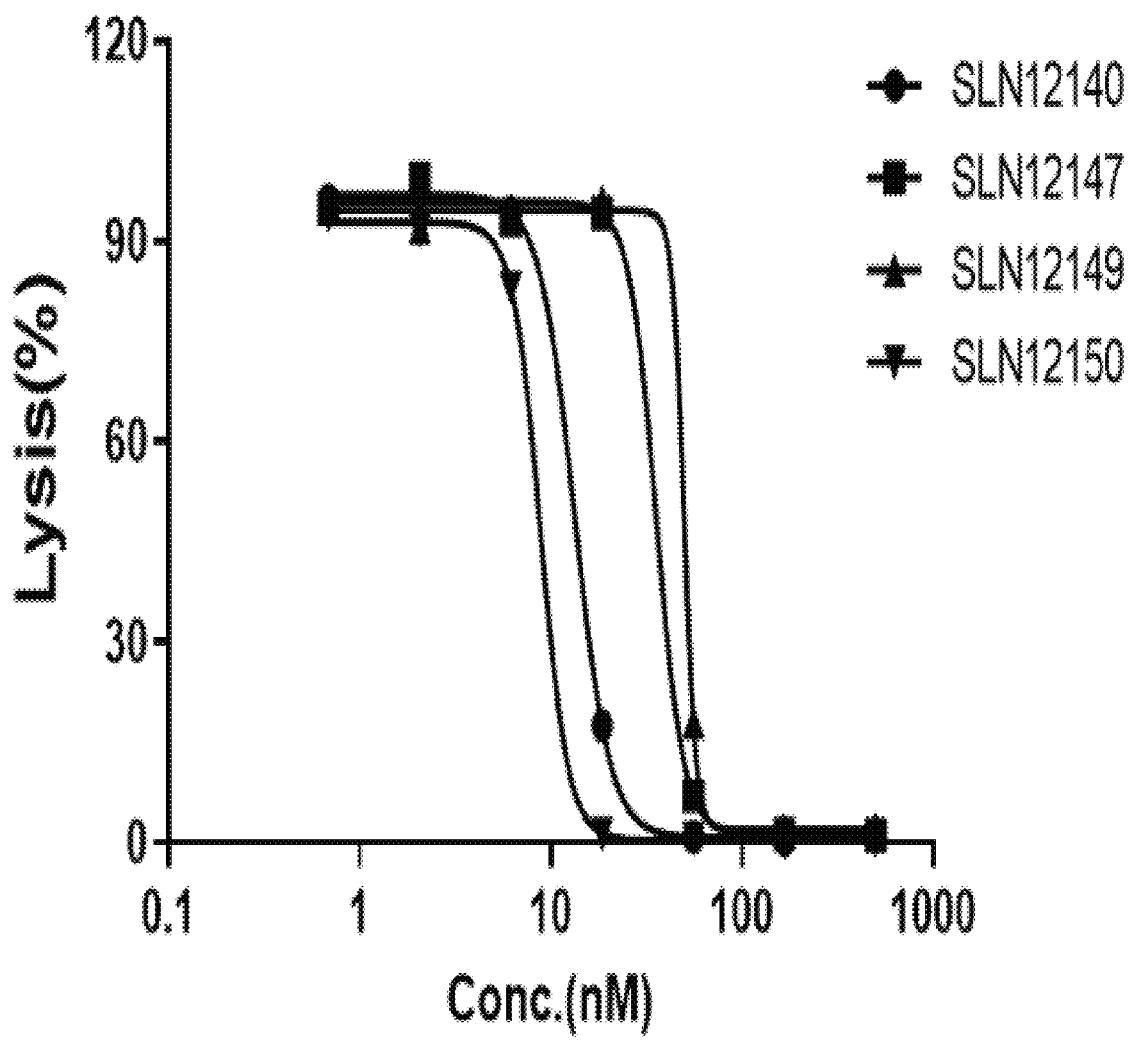
FIG. 31 Illustrates inhibiting different species AP activities with SLN12140, SLN12147, SLN12149 and SLN12150 in ELISA. A) Human AP activity with fusion proteins. B) Cynomolgus AP activity with fusion proteins. C) Mouse AP activity with fusion proteins.
Figure 31B:
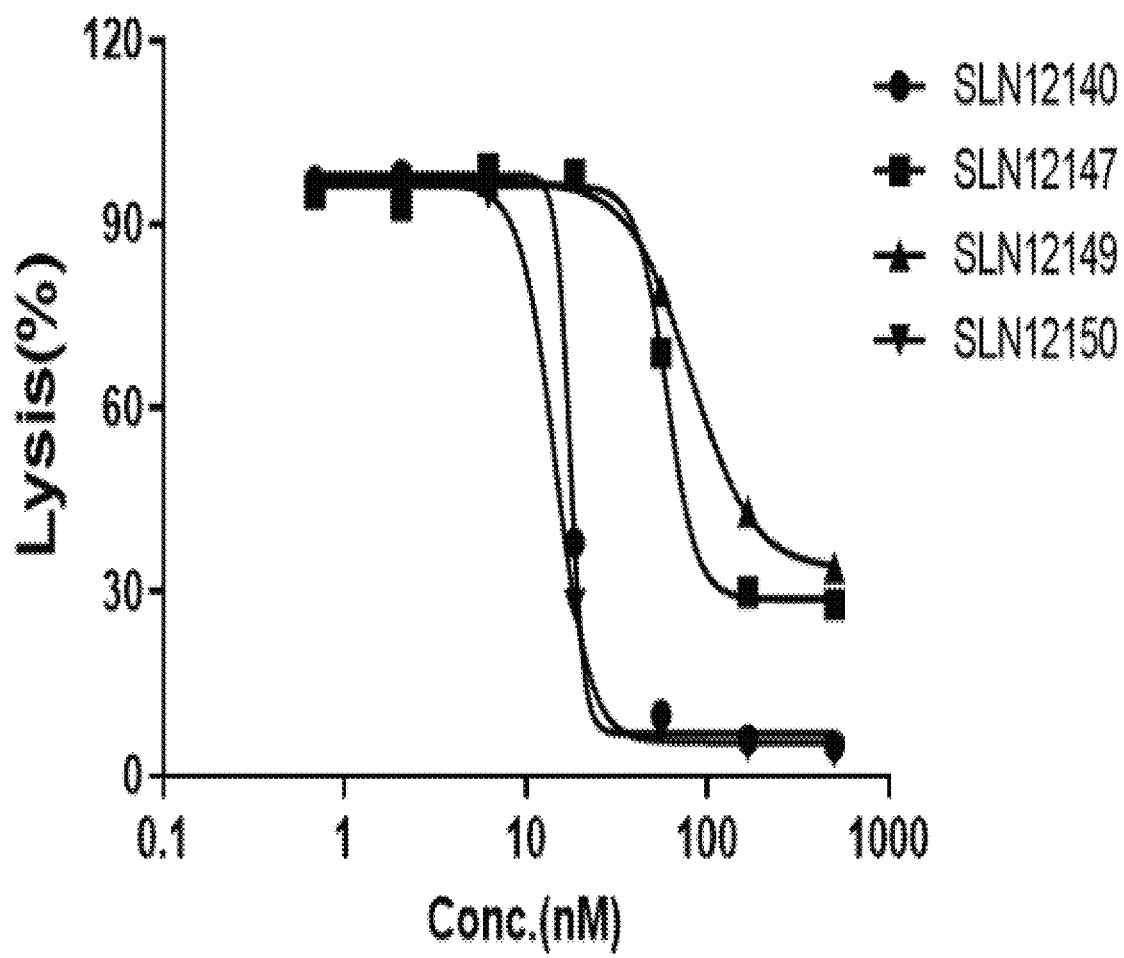
Figure 31C:
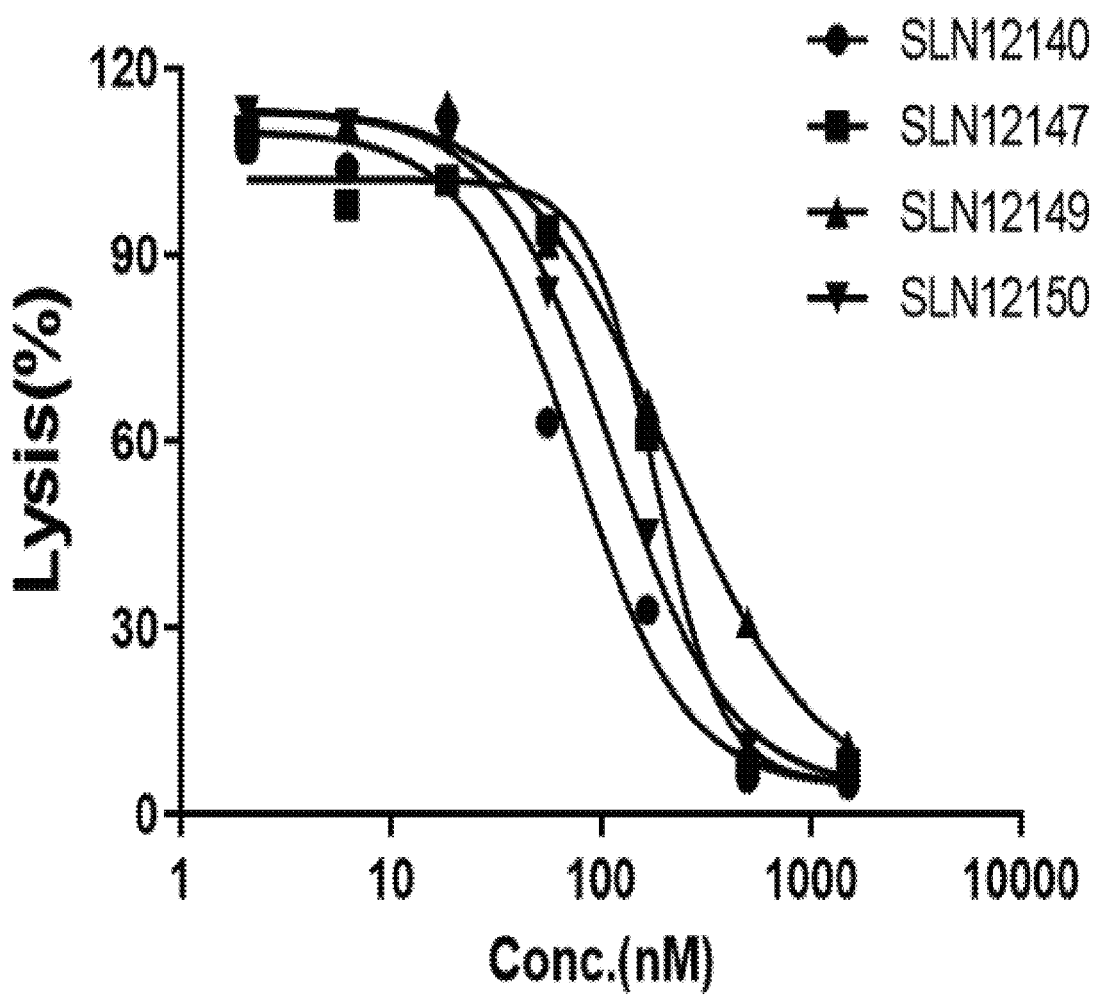
Figure 32A:
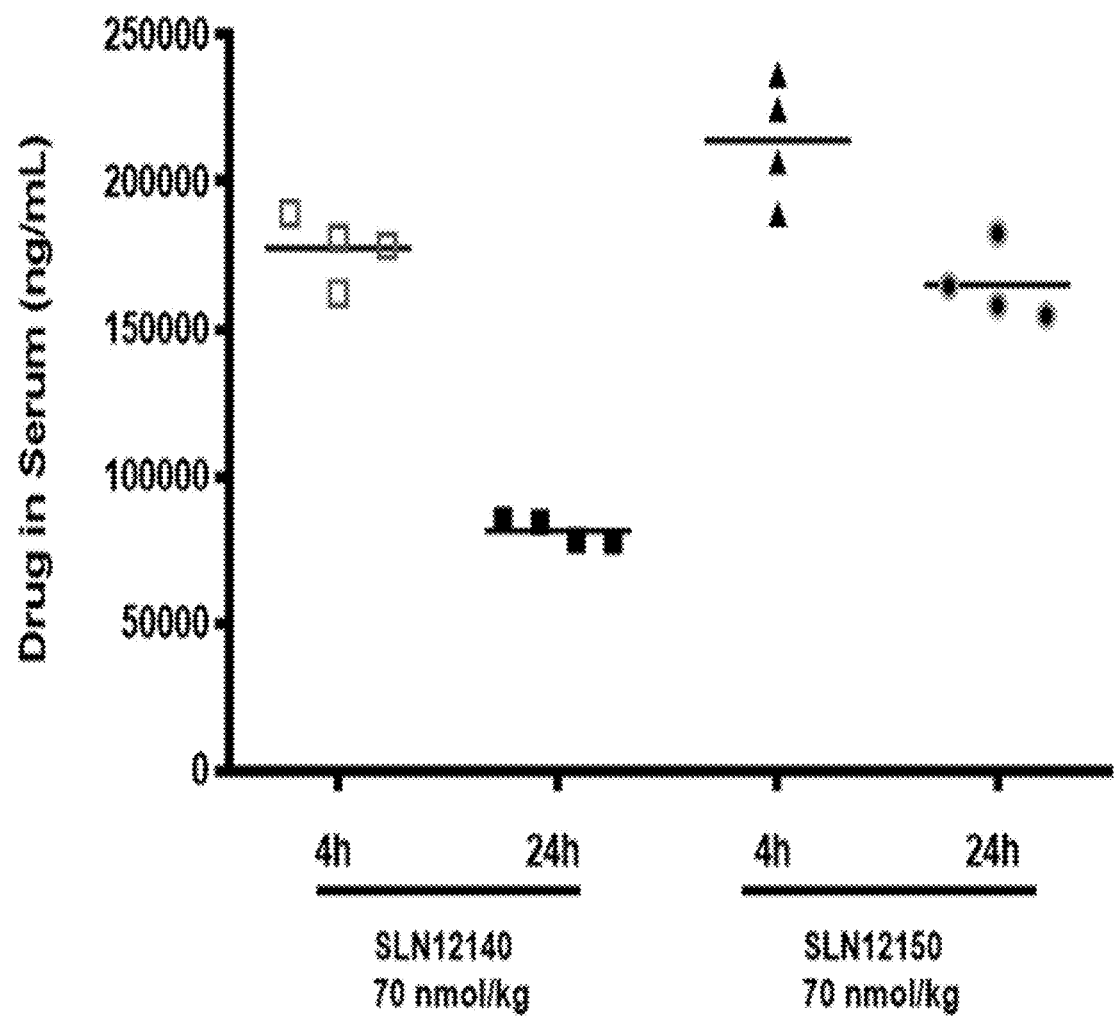
FIG. 32 Illustrates SLN12140 and SLN12150 PK results in Mouse. A) Drugs in Mouse serum. B) Drugs in Mouse Brain tissue. C) Drugs in Mouse CSF. D) Drugs ID % in Mouse Brain tissue.
Figure 32B:
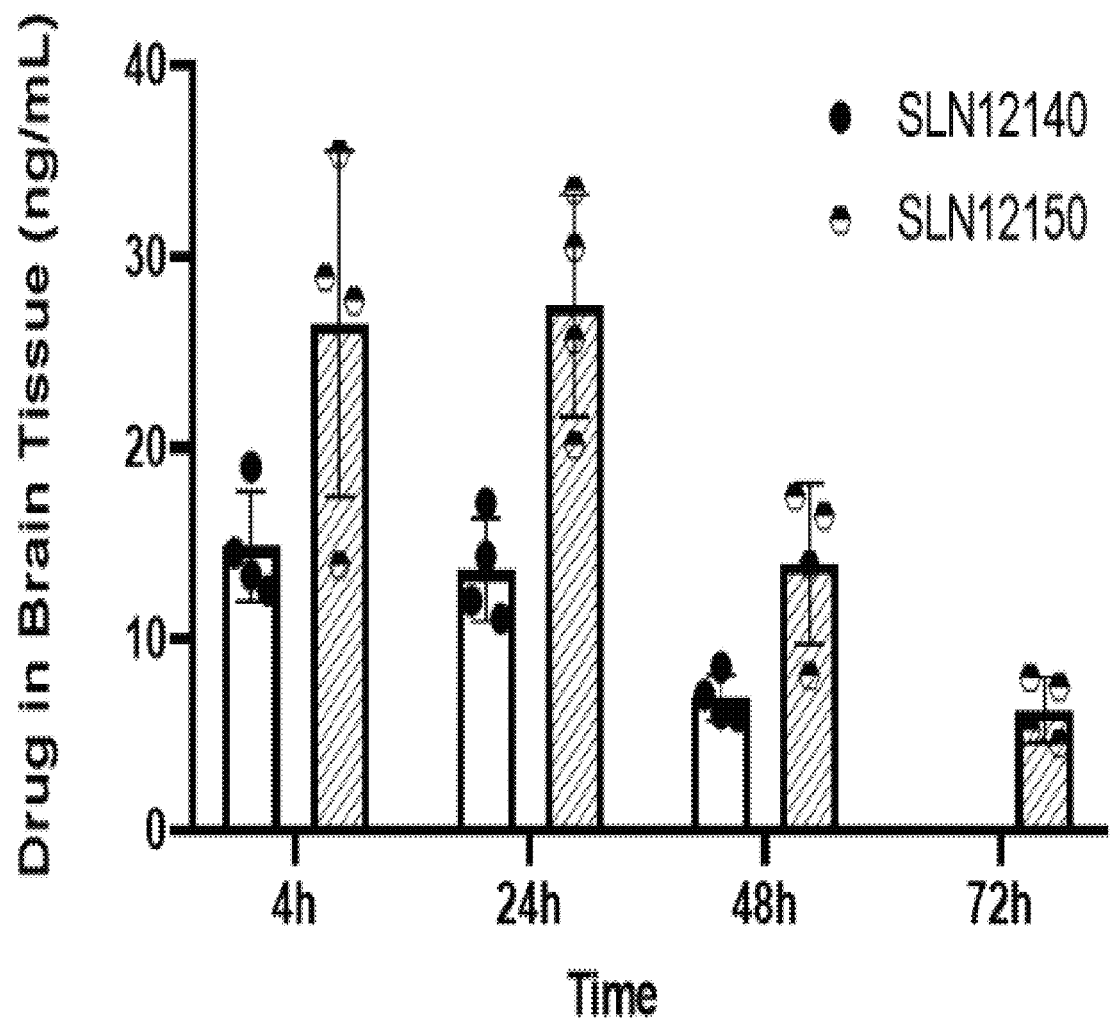
Figure 32C:
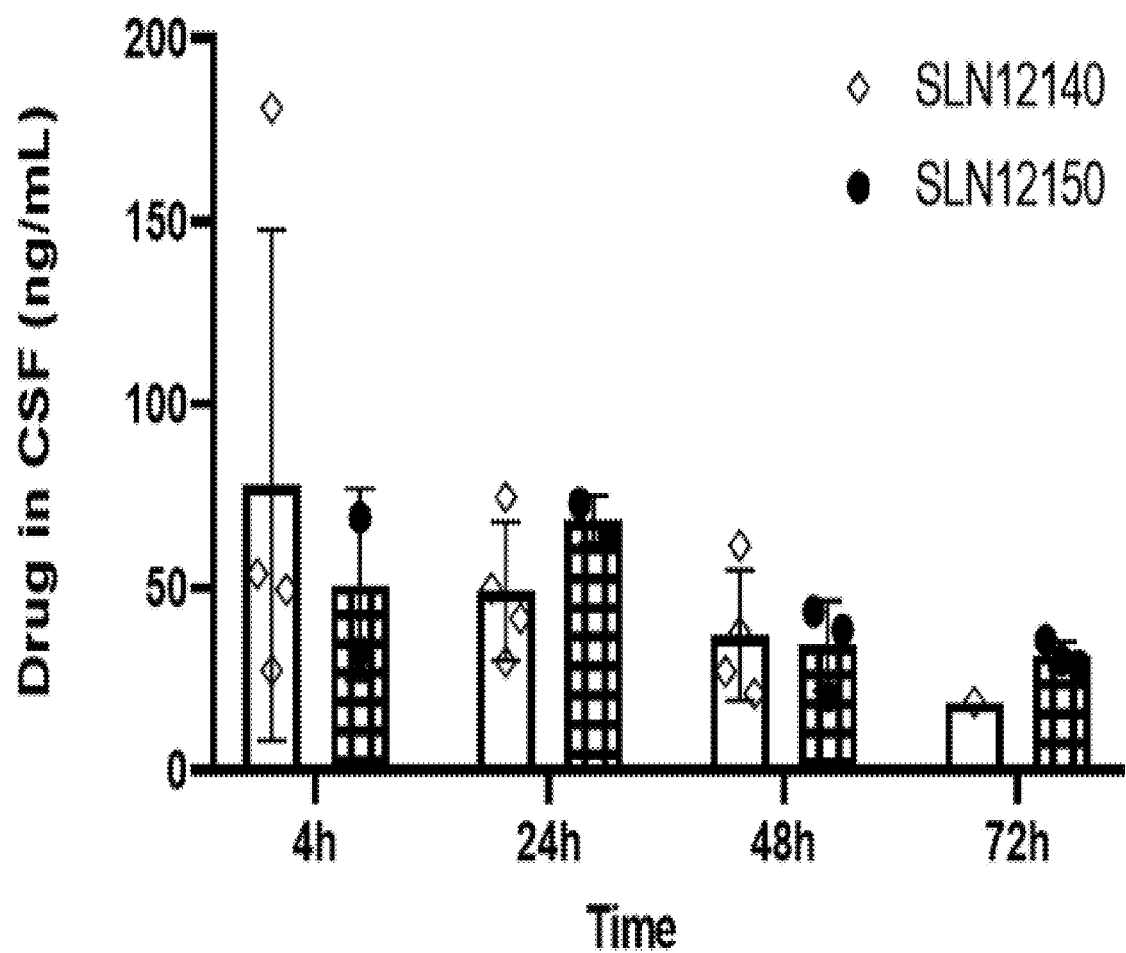
Figure 32D:
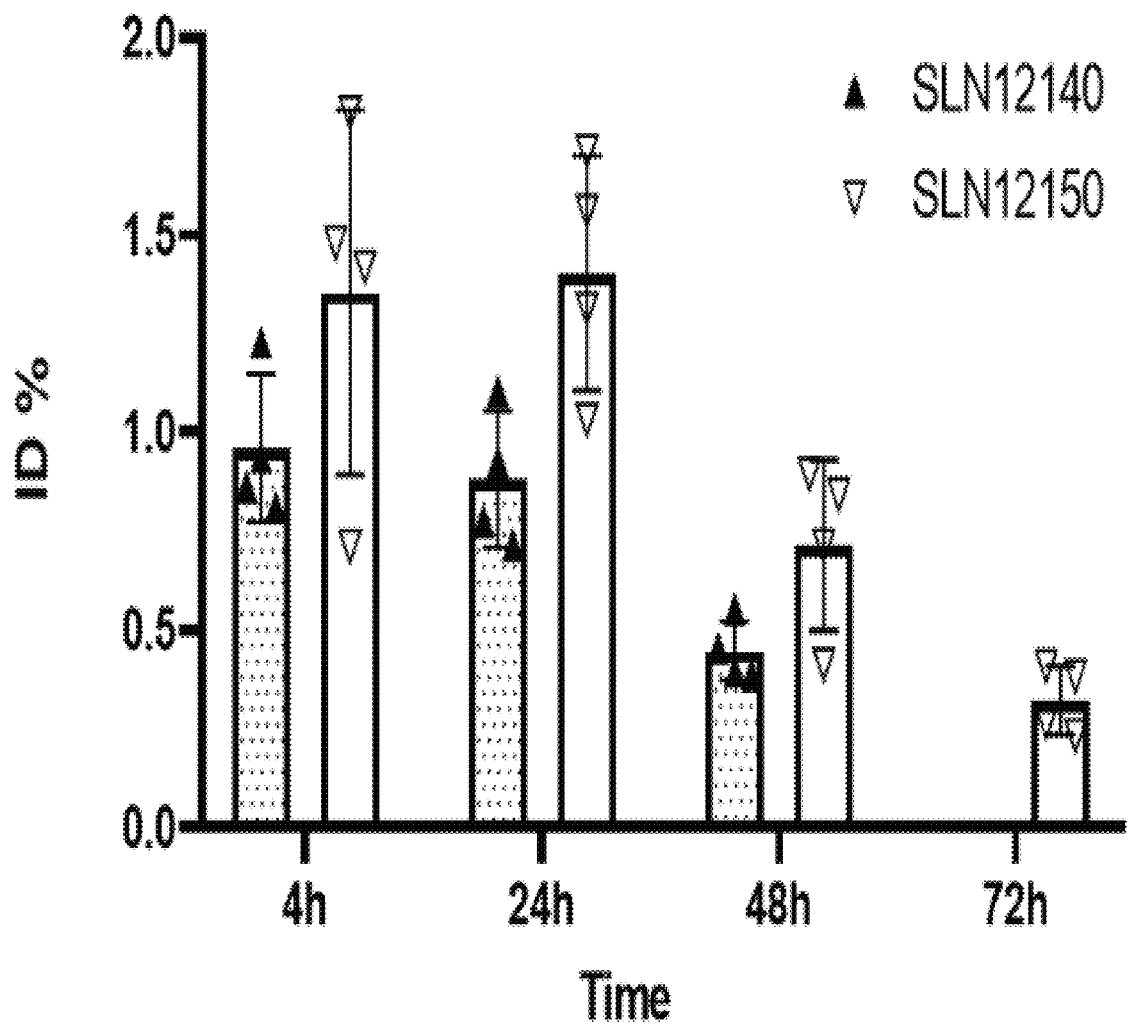

11.4 Inhibiting Human/Cynomolgus/Mouse AP Activity with the Recombinant Antibodies Recombinant antibodies were serially diluted with 1×PBS, then transfer to 96-well Plate with U bottom (50 µl/well). Prepare 20% human serum/20% cynomolgus serum with 1×AP buffer, 60% mouse serum with 2×AP buffer, incubate on ice for 30 minutes. Prepared the rabbit RBC during incubation of serum: 0.5 ml of rabbit erythrocytes ($4\times10^8$/ml) were washed three times with 1 ml of 1×AP buffer and resuspended to a final concentration of $5\times10^7$/ml (4 ml) in 1×AP buffer. Then the activated serum (50 µl/well) and red cell (50 µl/well) were added to sample well. The plate with human/cynomolgus serum were incubated 30 mins in 37° C., the plate with mouse serum were incubated 60 mins in 37° C. The plate was centrifuged at 600 rpm for 2 mins and 100 µL of the supernatant transferred to a new flat bottom 96-well plate. Hemoglobin release was determined at OD 405 nm using a microplate reader (FIG. 31).

11.5 Mouse BBB pK Assay in Mouse Tissues with the Recombinant Antibodies

11.5.1 Method Principle of PK Assay (SI.N12140/SLN12150/SLN12147/SLN12149)

This method utilizes an antibody sandwich mode by ELISA to detect analyte in mouse serum/brain tissue homogenate/CSF. The assay plate coated with SLN2102 is incubated overnight. On the next day, analyte in samples and STD/QC will be captured on the plate by SLN2102. After the sample incubation completed, detection antibody which Biotin labeled will be added to the plate. The plate is washed to remove excess detection antibody (Bio-SLN2108). SA-HRP is added to bind Biotin. After completion, TMB is added and the plate is read on Micro-plate Reader. The resulting OD is proportional to the amount of analyte presents in the samples and STD/QC (FIG. 32).

SLN12147 (SEQ ID NO: 116)
SLN12149 (SEQ ID NO: 117)
SLN12150 (SEQ ID NO: 118)

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

---

The invention claimed is:

1. An isolated antibody or an antigen-binding fragment thereof that specifically binds to properdin, wherein said antibody or the antigen-binding fragment thereof comprises a VHH, and said VHH comprises CDR1, CDR2 and CDR3, said CDR1 comprises the amino acid sequence $X_1 X_2 CMX_5$, wherein $X_1$ is H or S or T or Y, $X_2$ is G or Y, and $X_5$ is A or G, said CDR2 comprises the amino acid sequence of SEQ ID NO: 55, and said CDR3 comprises the amino acid sequence of SEQ ID NO: 12, SEQ ID NO: 13, SEQ ID NO: 14, SEQ ID NO: 15, SEQ ID NO: 16, or SEQ ID NO: 17.

2. The antibody or an antigen-binding fragment thereof of claim 1, wherein said VHH comprises CDR1, CDR2 and CDR3, said CDR1 comprises the amino acid sequence of SEQ ID NO: 1, SEQ ID NO: 2, SEQ ID NO: 3, SEQ ID NO: 4, or SEQ ID NO: 5, said CDR2 comprises the amino acid sequence of SEQ ID NO: 6, SEQ ID NO: 7, SEQ ID NO: 8, SEQ ID NO: 9, SEQ ID NO: 10, or SEQ ID NO: 11, and said CDR3 comprises the amino acid sequence of SEQ ID NO: 12, SEQ ID NO: 13, SEQ ID NO: 14, SEQ ID NO: 15, SEQ ID NO: 16, or SEQ ID NO: 17.

3. The antibody or an antigen-binding fragment thereof of claim 1, wherein said VHH comprises CDR1, CDR2 and CDR3, and said CDR1, CDR2 and CDR3comprises any set of amino acid sequences selected from the group consisting of:

1) CDR1: SEQ ID NO: 1, CDR2: SEQ ID NO: 6, CDR3: SEQ ID NO: 12;
2) CDR1: SEQ ID NO: 2, CDR2: SEQ ID NO: 7, CDR3: SEQ ID NO: 13;
3) CDR1: SEQ ID NO: 3, CDR2: SEQ ID NO: 8, CDR3: SEQ ID NO: 14;
4) CDR1: SEQ ID NO: 4, CDR2: SEQ ID NO: 9, CDR3: SEQ ID NO: 15;

5) CDR1: SEQ ID NO: 5, CDR2: SEQ ID NO: 10, CDR3: SEQ ID NO: 16; and
6) CDR1: SEQ ID NO: 3, CDR2: SEQ ID NO: 11, CDR3: SEQ ID NO: 17.

4. The antibody or an antigen-binding fragment thereof of claim 1, wherein said VHH comprises FR1, FR2, FR3 and FR4, said FR1 comprises the amino acid sequence of SEQ ID NO: 56, said FR2 comprises the amino acid sequence of SEQ ID NO: 57, said FR3 comprises the amino acid sequence of SEQ ID NO: 58, and said FR4 comprises the amino acid sequence of SEQ ID NO: 59.

5. The antibody or an antigen-binding fragment thereof of claim 1, wherein said VHH comprises FR1, FR2, FR3 and FR4, and said VHH comprises any set of amino acid sequences selected from the group consisting of:
1) FR1: SEQ ID NO: 18, FR2: SEQ ID NO: 31, FR3: SEQ ID NO: 41, FR4: SEQ ID NO: 52;
2) FR1: SEQ ID NO: 19, FR2: SEQ ID NO: 32, FR3: SEQ ID NO: 42, FR4: SEQ ID NO: 53;
3) FR1: SEQ ID NO: 19, FR2: SEQ ID NO: 32, FR3: SEQ ID NO: 43, FR4: SEQ ID NO: 53;
4) FR1: SEQ ID NO: 20, FR2: SEQ ID NO: 32, FR3: SEQ ID NO: 43, FR4: SEQ ID NO: 53;
5) FR1: SEQ ID NO: 20, FR2: SEQ ID NO: 31, FR3: SEQ ID NO: 43, FR4: SEQ ID NO: 53;
6) FR1: SEQ ID NO: 21, FR2: SEQ ID NO: 33, FR3: SEQ ID NO: 44, FR4: SEQ ID NO: 52;
7) FR1: SEQ ID NO: 22, FR2: SEQ ID NO: 34, FR3: SEQ ID NO: 42, FR4: SEQ ID NO: 53;
8) FR1: SEQ ID NO: 22, FR2: SEQ ID NO: 34, FR3: SEQ ID NO: 45, FR4: SEQ ID NO: 53;
9) FR1: SEQ ID NO: 22, FR2: SEQ ID NO: 33, FR3: SEQ ID NO: 45, FR4: SEQ ID NO: 53;
10) FR1: SEQ ID NO: 23, FR2: SEQ ID NO: 35, FR3: SEQ ID NO: 46, FR4: SEQ ID NO: 52;
11) FR1: SEQ ID NO: 24, FR2: SEQ ID NO: 36, FR3: SEQ ID NO: 47, FR4: SEQ ID NO: 53;
12) FR1: SEQ ID NO: 24, FR2: SEQ ID NO: 36, FR3: SEQ ID NO: 48, FR4: SEQ ID NO: 53;
13) FR1: SEQ ID NO: 25, FR2: SEQ ID NO: 36, FR3: SEQ ID NO: 48, FR4: SEQ ID NO: 53;
14) FR1: SEQ ID NO: 25, FR2: SEQ ID NO: 35, FR3: SEQ ID NO: 48, FR4: SEQ ID NO: 53;
15) FR1: SEQ ID NO: 26, FR2: SEQ ID NO: 37, FR3: SEQ ID NO: 49, FR4: SEQ ID NO: 52;
16) FR1: SEQ ID NO: 27, FR2: SEQ ID NO: 38, FR3: SEQ ID NO: 42, FR4: SEQ ID NO: 53;
17) FR1: SEQ ID NO: 27, FR2: SEQ ID NO: 39, FR3: SEQ ID NO: 42, FR4: SEQ ID NO: 53;
18) FR1: SEQ ID NO: 28, FR2: SEQ ID NO: 39, FR3: SEQ ID NO: 42, FR4: SEQ ID NO: 53;
19) FR1: SEQ ID NO: 28, FR2: SEQ ID NO: 39, FR3: SEQ ID NO: 43, FR4: SEQ ID NO: 53;
20) FR1: SEQ ID NO: 28, FR2: SEQ ID NO: 37, FR3: SEQ ID NO: 43, FR4: SEQ ID NO: 53;
21) FR1: SEQ ID NO: 29, FR2: SEQ ID NO: 31, FR3: SEQ ID NO: 50, FR4: SEQ ID NO: 52; and
22) FR1: SEQ ID NO: 30, FR2: SEQ ID NO: 40, FR3: SEQ ID NO: 51, FR4: SEQ ID NO: 52.

6. The antibody or an antigen-binding fragment thereof of claim 1, wherein said VHH comprises the amino acid sequence of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 92, and SEQ ID NO: 93.

7. The antibody or an antigen-binding fragment thereof of claim 1, wherein said antibody comprises an antibody heavy chain constant region, wherein said heavy-chain constant region comprises a human Fc region, wherein said human Fc region comprises the amino acid sequence of SEQ ID NO: 109.

8. The antibody or an antigen-binding fragment thereof of claim 1, which is directly or indirectly linked to a second antigen binding domain.

9. The antibody or an antigen-binding fragment thereof of claim 8, which comprises the amino acid sequence of SEQ ID NO: 81 or SEQ ID NO: 116.

10. The antibody or an antigen-binding fragment thereof of claim 1, which is indirectly linked to to a second antigen binding domain via a linker, wherein said linker is a poly-glycine linker, wherein said linker comprises the amino acid sequence of SEQ ID NO: 108: GGGGSGGGGSGGGGS.

11. A fusion protein, comprising antibody or an antigen-binding fragment thereof of claim 1.

12. The fusion protein of claim 11, which further comprises a functionally active protein, wherein said antibody or an antigen-binding fragment thereof is directly or indirectly linked to said functionally active protein.

13. The fusion protein of claim 12, wherein said functionally active protein is indirectly linked to the antibody or the antigen-binding fragment thereof via a linker, wherein said linker is a poly-glycine linker, wherein said linker comprises the amino acid sequence of SEQ ID NO: 108: GGGGSGGGGSGGGGS.

14. The fusion protein of claim 12, wherein said functionally active protein is factor H.

15. The fusion protein of claim 12, wherein said functionally active protein is VEGF inhibiting protein.

16. The fusion protein of claim 12, wherein said functionally active protein is transferrin binding protein.

17. The fusion protein of claim 11, which comprises the amino acid sequence of SEQ ID NO: 82, SEQ ID NO: 114, SEQ ID NO: 117 or SEQ ID NO: 118.

18. A polypeptide, comprising the antibody or the antigen-binding fragment thereof of claim 1.

19. An immunoconjugate, comprising the antibody or the antigen-binding fragment thereof of claim 1.

20. A cell, comprising the antibody or the antigen-binding fragment thereof of claim 1.

21. A pharmaceutical composition, comprising the antibody or the antigen-binding fragment thereof of claim 1, and a pharmaceutically acceptable adjuvant and/or excipient.

22. A pharmaceutical combination, comprising the antibody or the antigen-binding fragment thereof of claim 1 and at least one other active ingredient.

23. A method for detecting properdin, the method comprising:
contacting a sample with the antibody or the antigen-binding fragment thereof of claim 1, and
detecting the presence, a level of expression, or a combination thereof of properdin in the sample.

* * * * *

SEQUENCE LISTING

```
Sequence total quantity: 118
SEQ ID NO: 1            moltype = AA  length = 5
FEATURE                 Location/Qualifiers
REGION                  1..5
                        note = CDR1
source                  1..5
                        mol_type = protein
                        organism = synthetic construct
SEQUENCE: 1
YYCMG                                                                   5

SEQ ID NO: 2            moltype = AA  length = 5
FEATURE                 Location/Qualifiers
REGION                  1..5
                        note = CDR1
source                  1..5
                        mol_type = protein
                        organism = synthetic construct
```

```
SEQUENCE: 2
SYCMG                                                                              5

SEQ ID NO: 3             moltype = AA   length = 5
FEATURE                  Location/Qualifiers
REGION                   1..5
                         note = CDR1
source                   1..5
                         mol_type = protein
                         organism = synthetic construct
SEQUENCE: 3
HYCMG                                                                              5

SEQ ID NO: 4             moltype = AA   length = 5
FEATURE                  Location/Qualifiers
REGION                   1..5
                         note = CDR1
source                   1..5
                         mol_type = protein
                         organism = synthetic construct
SEQUENCE: 4
SYCMA                                                                              5

SEQ ID NO: 5             moltype = AA   length = 5
FEATURE                  Location/Qualifiers
REGION                   1..5
                         note = CDR1
source                   1..5
                         mol_type = protein
                         organism = synthetic construct
SEQUENCE: 5
TGCMA                                                                              5

SEQ ID NO: 6             moltype = AA   length = 16
FEATURE                  Location/Qualifiers
REGION                   1..16
                         note = CDR2
source                   1..16
                         mol_type = protein
                         organism = synthetic construct
SEQUENCE: 6
FDTSDGSKYY ADSVKG                                                                 16

SEQ ID NO: 7             moltype = AA   length = 15
FEATURE                  Location/Qualifiers
REGION                   1..15
                         note = CDR2
source                   1..15
                         mol_type = protein
                         organism = synthetic construct
SEQUENCE: 7
INSDGRTSYA DSVKG                                                                  15

SEQ ID NO: 8             moltype = AA   length = 15
FEATURE                  Location/Qualifiers
REGION                   1..15
                         note = CDR2
source                   1..15
                         mol_type = protein
                         organism = synthetic construct
SEQUENCE: 8
IRRDGVTRYA DSVKG                                                                  15

SEQ ID NO: 9             moltype = AA   length = 15
FEATURE                  Location/Qualifiers
REGION                   1..15
                         note = CDR2
source                   1..15
                         mol_type = protein
                         organism = synthetic construct
SEQUENCE: 9
IDTDGSTSYT DSVKG                                                                  15

SEQ ID NO: 10            moltype = AA   length = 16
FEATURE                  Location/Qualifiers
REGION                   1..16
                         note = CDR2
source                   1..16
                         mol_type = protein
```

```
                                              -continued
                            organism = synthetic construct
SEQUENCE: 10
IIRGERGEWY ADSVKG                                                          16

SEQ ID NO: 11               moltype = AA  length = 15
FEATURE                     Location/Qualifiers
REGION                      1..15
                            note = CDR2
source                      1..15
                            mol_type = protein
                            organism = synthetic construct
SEQUENCE: 11
ITSDGWTRYA DSVKG                                                           15

SEQ ID NO: 12               moltype = AA  length = 18
FEATURE                     Location/Qualifiers
REGION                      1..18
                            note = CDR3
source                      1..18
                            mol_type = protein
                            organism = synthetic construct
SEQUENCE: 12
RPFYVGGTCL PRLTDFSI                                                        18

SEQ ID NO: 13               moltype = AA  length = 22
FEATURE                     Location/Qualifiers
REGION                      1..22
                            note = CDR3
source                      1..22
                            mol_type = protein
                            organism = synthetic construct
SEQUENCE: 13
VILPPTDGME YSCNYPAAEY NY                                                   22

SEQ ID NO: 14               moltype = AA  length = 17
FEATURE                     Location/Qualifiers
REGION                      1..17
                            note = CDR3
source                      1..17
                            mol_type = protein
                            organism = synthetic construct
SEQUENCE: 14
QRDCGISGLL WQSSVGY                                                         17

SEQ ID NO: 15               moltype = AA  length = 19
FEATURE                     Location/Qualifiers
REGION                      1..19
                            note = CDR3
source                      1..19
                            mol_type = protein
                            organism = synthetic construct
SEQUENCE: 15
APWLLAYGDY CVTRPDFGE                                                       19

SEQ ID NO: 16               moltype = AA  length = 14
FEATURE                     Location/Qualifiers
REGION                      1..14
                            note = CDR3
source                      1..14
                            mol_type = protein
                            organism = synthetic construct
SEQUENCE: 16
DYRYPCDGRS NYDY                                                            14

SEQ ID NO: 17               moltype = AA  length = 18
FEATURE                     Location/Qualifiers
REGION                      1..18
                            note = CDR3
source                      1..18
                            mol_type = protein
                            organism = synthetic construct
SEQUENCE: 17
TPEGSCSTGV STPSTFRV                                                        18

SEQ ID NO: 18               moltype = AA  length = 27
FEATURE                     Location/Qualifiers
REGION                      1..27
                            note = FR1
source                      1..27
```

```
                        mol_type = protein
                        organism = synthetic construct
SEQUENCE: 18
HVQLVESGGG SVQAGGSLRL SCEAFEY                                            27

SEQ ID NO: 19           moltype = AA   length = 27
FEATURE                 Location/Qualifiers
REGION                  1..27
                        note = FR1
source                  1..27
                        mol_type = protein
                        organism = synthetic construct
SEQUENCE: 19
EVQLVESGGG LVQPGGSLRL SCAAFEY                                            27

SEQ ID NO: 20           moltype = AA   length = 27
FEATURE                 Location/Qualifiers
REGION                  1..27
                        note = FR1
source                  1..27
                        mol_type = protein
                        organism = synthetic construct
SEQUENCE: 20
EVQLVESGGG LVQPGGSLRL SCEAFEY                                            27

SEQ ID NO: 21           moltype = AA   length = 30
FEATURE                 Location/Qualifiers
REGION                  1..30
                        note = FR1
source                  1..30
                        mol_type = protein
                        organism = synthetic construct
SEQUENCE: 21
HVQLVESGGG SVQSGGSLRL SCAASAYIYS                                         30

SEQ ID NO: 22           moltype = AA   length = 30
FEATURE                 Location/Qualifiers
REGION                  1..30
                        note = FR1
source                  1..30
                        mol_type = protein
                        organism = synthetic construct
SEQUENCE: 22
EVQLVESGGG LVQPGGSLRL SCAASAYIYS                                         30

SEQ ID NO: 23           moltype = AA   length = 30
FEATURE                 Location/Qualifiers
REGION                  1..30
                        note = FR1
source                  1..30
                        mol_type = protein
                        organism = synthetic construct
SEQUENCE: 23
QVQLVESGGG SVQSGGSLRL SCVDSGYTYG                                         30

SEQ ID NO: 24           moltype = AA   length = 30
FEATURE                 Location/Qualifiers
REGION                  1..30
                        note = FR1
source                  1..30
                        mol_type = protein
                        organism = synthetic construct
SEQUENCE: 24
QVQLVESGGG VVQPGGSLRL SCAASGYTYG                                         30

SEQ ID NO: 25           moltype = AA   length = 30
FEATURE                 Location/Qualifiers
REGION                  1..30
                        note = FR1
source                  1..30
                        mol_type = protein
                        organism = synthetic construct
SEQUENCE: 25
QVQLVESGGG VVQPGGSLRL SCADSGYTYG                                         30

SEQ ID NO: 26           moltype = AA   length = 30
FEATURE                 Location/Qualifiers
REGION                  1..30
                        note = FR1
```

```
source                      1..30
                            mol_type = protein
                            organism = synthetic construct
SEQUENCE: 26
HVQLVESGGG SVQAGGSLRL SCAHPEYTSS                                        30

SEQ ID NO: 27               moltype = AA  length = 30
FEATURE                     Location/Qualifiers
REGION                      1..30
                            note = FR1
source                      1..30
                            mol_type = protein
                            organism = synthetic construct
SEQUENCE: 27
EVQLVESGGG LVQPGGSLRL SCAASEYTSS                                        30

SEQ ID NO: 28               moltype = AA  length = 30
FEATURE                     Location/Qualifiers
REGION                      1..30
                            note = FR1
source                      1..30
                            mol_type = protein
                            organism = synthetic construct
SEQUENCE: 28
EVQLVESGGG LVQPGGSLRL SCAHPEYTSS                                        30

SEQ ID NO: 29               moltype = AA  length = 30
FEATURE                     Location/Qualifiers
REGION                      1..30
                            note = FR1
source                      1..30
                            mol_type = protein
                            organism = synthetic construct
SEQUENCE: 29
QVQLVESGGG SVHAGGSLRL SCAVSGYTHS                                        30

SEQ ID NO: 30               moltype = AA  length = 30
FEATURE                     Location/Qualifiers
REGION                      1..30
                            note = FR1
source                      1..30
                            mol_type = protein
                            organism = synthetic construct
SEQUENCE: 30
DVQLVESGGG SVQVGGSLRL SCVDSGYTYT                                        30

SEQ ID NO: 31               moltype = AA  length = 15
FEATURE                     Location/Qualifiers
REGION                      1..15
                            note = FR2
source                      1..15
                            mol_type = protein
                            organism = synthetic construct
SEQUENCE: 31
WFRQAPGKER EGVAS                                                        15

SEQ ID NO: 32               moltype = AA  length = 15
FEATURE                     Location/Qualifiers
REGION                      1..15
                            note = FR2
source                      1..15
                            mol_type = protein
                            organism = synthetic construct
SEQUENCE: 32
WFRQAPGKGL EGVAS                                                        15

SEQ ID NO: 33               moltype = AA  length = 15
FEATURE                     Location/Qualifiers
REGION                      1..15
                            note = FR2
source                      1..15
                            mol_type = protein
                            organism = synthetic construct
SEQUENCE: 33
WFRQAPGKER ERVSV                                                        15

SEQ ID NO: 34               moltype = AA  length = 15
FEATURE                     Location/Qualifiers
REGION                      1..15
```

```
                        note = FR2
source                  1..15
                        mol_type = protein
                        organism = synthetic construct
SEQUENCE: 34
WFRQAPGKGL ERVSV                                                        15

SEQ ID NO: 35           moltype = AA  length = 15
FEATURE                 Location/Qualifiers
REGION                  1..15
                        note = FR2
source                  1..15
                        mol_type = protein
                        organism = synthetic construct
SEQUENCE: 35
WFRQAPGKER EGVAA                                                        15

SEQ ID NO: 36           moltype = AA  length = 15
FEATURE                 Location/Qualifiers
REGION                  1..15
                        note = FR2
source                  1..15
                        mol_type = protein
                        organism = synthetic construct
SEQUENCE: 36
WFRQAPGKGL EGVAA                                                        15

SEQ ID NO: 37           moltype = AA  length = 15
FEATURE                 Location/Qualifiers
REGION                  1..15
                        note = FR2
source                  1..15
                        mol_type = protein
                        organism = synthetic construct
SEQUENCE: 37
WIRQAPGKER EGVAA                                                        15

SEQ ID NO: 38           moltype = AA  length = 15
FEATURE                 Location/Qualifiers
REGION                  1..15
                        note = FR2
source                  1..15
                        mol_type = protein
                        organism = synthetic construct
SEQUENCE: 38
WIRQAPGKGL EGVSA                                                        15

SEQ ID NO: 39           moltype = AA  length = 15
FEATURE                 Location/Qualifiers
REGION                  1..15
                        note = FR2
source                  1..15
                        mol_type = protein
                        organism = synthetic construct
SEQUENCE: 39
WIRQAPGKGL EGVAA                                                        15

SEQ ID NO: 40           moltype = AA  length = 15
FEATURE                 Location/Qualifiers
REGION                  1..15
                        note = FR2
source                  1..15
                        mol_type = protein
                        organism = synthetic construct
SEQUENCE: 40
WFRQAPGEER EGVAV                                                        15

SEQ ID NO: 41           moltype = AA  length = 32
FEATURE                 Location/Qualifiers
REGION                  1..32
                        note = FR3
source                  1..32
                        mol_type = protein
                        organism = synthetic construct
SEQUENCE: 41
RFTISKDIAK NTLYLEMNIL QAEDTAMYYC AA                                     32

SEQ ID NO: 42           moltype = AA  length = 32
FEATURE                 Location/Qualifiers
```

```
REGION                     1..32
                           note = FR3
source                     1..32
                           mol_type = protein
                           organism = synthetic construct
SEQUENCE: 42
RFTISRDNSK NTLYLQMNSL RAEDTAVYYC AA                                32

SEQ ID NO: 43              moltype = AA  length = 32
FEATURE                    Location/Qualifiers
REGION                     1..32
                           note = FR3
source                     1..32
                           mol_type = protein
                           organism = synthetic construct
SEQUENCE: 43
RFTISKDNSK NTLYLQMNSL RAEDTAVYYC AA                                32

SEQ ID NO: 44              moltype = AA  length = 32
FEATURE                    Location/Qualifiers
REGION                     1..32
                           note = FR3
source                     1..32
                           mol_type = protein
                           organism = synthetic construct
SEQUENCE: 44
RFTISQDNAK NTLYLQMNSL KPEDTAMYYC AA                                32

SEQ ID NO: 45              moltype = AA  length = 32
FEATURE                    Location/Qualifiers
REGION                     1..32
                           note = FR3
source                     1..32
                           mol_type = protein
                           organism = synthetic construct
SEQUENCE: 45
RFTISQDNSK NTLYLQMNSL RAEDTAVYYC AA                                32

SEQ ID NO: 46              moltype = AA  length = 32
FEATURE                    Location/Qualifiers
REGION                     1..32
                           note = FR3
source                     1..32
                           mol_type = protein
                           organism = synthetic construct
SEQUENCE: 46
RFTISLDNAK STLYLQMNSL KAEDTAMYYC AT                                32

SEQ ID NO: 47              moltype = AA  length = 32
FEATURE                    Location/Qualifiers
REGION                     1..32
                           note = FR3
source                     1..32
                           mol_type = protein
                           organism = synthetic construct
SEQUENCE: 47
RFTISRDNSK NTLYLQMNSL RAEDTAVYYC AT                                32

SEQ ID NO: 48              moltype = AA  length = 32
FEATURE                    Location/Qualifiers
REGION                     1..32
                           note = FR3
source                     1..32
                           mol_type = protein
                           organism = synthetic construct
SEQUENCE: 48
RFTISLDNSK NTLYLQMNSL RAEDTAVYYC AT                                32

SEQ ID NO: 49              moltype = AA  length = 32
FEATURE                    Location/Qualifiers
REGION                     1..32
                           note = FR3
source                     1..32
                           mol_type = protein
                           organism = synthetic construct
SEQUENCE: 49
RFTISKDNAK NTLYLQMNNL KPEDTAMYYC AA                                32

SEQ ID NO: 50              moltype = AA  length = 32
```

```
FEATURE                 Location/Qualifiers
REGION                  1..32
                        note = FR3
source                  1..32
                        mol_type = protein
                        organism = synthetic construct
SEQUENCE: 50
RFTISQDNAE NTLYLQMNSL KSEDTAMYYC AA                                      32

SEQ ID NO: 51           moltype = AA  length = 32
FEATURE                 Location/Qualifiers
REGION                  1..32
                        note = FR3
source                  1..32
                        mol_type = protein
                        organism = synthetic construct
SEQUENCE: 51
RFTISKDNAL NTLYLQMNSL KPEDTAMYYC AT                                      32

SEQ ID NO: 52           moltype = AA  length = 11
FEATURE                 Location/Qualifiers
REGION                  1..11
                        note = FR4
source                  1..11
                        mol_type = protein
                        organism = synthetic construct
SEQUENCE: 52
WGQGTQVTVS S                                                             11

SEQ ID NO: 53           moltype = AA  length = 11
FEATURE                 Location/Qualifiers
REGION                  1..11
                        note = FR4
source                  1..11
                        mol_type = protein
                        organism = synthetic construct
SEQUENCE: 53
WGQGTLVTVS S                                                             11

SEQ ID NO: 54           moltype =  length =
SEQUENCE: 54
000

SEQ ID NO: 55           moltype = AA  length = 16
FEATURE                 Location/Qualifiers
REGION                  1..16
                        note = 1-CDR2; 2-CDR2; 3-CDR2; 4-CDR2; 5-CDR2; 6-CDR2
SITE                    1
                        note = misc_feature - Xaa = Phe, Ile or missing
SITE                    2
                        note = misc_feature - Xaa = Asp or Ile
SITE                    3
                        note = misc_feature - Xaa = Asp, Asn, Arg or Thr
SITE                    4
                        note = misc_feature - Xaa = Gly, Arg, Ser or Thr
SITE                    5
                        note = misc_feature - Xaa = Asp or Glu
SITE                    6
                        note = misc_feature - Xaa = Gly or Arg
SITE                    7
                        note = misc_feature - Xaa = Gly, Arg, Ser, Val or Trp
SITE                    8
                        note = misc_feature - Xaa = Glu, Lys or Thr
SITE                    9
                        note = misc_feature - Xaa = Arg, Ser, Trp or Tyr
SITE                    11
                        note = misc_feature - Xaa = Ala or Thr
source                  1..16
                        mol_type = protein
                        organism = synthetic construct
SEQUENCE: 55
XXXXXXXXXY XDSVKG                                                        16

SEQ ID NO: 56           moltype = AA  length = 30
FEATURE                 Location/Qualifiers
REGION                  1..30
                        note = 1-FR1-M; 1-FR1-H1; 1-FR1-H2; 1-FR1-H3; 1-FR1-H4;
                        1-FR1-H5; 2-FR1-M; 2-FR1-H1; 2-FR1-H2; 2-FR1-H3; 3-FR1-M;
                        3-FR1-H1; 3-FR1-H2; 3-FR1-H3; 3-FR1-H4; 4-FR1-M; 4-FR1-H1;
```

|  |  |
|---|---|
|  | 4-FR1-H2; 4-FR1-H3; 4-FR1-H4; 4-FR1-H5; 5-FR1; 6-FR1 |
| SITE | 1 |
|  | note = misc_feature - Xaa = Asp, Glu, His or Gln |
| SITE | 11 |
|  | note = misc_feature - Xaa = Leu, Ser or Val |
| SITE | 13 |
|  | note = misc_feature - Xaa = His or Gln |
| SITE | 14 |
|  | note = misc_feature - Xaa = Ala, Pro, Ser or Val |
| SITE | 23 |
|  | note = misc_feature - Xaa = Ala, Glu or Val |
| SITE | 24 |
|  | note = misc_feature - Xaa = Ala, Asp, His or Val |
| SITE | 25 |
|  | note = misc_feature - Xaa = Phe, Pro or Ser |
| SITE | 26 |
|  | note = misc_feature - Xaa = Ala, Glu or Gly |
| SITE | 28 |
|  | note = misc_feature - Xaa = Ile, Thr or missing |
| SITE | 29 |
|  | note = misc_feature - Xaa = His, Ser, Tyr or missing |
| SITE | 30 |
|  | note = misc_feature - Xaa = Gly, Ser, Thr or missing |
| source | 1..30 |
|  | mol_type = protein |
|  | organism = synthetic construct |
| SEQUENCE: 56 |  |
| XVQLVESGGG XVXXGGSLRL SCXXXXXYXXX | 30 |

| SEQ ID NO: 57 | moltype = AA  length = 15 |
|---|---|
| FEATURE | Location/Qualifiers |
| REGION | 1..15 |
|  | note = 1-FR2-M; 1-FR2-H5; 5-FR2; 1-FR2-H1; 1-FR2-H2; 1-FR2-H3; 1-FR2-H4; 2-FR2-M; 2-FR2-H3; 2-FR2-H1; 2-FR2-H2; 3-FR2-M; 3-FR2-H4; 3-FR2-H1; 3-FR2-H2; 3-FR2-H3; 4-FR2-M; 4-FR2-H5; 4-FR2-H1; 4-FR2-H2; 4-FR2-H3; 4-FR2-H4; 6-FR2 |
| SITE | 2 |
|  | note = misc_feature - Xaa = Phe or Ile |
| SITE | 8 |
|  | note = misc_feature - Xaa = Glu or Lys |
| SITE | 9 |
|  | note = misc_feature - Xaa = Glu or Gly |
| SITE | 10 |
|  | note = misc_feature - Xaa = Leu or Arg |
| SITE | 12 |
|  | note = misc_feature - Xaa = Gly or Arg |
| SITE | 14 |
|  | note = misc_feature - Xaa = Ala or Ser |
| SITE | 15 |
|  | note = misc_feature - Xaa = Ala, Ser or Val |
| source | 1..15 |
|  | mol_type = protein |
|  | organism = synthetic construct |
| SEQUENCE: 57 |  |
| WXRQAPGXXX EXVXX | 15 |

| SEQ ID NO: 58 | moltype = AA  length = 32 |
|---|---|
| FEATURE | Location/Qualifiers |
| REGION | 1..32 |
|  | note = 1-FR3-M; 1-FR3-H1; 1-FR3-H2; 2-FR3-H1; 4-FR3-H1; 4-FR3-H2; 4-FR3-H3; 1-FR3-H3; 1-FR3-H4; 1-FR3-H5; 4-FR3-H4; 4-FR3-H5; 2-FR3-M; 2-FR3-H2; 2-FR3-H3; 3-FR3-M; 3-FR3-H1; 3-FR3-H2; 3-FR3-H3; 3-FR3-H4; 4-FR3-M; 5-FR3; 6-FR3 |
| SITE | 6 |
|  | note = misc_feature - Xaa = Lys, Leu, Gln or Arg |
| SITE | 8 |
|  | note = misc_feature - Xaa = Ile or Asn |
| SITE | 9 |
|  | note = misc_feature - Xaa = Ala or Ser |
| SITE | 10 |
|  | note = misc_feature - Xaa = Glu, Lys or Leu |
| SITE | 11 |
|  | note = misc_feature - Xaa = Asn or Ser |
| SITE | 16 |
|  | note = misc_feature - Xaa = Glu or Gln |
| SITE | 19 |
|  | note = misc_feature - Xaa = Ile, Asn or Ser |
| SITE | 21 |

```
                        note = misc_feature - Xaa = Lys, Gln or Arg
SITE                    22
                        note = misc_feature - Xaa = Ala, Pro or Ser
SITE                    27
                        note = misc_feature - Xaa = Met or Val
SITE                    32
                        note = misc_feature - Xaa = Ala or Thr
source                  1..32
                        mol_type = protein
                        organism = synthetic construct
SEQUENCE: 58
RFTISXDXXX XTLYLXMNXL XXEDTAXYYC AX                                   32

SEQ ID NO: 59           moltype = AA   length = 11
FEATURE                 Location/Qualifiers
REGION                  1..11
                        note = 1-FR4-M; 2-FR4-M; 3-FR4-M; 4-FR4-M; 5-FR4; 6-FR4;
                         1-FR4-H1; 1-FR4-H2; 1-FR4-H3; 1-FR4-H4; 1-FR4-H5;
                         2-FR4-H1; 2-FR4-H2; 2-FR4-H3; 3-FR4-H1; 3-FR4-H2;
                         3-FR4-H3; 3-FR4-H4; 4-FR4-H1; 4-FR4-H2; 4-FR4-H3;
                         4-FR4-H4; 4-FR4-H5
SITE                    6
                        note = misc_feature - Xaa = Leu or Gln
source                  1..11
                        mol_type = protein
                        organism = synthetic construct
SEQUENCE: 59
WGQGTXVTVS S                                                          11

SEQ ID NO: 60           moltype = AA   length = 124
FEATURE                 Location/Qualifiers
REGION                  1..124
                        note = VHH
source                  1..124
                        mol_type = protein
                        organism = synthetic construct
SEQUENCE: 60
HVQLVESGGG SVQAGGSLRL SCEAFEYYYC MGWFRQAPGK EREGVASFDT SDGSKYYADS     60
VKGRFTISKD IAKNTLYLEM NILQAEDTAM YYCAARPFYV GGTCLPRLTD FSIWGQGTQV     120
TVSS                                                                  124

SEQ ID NO: 61           moltype = AA   length = 124
FEATURE                 Location/Qualifiers
REGION                  1..124
                        note = VHH
source                  1..124
                        mol_type = protein
                        organism = synthetic construct
SEQUENCE: 61
EVQLVESGGG LVQPGGSLRL SCAAFEYYYC MGWFRQAPGK GLEGVSSFDT SDGSKYYADS     60
VKGRFTISRD NSKNTLYLQM NSLRAEDTAV YYCAARPFYV GGTCLPRLTD FSIWGQGTLV     120
TVSS                                                                  124

SEQ ID NO: 62           moltype = AA   length = 124
FEATURE                 Location/Qualifiers
REGION                  1..124
                        note = VHH
source                  1..124
                        mol_type = protein
                        organism = synthetic construct
SEQUENCE: 62
EVQLVESGGG LVQPGGSLRL SCAAFEYYYC MGWFRQAPGK GLEGVASFDT SDGSKYYADS     60
VKGRFTISRD NSKNTLYLQM NSLRAEDTAV YYCAARPFYV GGTCLPRLTD FSIWGQGTLV     120
TVSS                                                                  124

SEQ ID NO: 63           moltype = AA   length = 124
FEATURE                 Location/Qualifiers
REGION                  1..124
                        note = VHH
source                  1..124
                        mol_type = protein
                        organism = synthetic construct
SEQUENCE: 63
EVQLVESGGG LVQPGGSLRL SCAAFEYYYC MGWFRQAPGK GLEGVASFDT SDGSKYYADS     60
VKGRFTISKD NSKNTLYLQM NSLRAEDTAV YYCAARPFYV GGTCLPRLTD FSIWGQGTLV     120
TVSS                                                                  124

SEQ ID NO: 64           moltype = AA   length = 124
FEATURE                 Location/Qualifiers
```

```
REGION                      1..124
                            note = VHH
source                      1..124
                            mol_type = protein
                            organism = synthetic construct
SEQUENCE: 64
EVQLVESGGG LVQPGGSLRL SCEAFEYYYC MGWFRQAPGK GLEGVASFDT SDGSKYYADS    60
VKGRFTISKD NSKNTLYLQM NSLRAEDTAV YYCAARPFYV GGTCLPRLTD FSIWGQGTLV   120
TVSS                                                                124

SEQ ID NO: 65               moltype = AA  length = 124
FEATURE                     Location/Qualifiers
REGION                      1..124
                            note = VHH
source                      1..124
                            mol_type = protein
                            organism = synthetic construct
SEQUENCE: 65
EVQLVESGGG LVQPGGSLRL SCEAFEYYYC MGWFRQAPGK EREGVASFDT SDGSKYYADS    60
VKGRFTISKD NSKNTLYLQM NSLRAEDTAV YYCAARPFYV GGTCLPRLTD FSIWGQGTLV   120
TVSS                                                                124

SEQ ID NO: 66               moltype = AA  length = 130
FEATURE                     Location/Qualifiers
REGION                      1..130
                            note = VHH
source                      1..130
                            mol_type = protein
                            organism = synthetic construct
SEQUENCE: 66
HVQLVESGGG SVQSGGSLRL SCAASAYIYS SYCMGWFRQA PGKERERVSV INSDGRTSYA    60
DSVKGRFTIS QDNAKNTLYL QMNSLKPEDT AMYYCAAVIL PPTDGMEYSC NYPAAEYNYW   120
GQGTQVTVSS                                                          130

SEQ ID NO: 67               moltype = AA  length = 130
FEATURE                     Location/Qualifiers
REGION                      1..130
                            note = VHH
source                      1..130
                            mol_type = protein
                            organism = synthetic construct
SEQUENCE: 67
EVQLVESGGG LVQPGGSLRL SCAASAYIYS SYCMGWFRQA PGKGLERVSV INSDGRTSYA    60
DSVKGRFTIS RDNSKNTLYL QMNSLRAEDT AVYYCAAVIL PPTDGMEYSC NYPAAEYNYW   120
GQGTLVTVSS                                                          130

SEQ ID NO: 68               moltype = AA  length = 130
FEATURE                     Location/Qualifiers
REGION                      1..130
                            note = VHH
source                      1..130
                            mol_type = protein
                            organism = synthetic construct
SEQUENCE: 68
EVQLVESGGG LVQPGGSLRL SCAASAYIYS SYCMGWFRQA PGKGLERVSV INSDGRTSYA    60
DSVKGRFTIS QDNSKNTLYL QMNSLRAEDT AVYYCAAVIL PPTDGMEYSC NYPAAEYNYW   120
GQGTLVTVSS                                                          130

SEQ ID NO: 69               moltype = AA  length = 130
FEATURE                     Location/Qualifiers
REGION                      1..130
                            note = VHH
source                      1..130
                            mol_type = protein
                            organism = synthetic construct
SEQUENCE: 69
EVQLVESGGG LVQPGGSLRL SCAASAYIYS SYCMGWFRQA PGKERERVSV INSDGRTSYA    60
DSVKGRFTIS QDNSKNTLYL QMNSLRAEDT AVYYCAAVIL PPTDGMEYSC NYPAAEYNYW   120
GQGTLVTVSS                                                          130

SEQ ID NO: 70               moltype = AA  length = 125
FEATURE                     Location/Qualifiers
REGION                      1..125
                            note = VHH
source                      1..125
                            mol_type = protein
                            organism = synthetic construct
SEQUENCE: 70
QVQLVESGGG SVQSGGSLRL SCVDSGYTYG HYCMGWFRQA PGKEREGVAA IRRDGVTRYA    60
```

```
DSVKGRFTIS LDNAKSTLYL QMNSLKAEDT AMYYCATQRD CGISGLLWQS SVGYWGQGTQ    120
VTVSS                                                                125

SEQ ID NO: 71           moltype = AA  length = 125
FEATURE                 Location/Qualifiers
REGION                  1..125
                        note = VHH
source                  1..125
                        mol_type = protein
                        organism = synthetic construct
SEQUENCE: 71
QVQLVESGGG VVQPGGSLRL SCAASGYTYG HYCMGWFRQA PGKGLEGVAA IRRDGVTRYA    60
DSVKGRFTIS RDNSKNTLYL QMNSLRAEDT AVYYCATQRD CGISGLLWQS SVGYWGQGTL    120
VTVSS                                                                125

SEQ ID NO: 72           moltype = AA  length = 125
FEATURE                 Location/Qualifiers
REGION                  1..125
                        note = VHH
source                  1..125
                        mol_type = protein
                        organism = synthetic construct
SEQUENCE: 72
QVQLVESGGG VVQPGGSLRL SCAASGYTYG HYCMGWFRQA PGKGLEGVAA IRRDGVTRYA    60
DSVKGRFTIS LDNSKNTLYL QMNSLRAEDT AVYYCATQRD CGISGLLWQS SVGYWGQGTL    120
VTVSS                                                                125

SEQ ID NO: 73           moltype = AA  length = 125
FEATURE                 Location/Qualifiers
REGION                  1..125
                        note = VHH
source                  1..125
                        mol_type = protein
                        organism = synthetic construct
SEQUENCE: 73
QVQLVESGGG VVQPGGSLRL SCADSGYTYG HYCMGWFRQA PGKGLEGVAA IRRDGVTRYA    60
DSVKGRFTIS LDNSKNTLYL QMNSLRAEDT AVYYCATQRD CGISGLLWQS SVGYWGQGTL    120
VTVSS                                                                125

SEQ ID NO: 74           moltype = AA  length = 125
FEATURE                 Location/Qualifiers
REGION                  1..125
                        note = VHH
source                  1..125
                        mol_type = protein
                        organism = synthetic construct
SEQUENCE: 74
QVQLVESGGG VVQPGGSLRL SCADSGYTYG HYCMGWFRQA PGKEREGVAA IRRDGVTRYA    60
DSVKGRFTIS LDNSKNTLYL QMNSLRAEDT AVYYCATQRD CGISGLLWQS SVGYWGQGTL    120
VTVSS                                                                125

SEQ ID NO: 75           moltype = AA  length = 127
FEATURE                 Location/Qualifiers
REGION                  1..127
                        note = VHH
source                  1..127
                        mol_type = protein
                        organism = synthetic construct
SEQUENCE: 75
HVQLVESGGG SVQAGGSLRL SCAHPEYTSS SYCMAWIRQA PGKEREGVAA IDTDGSTSYT    60
DSVKGRFTIS KDNAKNTLYL QMNNLKPEDT AMYYCAAAPW LLAYGDYCVT RPDFGEWGQG    120
TQVTVSS                                                              127

SEQ ID NO: 76           moltype = AA  length = 127
FEATURE                 Location/Qualifiers
REGION                  1..127
                        note = VHH
source                  1..127
                        mol_type = protein
                        organism = synthetic construct
SEQUENCE: 76
EVQLVESGGG LVQPGGSLRL SCAASEYTSS SYCMAWIRQA PGKGLEGVSA IDTDGSTSYT    60
DSVKGRFTIS RDNSKNTLYL QMNSLRAEDT AVYYCAAAPW LLAYGDYCVT RPDFGEWGQG    120
TLVTVSS                                                              127

SEQ ID NO: 77           moltype = AA  length = 127
FEATURE                 Location/Qualifiers
REGION                  1..127
                        note = VHH
```

-continued

```
source                  1..127
                        mol_type = protein
                        organism = synthetic construct
SEQUENCE: 77
EVQLVESGGG LVQPGGSLRL SCAASEYTSS SYCMAWIRQA PGKGLEGVAA IDTDGSTSYT    60
DSVKGRFTIS RDNSKNTLYL QMNSLRAEDT AVYYCAAAPW LLAYGDYCVT RPDFGEWGQG   120
TLVTVSS                                                             127

SEQ ID NO: 78           moltype = AA  length = 127
FEATURE                 Location/Qualifiers
REGION                  1..127
                        note = VHH
source                  1..127
                        mol_type = protein
                        organism = synthetic construct
SEQUENCE: 78
EVQLVESGGG LVQPGGSLRL SCAHPEYTSS SYCMAWIRQA PGKGLEGVAA IDTDGSTSYT    60
DSVKGRFTIS RDNSKNTLYL QMNSLRAEDT AVYYCAAAPW LLAYGDYCVT RPDFGEWGQG   120
TLVTVSS                                                             127

SEQ ID NO: 79           moltype = AA  length = 127
FEATURE                 Location/Qualifiers
REGION                  1..127
                        note = VHH
source                  1..127
                        mol_type = protein
                        organism = synthetic construct
SEQUENCE: 79
EVQLVESGGG LVQPGGSLRL SCAHPEYTSS SYCMAWIRQA PGKGLEGVAA IDTDGSTSYT    60
DSVKGRFTIS KDNSKNTLYL QMNSLRAEDT AVYYCAAAPW LLAYGDYCVT RPDFGEWGQG   120
TLVTVSS                                                             127

SEQ ID NO: 80           moltype = AA  length = 127
FEATURE                 Location/Qualifiers
REGION                  1..127
                        note = VHH
source                  1..127
                        mol_type = protein
                        organism = synthetic construct
SEQUENCE: 80
EVQLVESGGG LVQPGGSLRL SCAHPEYTSS SYCMAWIRQA PGKEREGVAA IDTDGSTSYT    60
DSVKGRFTIS KDNSKNTLYL QMNSLRAEDT AVYYCAAAPW LLAYGDYCVT RPDFGEWGQG   120
TLVTVSS                                                             127

SEQ ID NO: 81           moltype = AA  length = 516
FEATURE                 Location/Qualifiers
REGION                  1..516
                        note = VHH
source                  1..516
                        mol_type = protein
                        organism = synthetic construct
SEQUENCE: 81
EVQLVESGGG LVQPGGSLRL SCAASAYIYS SYCMGWFRQA PGKGLERVSV INSDGRTSYA    60
DSVKGRFTIS RDNSKNTLYL QMNSLRAEDT AVYYCAAVIL PPTDGMEYSC NYPAAEYNYW   120
GQGTLVTVSS GGGGSGGGGS GGGGSEVQLV ESGGGLVQPG GSLRLSCAAS EYTSSSYCMA   180
WIRQAPGKGL EGVAAIDTDG STSYTDSVKG RFTISRDNSK NTLYLQMNSL RAEDTAVYYC   240
AAAPWLLAYG DYCVTRPDFG EWGQGTLVTV SSGGGGSGGG GSGGGGSESK YGPPCPPCPA   300
PEFLGGPSVF LFPPKPKDTL MISRTPEVTC VVVDVSQEDP EVQFNWYVDG VEVHNAKTKP   360
REEQFNSTYR VVSVLTVLHQ DWLNGKEYKC KVSNKGLPSS IEKTISKAKG QPREPQVYTL   420
PPSQEEMTKN QVSLTCLVKG FYPSDIAVEW ESNGQPENNY KTTPPVLDSD GSFFLYSRLT   480
VDKSRWQEGN VFSCSVMHEA LHNHYTQKSL SLSLGK                             516

SEQ ID NO: 82           moltype = AA  length = 777
FEATURE                 Location/Qualifiers
REGION                  1..777
                        note = VHH
source                  1..777
                        mol_type = protein
                        organism = synthetic construct
SEQUENCE: 82
EVQLVESGGG LVQPGGSLRL SCAASAYIYS SYCMGWFRQA PGKGLERVSV INSDGRTSYA    60
DSVKGRFTIS RDNSKNTLYL QMNSLRAEDT AVYYCAAVIL PPTDGMEYSC NYPAAEYNYW   120
GQGTLVTVSS GGGGSGGGGS GGGGSEVQLV ESGGGLVQPG GSLRLSCAAS EYTSSSYCMA   180
WIRQAPGKGL EGVAAIDTDG STSYTDSVKG RFTISRDNSK NTLYLQMNSL RAEDTAVYYC   240
AAAPWLLAYG DYCVTRPDFG EWGQGTLVTV SSGGGGSGGG GSGGGGSESK YGPPCPPCPA   300
PEFLGGPSVF LFPPKPKDTL MISRTPEVTC VVVDVSQEDP EVQFNWYVDG VEVHNAKTKP   360
REEQFNSTYR VVSVLTVLHQ DWLNGKEYKC KVSNKGLPSS IEKTISKAKG QPREPQVYTL   420
PPSQEEMTKN QVSLTCLVKG FYPSDIAVEW ESNGQPENNY KTTPPVLDSD GSFFLYSRLT   480
VDKSRWQEGN VFSCSVLHEA LHSHYTQKSL SLSLGKGGGG SGGGGSGGGG SEDCNELPPR   540
```

```
RNTEILTGSW SDQTYPEGTQ AIYKCRPGYR SLGNVIMVCR KGEWVALNPL RKCQKRPCGH    600
PGDTPFGTFT LTGGNVFEYG VKAVYTCNEG YQLLGEINYR ECDTDGWTND IPICEVVKCL    660
PVTAPENGKI VSSAMEPDRE YHFGQAVRFV CNSGYKIEGD EEMHCSDDGF WSKEKPKCVE    720
ISCKSPDVIN GSPISQKIIY KENERFQYKC NMGYEYSERG DAVCTESGWR PLPSCEE      777

SEQ ID NO: 83           moltype = AA   length = 126
FEATURE                 Location/Qualifiers
REGION                  1..126
                        note = VHH
source                  1..126
                        mol_type = protein
                        organism = synthetic construct
SEQUENCE: 83
EVQLVESGGG SVQVGGSLRL SCVDTSYTYT HYCMGWFRQA PGKEREGVAV MTTDGWTRYA    60
DSVKGRFIIS KDNAKNTLYL QMNSLKLEDT AMYYCATNPG DSCTTGISTP PTFRTWGQGT   120
QVTVSS                                                              126

SEQ ID NO: 84           moltype = AA   length = 126
FEATURE                 Location/Qualifiers
REGION                  1..126
                        note = VHH
source                  1..126
                        mol_type = protein
                        organism = synthetic construct
SEQUENCE: 84
DVQLVESGGG SVQVGGSLRL SCVDTSYTYT HYCMGWFRQA PGKEREGVAV MTTDGWTRYA    60
DSVKGRFIIS KDNAKNTLYL QMNSLKLEDT AMYYCATNPW DSCTTGISTP STFRTWGQGT   120
QVTVSS                                                              126

SEQ ID NO: 85           moltype = AA   length = 127
FEATURE                 Location/Qualifiers
REGION                  1..127
                        note = VHH
source                  1..127
                        mol_type = protein
                        organism = synthetic construct
SEQUENCE: 85
EVQLVESGGG SVQAGGSLRL SCAASISIRS FNYMAWFRQA PGKEREGVAA SYAGGVSTYY    60
TDSVKGRFTI SQDNAQKRVY LQMNSLKPED TAVYYCAATQ DVIWRTGPLE SDEYRYWGQG   120
TQVTVSS                                                             127

SEQ ID NO: 86           moltype = AA   length = 122
FEATURE                 Location/Qualifiers
REGION                  1..122
                        note = VHH
source                  1..122
                        mol_type = protein
                        organism = synthetic construct
SEQUENCE: 86
EVQLVESGGG SVQAGGSLKL SCVVSAYTYS VACMGWVRQA PGKEREGVAA IDSYGRTSYP    60
DSVKGRFTIS RDNTKNTLYL QTNSLKPEDT GMYYCAADLT RTLVDGCNWT HWGQGTQVTV   120
SS                                                                  122

SEQ ID NO: 87           moltype = AA   length = 129
FEATURE                 Location/Qualifiers
REGION                  1..129
                        note = VHH
source                  1..129
                        mol_type = protein
                        organism = synthetic construct
SEQUENCE: 87
KVQLVESGGG SVQAGGSLRL SCAASGYTYS IGCMGWFRQA PGKEREGVAA IDSDGSTSYA    60
DSVKGRFTIS KHNAKNTLYL QMDSLKPEDT AMYYCAADVH PIGHPVAGPH LKSADFGYWG   120
QGTQVTVSS                                                           129

SEQ ID NO: 88           moltype = AA   length = 124
FEATURE                 Location/Qualifiers
REGION                  1..124
                        note = VHH
source                  1..124
                        mol_type = protein
                        organism = synthetic construct
SEQUENCE: 88
DVQLVESGGG SVQAGGSLRL SCAASTYTGS RINMAWFRQA TGKEREGVAT IMIGGPYTHY    60
ADSLKGRLTI SQDSAKNTMY LQMNSLKPED TAVYYCAADS RIVGSLVDSD YKYWGQGTQV   120
TVSS                                                                124

SEQ ID NO: 89           moltype = AA   length = 126
FEATURE                 Location/Qualifiers
```

```
REGION                  1..126
                        note = VHH
source                  1..126
                        mol_type = protein
                        organism = synthetic construct
SEQUENCE: 89
DVQLVESGGG SVQVGGSLKL SCVDSGYTYS HYCMAWFRQA PGKEREGVAV IASDGWTRYA    60
DSVKGRFTIS KDSAKNTLYL QMNSLKPEDT AMYYCASDPT DLCTTGLSTP SKFLNWGQGT   120
QVTVSS                                                              126

SEQ ID NO: 90           moltype = AA   length = 125
FEATURE                 Location/Qualifiers
REGION                  1..125
                        note = VHH
source                  1..125
                        mol_type = protein
                        organism = synthetic construct
SEQUENCE: 90
EVQLVESGGG SVQSGGSLRL SCAASGDTYS RSCMGWFRQA PGKEREGVAD IDSDGSRTYA    60
DSVKGRFTIS QDNDKNTLYL QMNSLKPEDT AMYYCAADRV SIDGGCHESV HLNFWGQGTQ   120
VTVSS                                                               125

SEQ ID NO: 91           moltype = AA   length = 124
FEATURE                 Location/Qualifiers
REGION                  1..124
                        note = VHH
source                  1..124
                        mol_type = protein
                        organism = synthetic construct
SEQUENCE: 91
QVQLVESGGG SVQAGGSLRL FCAASGYDYD TWFYMAWFRQ APGKEREGVA AIDTIGNTNY    60
ADSVKGRFTI SKGNAKNSLY LQINSLKPED TAIYFCAAGQ SLPLALSSNE YEFWGQGTQV   120
TVSS                                                                124

SEQ ID NO: 92           moltype = AA   length = 123
FEATURE                 Location/Qualifiers
REGION                  1..123
                        note = VHH
source                  1..123
                        mol_type = protein
                        organism = synthetic construct
SEQUENCE: 92
QVQLVESGGG SVHAGGSLRL SCAVSGYTHS TGCMAWFRQA PGKEREGVAS IIRGERGEWY    60
ADSVKGRFTI SQDNAENTLY LQMNSLKSED TAMYYCAADY RYPCDGRSNY DYWGQGTQVT   120
VSS                                                                 123

SEQ ID NO: 93           moltype = AA   length = 126
FEATURE                 Location/Qualifiers
REGION                  1..126
                        note = VHH
source                  1..126
                        mol_type = protein
                        organism = synthetic construct
SEQUENCE: 93
DVQLVESGGG SVQVGGSLRL SCVDSGYTYT HYCMGWFRQA PGEEREGVAV ITSDGWTRYA    60
DSVKGRFTIS KDNALNTLYL QMNSLKPEDT AMYYCATTPE GSCSTGVSTP STFRVWGQGT   120
QVTVSS                                                              126

SEQ ID NO: 94           moltype = AA   length = 136
FEATURE                 Location/Qualifiers
REGION                  1..136
                        note = VHH
source                  1..136
                        mol_type = protein
                        organism = synthetic construct
SEQUENCE: 94
DVQLVESGGG SVQSGGSLRL SCAASGRTWS NYCMGWFRQA PGKEREGVAV IDSDGSTSYV    60
DSVKGRFTIS EDNAKNTLYL QMNSLKPEDT AMYYCAAAGV IRYDDDRALS DLCGVEVTSA   120
ADFAYWGQGT QVTVSS                                                   136

SEQ ID NO: 95           moltype = AA   length = 134
FEATURE                 Location/Qualifiers
REGION                  1..134
                        note = VHH
source                  1..134
                        mol_type = protein
                        organism = synthetic construct
SEQUENCE: 95
HVQLVESGGG SVQSGGSLRL SCVASGYTSG YTYSSYCIAW FRQAPGKERE GVAQIDSDGS    60
```

```
TTYADSVKGR FTISQDNVKN TLYLQMNSLK PDDTAMYYCA AEPRPHTYYS CTYLNHGSLD    120
FGYWGQGTQV TVSS                                                      134

SEQ ID NO: 96           moltype = AA  length = 129
FEATURE                 Location/Qualifiers
REGION                  1..129
                        note = VHH
source                  1..129
                        mol_type = protein
                        organism = synthetic construct
SEQUENCE: 96
HVQLVESGGG SVQSGGSLRL SCAASGMTWS RYCMGWFRQA SGKEREGVAA IGSDGDTSYA    60
DSVKGRFTIS QDNAKKTLYL QMNSLKPEDT AMYYCAAAGV AGTFEGLTCP TVEYYYAYWG    120
QGTQVTVSS                                                            129

SEQ ID NO: 97           moltype = AA  length = 125
FEATURE                 Location/Qualifiers
REGION                  1..125
                        note = VHH
source                  1..125
                        mol_type = protein
                        organism = synthetic construct
SEQUENCE: 97
QVQLVESGGG SVQAGGSLRL SCAASGITWS RYCMAWFRQV PGKEREGVAA MNNAGSTSYI    60
ESVKARFTIS EDNAKNTLYL QMNSLKPEDT AMYYCAVAGS TDGTCAYEAY LFANWGRGTQ    120
VTVSS                                                                125

SEQ ID NO: 98           moltype = AA  length = 512
FEATURE                 Location/Qualifiers
REGION                  1..512
                        note = VHH
source                  1..512
                        mol_type = protein
                        organism = synthetic construct
SEQUENCE: 98
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKG GGGSGGGSSG    240
GGGSHVQLVE SGGGSVQAGG SLRLSCEAFE YYYCMGWFRQ APGKEREGVA SFDTSDGSKY    300
YADSVKGRFT ISKDIAKNTL YLEMNILQAE DTAMYYCAAR PFYVGGTCLP RLTDFSIWGQ    360
GTQVTVSSGG GGSGGGGSGG GGSKVQLVES GGGSVQAGGS LRLSCAASGY TYSIGCMGWF    420
RQAPGKEREG VAAIDSDGST SYADSVKGRF TISKHNAKNT LYLQMDSLKP EDTAMYYCAA    480
DVHPIGHPVA GPHLKSADFG YWGQGTQVTV SS                                  512

SEQ ID NO: 99           moltype = AA  length = 513
FEATURE                 Location/Qualifiers
REGION                  1..513
                        note = VHH
source                  1..513
                        mol_type = protein
                        organism = synthetic construct
SEQUENCE: 99
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKG GGGSGGGSSG    240
GGGSHVQLVE SGGGSVQAGG SLRLSCEAFE YYYCMGWFRQ APGKEREGVA SFDTSDGSKY    300
YADSVKGRFT ISKDIAKNTL YLEMNILQAE DTAMYYCAAR PFYVGGTCLP RLTDFSIWGQ    360
GTQVTVSSGG GGSGGGGSGG GGSHVQLVES GGGSVQSGGS LRLSCAASAY IYSSYCMGWF    420
RQAPGKERER VSVINSDGRT SYADSVKGRF TISQDNAKNT LYLQMNSLKP EDTAMYYCAA    480
VILPPTDGME YSCNYPAAEY NYWGQGTQVT VSS                                 513

SEQ ID NO: 100          moltype = AA  length = 508
FEATURE                 Location/Qualifiers
REGION                  1..508
                        note = VHH
source                  1..508
                        mol_type = protein
                        organism = synthetic construct
SEQUENCE: 100
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKG GGGSGGGSSG    240
GGGSHVQLVE SGGGSVQAGG SLRLSCEAFE YYYCMGWFRQ APGKEREGVA SFDTSDGSKY    300
YADSVKGRFT ISKDIAKNTL YLEMNILQAE DTAMYYCAAR PFYVGGTCLP RLTDFSIWGQ    360
GTQVTVSSGG GGSGGGGSGG GGSQVQLVES GGGSVQSGGS LRLSCVDSGY TYGHYCMGWF    420
RQAPGKEREG VAAIRRDGVT RYADSVKGRF TISLDNAKST LYLQMNSLKA EDTAMYYCAT    480
```

```
QRDCGISGLL WQSSVGYWGQ GTQVTVSS                                         508

SEQ ID NO: 101             moltype = AA  length = 514
FEATURE                    Location/Qualifiers
REGION                     1..514
                           note = VHH
source                     1..514
                           mol_type = protein
                           organism = synthetic construct
SEQUENCE: 101
ESKYGPPCPP CPAPEFLGGP SVFLFPPKPK DTLMISRTPE VTCVVVDVSQ EDPEVQFNWY      60
VDGVEVHNAK TKPREEQFNS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGKG GGGSGGGSSG     240
GGGSDVQLVE SGGGSVQVGG SLRLSCVDTS YTYTHYCMGW FRQAPGKERE GVAVMTTDGW     300
TRYADSVKGR FIISKDNAKN TLYLQMNSLK LEDTAMYYCA TNPWDSCTTG ISTPSTFRTW     360
GQGTQVTVSS GGGGSGGGGS GGGGSKVQLV ESGGGSVQAG GSLRLSCAAS GYTYSIGCMG     420
WFRQAPGKER EGVAAIDSDG STSYADSVKG RFTISKHNAK NTLYLQMDSL KPEDTAMYYC     480
AADVHPIGHP VAGPHLKSAD FGYWGQGTQV TVSS                                 514

SEQ ID NO: 102             moltype = AA  length = 515
FEATURE                    Location/Qualifiers
REGION                     1..515
                           note = VHH
source                     1..515
                           mol_type = protein
                           organism = synthetic construct
SEQUENCE: 102
ESKYGPPCPP CPAPEFLGGP SVFLFPPKPK DTLMISRTPE VTCVVVDVSQ EDPEVQFNWY      60
VDGVEVHNAK TKPREEQFNS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGKG GGGSGGGSSG     240
GGGSDVQLVE SGGGSVQVGG SLRLSCVDTS YTYTHYCMGW FRQAPGKERE GVAVMTTDGW     300
TRYADSVKGR FIISKDNAKN TLYLQMNSLK LEDTAMYYCA TNPWDSCTTG ISTPSTFRTW     360
GQGTQVTVSS GGGGSGGGGS GGGGSHVQLV ESGGGSVQSG GSLRLSCAAS AYIYSSYCMG     420
WFRQAPGKER ERVSVINSDG RTSYADSVKG RFTISQDNAK NTLYLQMNSL KPEDTAMYYC     480
AAVILPPTDG MEYSCNYPAA EYNYWGQGTQ VTVSS                                515

SEQ ID NO: 103             moltype = AA  length = 510
FEATURE                    Location/Qualifiers
REGION                     1..510
                           note = VHH
source                     1..510
                           mol_type = protein
                           organism = synthetic construct
SEQUENCE: 103
ESKYGPPCPP CPAPEFLGGP SVFLFPPKPK DTLMISRTPE VTCVVVDVSQ EDPEVQFNWY      60
VDGVEVHNAK TKPREEQFNS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGKG GGGSGGGSSG     240
GGGSDVQLVE SGGGSVQVGG SLRLSCVDTS YTYTHYCMGW FRQAPGKERE GVAVMTTDGW     300
TRYADSVKGR FIISKDNAKN TLYLQMNSLK LEDTAMYYCA TNPWDSCTTG ISTPSTFRTW     360
GQGTQVTVSS GGGGSGGGGS GGGGSQVQLV ESGGGSVQSG GSLRLSCVDS GYTYGHYCMG     420
WFRQAPGKER EGVAAIRRDG VTRYADSVKG RFTISLDNAK STLYLQMNSL KAEDTAMYYC     480
ATQRDCGISG LLWQSSVGYW GQGTQVTVSS                                      510

SEQ ID NO: 104             moltype = AA  length = 515
FEATURE                    Location/Qualifiers
REGION                     1..515
                           note = VHH
source                     1..515
                           mol_type = protein
                           organism = synthetic construct
SEQUENCE: 104
ESKYGPPCPP CPAPEFLGGP SVFLFPPKPK DTLMISRTPE VTCVVVDVSQ EDPEVQFNWY      60
VDGVEVHNAK TKPREEQFNS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGKG GGGSGGGSSG     240
GGGSHVQLVE SGGGSVQAGG SLRLSCAHPE YTSSSYCMAW IRQAPGKERE GVAAIDTDGS     300
TSYTDSVKGR FTISKDNAKN TLYLQMNNLK PEDTAMYYCA AAPWLLAYGD YCVTRPDFGE     360
WGQGTQVTVS SGGGGSGGGG SGGGGSKVQL VESGGGSVQA GGSLRLSCAA SGYTYSIGCM     420
GWFRQAPGKE REGVAAIDSD GSTSYADSVK GRFTISKHNA KNTLYLQMDS LKPEDTAMYY     480
CAADVHPIGH PVAGPHLKSA DFGYWGQGTQ VTVSS                                515

SEQ ID NO: 105             moltype = AA  length = 516
FEATURE                    Location/Qualifiers
REGION                     1..516
                           note = VHH
source                     1..516
```

```
                         mol_type = protein
                         organism = synthetic construct
SEQUENCE: 105
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKG  GGGSGGGSSG  240
GGGSHVQLVE  SGGGSVQAGG  SLRLSCAHPE  YTSSSYCMAW  IRQAPGKERE  GVAAIDTDGS  300
TSYTDSVKGR  FTISKDNAKN  TLYLQMNNLK  PEDTAMYYCA  AAPWLLAYGD  YCVTRPDFGE  360
WGQGTQVTVS  SGGGGSGGGG  SGGGGSHVQL  VESGGGSVQS  GGSLRLSCAA  SAYIYSSYCM  420
GWFRQAPGKE  RERVSVINSD  GRTSYADSVK  GRFTISQDNA  KNTLYLQMNS  LKPEDTAMYY  480
CAAVILPPTD  GMEYSCNYPA  AEYNYWGQGT  QVTVSS                              516

SEQ ID NO: 106           moltype = AA  length = 511
FEATURE                  Location/Qualifiers
REGION                   1..511
                         note = VHH
source                   1..511
                         mol_type = protein
                         organism = synthetic construct
SEQUENCE: 106
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKG  GGGSGGGSSG  240
GGGSHVQLVE  SGGGSVQAGG  SLRLSCAHPE  YTSSSYCMAW  IRQAPGKERE  GVAAIDTDGS  300
TSYTDSVKGR  FTISKDNAKN  TLYLQMNNLK  PEDTAMYYCA  AAPWLLAYGD  YCVTRPDFGE  360
WGQGTQVTVS  SGGGGSGGGG  SGGGGSQVQL  VESGGGSVQS  GGSLRLSCVD  SGYTYGHYCM  420
GWFRQAPGKE  REGVAAIRRD  GVTRYADSVK  GRFTISLDNA  KSTLYLQMNS  LKAEDTAMYY  480
CATQRDCGIS  GLLWQSSVGY  WGQGTQVTVS  S                                   511

SEQ ID NO: 107           moltype = AA  length = 510
FEATURE                  Location/Qualifiers
REGION                   1..510
                         note = VHH
source                   1..510
                         mol_type = protein
                         organism = synthetic construct
SEQUENCE: 107
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKG  GGGSGGGSSG  240
GGGSHVQLVE  SGGGSVQAGG  SLRLSCEAFE  YYYCMGWFRQ  APGKEREGVA  SFDTSDGSKY  300
YADSVKGRFT  ISKDIAKNTL  YLEMNILQAE  DTAMYYCAAR  PFYVGGTCLP  RLTDFSIWGQ  360
GTQVTVSSGG  GGSGGGGSGG  GGSHVQLVES  GGGSVQAGGS  LRLSCAHPEY  TSSSYCMAWI  420
RQAPGKEREG  VAAIDTDGST  SYTDSVKGRF  TISKDNAKNT  LYLQMNNLKP  EDTAMYYCAA  480
APWLLAYGDY  CVTRPDFGEW  GQGTQVTVSS                                      510

SEQ ID NO: 108           moltype = AA  length = 15
FEATURE                  Location/Qualifiers
REGION                   1..15
                         note = linker
source                   1..15
                         mol_type = protein
                         organism = synthetic construct
SEQUENCE: 108
GGGGSGGGGS  GGGGS                                                        15

SEQ ID NO: 109           moltype = AA  length = 229
FEATURE                  Location/Qualifiers
REGION                   1..229
                         note = Fc
source                   1..229
                         mol_type = protein
                         organism = synthetic construct
SEQUENCE: 109
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGK                229

SEQ ID NO: 110           moltype = AA  length = 246
FEATURE                  Location/Qualifiers
REGION                   1..246
                         note = factorH
source                   1..246
                         mol_type = protein
                         organism = synthetic construct
```

```
SEQUENCE: 110
EDCNELPPRR NTEILTGSWS DQTYPEGTQA IYKCRPGYRS LGNVIMVCRK GEWVALNPLR    60
KCQKRPCGHP GDTPFGTFTL TGGNVFEYGV KAVYTCNEGY QLLGEINYRE CDTDGWTNDI   120
PICEVVKCLP VTAPENGKIV SSAMEPDREY HFGQAVRFVC NSGYKIEGDE EMHCSDDGFW   180
SKEKPKCVEI SCKSPDVING SPISQKIIYK ENERFQYKCN MGYEYSERGD AVCTESGWRP   240
LPSCEE                                                              246

SEQ ID NO: 111          moltype = DNA  length = 48
FEATURE                 Location/Qualifiers
misc_feature            1..48
                        note = Forward primer
misc_feature            31
                        note = n = c or g
misc_feature            33
                        note = n = g or t
source                  1..48
                        mol_type = other DNA
                        organism = synthetic construct
SEQUENCE: 111
ggcggtggca gctcaggagg cggcggatcc nangtgcagc tggtggag                 48

SEQ ID NO: 112          moltype = DNA  length = 46
FEATURE                 Location/Qualifiers
misc_feature            1..46
                        note = Reverse primer
misc_feature            40
                        note = n = a or g
source                  1..46
                        mol_type = other DNA
                        organism = synthetic construct
SEQUENCE: 112
aatccagagg ttgattgtcg acgtacgcta tgaggagacn gtgacc                   46

SEQ ID NO: 113          moltype = AA  length = 495
FEATURE                 Location/Qualifiers
REGION                  1..495
                        note = VEGF inhibiting VHHs
source                  1..495
                        mol_type = protein
                        organism = synthetic construct
SEQUENCE: 113
EVQLVESGGG LVQPGGSLRL SCAASVYTSS TYYMAWFRQA PGKGREGVAA AYAGGGGTVY    60
ADSVKGRFTI SQDNSKNTLY LQMNSLRAED TAVYYCAARM SRLLGMAPLL PEHYDSWGQG   120
TLVTVSSGGG GSGGGGSGGG GSEVQLVESG GGLVQPGGSL RLSCAASRDA YFNNYMAWFR   180
QAPGKGLEGV SSIATNTGND YYADSVKGRF TISRDNSKNT IYLQMNSLRA EDTAVYYCAA   240
GWRGGSFWTP SKYSYWGQGT LVTVSSESKY GPPCPPCPAP EFLGGPSVFL FPPKPKDTLM   300
ISRTPEVTCV VVDVSQEDPE VQFNWYVDGV EVHNAKTKPR EEQFNSTYRV VSVLTVLHQD   360
WLNGKEYKCK VSNKGLPSSI EKTISKAKGQ PREPQVYTLP PSQEEMTKNQ VSLTCLVKGF   420
YPSDIAVEWE SNGQPENNYK TTPPVLDSDG SFFLYSRLTV DKSRWQEGNV FSCSVMHEAL   480
HNHYTQKSLS LSLGK                                                    495

SEQ ID NO: 114          moltype = AA  length = 782
FEATURE                 Location/Qualifiers
REGION                  1..782
                        note = SLN12140 and VEGF inhibiting VHHs
source                  1..782
                        mol_type = protein
                        organism = synthetic construct
SEQUENCE: 114
EVQLVESGGG LVQPGGSLRL SCAASVYTSS TYYMAWFRQA PGKGREGVAA AYAGGGGTVY    60
ADSVKGRFTI SQDNSKNTLY LQMNSLRAED TAVYYCAARM SRLLGMAPLL PEHYDSWGQG   120
TLVTVSSGGG GSGGGGSGGG GSEVQLVESG GGLVQPGGSL RLSCAASRDA YFNNYMAWFR   180
QAPGKGLEGV SSIATNTGND YYADSVKGRF TISRDNSKNT IYLQMNSLRA EDTAVYYCAA   240
GWRGGSFWTP SKYSYWGQGT LVTVSSESKY GPPCPPCPAP EFLGGPSVFL FPPKPKDTLM   300
ISRTPEVTCV VVDVSQEDPE VQFNWYVDGV EVHNAKTKPR EEQFNSTYRV VSVLTVLHQD   360
WLNGKEYKCK VSNKGLPSSI EKTISKAKGQ PREPQVYTLP PSQEEMTKNQ VSLTCLVKGF   420
YPSDIAVEWE SNGQPENNYK TTPPVLDSDG SFFLYSRLTV DKSRWQEGNV FSCSVMHEAL   480
HNHYTQKSLS LSLGKGGGGS GGGGSGGGGS EVQLVESGGG LVQPGGSLRL SCAASAYIYS   540
SYCMGWFRQA PGKGLERVSV INSDGRTSYA DSVKGRFTIS RDNSKNTLYL QMNSLRAEDT   600
AVYYCAAVIL PPTDGMEYSC NYPAAEYNYW GQGTLVTVSS GGGGSGGGGS GGGGSEVQLV   660
ESGGGLVQPG GSLRLSCAAS EYTSSSYCMA WIRQAPGKGL EGVAAIDTDG STSYTDSVKG   720
RFTISRDNSK NTLYLQMNSL RAEDTAVYYC AAAPWLLAYG DYCVTRPDFG EWGQGTLVTV   780
SS                                                                  782

SEQ ID NO: 115          moltype = AA  length = 128
FEATURE                 Location/Qualifiers
REGION                  1..128
                        note = hTf binding VHH
source                  1..128
```

```
                        mol_type = protein
                        organism = synthetic construct
SEQUENCE: 115
EVQLVESGGG LVQPGGSLRL SCAASGHAYG GNYMGWFRQA PGKGLEGVAV LYTGGGSTYY      60
ADSVKGRFTI SEDNSKNTVY LQMNSLRAED TAVYYCALAL GSARWYTSSL DARAYNIWGQ     120
GTLVTVSS                                                              128

SEQ ID NO: 116          moltype = AA  length = 272
FEATURE                 Location/Qualifiers
REGION                  1..272
                        note = properdin inhibiting VHHs
source                  1..272
                        mol_type = protein
                        organism = synthetic construct
SEQUENCE: 116
EVQLVESGGG LVQPGGSLRL SCAASAYIYS SYCMGWFRQA PGKGLERVSV INSDGRTSYA      60
DSVKGRFTIS RDNSKNTLYL QMNSLRAEDT AVYYCAAVIL PPTDGMEYSC NYPAAEYNYW     120
GQGTLVTVSS GGGGSGGGGS GGGGSEVQLV ESGGGLVQPG GSLRLSCAAS EYTSSSYCMA     180
WIRQAPGKGL EGVAAIDTDG STSYTDSVKG RFTISRDNSK NTLYLQMNSL RAEDTAVYYC     240
AAAPWLLAYG DYCVTRPDFG EWGQGTLVTV SS                                   272

SEQ ID NO: 117          moltype = AA  length = 415
FEATURE                 Location/Qualifiers
REGION                  1..415
                        note = SLN12147 and hTf binding VHH
source                  1..415
                        mol_type = protein
                        organism = synthetic construct
SEQUENCE: 117
EVQLVESGGG LVQPGGSLRL SCAASAYIYS SYCMGWFRQA PGKGLERVSV INSDGRTSYA      60
DSVKGRFTIS RDNSKNTLYL QMNSLRAEDT AVYYCAAVIL PPTDGMEYSC NYPAAEYNYW     120
GQGTLVTVSS GGGGSGGGGS GGGGSEVQLV ESGGGLVQPG GSLRLSCAAS EYTSSSYCMA     180
WIRQAPGKGL EGVAAIDTDG STSYTDSVKG RFTISRDNSK NTLYLQMNSL RAEDTAVYYC     240
AAAPWLLAYG DYCVTRPDFG EWGQGTLVTV SSGGGGSGGG GSGGGGSEVQ LVESGGGLVQ     300
PGGSLRLSCA ASGHAYGGNY MGWFRQAPGK GLEGVAVLYT GGGSTYYADS VKGRFTISED     360
NSKNTVYLQM NSLRAEDTAV YYCALALGSA RWYTSSLDAR AYNIWGQGTL VTVSS          415

SEQ ID NO: 118          moltype = AA  length = 659
FEATURE                 Location/Qualifiers
REGION                  1..659
                        note = SLN12140 and hTf binding VHH
source                  1..659
                        mol_type = protein
                        organism = synthetic construct
SEQUENCE: 118
EVQLVESGGG LVQPGGSLRL SCAASAYIYS SYCMGWFRQA PGKGLERVSV INSDGRTSYA      60
DSVKGRFTIS RDNSKNTLYL QMNSLRAEDT AVYYCAAVIL PPTDGMEYSC NYPAAEYNYW     120
GQGTLVTVSS GGGGSGGGGS GGGGSEVQLV ESGGGLVQPG GSLRLSCAAS EYTSSSYCMA     180
WIRQAPGKGL EGVAAIDTDG STSYTDSVKG RFTISRDNSK NTLYLQMNSL RAEDTAVYYC     240
AAAPWLLAYG DYCVTRPDFG EWGQGTLVTV SSGGGGSGGG GSGGGGSESK YGPPCPPCPA     300
PEFLGGPSVF LFPPKPKDTL MISRTPEVTC VVVDVSQEDP EVQFNWYVDG VEVHNAKTKP     360
REEQFNSTYR VVSVLTVLHQ DWLNGKEYKC KVSNKGLPSS IEKTISKAKG QPREPQVYTL     420
PPSQEEMTKN QVSLTCLVKG FYPSDIAVEW ESNGQPENNY KTTPPVLDSD GSFFLYSRLT     480
VDKSRWQEGN VFSCSVMHEA LHNHYTQKSL SLSLGKGGGG SGGGGSGGGG SEVQLVESGG     540
GLVQPGGSLR LSCAASGHAY GGNYMGWFRQ APGKGLEGVA VLYTGGGSTY YADSVKGRFT     600
ISEDNSKNTV YLQMNSLRAE DTAVYYCALA LGSARWYTSS LDARAYNIWG QGTLVTVSS      659
```